United States Patent
Lonberg et al.

(10) Patent No.: US 7,135,287 B1
(45) Date of Patent: *Nov. 14, 2006

(54) HUMAN ANTIBODIES

(75) Inventors: Nils Lonberg, Woodside, CA (US); Joe Buechler, Carlsbad, CA (US); Jeff Gray, Solana Beach, CA (US); Gunars Valkirs, Escondido, CA (US)

(73) Assignees: Biosite, Inc., San Diego, CA (US); Medarex, Inc., Milpitas, CA (US)

( * ) Notice: Subject to any disclaimer, the term of this patent is extended or adjusted under 35 U.S.C. 154(b) by 509 days.

This patent is subject to a terminal disclaimer.

(21) Appl. No.: 10/111,365

(22) PCT Filed: Oct. 2, 2000

(86) PCT No.: PCT/US00/27237

§ 371 (c)(1),
(2), (4) Date: Apr. 1, 2002

(87) PCT Pub. No.: WO01/25492

PCT Pub. Date: Apr. 12, 2001

Related U.S. Application Data

(63) Continuation-in-part of application No. 09/453,234, filed on Dec. 1, 1999, now Pat. No. 6,794,132.

(60) Provisional application No. 60/157,414, filed on Oct. 2, 1999.

(51) Int. Cl.
*C12Q 1/68* (2006.01)
*G01N 33/53* (2006.01)
*C12N 15/70* (2006.01)
*C12N 15/74* (2006.01)
*A01K 67/02* (2006.01)
*A61K 31/711* (2006.01)

(52) U.S. Cl. ............ 435/6; 435/7.1; 435/472; 800/18; 514/44

(58) Field of Classification Search .............. 800/4; 435/6, 455, 471
See application file for complete search history.

(56) References Cited

U.S. PATENT DOCUMENTS

| | | | |
|---|---|---|---|
| 3,654,090 A | 4/1972 | Schuurs et al. | |
| 4,376,110 A | 3/1983 | David et al. | |
| 4,486,530 A | 12/1984 | David et al. | |
| 4,514,505 A | 4/1985 | Cranfield et al. | |
| 5,173,418 A | 12/1992 | Molin et al. | |
| 5,427,908 A | 6/1995 | Dower | |
| 5,486,452 A | 1/1996 | Gordon et al. | |
| 5,545,807 A | 8/1996 | Surani et al. | |
| 5,565,332 A | 10/1996 | Hoogenboom et al. | |
| 5,571,698 A | 11/1996 | Ladner et al. | |
| 5,595,898 A | 1/1997 | Robinson et al. | |
| 5,625,126 A | 4/1997 | Lonberg et al. | |
| 5,658,727 A | 8/1997 | Barbas et al. | |
| 5,667,988 A | 9/1997 | Barbas et al. | |
| 5,766,905 A | 6/1998 | Studier et al. | |
| 5,770,429 A | 6/1998 | Lonberg et al. | |
| 5,789,208 A | 8/1998 | Sharon | |
| 5,874,312 A | 2/1999 | Sredni et al. | |
| 5,914,241 A | 6/1999 | Valkirs | |
| 5,939,807 A | 8/1999 | Patyk et al. | |
| 6,057,098 A | 5/2000 | Buechler et al. | |
| 6,090,382 A | 7/2000 | Salfeld | |
| 6,261,558 B1 | 7/2001 | Barbas et al. | |
| 6,794,132 B1 * | 9/2004 | Buechler et al. | 435/6 |

FOREIGN PATENT DOCUMENTS

| | | |
|---|---|---|
| EP | 934 953 | 8/1999 |
| WO | WO 91/19818 | 2/1991 |
| WO | WO 92/06204 | 4/1992 |
| WO | WO 94/26787 | 11/1994 |
| WO | WO 95/11317 A1 | 4/1995 |
| WO | WO 96/33735 | 10/1996 |
| WO | WO 98/06704 | 2/1998 |
| WO | WO 98/47343 | 10/1998 |
| WO | WO 99/53049 | 10/1999 |

OTHER PUBLICATIONS

Mendez, M.J. et al. "Functional transplant of megabase human immunoglobulin loci recapitulates human antibody response in mice" 1997, Nat. Genetics; vol. 15 p. 146-156.*

Moreadith, R.W. et al, "Gene targeting in embryonic stem cells: the new physiology and metabolism", 1997, J. Mol. Med., vol. 75: pp. 208-216.*

Mullins, L.J. et al., "Perspective series: Molecular Medicine in Genetically Engineered Animals", 1996, J. Clin. Invest., vol. 97: pp. 1557-1560.*

Donnelly, J.J. et al., "DNA Vaccines", 1997, Annu. Rev. Immunol., vol. 15: pp. 617-648.*

Cwirla et al., "Peptides on Phage: A Vast Library of Peptides for Identifying Ligands," *PNAS*, 87:6378-82 (1990).

Devlin et al., "Random Peptide Libraries: A Source of Specific Protein Binding Molecules," *Science*, 249:404-406 (1990).

(Continued)

*Primary Examiner*—Scott D. Priebe
*Assistant Examiner*—Michael Burkhart
(74) *Attorney, Agent, or Firm*—Townsend and Townsend and Crew, LLP

(57) ABSTRACT

The invention uses the power of display selection methods to screen libraries of human immunoglobulin genes from nonhuman transgenic animals expressing human immunoglobulins. Such screening produces unlimited numbers of high affinity human antibodies to any target of interest.

12 Claims, 10 Drawing Sheets

OTHER PUBLICATIONS

Georgiou et al., "Display of Heterologous Proteins on the Surface of Microorganisms: From the Screening of Combinatorial Libraries to Live Recombinant Vaccines," *Nature Biotech.*, 15:29-34 (1997).

Kricka, L.J., "Human Anti-Animal Antibody Interferences in Immunological Assays," *Clinical Chemistry*, 45(7):942-956 (1999).

Kuijper et al., "Functional cloning vectors for use in directional cDNA cloning using cohesive ends produced with T4 DNA polymerase," *Gene*, 112(2):147-155 (1992).

McCafferty et al., "Selection and Rapid Purification of Murine Antibody Fragments That Bind a Transition-State Analog by Phage Display," *Applied Biochem. & Biotech.*, 47:157-173 (1994).

Rader et al., "Phage display of combinatorial antibody libraries," *Current Opinionin Biotech.* 8:503-508 (1997).

Scott et al., "Searching for Peptide Ligands With An Epitope Library," *Science*, 249:386-388 (1990).

Winter et al., "Making Antibodies by Phage Display Technology," *Annu. Rev. Immunol.*, 12:433-455 (1994).

Dziegiel et al., "Phage display used for gene cloning of human recombinant antibody against the erythrocyte surface antigen, rhesus D," *J. Immunol. Methods*, 182:7-19 (1995).

Fishweld et al., "High-avidity human IgGk monoclonal antibodies from a novel strain of minilocus transgenic mice," *Nature Biotechnology*, 14:845-851 (1996).

He et al., "Selection of a human anti-progesterone antibody fragment from a transgenic mouse library by ARM ribosome display," *J. Immunol. Methods*, 231:105-117 (1999).

Mendez et al., "Functional transplant of megabase human immunoglobin loci recapitulates human antibody response in mice," *Nature Genetics*, 15(2):146-156 (1997).

Popov et al., "A Human Immunoglobulin λ locus Is Similarly Well Expressed in Mice and Humans," *J. Exp. Med.*, 189(10):1611-1619 (1999).

* cited by examiner

DNA Sequences of Oligos used to delete CDR1-CDR3 regions of 668-4

Kappa Chain

Framework 4                                                Stop Stop Stop  Framework 1
TAT TTC CAG CTT GGT CCC TCT AGA GTT AAC GAT ATC AA CGT TTA T CTA A TCA GCA AGA GAT GGA GGC TTG Heavy Chain Framework 4                                                Stop Stop Stop  Framework 4
TGA GGT TCC TTG ACC CCA CTG CAG AGT ACT AGG CCT CT GAG CTA C TCA G TTA GGT GAT TGA GTA GCC AGT

FIG. 2

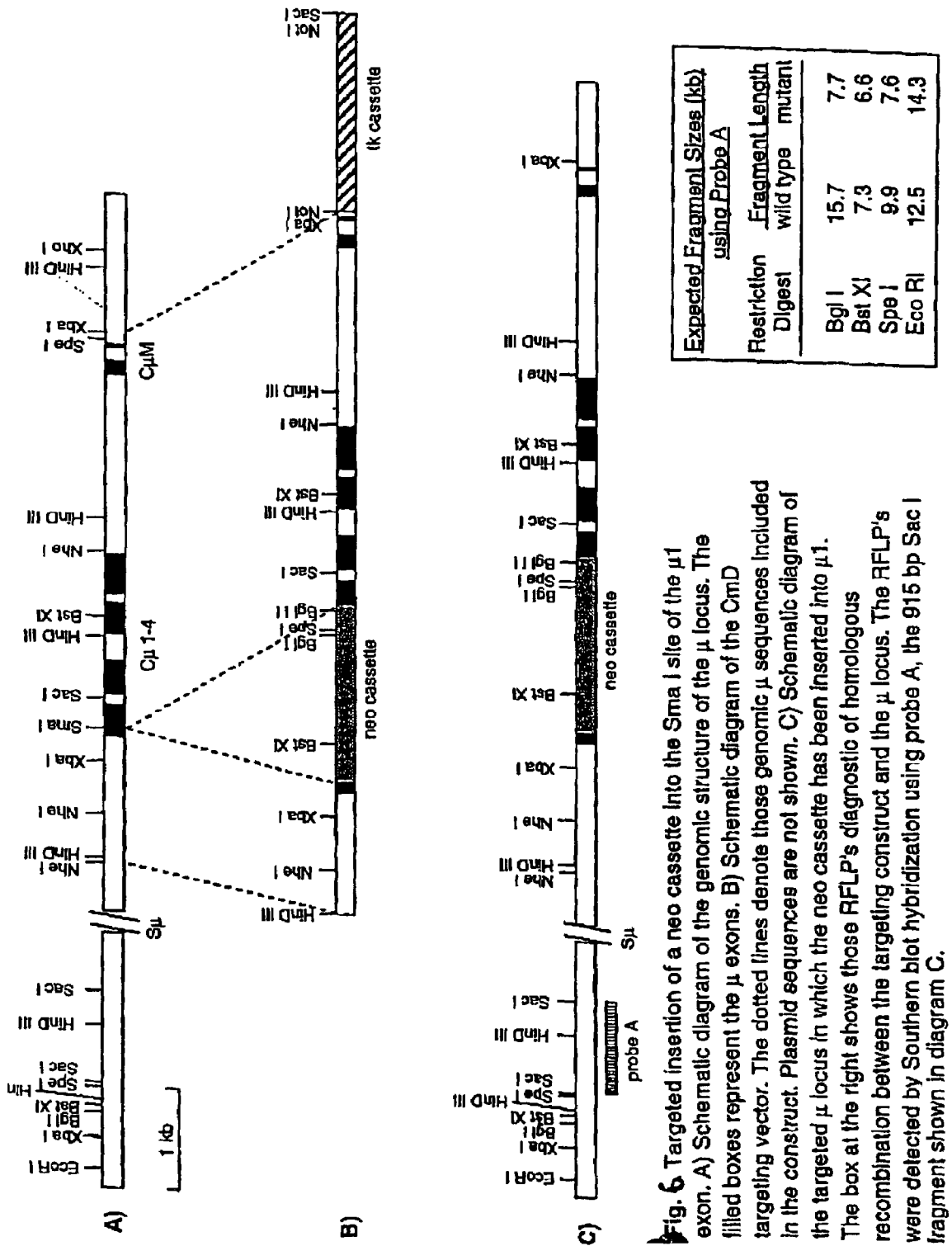

Fig. 6 Targeted insertion of a neo cassette into the Sma I site of the μ1 exon. A) Schematic diagram of the genomic structure of the μ locus. The filled boxes represent the μ exons. B) Schematic diagram of the CmD targeting vector. The dotted lines denote those genomic μ sequences included in the construct. Plasmid sequences are not shown. C) Schematic diagram of the targeted μ locus in which the neo cassette has been inserted into μ1. The box at the right shows those RFLP's diagnostic of homologous recombination between the targeting construct and the μ locus. The RFLP's were detected by Southern blot hybridization using probe A, the 915 bp Sac I fragment shown in diagram C.

SEQUENCE LISTING

<160> NUMBER OF SEQ ID NOS: 172

<210> SEQ ID NO 1
<211> LENGTH: 43
<212> TYPE: DNA
<213> ORGANISM: Artificial Sequence
<220> FEATURE:
<223> OTHER INFORMATION: Oligo 188

<400> SEQUENCE: 1
ttacccctgt ggcaaaagcc gaagtgcagc tggtggagtc tgg          43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Oligo 944

<400> SEQUENCE: 2
ttacccctgt ggcaaaagcc caggtgcagc tggtgcagtc tgg          43

<210> SEQ ID NO 3
<211> LENGTH: 43
<212> TYPE: DNA
<213> ORGANISM: Artificial Sequence

```
<220> FEATURE:
<223> OTHER INFORMATION: Description of Artificial Sequence: Oligo 948

<400> SEQUENCE: 3
ttacccctgt ggcaaaagcc caggtgcagc tggtggagtc tgg                    43

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Oligo 952

<400> SEQUENCE: 4
gatgggccct tggtggaggc                                              20

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Oligo 189

<400> SEQUENCE: 5
ctgcccaacc agccatggcc gaaattgtgc tcacccagtc tcc                    43

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Oligo 931

<400> SEQUENCE: 6
tcgctgccca accagccatg gccgtcatct ggatgaccca gtctcc                 46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Oligo 932

<400> SEQUENCE: 7
tcgctgccca accagccatg gccaacatcc agatgaccca gtctcc                 46

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Oligo 933

<400> SEQUENCE: 8
tcgctgccca accagccatg gccgccatcc ggatgaccca gtctcc                 46

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Oligo 934

<400> SEQUENCE: 9
tcgctgccca accagccatg gccgccatcc agttgaccca gtctcc                 46
```

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Oligo 935

<400> SEQUENCE: 10
tcgctgccca accagccatg gccgaaatag tgatgacgca gtctcc        46

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Oligo 936

<400> SEQUENCE: 11
tcgctgccca accagccatg gccgatgttg tgatgacaca gtctcc        46

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Oligo 937

<400> SEQUENCE: 12
tcgctgccca accagccatg gccgaaattg tgttgacgca gtctcc        46

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Oligo 955

<400> SEQUENCE: 13
tcgctgccca accagccatg gccgacatcc agatgatcca gtctcc        46

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Oligo 956

<400> SEQUENCE: 14
tcgctgccca accagccatg gccgatattg tgatgaccca gactcc        46

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Oligo 973

<400> SEQUENCE: 15
cagcaggcac acaacagagg c        21

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Oligo 945

```
<400> SEQUENCE: 16
ttacccctgt ggcaaaagcc gaggtgcagc tgttggagtc tgg                    43

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Oligo 946

<400> SEQUENCE: 17
ttacccctgt ggcaaaagcc gaggtgcagc tggtgcagtc tgg                    43

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Oligo 947

<400> SEQUENCE: 18
ttacccctgt ggcaaaagcc caggtgcagc tacagcagtg ggg                    43

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Oligo 953

<400> SEQUENCE: 19
gacagatggt gcagccacag t                                            21

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence: Oligo 864

<400> SEQUENCE: 20
atctggcaca tcatatggat aagtttcgtg tacaaaatgc cagacctaga ggaattttat  60
ttccagcttg gtccc                                                   75

<210> SEQ ID NO 21
<211> LENGTH: 69
<212> TYPE: DNA
<213> ORGANISM: Artificial Sequence
<220> FEATURE:
<223> OTHER INFORMATION: Description of Artificial Sequence: Oligo 862

<400> SEQUENCE: 21
gtgatggtga tggtgatgga tcggagtacc aggttatcga gccctcgata ttgaggagac  60
ggtgactga                                                          69

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:  Primer 5

<400> SEQUENCE: 22
```
gcaactgttg ggaaggg                                                    17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer 197

<400> SEQUENCE: 23
tcgctgccca accagccatg                                                 20

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Primer 869

<400> SEQUENCE: 24
gggaccaagc tggaaataaa acgggctgtg gctgcaccat ctgtct                    46

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Primer 870

<400> SEQUENCE: 25
atctggcaca tcatatggat aagactctcc cctgttgaag ctctt                     45

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:Primer 867

<400> SEQUENCE: 26
tcagtcaccg tctcctcagc ctccaccaag ggcccatc                             38

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Primer 876

<400> SEQUENCE: 27
gtgatggtga tggtgatgag atttgggctc tgctttcttg tcc                       43

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer 885

<400> SEQUENCE: 28
taagagcggt aagagtgcca g                                               21

<210> SEQ ID NO 29
<211> LENGTH: 69
<212> TYPE: DNA
<213> ORGANISM: Artificial Sequence

```
<220> FEATURE:
<223> OTHER INFORMATION: Description of Artificial Sequence: Primer 970

<400> SEQUENCE: 29
gtgataaact accgtaaagc ttatcgatga taagctgtca attagtgatg gtgatggtga    60
tgagatttg                                                            69

<210> SEQ ID NO 30
<211> LENGTH: 10
<212> TYPE: PRT
<213> ORGANISM: Artificial Sequence
<220> FEATURE:
<223> OTHER INFORMATION: Example 17 Decapeptide

<400> SEQUENCE: 30

Tyr Pro Tyr Asp Val Pro Asp Tyr Ala Ser
  1               5                  10

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence: Example 19
      Primer A

<400> SEQUENCE: 31
tcgctgccca accagccatg gccagtgcta aagaacttag atctcag                  47

<210> SEQ ID NO 32
<211> LENGTH: 86
<212> TYPE: DNA
<213> ORGANISM: Artificial Sequence
<220> FEATURE:
<223> OTHER INFORMATION: Description of Artificial Sequence: Example 19
      Primer B

<400> SEQUENCE: 32
gtgataaact accgcattaa agcttatcga tgataagctg tcaattagtg atggtgatgg    60
tgatgtgaat tctcagccct cttcaa                                         86

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Example 19
      Primer C

<400> SEQUENCE: 33
gcaactctct actgtttctc c                                              21

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Example 19
      Primer D

<400> SEQUENCE: 34
gaggatgacg atgagcgc                                                  18

<210> SEQ ID NO 35
<211> LENGTH: 672
```

```
<212> TYPE: DNA
<213> ORGANISM: Homo sapiens
<220> FEATURE:
<223> OTHER INFORMATION: M1-1L

<400> SEQUENCE: 35
gaaattgtgt tgacgcagtc tccagccacc ctgtctttgt ctccagggga aagagccacc      60
ctctcctgca gggccagtca gggtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctcggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaacacaaa gtctacgcct gcgaagtcac ccatcagggc    600
ctgagctcgc ccgtcacaaa gagcttcaac aggggagagt cttatccata tgatgtgcca    660
gattatgcga gc                                                        672

<210> SEQ ID NO 36
<211> LENGTH: 224
<212> TYPE: PRT
<213> ORGANISM: Homo sapiens

<400> SEQUENCE: 36

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Gly Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
```

<210> SEQ ID NO 37
<211> LENGTH: 678
<212> TYPE: DNA
<213> ORGANISM: Homo sapiens
<220> FEATURE:
<223> OTHER INFORMATION: M1-3L
<220> FEATURE:
<221> NAME/KEY: CDS
<222> LOCATION: (1)..(678)

<400> SEQUENCE: 37

| | | | | | | | | | | | | | | | | |
|---|---|---|---|---|---|---|---|---|---|---|---|---|---|---|---|---|
| gaa | ata | gtg | atg | acg | cag | tct | cca | gcc | acc | ctg | tct | ttg | tct | cca | ggg | 48 |
| Glu | Ile | Val | Met | Thr | Gln | Ser | Pro | Ala | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agc | agc | agc | 96 |
| Glu | Arg | Ala | Thr | Leu | Ser | Cys | Arg | Ala | Ser | Gln | Ser | Val | Ser | Ser | Ser | |
| | | | 20 | | | | | 25 | | | | | 30 | | | |
| tac | tta | gcc | tgg | tac | cag | cag | aaa | cct | ggc | cag | gct | ccc | agg | ctc | ctc | 144 |
| Tyr | Leu | Ala | Trp | Tyr | Gln | Gln | Lys | Pro | Gly | Gln | Ala | Pro | Arg | Leu | Leu | |
| | | 35 | | | | | 40 | | | | | 45 | | | | |
| atc | tat | ggt | gca | tcc | agc | agg | gcc | act | ggc | atc | cca | gac | agg | ttc | agt | 192 |
| Ile | Tyr | Gly | Ala | Ser | Ser | Arg | Ala | Thr | Gly | Ile | Pro | Asp | Arg | Phe | Ser | |
| | 50 | | | | | 55 | | | | | 60 | | | | | |
| ggc | agt | ggg | tct | ggg | aca | gac | ttc | act | ctc | acc | atc | agc | aga | ctg | gag | 240 |
| Gly | Ser | Gly | Ser | Gly | Thr | Asp | Phe | Thr | Leu | Thr | Ile | Ser | Arg | Leu | Glu | |
| 65 | | | | | 70 | | | | | 75 | | | | | 80 | |
| cct | gaa | gat | ttt | gca | gtg | tat | tac | tgt | cag | cag | tat | ggt | agc | tca | cct | 288 |
| Pro | Glu | Asp | Phe | Ala | Val | Tyr | Tyr | Cys | Gln | Gln | Tyr | Gly | Ser | Ser | Pro | |
| | | | | 85 | | | | | 90 | | | | | 95 | | |
| cca | ttc | act | ttc | ggc | cct | ggg | acc | aaa | gtg | gat | atc | aaa | cga | act | gtg | 336 |
| Pro | Phe | Thr | Phe | Gly | Pro | Gly | Thr | Lys | Val | Asp | Ile | Lys | Arg | Thr | Val | |
| | | | 100 | | | | | 105 | | | | | 110 | | | |
| gct | gca | cca | tct | gtc | ttc | atc | ttc | ccg | cca | tct | gat | gag | cag | ttg | aaa | 384 |
| Ala | Ala | Pro | Ser | Val | Phe | Ile | Phe | Pro | Pro | Ser | Asp | Glu | Gln | Leu | Lys | |
| | | 115 | | | | | 120 | | | | | 125 | | | | |
| tct | gga | act | gcc | tct | gtt | gtg | tgc | ctg | ctg | aat | aac | ttc | tat | ccc | aga | 432 |
| Ser | Gly | Thr | Ala | Ser | Val | Val | Cys | Leu | Leu | Asn | Asn | Phe | Tyr | Pro | Arg | |
| | 130 | | | | | 135 | | | | | 140 | | | | | |
| gag | gcc | aaa | gta | cag | tgg | aag | gtg | gat | aac | gcc | ctc | caa | tcg | ggt | aac | 480 |
| Glu | Ala | Lys | Val | Gln | Trp | Lys | Val | Asp | Asn | Ala | Leu | Gln | Ser | Gly | Asn | |
| 145 | | | | | 150 | | | | | 155 | | | | | 160 | |
| tcc | cag | gag | agt | gtc | aca | gag | cag | gac | agc | aag | gac | agc | acc | tac | agc | 528 |
| Ser | Gln | Glu | Ser | Val | Thr | Glu | Gln | Asp | Ser | Lys | Asp | Ser | Thr | Tyr | Ser | |
| | | | | 165 | | | | | 170 | | | | | 175 | | |
| ctc | agc | agc | acc | ctg | acg | ctg | agc | aaa | gca | gac | tac | gag | aaa | cac | aaa | 576 |
| Leu | Ser | Ser | Thr | Leu | Thr | Leu | Ser | Lys | Ala | Asp | Tyr | Glu | Lys | His | Lys | |
| | | | 180 | | | | | 185 | | | | | 190 | | | |
| gtc | tac | gcc | tgc | gaa | gtc | acc | cat | cag | ggc | ctg | agc | tcg | ccc | gtc | aca | 624 |
| Val | Tyr | Ala | Cys | Glu | Val | Thr | His | Gln | Gly | Leu | Ser | Ser | Pro | Val | Thr | |
| | | 195 | | | | | 200 | | | | | 205 | | | | |
| aag | agc | ttc | aac | agg | gga | gag | tct | tat | cca | tat | gat | gtg | cca | gat | tat | 672 |
| Lys | Ser | Phe | Asn | Arg | Gly | Glu | Ser | Tyr | Pro | Tyr | Asp | Val | Pro | Asp | Tyr | |
| | 210 | | | | | 215 | | | | | 220 | | | | | |
| gcg | agc | | | | | | | | | | | | | | | 678 |
| Ala | Ser | | | | | | | | | | | | | | | |
| 225 | | | | | | | | | | | | | | | | |

<210> SEQ ID NO 38
<211> LENGTH: 226
<212> TYPE: PRT

```
<213> ORGANISM: Homo sapiens
<220> FEATURE:
<223> OTHER INFORMATION: M1-3L

<400> SEQUENCE: 38

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Pro Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 39
<211> LENGTH: 672
<212> TYPE: DNA
<213> ORGANISM: Homo sapiens
<220> FEATURE:
<223> OTHER INFORMATION: M1-4L
<220> FEATURE:
<221> NAME/KEY: CDS
<222> LOCATION: (1)..(672)

<400> SEQUENCE: 39 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc cac     144
Tyr Leu Ala Trp Tyr Gln Gln Lys Pro Gly Gln Ala Pro Arg Leu His
            35                  40                  45 atc tat ggt gca tcc aga agg gcc act ggc atc cca gac agg ttc agt     192
Ile Tyr Gly Ala Ser Arg Arg Ala Thr Gly Ile Pro Asp Arg Phe Ser
    50                  55                  60
```

```
ggc agt ggg tct ggg aca gac ttc act ctc acc atc agc aga ctg gag    240
Gly Ser Gly Ser Gly Thr Asp Phe Thr Leu Thr Ile Ser Arg Leu Glu
 65                  70                  75                  80 cct gaa gat ttt gca gtg tat tac tgt cag cag ttt ggt agc tca ttc    288
Pro Glu Asp Phe Ala Val Tyr Tyr Cys Gln Gln Phe Gly Ser Ser Phe
                 85                  90                  95 act ttc ggc cct ggg acc aaa gtg gat atc aaa cga act gtg gct gca    336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc    672
Phe Asn Arg Gly Glu Ser Tyr Pro Tyr Asp Val Pro Asp Tyr Ala Ser
    210                 215                 220

<210> SEQ ID NO 40
<211> LENGTH: 224
<212> TYPE: PRT
<213> ORGANISM: Homo sapiens
<220> FEATURE:
<223> OTHER INFORMATION: M1-4L

<400> SEQUENCE: 40

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu His
         35                  40                  45

Ile Tyr Gly Ala Ser Arg Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 41
<211> LENGTH: 678
<212> TYPE: DNA
<213> ORGANISM: Homo sapiens
<220> FEATURE:
<221> NAME/KEY: CDS
<222> LOCATION: (1)..(678)
<220> FEATURE:
<223> OTHER INFORMATION: M1-5L

<400> SEQUENCE: 41
```

| | | | | | | | | | | | | | | | | |
|---|---|---|---|---|---|---|---|---|---|---|---|---|---|---|---|---|
| gaa | ata | gtg | atg | acg | cag | tct | cca | ggc | acc | ctg | tct | ttg | tct | cca | ggg | 48 |
| Glu | Ile | Val | Met | Thr | Gln | Ser | Pro | Gly | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agc | agc | agc | 96 |
| Glu | Arg | Ala | Thr | Leu | Ser | Cys | Arg | Ala | Ser | Gln | Ser | Val | Ser | Ser | Ser | |
| | | | 20 | | | | | 25 | | | | | 30 | | | |
| tac | tta | gcc | tgg | tac | cag | cag | aaa | cct | ggc | cag | gct | ccc | agg | ctc | ctc | 144 |
| Tyr | Leu | Ala | Trp | Tyr | Gln | Gln | Lys | Pro | Gly | Gln | Ala | Pro | Arg | Leu | Leu | |
| | | 35 | | | | | 40 | | | | | 45 | | | | |
| atc | tat | ggt | gca | tcc | agc | agg | gcc | act | ggc | atc | cca | gac | agg | ttc | agt | 192 |
| Ile | Tyr | Gly | Ala | Ser | Ser | Arg | Ala | Thr | Gly | Ile | Pro | Asp | Arg | Phe | Ser | |
| | 50 | | | | | 55 | | | | | 60 | | | | | |
| ggc | agt | ggg | tct | ggg | aca | gac | ttc | act | ctc | acc | atc | agc | aga | ctg | gag | 240 |
| Gly | Ser | Gly | Ser | Gly | Thr | Asp | Phe | Thr | Leu | Thr | Ile | Ser | Arg | Leu | Glu | |
| 65 | | | | | 70 | | | | | 75 | | | | | 80 | |
| cct | gaa | gat | ttt | gca | gtg | tat | tac | tgt | cag | cag | tat | ggt | agc | tca | cct | 288 |
| Pro | Glu | Asp | Phe | Ala | Val | Tyr | Tyr | Cys | Gln | Gln | Tyr | Gly | Ser | Ser | Pro | |
| | | | | 85 | | | | | 90 | | | | | 95 | | |
| ata | ttc | act | ttc | ggc | cct | ggg | acc | aaa | gtg | gat | atc | aaa | cga | act | gtg | 336 |
| Ile | Phe | Thr | Phe | Gly | Pro | Gly | Thr | Lys | Val | Asp | Ile | Lys | Arg | Thr | Val | |
| | | | 100 | | | | | 105 | | | | | 110 | | | |
| gct | gca | cca | tct | gtc | ttc | atc | ttc | ccg | cca | tct | gat | gag | cag | ttg | aaa | 384 |
| Ala | Ala | Pro | Ser | Val | Phe | Ile | Phe | Pro | Pro | Ser | Asp | Glu | Gln | Leu | Lys | |
| | | 115 | | | | | 120 | | | | | 125 | | | | |
| tct | gga | act | gcc | tct | gtt | gtg | tgc | ctg | ctg | aat | aac | ttc | tat | ccc | aga | 432 |
| Ser | Gly | Thr | Ala | Ser | Val | Val | Cys | Leu | Leu | Asn | Asn | Phe | Tyr | Pro | Arg | |
| | 130 | | | | | 135 | | | | | 140 | | | | | |
| gag | gcc | aaa | gta | cag | tgg | aag | gtg | gat | aac | gcc | ctc | caa | tcg | ggt | aac | 480 |
| Glu | Ala | Lys | Val | Gln | Trp | Lys | Val | Asp | Asn | Ala | Leu | Gln | Ser | Gly | Asn | |
| 145 | | | | | 150 | | | | | 155 | | | | | 160 | |
| tcc | cag | gag | agt | gtc | aca | gag | cag | gac | agc | aag | gac | agc | acc | tac | agc | 528 |
| Ser | Gln | Glu | Ser | Val | Thr | Glu | Gln | Asp | Ser | Lys | Asp | Ser | Thr | Tyr | Ser | |
| | | | | 165 | | | | | 170 | | | | | 175 | | |
| ctc | agc | agc | acc | ctg | acg | ctg | agc | aaa | gca | gac | tac | gag | aaa | cac | aaa | 576 |
| Leu | Ser | Ser | Thr | Leu | Thr | Leu | Ser | Lys | Ala | Asp | Tyr | Glu | Lys | His | Lys | |
| | | | 180 | | | | | 185 | | | | | 190 | | | |
| gtc | tac | gcc | tgc | gaa | gtc | acc | cat | cag | ggc | ctg | agc | tcg | ccc | gtc | aca | 624 |
| Val | Tyr | Ala | Cys | Glu | Val | Thr | His | Gln | Gly | Leu | Ser | Ser | Pro | Val | Thr | |
| | | 195 | | | | | 200 | | | | | 205 | | | | |
| aag | agc | ttc | aac | agg | gga | gag | tct | tat | cca | tat | gat | gtg | cca | gat | tat | 672 |

```
Lys Ser Phe Asn Arg Gly Glu Ser Tyr Pro Tyr Asp Val Pro Asp Tyr
        210                 215                 220 gcg agc                                                                    678
Ala Ser
225

<210> SEQ ID NO 42
<211> LENGTH: 226
<212> TYPE: PRT
<213> ORGANISM: Homo sapiens
<220> FEATURE:
<223> OTHER INFORMATION: M1-5L

<400> SEQUENCE: 42

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 43
<211> LENGTH: 672
<212> TYPE: DNA
<213> ORGANISM: Homo sapiens
<220> FEATURE:
<223> OTHER INFORMATION: M1-8L
<220> FEATURE:
<221> NAME/KEY: CDS
<222> LOCATION: (1)..(672)

<400> SEQUENCE: 43 gaa ata gtg atg acg cag tct cca ggc acc ctg tct ttg tct cca ggg    48
Glu Ile Val Met Thr Gln Ser Pro Gly Thr Leu Ser Leu Ser Pro Gly
  1               5                  10                  15
```

```
gaa aga gcc acc ctc tcc tgc agg gcc agt cag agt gtt agc agc acc      96
Glu Arg Ala Thr Leu Ser Cys Arg Ala Ser Gln Ser Val Ser Ser Thr
         20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
     35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat gtt agc tca ttc     288
Pro Glu Asp Phe Ala Val Tyr Tyr Cys Gln Gln Tyr Val Ser Ser Phe
             85                  90                  95 act ttc ggc cct ggg acc aaa gtg gat atc aaa cga act gtg gct gca     336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc     672
Phe Asn Arg Gly Glu Ser Tyr Pro Tyr Asp Val Pro Asp Tyr Ala Ser
    210                 215                 220
```

<210> SEQ ID NO 44
<211> LENGTH: 224
<212> TYPE: PRT
<213> ORGANISM: Homo sapiens
<220> FEATURE:
<223> OTHER INFORMATION: M1-8L

<400> SEQUENCE: 44

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Ser Phe
             85                  90                  95
```

```
Thr Phe Gly Pro Gly Thr Lys Val Asp Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Ser Tyr Pro Tyr Asp Val Pro Asp Tyr Ala Ser
            210                 215                 220
```

<210> SEQ ID NO 45
<211> LENGTH: 672
<212> TYPE: DNA
<213> ORGANISM: Homo sapiens
<220> FEATURE:
<223> OTHER INFORMATION: M1-10L
<220> FEATURE:
<221> NAME/KEY: CDS
<222> LOCATION: (1)..(672)

<400> SEQUENCE: 45

```
gat gtt gtg atg aca cag tct cca gcc acc ctg tct ttg tct cca ggg      48
Asp Val Val Met Thr Gln Ser Pro Ala Thr Leu Ser Leu Ser Pro Gly
1               5                   10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ccc     288
Glu Asp Phe Ala Val Tyr Tyr Cys Gln Gln Arg Ser Asn Trp Pro Pro
                85                  90                  95 act ttc ggc gga ggg acc aag gtg gag atc aaa cga act gtg gct gca     336
Thr Phe Gly Gly Gly Thr Lys Val Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
            130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
```

```
                Glu Ser Val Thr Glu Gln Asp Ser Lys Asp Ser Thr Tyr Ser Leu Ser
                            165                 170                 175 agc acc ctg acg ctg agc aaa gca gac tac gag aaa cac aaa gtc tac                     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc                     624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc                     672
Phe Asn Arg Gly Glu Ser Tyr Pro Tyr Asp Val Pro Asp Tyr Ala Ser
    210                 215                 220
```

<210> SEQ ID NO 46
<211> LENGTH: 224
<212> TYPE: PRT
<213> ORGANISM: Homo sapiens
<220> FEATURE:
<223> OTHER INFORMATION: M1-10L

<400> SEQUENCE: 46

```
Asp Val Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 47
<211> LENGTH: 672
<212> TYPE: DNA
<213> ORGANISM: Homo sapiens
<220> FEATURE:
<223> OTHER INFORMATION: M1-21L
<220> FEATURE:
<221> NAME/KEY: CDS
<222> LOCATION: (1)..(672)

<400> SEQUENCE: 47

```
gcc atc cgg atg acc cag tct cca tcc ttc ctg tct gca tct gta gga      48
Ala Ile Arg Met Thr Gln Ser Pro Ser Phe Leu Ser Ala Ser Val Gly
 1               5                  10                  15 gac aga gtc acc atc act tgc cgg gca agt cag agc att agc agc tat      96
Asp Arg Val Thr Ile Thr Cys Arg Ala Ser Gln Ser Ile Ser Ser Tyr
             20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
         35                  40                  45 tat gct gca tcc agt ttg caa agt ggg gtc cca tca agg ttc agt gtc     192
Tyr Ala Ala Ser Ser Leu Gln Ser Gly Val Pro Ser Arg Phe Ser Val
 50                  55                  60 agt gga tct ggg aca gat ctc act ctc acc atc agc agt ctg caa cct     240
Ser Gly Ser Gly Thr Asp Leu Thr Leu Thr Ile Ser Ser Leu Gln Pro
 65                  70                  75                  80 gaa gat ttt gca act tat tac tgt cag tgt ggt tac agt aca cca ttc     288
Glu Asp Phe Ala Thr Tyr Tyr Cys Gln Cys Gly Tyr Ser Thr Pro Phe
                 85                  90                  95 act ttc ggc cct ggg acc aaa gtg gat atc aaa cga act gtg gct gca     336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc     672
Phe Asn Arg Gly Glu Ser Tyr Pro Tyr Asp Val Pro Asp Tyr Ala Ser
    210                 215                 220
```

<210> SEQ ID NO 48
<211> LENGTH: 224
<212> TYPE: PRT
<213> ORGANISM: Homo sapiens
<220> FEATURE:
<223> OTHER INFORMATION: M1-21L

<400> SEQUENCE: 48

```
Ala Ile Arg Met Thr Gln Ser Pro Ser Phe Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Val
 50                  55                  60
```

```
Ser Gly Ser Gly Thr Asp Leu Thr Leu Thr Ile Ser Ser Leu Gln Pro
 65                  70                  75                  80

Glu Asp Phe Ala Thr Tyr Tyr Cys Gln Cys Gly Tyr Ser Thr Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 49
<211> LENGTH: 678
<212> TYPE: DNA
<213> ORGANISM: Homo sapiens
<220> FEATURE:
<223> OTHER INFORMATION: M1-23L
<220> FEATURE:
<221> NAME/KEY: CDS
<222> LOCATION: (1)..(678)

<400> SEQUENCE: 49

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
                 85                  90                  95 ccg tac act ttt ggc cag ggg acc aag ctg gag atc aaa cga act gtg     336
Pro Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa     384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga     432
Ser Gly Thr Ala Ser Val Val Cys Leu Leu Asn Asn Phe Tyr Pro Arg
    130                 135                 140
```

```
gag gcc aaa gta cag tgg agg gtg gat aac gcc ctc caa tcg ggt aac      480
Glu Ala Lys Val Gln Trp Arg Val Asp Asn Ala Leu Gln Ser Gly Asn
145                 150                 155                 160 tcc cag gag agt gtc aca gag cag gac agc aag gac agc acc tac agc      528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa      576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca      624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat      672
Lys Ser Phe Asn Arg Gly Glu Ser Tyr Pro Tyr Asp Val Pro Asp Tyr
    210                 215                 220 gcg agc                                                              678
Ala Ser
225

<210> SEQ ID NO 50
<211> LENGTH: 226
<212> TYPE: PRT
<213> ORGANISM: Homo sapiens
<220> FEATURE:
<223> OTHER INFORMATION: M1-23L

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Arg Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225
```

<210> SEQ ID NO 51
<211> LENGTH: 672
<212> TYPE: DNA
<213> ORGANISM: Homo sapiens
<220> FEATURE:
<223> OTHER INFORMATION: M1-25L

<400> SEQUENCE: 51

```
gaaattgtgt tgacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtgcatcca gcagggccac tggcatccca       180
aacaggttca gtggcagtgg gtctgggaca gacttcactc tcaccatcag cagactggag       240
cctgaagatt ttgcagtgta ttactgtcag cagtatggta gctcattcac tttcggccct       300
gggaccaaag tggatatcaa acgaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccctgacg      540
ctgagcaaag cagactacga gaaacacaaa gtctacgcct gcgaagtcac ccatcagggc       600
ctgagctcgc ccgtcacaaa gagcttcaac aggggagagt cttatcccata tgatgtgcca       660
gattatgcga gc                                                           672
```

<210> SEQ ID NO 52
<211> LENGTH: 224
<212> TYPE: PRT
<213> ORGANISM: Homo sapiens
<220> FEATURE:
<223> OTHER INFORMATION: M1-25L

<400> SEQUENCE: 52

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asn Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205
Phe Asn Arg Gly Glu Ser Tyr Pro Tyr Asp Val Pro Asp Tyr Ala Asn
    210                 215                 220

<210> SEQ ID NO 53
<211> LENGTH: 675
<212> TYPE: DNA
<213> ORGANISM: Homo sapiens
<220> FEATURE:
<223> OTHER INFORMATION: M1-1H
<220> FEATURE:
<221> NAME/KEY: CDS
<222> LOCATION: (1)..(675)

<400> SEQUENCE: 53 cag gtg cag ctg gtg gag tct ggg gga ggc gtg gtc cag cct ggg aag        48
Gln Val Gln Leu Val Glu Ser Gly Gly Gly Val Val Gln Pro Gly Lys
  1               5                  10                  15 tcc ctg aga ctc tcc tgt gca gcg tct gaa ttc acc atc agt tac tat        96
Ser Leu Arg Leu Ser Cys Ala Ala Ser Glu Phe Thr Ile Ser Tyr Tyr
             20                  25                  30 ggc atg cac tgg gtc cgc cag gtt cca ggc aag ggg ctg gag tgg gtg       144
Gly Met His Trp Val Arg Gln Val Pro Gly Lys Gly Leu Glu Trp Val
         35                  40                  45 gca gct gtc tgg tat gat gaa agt act aca tat tct cca gac tcc gtg       192
Ala Ala Val Trp Tyr Asp Glu Ser Thr Thr Tyr Ser Pro Asp Ser Val
     50                  55                  60 aag ggc cga ttc acc atc tcc aga gac gat tcc aag aac acg ctg tat       240
Lys Gly Arg Phe Thr Ile Ser Arg Asp Asp Ser Lys Asn Thr Leu Tyr
 65                  70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg       336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc       432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat       672
Thr Lys Val Asp Lys Lys Ala Glu Pro Lys Ser His His His His His
    210                 215                 220 cac                                                                   675
His
225
```

```
<210> SEQ ID NO 54
<211> LENGTH: 225
<212> TYPE: PRT
<213> ORGANISM: Homo sapiens
<220> FEATURE:
<223> OTHER INFORMATION: M1-1H

<400> SEQUENCE: 54

Gln Val Gln Leu Val Glu Ser Gly Gly Gly Val Val Gln Pro Gly Lys
  1               5                  10                  15

Ser Leu Arg Leu Ser Cys Ala Ala Ser Glu Phe Thr Ile Ser Tyr Tyr
             20                  25                  30

Gly Met His Trp Val Arg Gln Val Pro Gly Lys Gly Leu Glu Trp Val
         35                  40                  45

Ala Ala Val Trp Tyr Asp Glu Ser Thr Thr Tyr Ser Pro Asp Ser Val
     50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 55
<211> LENGTH: 677
<212> TYPE: DNA
<213> ORGANISM: Homo sapiens
<220> FEATURE:
<223> OTHER INFORMATION: M1-3H
<220> FEATURE:
<221> NAME/KEY: CDS
<222> LOCATION: (3)..(677)

<400> SEQUENCE: 55 cc gat gtg cag ctg gtg cag tct ggg gga ggc gtg gtc cag cct ggg        47
   Asp Val Gln Leu Val Gln Ser Gly Gly Gly Val Val Gln Pro Gly
    1               5                  10                  15 agg tcc ctg aga ctc tcc tgt gca gcg tct gga ttc acc ttc agt tac        95
Arg Ser Leu Arg Leu Ser Cys Ala Ala Ser Gly Phe Thr Phe Ser Tyr
             20                  25                  30 tat ggc atg cac tgg gtc cgc cag gct cca ggc aag ggg ctg gag tgg       143
Tyr Gly Met His Trp Val Arg Gln Ala Pro Gly Lys Gly Leu Glu Trp
```

```
                    35                  40                  45
gtg aca ctt ata acc tat gat gga gat aat aaa tac tat gca gac tcc      191
Val Thr Leu Ile Thr Tyr Asp Gly Asp Asn Lys Tyr Tyr Ala Asp Ser
         50                  55                  60 gtg aag ggc cga ttc acc atc tcc aga gac aat tcc aag aac acg ctg      239
Val Lys Gly Arg Phe Thr Ile Ser Arg Asp Asn Ser Lys Asn Thr Leu
 65                  70                  75 tat ctg caa atg aac agc ctg aga gcc gag gac acg gct gtg tat tac      287
Tyr Leu Gln Met Asn Ser Leu Arg Ala Glu Asp Thr Ala Val Tyr Tyr
 80                  85                  90                  95 tgt gcg aga gac ggg atc ggg tac ttt gac tat tgg ggc cag gga acc      335
Cys Ala Arg Asp Gly Ile Gly Tyr Phe Asp Tyr Trp Gly Gln Gly Thr
                100                 105                 110 ctg gtc acc gtc tcc tca gcc tcc acc aag ggc cca tcg gtc ttc ccc      383
Leu Val Thr Val Ser Ser Ala Ser Thr Lys Gly Pro Ser Val Phe Pro
            115                 120                 125 ctg gca ccc tcc tcc aag agc acc tct ggg ggc aca gcg gcc ctg ggc      431
Leu Ala Pro Ser Ser Lys Ser Thr Ser Gly Gly Thr Ala Ala Leu Gly
        130                 135                 140 tgc ctg gtc aag gac tac ttc ccc gaa ccg gtg acg gtg tcg tgg aac      479
Cys Leu Val Lys Asp Tyr Phe Pro Glu Pro Val Thr Val Ser Trp Asn
145                 150                 155 tca ggc gcc ctg acc agc ggc gtg cac acc ttc ccg gct gtc cta cag      527
Ser Gly Ala Leu Thr Ser Gly Val His Thr Phe Pro Ala Val Leu Gln
160                 165                 170                 175 tcc tca gga ctc tac tcc ctc agc agc gtg gtg acc gtg ccc tcc agc      575
Ser Ser Gly Leu Tyr Ser Leu Ser Ser Val Val Thr Val Pro Ser Ser
            180                 185                 190 agc ttg ggc acc cag acc tac atc tgc aac gtg aat cac aag ccc agc      623
Ser Leu Gly Thr Gln Thr Tyr Ile Cys Asn Val Asn His Lys Pro Ser
        195                 200                 205 aac acc aag gtg gac aag aaa gca gag ccc aaa tct cat cac cat cac      671
Asn Thr Lys Val Asp Lys Lys Ala Glu Pro Lys Ser His His His His
    210                 215                 220 cat cac                                                              677
His His
    225
```

<210> SEQ ID NO 56
<211> LENGTH: 225
<212> TYPE: PRT
<213> ORGANISM: Homo sapiens
<220> FEATURE:
<223> OTHER INFORMATION: M1-3H

<400> SEQUENCE: 56

```
Asp Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Val
         35                  40                  45

Thr Leu Ile Thr Tyr Asp Gly Asp Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Gly Ile Gly Tyr Phe Asp Tyr Trp Gly Gln Gly Thr Leu
```

-continued

```
                100                 105                 110
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
        180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225
```

<210> SEQ ID NO 57
<211> LENGTH: 675
<212> TYPE: DNA
<213> ORGANISM: Homo sapiens
<220> FEATURE:
<223> OTHER INFORMATION: M1-4H
<220> FEATURE:
<221> NAME/KEY: CDS
<222> LOCATION: (1)..(675)

<400> SEQUENCE: 57

```
cag gtg cag ctg gtg gag tct ggg gga ggc gtg gtc cag cct ggg aag      48
Gln Val Gln Leu Val Glu Ser Gly Gly Gly Val Val Gln Pro Gly Lys
  1               5                  10                  15 tcc ctg aga ctc tcc tgt gca gcg tct gga ttc acc ttc agt tac tat      96
Ser Leu Arg Leu Ser Cys Ala Ala Ser Gly Phe Thr Phe Ser Tyr Tyr
            20                  25                  30 ggc atg cac tgg gtc cgc cag gtt cca ggc aag ggg ctg gag tgg gtg     144
Gly Met His Trp Val Arg Gln Val Pro Gly Lys Gly Leu Glu Trp Val
        35                  40                  45 gca gct gtc tgg tat gat gga agt act aca tat tct cca gac tcc gtg     192
Ala Ala Val Trp Tyr Asp Gly Ser Thr Thr Tyr Ser Pro Asp Ser Val
    50                  55                  60 aag ggc cga ttc acc atc tcc aga gac gat tcc aag aac acg ctg tat     240
Lys Gly Arg Phe Thr Ile Ser Arg Asp Asp Ser Lys Asn Thr Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga gat agg gtg ggc ctc ttt gac tac tgg ggc cag gga acc ctg     336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160
```

```
ggc gcc ctg acc agc ggc gtg cac acc ttc ccg gct gtc cta cag tcc      528
Gly Ala Leu Thr Ser Gly Val His Thr Phe Pro Ala Val Leu Gln Ser
            165                 170                 175 tca gga ctc tac tcc ctc agc agc gtg gtg acc gtg ccc tcc agc agc      576
Ser Gly Leu Tyr Ser Leu Ser Ser Val Val Thr Val Pro Ser Ser Ser
        180                 185                 190 ttg ggc acc cag acc tac atc tgc aac gtg aat cac aag ccc agc aac      624
Leu Gly Thr Gln Thr Tyr Ile Cys Asn Val Asn His Lys Pro Ser Asn
            195                 200                 205 acc aag gtg gac aag aaa gca ggg ccc aaa tct cat cac cat cac cat      672
Thr Lys Val Asp Lys Lys Ala Gly Pro Lys Ser His His His His His
        210                 215                 220 cac                                                                  675
His
225

<210> SEQ ID NO 58
<211> LENGTH: 225
<212> TYPE: PRT
<213> ORGANISM: Homo sapiens
<220> FEATURE:
<223> OTHER INFORMATION: M1-4H

<400> SEQUENCE: 58

Gln Val Gln Leu Val Glu Ser Gly Gly Val Val Gln Pro Gly Lys
  1               5                  10                  15

Ser Leu Arg Leu Ser Cys Ala Ala Ser Gly Phe Thr Phe Ser Tyr Tyr
                 20                  25                  30

Gly Met His Trp Val Arg Gln Val Pro Gly Lys Gly Leu Glu Trp Val
             35                  40                  45

Ala Ala Val Trp Tyr Asp Gly Ser Thr Thr Tyr Ser Pro Asp Ser Val
         50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Gly Pro Lys Ser His His His His His
    210                 215                 220

His
225

<210> SEQ ID NO 59
<211> LENGTH: 675
<212> TYPE: DNA
```

```
<213> ORGANISM: Homo sapiens
<220> FEATURE:
<223> OTHER INFORMATION: M1-5H
<220> FEATURE:
<221> NAME/KEY: CDS
<222> LOCATION: (1)..(675)

<400> SEQUENCE: 59 cag gtg cag ctg gtg gag tct ggg gga ggc gtg gtc cag cct ggg agg      48
Gln Val Gln Leu Val Glu Ser Gly Gly Gly Val Val Gln Pro Gly Arg
  1               5                  10                  15 tcc ctg aga ctc tcc tgt gca gcg tct gga ttt acc ttc agt tac tat      96
Ser Leu Arg Leu Ser Cys Ala Ala Ser Gly Phe Thr Phe Ser Tyr Tyr
                 20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
             35                  40                  45 aca ctt ata acc tat gat gga gat aat aaa tac tat gca gac tcc gtg     192
Thr Leu Ile Thr Tyr Asp Gly Asp Asn Lys Tyr Tyr Ala Asp Ser Val
         50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg aga gac ggg atc ggg tac ttt gac tat tgg ggc cag gga acc ctg     336
Ala Arg Asp Gly Ile Gly Tyr Phe Asp Tyr Trp Gly Gln Gly Thr Leu
                100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
            115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
        130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc     576
Ser Gly Leu Tyr Ser Leu Ser Ser Val Val Thr Val Pro Ser Ser Ser
                180                 185                 190 ttg ggc acc cag acc tac atc tgc aac gtg aat cac aag ccc agc aac     624
Leu Gly Thr Gln Thr Tyr Ile Cys Asn Val Asn His Lys Pro Ser Asn
            195                 200                 205 acc aag gtg gac aag aaa gca gag ccc aaa tct cat cac cat cac cat     672
Thr Lys Val Asp Lys Lys Ala Glu Pro Lys Ser His His His His His
        210                 215                 220 cac                                                                  675
His
225

<210> SEQ ID NO 60
<211> LENGTH: 225
<212> TYPE: PRT
<213> ORGANISM: Homo sapiens
<220> FEATURE:
<223> OTHER INFORMATION: M1-5H

<400> SEQUENCE: 60
```

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Val
         35                  40                  45

Thr Leu Ile Thr Tyr Asp Gly Asp Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 61
<211> LENGTH: 675
<212> TYPE: DNA
<213> ORGANISM: Homo sapiens
<220> FEATURE:
<223> OTHER INFORMATION: M1-8H
<220> FEATURE:
<221> NAME/KEY: CDS
<222> LOCATION: (1)..(675)

<400> SEQUENCE: 61 cag gtg cag ctg gtg cag tct ggg gga ggc gtg gtc cag cct ggg aag      48
Gln Val Gln Leu Val Gln Ser Gly Gly Gly Val Val Gln Pro Gly Lys
  1               5                  10                  15 tcc ctg aaa ctc tcc tgt gca gcg tct gga ttc acc ttc agt tac tat      96
Ser Leu Lys Leu Ser Cys Ala Ala Ser Gly Phe Thr Phe Ser Tyr Tyr
             20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
         35                  40                  45 gca gct gta tgg tat gat gga agt aac aca tac tct cca gac tcc gtg     192
Ala Ala Val Trp Tyr Asp Gly Ser Asn Thr Tyr Ser Pro Asp Ser Val
     50                  55                  60 aag ggc cga ttc acc atc tcc aga gac gat tcc aag aac acg gtg tat     240
Lys Gly Arg Phe Thr Ile Ser Arg Asp Asp Ser Lys Asn Thr Val Tyr
 65                  70                  75                  80 ctg caa atg aac agc ctg aga gcc gag gac acg gct gtg tat tac tgt     288
```

```
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg      336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
            115                 120                 125 gca ccc tcc tcc aag agc acc tct ggg ggc aca gcg gcc ctg ggc tgc      432
Ala Pro Ser Ser Lys Ser Thr Ser Gly Gly Thr Ala Ala Leu Gly Cys
        130                 135                 140 ctg gtc aag gac tac ttc ccc gaa ccg gtg acg gtg tcg tgg aac tca      480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc      528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc      576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac      624
Leu Gly Thr Gln Thr Tyr Ile Cys Asn Val Asn His Lys Pro Ser Asn
            195                 200                 205 acc aag gtg gac aag aaa gca gag ccc aaa tct cat cac cat cac cat      672
Thr Lys Val Asp Lys Lys Ala Glu Pro Lys Ser His His His His His
        210                 215                 220 cac                                                                  675
His
225

<210> SEQ ID NO 62
<211> LENGTH: 225
<212> TYPE: PRT
<213> ORGANISM: Homo sapiens
<220> FEATURE:
<223> OTHER INFORMATION: M1-8H

<400> SEQUENCE: 62

Gln Val Gln Leu Val Gln Ser Gly Gly Gly Val Val Gln Pro Gly Lys
  1               5                  10                  15

Ser Leu Lys Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Val
         35                  40                  45

Ala Ala Val Trp Tyr Asp Gly Ser Asn Thr Tyr Ser Pro Asp Ser Val
     50                  55                  60

Lys Gly Arg Phe Thr Ile Ser Arg Asp Asp Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 63
<211> LENGTH: 708
<212> TYPE: DNA
<213> ORGANISM: Homo sapiens
<220> FEATURE:
<223> OTHER INFORMATION: M1-10H
<220> FEATURE:
<221> NAME/KEY: CDS
<222> LOCATION: (1)..(708)

<400> SEQUENCE: 63 cag gtg cag ctg gtg cag tct ggg gga ggc ttg gta cat cct ggg ggg       48
Gln Val Gln Leu Val Gln Ser Gly Gly Gly Leu Val His Pro Gly Gly
 1               5                  10                  15 tcc ctg aga ctc tcc tgt gaa ggc tct gga ttc atc ttc agg aac cat       96
Ser Leu Arg Leu Ser Cys Glu Gly Ser Gly Phe Ile Phe Arg Asn His
             20                  25                  30 cct ata cac tgg gtt cgc cag gct cca gga aaa ggt ctg gag tgg gta      144
Pro Ile His Trp Val Arg Gln Ala Pro Gly Lys Gly Leu Glu Trp Val
         35                  40                  45 tca gtt agt ggt att ggt ggt gac aca tac tat gca gac tcc gtg aag      192
Ser Val Ser Gly Ile Gly Gly Asp Thr Tyr Tyr Ala Asp Ser Val Lys
     50                  55                  60 ggc cga ttc tcc atc tcc aga gac aat gcc aag aac tcc ttg tat ctt      240
Gly Arg Phe Ser Ile Ser Arg Asp Asn Ala Lys Asn Ser Leu Tyr Leu
 65                  70                  75                  80 caa atg aac agc ctg aga gcc gag gac atg gct gtg tat tac tgt gca      288
Gln Met Asn Ser Leu Arg Ala Glu Asp Met Ala Val Tyr Tyr Cys Ala
                 85                  90                  95 aga gaa tat tac tat ggt tcg ggg agt tat cgc gtt gac tac tac tac      336
Arg Glu Tyr Tyr Tyr Gly Ser Gly Ser Tyr Arg Val Asp Tyr Tyr Tyr
            100                 105                 110 tac ggt atg gac gtc tgg ggc caa ggg acc acg gtc acc gtc tcc tca      384
Tyr Gly Met Asp Val Trp Gly Gln Gly Thr Thr Val Thr Val Ser Ser
        115                 120                 125 gcc tcc acc aag ggc cca tcg gtc ttc ccc ctg gca ccc tcc tcc aag      432
Ala Ser Thr Lys Gly Pro Ser Val Phe Pro Leu Ala Pro Ser Ser Lys
    130                 135                 140 agc acc tct ggg ggc aca gcg gcc ctg ggc tgc ctg gtc aag gac tac      480
Ser Thr Ser Gly Gly Thr Ala Ala Leu Gly Cys Leu Val Lys Asp Tyr
145                 150                 155                 160 ttc ccc gaa ccg gtg acg gtg tcg tgg aac tca ggc gcc ctg acc agc      528
Phe Pro Glu Pro Val Thr Val Ser Trp Asn Ser Gly Ala Leu Thr Ser
                165                 170                 175 ggc gtg cac acc ttc ccg gct gtc cta cag tcc tca gga ctc tac tcc      576
Gly Val His Thr Phe Pro Ala Val Leu Gln Ser Ser Gly Leu Tyr Ser
            180                 185                 190 ctc agc agc gtg gtg acc gtg ccc tcc agc agc ttg ggc acc cag acc      624
Leu Ser Ser Val Val Thr Val Pro Ser Ser Ser Leu Gly Thr Gln Thr
        195                 200                 205
```

```
tac atc tgc aac gtg aat cac aag ccc agc aac acc aag gtg gac aag      672
Tyr Ile Cys Asn Val Asn His Lys Pro Ser Asn Thr Lys Val Asp Lys
210                 215                 220 aaa gca gag ccc aaa tct cat cac cat cac cat cac                      708
Lys Ala Glu Pro Lys Ser His His His His His His
225                 230                 235
```

<210> SEQ ID NO 64
<211> LENGTH: 236
<212> TYPE: PRT
<213> ORGANISM: Homo sapiens
<220> FEATURE:
<223> OTHER INFORMATION: M1-10H

<400> SEQUENCE: 64

```
Gln Val Gln Leu Val Gln Ser Gly Gly Gly Leu Val His Pro Gly Gly
1               5                   10                  15

Ser Leu Arg Leu Ser Cys Glu Gly Ser Gly Phe Ile Phe Arg Asn His
                20                  25                  30

Pro Ile His Trp Val Arg Gln Ala Pro Gly Lys Gly Leu Glu Trp Val
            35                  40                  45

Ser Val Ser Gly Ile Gly Gly Asp Thr Tyr Tyr Ala Asp Ser Val Lys
    50                  55                  60

Gly Arg Phe Ser Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Glu Tyr Tyr Tyr Gly Ser Gly Ser Tyr Arg Val Asp Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Ala Glu Pro Lys Ser His His His His His His
225                 230                 235
```

<210> SEQ ID NO 65
<211> LENGTH: 675
<212> TYPE: DNA
<213> ORGANISM: Homo sapiens
<220> FEATURE:
<223> OTHER INFORMATION: M1-21H
<220> FEATURE:
<221> NAME/KEY: CDS
<222> LOCATION: (1)..(675)

<400> SEQUENCE: 65

```
cag gtg cag ctg gtg cag tct ggg gga ggc gtg gtc cag cct ggg aag       48
Gln Val Gln Leu Val Gln Ser Gly Gly Gly Val Val Gln Pro Gly Lys
```

```
                1               5              10              15
tcc ctg aga ctc tcc tgt gca gcg tct gga ttc acc ttc agt tac tat    96
Ser Leu Arg Leu Ser Cys Ala Ala Ser Gly Phe Thr Phe Ser Tyr Tyr
            20                  25                  30 ggc atg cac tgg gtc cgc cag gtt cca ggc aag ggg ctg gag tgg gtg   144
Gly Met His Trp Val Arg Gln Val Pro Gly Lys Gly Leu Glu Trp Val
        35                  40                  45 gca gct gtc tgg tat gat gga agt act aca tat tct cca gac tcc gtg   192
Ala Ala Val Trp Tyr Asp Gly Ser Thr Thr Tyr Ser Pro Asp Ser Val
    50                  55                  60 aag ggc cga ttc acc atc tcc aga gac gat tcc aag aac acg ctg tat   240
Lys Gly Arg Phe Thr Ile Ser Arg Asp Asp Ser Lys Asn Thr Leu Tyr
65                  70                  75                  80 ctg caa atg agc agc ctg aga gcc gag gac acg gct gtg tat tac tgt   288
Leu Gln Met Ser Ser Leu Arg Ala Glu Asp Thr Ala Val Tyr Tyr Cys
                85                  90                  95 gcg aga gat agg gtg ggc ctc ttt gac tac tgg ggc cag gga acc ctg   336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg   384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc   432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca   480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc   528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc   576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac   624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat   672
Thr Lys Val Asp Lys Lys Ala Glu Pro Lys Ser His His His His His
    210                 215                 220 cac                                                                675
His
225

<210> SEQ ID NO 66
<211> LENGTH: 225
<212> TYPE: PRT
<213> ORGANISM: Homo sapiens
<220> FEATURE:
<223> OTHER INFORMATION: M1-21H

<400> SEQUENCE: 66

Gln Val Gln Leu Val Gln Ser Gly Gly Gly Val Val Gln Pro Gly Lys
 1               5                  10                  15

Ser Leu Arg Leu Ser Cys Ala Ala Ser Gly Phe Thr Phe Ser Tyr Tyr
            20                  25                  30

Gly Met His Trp Val Arg Gln Val Pro Gly Lys Gly Leu Glu Trp Val
        35                  40                  45

Ala Ala Val Trp Tyr Asp Gly Ser Thr Thr Tyr Ser Pro Asp Ser Val
    50                  55                  60
```

```
Lys Gly Arg Phe Thr Ile Ser Arg Asp Asp Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 67
<211> LENGTH: 675
<212> TYPE: DNA
<213> ORGANISM: Homo sapiens
<220> FEATURE:
<223> OTHER INFORMATION: M1-23H
<220> FEATURE:
<221> NAME/KEY: CDS
<222> LOCATION: (1)..(675)

<400> SEQUENCE: 67 cag gtg cag ctg gtg cag tct ggg gga ggc gtg gtc cag cct ggg agg      48
Gln Val Gln Leu Val Gln Ser Gly Gly Gly Val Val Gln Pro Gly Arg
  1               5                  10                  15 tcc ctg aga ctc tcc tgt gca gcg tct gga ttc acc ttc agt aac tat      96
Ser Leu Arg Leu Ser Cys Ala Ala Ser Gly Phe Thr Phe Ser Asn Tyr
             20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
         35                  40                  45 gca gct ata tgg tat gat gga agt aaa aca tac aat gca gac tcc gtg     192
Ala Ala Ile Trp Tyr Asp Gly Ser Lys Thr Tyr Asn Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg aga gat ggg ata ggc tac ttt gac tac tgg ggc cag gga acc ctg     336
Ala Arg Asp Gly Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125
```

```
gca ccc tcc tcc aag agc acc tct ggg gga aca gcg gcc ctg ggc tgc        432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca        480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc        528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc        576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac        624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat        672
Thr Lys Val Asp Lys Lys Ala Glu Pro Lys Ser His His His His His
    210                 215                 220 cac                                                                    675
His
225

<210> SEQ ID NO 68
<211> LENGTH: 225
<212> TYPE: PRT
<213> ORGANISM: Homo sapiens
<220> FEATURE:
<223> OTHER INFORMATION: M1-23H

<400> SEQUENCE: 68

Gln Val Gln Leu Val Gln Ser Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Ala Ile Trp Tyr Asp Gly Ser Lys Thr Tyr Asn Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220
```

His
225

<210> SEQ ID NO 69
<211> LENGTH: 675
<212> TYPE: DNA
<213> ORGANISM: Homo sapiens
<220> FEATURE:
<223> OTHER INFORMATION: M1-25H
<220> FEATURE:
<221> NAME/KEY: CDS
<222> LOCATION: (1)..(675)

<400> SEQUENCE: 69

| | | | | | | | | | | | | | | | | |
|---|---|---|---|---|---|---|---|---|---|---|---|---|---|---|---|---|
| cag | gtg | cag | ctg | gtg | gag | tct | ggg | gga | ggc | ttg | gtc | cag | cct | ggg | ggg | 48 |
| Gln | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |
| tcc | ctg | aga | ctc | tcc | tgt | gca | gcg | tct | gga | ttc | acc | ttc | agt | tac | tat | 96 |
| Ser | Leu | Arg | Leu | Ser | Cys | Ala | Ala | Ser | Gly | Phe | Thr | Phe | Ser | Tyr | Tyr | |
| | | | 20 | | | | | 25 | | | | | 30 | | | |
| ggc | atg | cac | tgg | gtc | cgc | cag | gtt | cca | ggc | aag | ggg | ctg | gag | tgg | gtg | 144 |
| Gly | Met | His | Trp | Val | Arg | Gln | Val | Pro | Gly | Lys | Gly | Leu | Glu | Trp | Val | |
| | | 35 | | | | | 40 | | | | | 45 | | | | |
| gca | gct | gtc | tgg | tat | gat | gga | agt | act | aca | tat | cct | cca | gac | tcc | gtg | 192 |
| Ala | Ala | Val | Trp | Tyr | Asp | Gly | Ser | Thr | Thr | Tyr | Pro | Pro | Asp | Ser | Val | |
| 50 | | | | | 55 | | | | | 60 | | | | | | |
| aag | ggc | cga | ttc | acc | atc | tcc | aga | gac | gat | tcc | aag | aac | acg | ctg | tat | 240 |
| Lys | Gly | Arg | Phe | Thr | Ile | Ser | Arg | Asp | Asp | Ser | Lys | Asn | Thr | Leu | Tyr | |
| 65 | | | | 70 | | | | | 75 | | | | | 80 | | |
| ctg | caa | atg | aac | agc | ctg | aga | gcc | gag | gac | acg | gct | gtt | tat | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gcg | aga | gat | agg | gtg | ggc | ctc | ttt | gac | tac | tgg | ggc | cag | gga | acc | ctg | 336 |
| Ala | Arg | Asp | Arg | Val | Gly | Leu | Phe | Asp | Tyr | Trp | Gly | Gln | Gly | Thr | Leu | |
| | | | 100 | | | | | 105 | | | | | 110 | | | |
| gtc | acc | gtc | tcc | tca | gcc | tcc | acc | aag | ggc | cca | tcg | gtc | ttc | ccc | ctg | 384 |
| Val | Thr | Val | Ser | Ser | Ala | Ser | Thr | Lys | Gly | Pro | Ser | Val | Phe | Pro | Leu | |
| | | 115 | | | | | 120 | | | | | 125 | | | | |
| gca | ccc | tcc | tcc | aag | agc | acc | tct | ggg | ggc | aca | gcg | gcc | ctg | ggc | tgc | 432 |
| Ala | Pro | Ser | Ser | Lys | Ser | Thr | Ser | Gly | Gly | Thr | Ala | Ala | Leu | Gly | Cys | |
| 130 | | | | | 135 | | | | | 140 | | | | | | |
| ctg | gtc | aag | gac | tac | ttc | ccc | gaa | ccg | gtg | acg | gtg | tcg | tgg | aac | tca | 480 |
| Leu | Val | Lys | Asp | Tyr | Phe | Pro | Glu | Pro | Val | Thr | Val | Ser | Trp | Asn | Ser | |
| 145 | | | | | 150 | | | | | 155 | | | | | 160 | |
| ggc | gcc | ctg | acc | agc | ggc | gtg | cac | acc | ttc | ccg | gct | gtc | cta | cag | tcc | 528 |
| Gly | Ala | Leu | Thr | Ser | Gly | Val | His | Thr | Phe | Pro | Ala | Val | Leu | Gln | Ser | |
| | | | | 165 | | | | | 170 | | | | | 175 | | |
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | | | 180 | | | | | 185 | | | | | 190 | | |
| ttg | ggc | acc | cag | acc | tac | atc | tgc | aac | gtg | aat | cac | aag | ccc | agc | aac | 624 |
| Leu | Gly | Thr | Gln | Thr | Tyr | Ile | Cys | Asn | Val | Asn | His | Lys | Pro | Ser | Asn | |
| | | | 195 | | | | | 200 | | | | | 205 | | | |
| acc | aag | gtg | gac | aag | aaa | gca | gag | ccc | aaa | tct | cat | cac | cat | cac | cat | 672 |
| Thr | Lys | Val | Asp | Lys | Lys | Ala | Glu | Pro | Lys | Ser | His | His | His | His | His | |
| | 210 | | | | | 215 | | | | | 220 | | | | | |
| cac | | | | | | | | | | | | | | | | 675 |
| His | | | | | | | | | | | | | | | | |
| 225 | | | | | | | | | | | | | | | | |

<210> SEQ ID NO 70

<211> LENGTH: 225
<212> TYPE: PRT
<213> ORGANISM: Homo sapiens
<220> FEATURE:
<223> OTHER INFORMATION: M1-25H

<400> SEQUENCE: 70

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Tyr Tyr
             20                  25                  30

Gly Met His Trp Val Arg Gln Val Pro Gly Lys Gly Leu Glu Trp Val
         35                  40                  45

Ala Ala Val Trp Tyr Asp Gly Ser Thr Thr Tyr Pro Pro Asp Ser Val
     50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225
```

<210> SEQ ID NO 71
<211> LENGTH: 678
<212> TYPE: DNA
<213> ORGANISM: Homo sapiens
<220> FEATURE:
<221> NAME/KEY: CDS
<222> LOCATION: (1)..(678)
<220> FEATURE:
<223> OTHER INFORMATION: M2-11L

<400> SEQUENCE: 71

```
gaa ata gtg atg acg cag tct cca ggc acc ctg tct ttg tct cca ggg      48
Glu Ile Val Met Thr Gln Ser Pro Gly Thr Leu Ser Leu Ser Pro Gly
  1               5                  10                  15 gaa aga gcc acc ctc tcc tgc agg gcc agt cag ggt gtt agc agc agc      96
Glu Arg Ala Thr Leu Ser Cys Arg Ala Ser Gln Gly Val Ser Ser Ser
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
```

-continued

```
               Ile Tyr Gly Ala Ser Ser Arg Ala Thr Gly Ile Pro Asp Arg Phe Ser
                   50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct      288
Pro Glu Asp Phe Ala Val Tyr Tyr Cys Gln Gln Tyr Gly Ser Ser Pro
                 85                  90                  95 cca ttc act ttc ggc cct ggg acc aaa gtg gat atc aaa cga act gtg      336
Pro Phe Thr Phe Gly Pro Gly Thr Lys Val Asp Ile Lys Arg Thr Val
            100                 105                 110 gct gca cca tct gtc ttc atc ttc ccg cca tct gat gag cag ttg aga      384
Ala Ala Pro Ser Val Phe Ile Phe Pro Pro Ser Asp Glu Gln Leu Arg
        115                 120                 125 tct gga act gcc tct gtt gtg tgc ctg ctg aat aac ttc tat ccc aga      432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac      480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc      528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa      576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca      624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat      672
Lys Ser Phe Asn Arg Gly Glu Ser Tyr Pro Tyr Asp Val Pro Asp Tyr
    210                 215                 220 gcg agc                                                              678
Ala Ser
225

<210> SEQ ID NO 72
<211> LENGTH: 226
<212> TYPE: PRT
<213> ORGANISM: Homo sapiens
<220> FEATURE:
<223> OTHER INFORMATION: M2-11L

<400> SEQUENCE: 72

Glu Ile Val Met Thr Gln Ser Pro Gly Thr Leu Ser Leu Ser Pro Gly
  1               5                  10                  15

Glu Arg Ala Thr Leu Ser Cys Arg Ala Ser Gln Gly Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Arg
```

```
                115                 120                 125
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 73
<211> LENGTH: 678
<212> TYPE: DNA
<213> ORGANISM: Homo sapiens
<220> FEATURE:
<221> NAME/KEY: CDS
<222> LOCATION: (1)..(678)
<220> FEATURE:
<223> OTHER INFORMATION: M2-12L

<400> SEQUENCE: 73 gaa ata gtg atg acg cag tct cca ggc acc ctg tct ttg tct cca ggg      48
Glu Ile Val Met Thr Gln Ser Pro Gly Thr Leu Ser Leu Ser Pro Gly
  1               5                  10                  15 gaa aga gcc acc ctc tcc tgc agg gcc agt cag ggt gtt agc agc agc      96
Glu Arg Ala Thr Leu Ser Cys Arg Ala Ser Gln Gly Val Ser Ser Ser
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc agc cta gag     240
Gly Ser Gly Ser Gly Thr Asp Phe Thr Leu Thr Ile Ser Ser Leu Glu
 65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
                 85                  90                  95 ccg tac act ttt ggc cag ggg acc aag ctg gag atc aaa cga act gtg     336
Pro Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa     384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga     432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac     480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc     528
Ser Gln Glu Ser Val Thr Glu Gln Asp Ser Lys Asp Ser Thr Tyr Ser
                165                 170                 175
```

```
ctc agc agc acc ctg acg ctg agc aaa gca gac tac gag aaa cac aaa      576
Leu Ser Ser Thr Leu Thr Leu Ser Lys Ala Asp Tyr Glu Lys His Lys
        180                 185                 190 gtc tac gcc tgc gaa gtc acc cat cag ggc ctg agc tcg ccc gtc aca      624
Val Tyr Ala Cys Glu Val Thr His Gln Gly Leu Ser Ser Pro Val Thr
            195                 200                 205 aag agc ttc aac agg gga gag tct tat cca tat gat gtg cca gat tat      672
Lys Ser Phe Asn Arg Gly Glu Ser Tyr Pro Tyr Asp Val Pro Asp Tyr
210                 215                 220 gcg agc                                                               678
Ala Ser
225

<210> SEQ ID NO 74
<211> LENGTH: 226
<212> TYPE: PRT
<213> ORGANISM: Homo sapiens
<220> FEATURE:
<223> OTHER INFORMATION: M2-12L

<400> SEQUENCE: 74

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Gly Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
 65                 70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 75
<211> LENGTH: 672
<212> TYPE: DNA
<213> ORGANISM: Homo sapiens
<220> FEATURE:
<221> NAME/KEY: CDS
```

<222> LOCATION: (1)..(672)
<220> FEATURE:
<223> OTHER INFORMATION: M2-16L

<400> SEQUENCE: 75

| | | |
|---|---|---|
| gaa ata gtg atg acg cag tct cca ggc acc ctg tct ttg tct cca ggg<br>Glu Ile Val Met Thr Gln Ser Pro Gly Thr Leu Ser Leu Ser Pro Gly<br>1               5                  10                  15 | | 48 |
| gaa aga gcc acc ctc tcc tgc agg gcc agt cag agt gtt agc agc agc<br>Glu Arg Ala Thr Leu Ser Cys Arg Ala Ser Gln Ser Val Ser Ser Ser<br>            20                  25                  30 | | 96 |
| tac tta gcc tgg tac cag cag aaa cct ggc cag gct ccc agg ctc ctc<br>Tyr Leu Ala Trp Tyr Gln Gln Lys Pro Gly Gln Ala Pro Arg Leu Leu<br>        35                  40                  45 | | 144 |
| atc tat ggt gca tcc agc agg gcc act ggc atc cca gac agg ttc agt<br>Ile Tyr Gly Ala Ser Ser Arg Ala Thr Gly Ile Pro Asp Arg Phe Ser<br>    50                  55                  60 | | 192 |
| gtc agt ggg tct ggg aca gac ttc act ctc acc atc agc aga ctg gag<br>Val Ser Gly Ser Gly Thr Asp Phe Thr Leu Thr Ile Ser Arg Leu Glu<br>65                  70                  75                  80 | | 240 |
| cct gaa gat ttt gca gtg tat tac tgt cag cag tat ggt agc tca ttc<br>Pro Glu Asp Phe Ala Val Tyr Tyr Cys Gln Gln Tyr Gly Ser Ser Phe<br>                85                  90                  95 | | 288 |
| act ttc ggc cct ggg acc aaa gtg gat atc aaa cga act gtg gct gca<br>Thr Phe Gly Pro Gly Thr Lys Val Asp Ile Lys Arg Thr Val Ala Ala<br>            100                 105                 110 | | 336 |
| cca tct gtc ttc atc ttc ccg cca tct gat gag cag ttg aaa tct gga<br>Pro Ser Val Phe Ile Phe Pro Pro Ser Asp Glu Gln Leu Lys Ser Gly<br>        115                 120                 125 | | 384 |
| act gcc tct gtt gtg tgc ctg ctg aat aac ttc tat ccc aga gag gcc<br>Thr Ala Ser Val Val Cys Leu Leu Asn Asn Phe Tyr Pro Arg Glu Ala<br>    130                 135                 140 | | 432 |
| aaa gta cag tgg aag gtg gat aac gcc ctc caa tcg ggt aac tcc cag<br>Lys Val Gln Trp Lys Val Asp Asn Ala Leu Gln Ser Gly Asn Ser Gln<br>145                 150                 155                 160 | | 480 |
| gag agt gtc aca gag cag gac agc aag gac agc acc tac agc ctc agc<br>Glu Ser Val Thr Glu Gln Asp Ser Lys Asp Ser Thr Tyr Ser Leu Ser<br>                165                 170                 175 | | 528 |
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>            180                 185                 190 | | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>        195                 200                 205 | | 624 |
| ttc aac agg gga gag tct tat cca tat gat gtg cca gat tat gcg agc<br>Phe Asn Arg Gly Glu Ser Tyr Pro Tyr Asp Val Pro Asp Tyr Ala Ser<br>    210                 215                 220 | | 672 |

<210> SEQ ID NO 76
<211> LENGTH: 224
<212> TYPE: PRT
<213> ORGANISM: Homo sapiens
<220> FEATURE:
<223> OTHER INFORMATION: M2-16L

<400> SEQUENCE: 76

Glu Ile Val Met Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
    50                  55                  60

Val Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Phe
                 85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 77
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: M2-18L

<400> SEQUENCE: 77 gaa ata gtg atg acg cag tct cca ggc acc ctg tct ttg tct cca ggg     48
Glu Ile Val Met Thr Gln Ser Pro Gly Thr Leu Ser Leu Ser Pro Gly
 1               5                  10                  15 gaa aga gcc acc ctc tcc tgc agg gcc agt cag agt gtt agc agc acc    96
Glu Arg Ala Thr Leu Ser Cys Arg Ala Ser Gln Ser Val Ser Ser Thr
             20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat gtt agc tca ttc    288
Pro Glu Asp Phe Ala Val Tyr Tyr Cys Gln Gln Tyr Val Ser Ser Phe
                 85                  90                  95 act ttc ggc cct ggg acc aaa gtg gat atc aaa cga act gtg gct gca    336
Thr Phe Gly Pro Gly Thr Lys Val Asp Ile Lys Arg Thr Val Ala Ala
                100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
            115                 120                 125
```

```
act gcc tct gtt gtg tgc ctg ctg aat aac ttc tat ccc aga gag gcc      432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag      480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc      528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac      576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc      624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc      672
Phe Asn Arg Gly Glu Ser Tyr Pro Tyr Asp Val Pro Asp Tyr Ala Ser
    210                 215                 220
```

<210> SEQ ID NO 78
<211> LENGTH: 224
<212> TYPE: PRT
<213> ORGANISM: Homo sapiens
<220> FEATURE:
<223> OTHER INFORMATION: M2-18L

<400> SEQUENCE: 78

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 79

<211> LENGTH: 678
<212> TYPE: DNA
<213> ORGANISM: Homo sapiens
<220> FEATURE:
<221> NAME/KEY: CDS
<222> LOCATION: (1)..(678)
<220> FEATURE:
<223> OTHER INFORMATION: M2-20L

<400> SEQUENCE: 79

| | | | | | | | | | | | | | | | | |
|---|---|---|---|---|---|---|---|---|---|---|---|---|---|---|---|---|
| gaa | ata | gtg | atg | acg | cag | tct | cca | ggc | acc | ctg | tct | ttg | tct | cca | ggg | 48 |
| Glu | Ile | Val | Met | Thr | Gln | Ser | Pro | Gly | Thr | Leu | Ser | Leu | Ser | Pro | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gaa | aga | gcc | acc | ctc | tcc | tgc | agg | gcc | agt | cag | agt | gtt | agc | agc | agc | 96 |
| Glu | Arg | Ala | Thr | Leu | Ser | Cys | Arg | Ala | Ser | Gln | Ser | Val | Ser | Ser | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | tta | gcc | tgg | tac | cag | cag | aaa | cct | ggc | cag | gct | ccc | agg | ctc | ctc | 144 |
| Tyr | Leu | Ala | Trp | Tyr | Gln | Gln | Lys | Pro | Gly | Gln | Ala | Pro | Arg | Leu | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| atc | tac | ggt | gca | tcc | agg | agg | gcc | act | ggc | atc | cca | gac | agg | ttc | agt | 192 |
| Ile | Tyr | Gly | Ala | Ser | Arg | Arg | Ala | Thr | Gly | Ile | Pro | Asp | Arg | Phe | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| ggc | agt | ggg | tct | ggg | aca | gac | ttc | act | ctc | acc | atc | agc | aga | ctg | gag | 240 |
| Gly | Ser | Gly | Ser | Gly | Thr | Asp | Phe | Thr | Leu | Thr | Ile | Ser | Arg | Leu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cct | gaa | gat | ttt | gca | gtg | tat | tac | tgt | cag | cag | tat | ggt | agc | tca | ccc | 288 |
| Pro | Glu | Asp | Phe | Ala | Val | Tyr | Tyr | Cys | Gln | Gln | Tyr | Gly | Ser | Ser | Pro | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | tac | act | ttt | ggc | cag | ggg | acc | aag | ctg | gag | atc | aaa | cga | act | gtg | 336 |
| Met | Tyr | Thr | Phe | Gly | Gln | Gly | Thr | Lys | Leu | Glu | Ile | Lys | Arg | Thr | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| gct | gca | cca | tct | gtc | ttc | atc | ttc | ccg | cca | tct | gat | gag | cag | ttg | aaa | 384 |
| Ala | Ala | Pro | Ser | Val | Phe | Ile | Phe | Pro | Pro | Ser | Asp | Glu | Gln | Leu | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| tct | gga | act | gcc | tct | gtt | gtg | tgc | ctg | ctg | aat | aac | ttc | tat | ccc | aga | 432 |
| Ser | Gly | Thr | Ala | Ser | Val | Val | Cys | Leu | Leu | Asn | Asn | Phe | Tyr | Pro | Arg | |
| 130 | | | | | 135 | | | | | 140 | | | | | | |

| | | | | | | | | | | | | | | | | |
|---|---|---|---|---|---|---|---|---|---|---|---|---|---|---|---|---|
| gag | gcc | aaa | gta | cag | tgg | aag | gtg | gat | aac | gcc | ctc | caa | tcg | ggt | aac | 480 |
| Glu | Ala | Lys | Val | Gln | Trp | Lys | Val | Asp | Asn | Ala | Leu | Gln | Ser | Gly | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | cag | gag | agt | gtc | aca | gag | cag | gac | agc | aag | gac | agc | acc | tac | agc | 528 |
| Ser | Gln | Glu | Ser | Val | Thr | Glu | Gln | Asp | Ser | Lys | Asp | Ser | Thr | Tyr | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| ctc | agc | agc | acc | ctg | acg | ctg | agc | aaa | gca | gac | tac | gag | aaa | cac | aaa | 576 |
| Leu | Ser | Ser | Thr | Leu | Thr | Leu | Ser | Lys | Ala | Asp | Tyr | Glu | Lys | His | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | tac | gcc | tgc | gaa | gtc | acc | cat | cag | ggc | ctg | agc | tcg | ccc | gtc | aca | 624 |
| Val | Tyr | Ala | Cys | Glu | Val | Thr | His | Gln | Gly | Leu | Ser | Ser | Pro | Val | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | agc | ttc | aac | agg | gga | gag | tct | tat | cca | tat | gat | gtg | cca | gat | tat | 672 |
| Lys | Ser | Phe | Asn | Arg | Gly | Glu | Ser | Tyr | Pro | Tyr | Asp | Val | Pro | Asp | Tyr | |
| 210 | | | | | 215 | | | | | 220 | | | | | | |

| | | | |
|---|---|---|---|
| gcg | agc | | 678 |
| Ala | Ser | | |
| 225 | | | |

<210> SEQ ID NO 80
<211> LENGTH: 226
<212> TYPE: PRT
<213> ORGANISM: Homo sapiens
<220> FEATURE:
<223> OTHER INFORMATION: M2-20L

```
<400> SEQUENCE: 80

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
             35                  40                  45

Ile Tyr Gly Ala Ser Arg Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 81
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: M2-31L

<400> SEQUENCE: 81 gaa att gtg ttg acg cag tct cca gcc acc ctg tct ttg tct cca ggg      48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
             35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
         50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80
```

-continued

| | |
|---|---|
| gaa gat ttt gca gtt tat tac tgt cag cag cgt acg aac tgg cct cgg<br>Glu Asp Phe Ala Val Tyr Tyr Cys Gln Gln Arg Thr Asn Trp Pro Arg<br>                        85                      90                    95 | 288 |
| acg ttc ggc caa ggg acc aag gtg gaa atc aaa cga act gtg gct gca<br>Thr Phe Gly Gln Gly Thr Lys Val Glu Ile Lys Arg Thr Val Ala Ala<br>                100                    105                   110 | 336 |
| cca tct gtc ttc atc ttc ccg cca tct gat gag cag ttg aaa tct gga<br>Pro Ser Val Phe Ile Phe Pro Pro Ser Asp Glu Gln Leu Lys Ser Gly<br>          115                    120                    125 | 384 |
| act gcc tct gtt gtg tgc ctg ctg aat aac ttc tat ccc aga gag gcc<br>Thr Ala Ser Val Val Cys Leu Leu Asn Asn Phe Tyr Pro Arg Glu Ala<br>130                   135                    140 | 432 |
| aaa gta cag tgg aag gtg gat aac gcc ctc caa tcg ggt aac tcc cag<br>Lys Val Gln Trp Lys Val Asp Asn Ala Leu Gln Ser Gly Asn Ser Gln<br>145                   150                   155                   160 | 480 |
| gag agt gtc aca gag cag gac agc aag gac agc acc tac agc ctc agc<br>Glu Ser Val Thr Glu Gln Asp Ser Lys Asp Ser Thr Tyr Ser Leu Ser<br>                165                    170                   175 | 528 |
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>          180                    185                    190 | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>               195                    200                   205 | 624 |
| ttc aac agg gga gag tct tat cca tat gat gtg cca gat tat gcg agc<br>Phe Asn Arg Gly Glu Ser Tyr Pro Tyr Asp Val Pro Asp Tyr Ala Ser<br>          210                    215                    220 | 672 |

<210> SEQ ID NO 82
<211> LENGTH: 224
<212> TYPE: PRT
<213> ORGANISM: Homo sapiens
<220> FEATURE:
<223> OTHER INFORMATION: M2-31L

<400> SEQUENCE: 82

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
        210                 215                 220

<210> SEQ ID NO 83
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: M2-32L

<400> SEQUENCE: 83 gaa att gtg ttg acg cag tct cca gcc acc ctg tct ttg tct cca ggg        48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
         35                  40                  45 tat gat gca tcc aac agg gcc gct ggc atc cca gcc agg ttc agt ggc       192
Tyr Asp Ala Ser Asn Arg Ala Ala Gly Ile Pro Ala Arg Phe Ser Gly
     50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca gtt tat tac tgt cag caa cgt aac aac tgg cct ctc       288
Glu Asp Phe Ala Val Tyr Tyr Cys Gln Gln Arg Asn Asn Trp Pro Leu
                 85                  90                  95 act ttc ggc gga ggg acc aag gtg gag atc aaa cga act gtg gct gca       336
Thr Phe Gly Gly Gly Thr Lys Val Glu Ile Lys Arg Thr Val Ala Ala
            100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc       624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc       672
Phe Asn Arg Gly Glu Ser Tyr Pro Tyr Asp Val Pro Asp Tyr Ala Ser
    210                 215                 220
```

```
<210> SEQ ID NO 84
<211> LENGTH: 224
<212> TYPE: PRT
<213> ORGANISM: Homo sapiens
<220> FEATURE:
<223> OTHER INFORMATION: M2-32L

<400> SEQUENCE: 84

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
210                 215                 220

<210> SEQ ID NO 85
<211> LENGTH: 678
<212> TYPE: DNA
<213> ORGANISM: Homo sapiens
<220> FEATURE:
<221> NAME/KEY: CDS
<222> LOCATION: (1)..(678)
<220> FEATURE:
<223> OTHER INFORMATION: M2-33L

<400> SEQUENCE: 85 gaa att gtg ttg acg cag tct cca ggc acc ctg tct ttg tct cca ggg        48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
```

-continued

```
                   50                  55                  60
ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct      288
Pro Glu Asp Phe Ala Val Tyr Tyr Cys Gln Gln Tyr Gly Ser Ser Pro
                 85                  90                  95 ccg tac act ttt ggc cag ggg acc aag ctg gag atc aaa cga act gtg      336
Pro Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa      384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga      432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac      480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc      528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa      576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca      624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat      672
Lys Ser Phe Asn Arg Gly Glu Ser Tyr Pro Tyr Asp Val Pro Asp Tyr
    210                 215                 220 gcg agc                                                              678
Ala Ser
225
```

<210> SEQ ID NO 86
<211> LENGTH: 226
<212> TYPE: PRT
<213> ORGANISM: Homo sapiens
<220> FEATURE:
<223> OTHER INFORMATION: M2-33L

<400> SEQUENCE: 86

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125
```

```
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 87
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: M2-34L

<400> SEQUENCE: 87 gaa att gtg ttg acg cag tct cca gcc acc ctg tct ttg tct cca ggg     48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gtt agc agc tac     96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acg aac tgg cct cgg    288
Glu Asp Phe Ala Val Tyr Tyr Cys Gln Gln Arg Thr Asn Trp Pro Arg
                 85                  90                  95 acg ttc ggc caa ggg acc aag gtg gaa atc aaa cga act gtg gct gca    336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175
```

```
agc acc ctg acg ctg agc aaa gca gac tac gag aaa cac aaa gtc tac    576
Ser Thr Leu Thr Leu Ser Lys Ala Asp Tyr Glu Lys His Lys Val Tyr
        180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
            195                 200                 205 ttc aac agg gga gag tct tat cca tat gat gtg cca gat tat gcg agc    672
Phe Asn Arg Gly Glu Ser Tyr Pro Tyr Asp Val Pro Asp Tyr Ala Ser
    210                 215                 220
```

<210> SEQ ID NO 88
<211> LENGTH: 224
<212> TYPE: PRT
<213> ORGANISM: Homo sapiens
<220> FEATURE:
<223> OTHER INFORMATION: M2-34L

<400> SEQUENCE: 88

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 89
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: M2-35L

<400> SEQUENCE: 89

```
gaa att gtg ttg acg cag tct cca gcc acc ctg tct ttg tct cca ggg     48
Glu Ile Val Leu Thr Gln Ser Pro Ala Thr Leu Ser Leu Ser Pro Gly
```

```
                1               5                    10                   15
gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc        144
Leu Ala Trp Tyr Gln Gln Lys Pro Gly Gln Ala Pro Arg Leu Leu Ile
            35                  40                  45 tat gat gca tcc aac agg gcc act ggc atc cca gcc agg ttc agt ggc        192
Tyr Asp Ala Ser Asn Arg Ala Thr Gly Ile Pro Ala Arg Phe Ser Gly
        50                  55                  60 agt ggg tct ggg aca gac ttc act ctc acc atc agc agc cta gag cct        240
Ser Gly Ser Gly Thr Asp Phe Thr Leu Thr Ile Ser Ser Leu Glu Pro
    65                  70                  75                  80 gaa gat ttt gca gtt tat tac tgt cag cag cgt acg aac tgg cct cgg        288
Glu Asp Phe Ala Val Tyr Tyr Cys Gln Gln Arg Thr Asn Trp Pro Arg
                85                  90                  95 acg ttc ggc caa ggg acc aag gtg gaa atc aaa cga act gtg gct gca        336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga        384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc        432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag        480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc        528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac        576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc        624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc        672
Phe Asn Arg Gly Glu Ser Tyr Pro Tyr Asp Val Pro Asp Tyr Ala Ser
    210                 215                 220
```

<210> SEQ ID NO 90
<211> LENGTH: 224
<212> TYPE: PRT
<213> ORGANISM: Homo sapiens
<220> FEATURE:
<223> OTHER INFORMATION: M2-35L

<400> SEQUENCE: 90

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
    65                  70                  75                  80
```

```
Glu Asp Phe Ala Val Tyr Tyr Cys Gln Gln Arg Thr Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Ser Tyr Pro Tyr Asp Val Pro Asp Tyr Ala Ser
210                 215                 220

<210> SEQ ID NO 91
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-11H

<400> SEQUENCE: 91 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcg tct gga ttt acc ttc agt tac tat      96
Ser Leu Arg Leu Ser Cys Ala Ala Ser Gly Phe Thr Phe Ser Tyr Tyr
                20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
            35                  40                  45 aca ctt ata acc tat gat gga gat aat aaa tac tat gca gac tcc gtg     192
Thr Leu Ile Thr Tyr Asp Gly Asp Asn Lys Tyr Tyr Ala Asp Ser Val
        50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga gac ggg atc ggg tac ttt gac tat tgg ggc cag gga acc ctg     336
Ala Arg Asp Gly Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160
```

```
ggc gcc ctg acc agc ggc gtg cac acc ttc ccg gct gtc cta cag tcc    528
Gly Ala Leu Thr Ser Gly Val His Thr Phe Pro Ala Val Leu Gln Ser
            165                 170                 175 tca gga ctc tac tcc ctc agc agc gtg gtg acc gtg ccc tcc agc agc    576
Ser Gly Leu Tyr Ser Leu Ser Ser Val Val Thr Val Pro Ser Ser Ser
        180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat    672
Thr Lys Val Asp Lys Lys Ala Glu Pro Lys Ser His His His His His
    210                 215                 220 cac                                                                675
His
225

<210> SEQ ID NO 92
<211> LENGTH: 225
<212> TYPE: PRT
<213> ORGANISM: Homo sapiens
<220> FEATURE:
<223> OTHER INFORMATION: M2-11H

<400> SEQUENCE: 92

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Tyr Tyr
                20                  25                  30

Gly Met His Trp Val Arg Gln Ala Pro Gly Lys Gly Leu Glu Trp Val
            35                  40                  45

Thr Leu Ile Thr Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
225

<210> SEQ ID NO 93
<211> LENGTH: 675
```

<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-12H

<400> SEQUENCE: 93

| | | |
|---|---|---|
| gat gtg cag ctg gtg gag tct ggg gga ggc gtg gtc cat cct ggg agg<br>Asp Val Gln Leu Val Glu Ser Gly Gly Gly Val Val His Pro Gly Arg<br>1                 5                    10                  15 | 48 |
| tcc ctg aga ctc tcc tgt gca gcg tct gga ttt acc ttc agt tac tat<br>Ser Leu Arg Leu Ser Cys Ala Ala Ser Gly Phe Thr Phe Ser Tyr Tyr<br>               20                    25                    30 | 96 |
| ggc atg cac tgg gtc cgc cag gct cca ggc aag ggg ctg gaa tgg atg<br>Gly Met His Trp Val Arg Gln Ala Pro Gly Lys Gly Leu Glu Trp Met<br>        35                    40                    45 | 144 |
| aca ctt ata tcc tat gat gga gat aat aaa tac tat gca gac tcc gtg<br>Thr Leu Ile Ser Tyr Asp Gly Asp Asn Lys Tyr Tyr Ala Asp Ser Val<br>    50                    55                    60 | 192 |
| aag ggc cga ttc acc atc tcc aga gaa aat tcc aag aac acg ctg tat<br>Lys Gly Arg Phe Thr Ile Ser Arg Glu Asn Ser Lys Asn Thr Leu Tyr<br>65                  70                    75                  80 | 240 |
| ctg caa atg aac agt ctg aga gcc gag gac acg gct gtg tat tac tgt<br>Leu Gln Met Asn Ser Leu Arg Ala Glu Asp Thr Ala Val Tyr Tyr Cys<br>               85                    90                    95 | 288 |
| gcg aga gac ggg atc ggg tac ttt gac tat tgg ggc cag gga acc ctg<br>Ala Arg Asp Gly Ile Gly Tyr Phe Asp Tyr Trp Gly Gln Gly Thr Leu<br>        100                    105                 110 | 336 |
| gtc acc gtc tcc tca gcc tcc acc aag ggc cca tcg gtc ttc ccc ctg<br>Val Thr Val Ser Ser Ala Ser Thr Lys Gly Pro Ser Val Phe Pro Leu<br>            115                    120                 125 | 384 |
| gca ccc tcc tcc aag agc acc tct ggg ggc aca gcg gcc ctg ggc tgc<br>Ala Pro Ser Ser Lys Ser Thr Ser Gly Gly Thr Ala Ala Leu Gly Cys<br>130                  135                    140 | 432 |
| ctg gtc aag gac tac ttc ccc gaa ccg gtg acg gtg tcg tgg aac tca<br>Leu Val Lys Asp Tyr Phe Pro Glu Pro Val Thr Val Ser Trp Asn Ser<br>145                  150                    155                160 | 480 |
| ggc gcc ctg acc agc ggc gtg cac acc ttc ccg gct gtc cta cag tcc<br>Gly Ala Leu Thr Ser Gly Val His Thr Phe Pro Ala Val Leu Gln Ser<br>                165                    170                 175 | 528 |
| tca gga ctc tac tcc ctc agc agc gtg gtg acc gtg ccc tcc agc agc<br>Ser Gly Leu Tyr Ser Leu Ser Ser Val Val Thr Val Pro Ser Ser Ser<br>                  180                    185                 190 | 576 |
| ttg ggc acc cag acc tac atc tgc aac gtg aat cac aag ccc agc agc<br>Leu Gly Thr Gln Thr Tyr Ile Cys Asn Val Asn His Lys Pro Ser Ser<br>                    195                    200                205 | 624 |
| acc aag gtg gac aag aaa gca gag ccc aaa tct cat cac cat cac cat<br>Thr Lys Val Asp Lys Lys Ala Glu Pro Lys Ser His His His His His<br>    210                      215                    220 | 672 |
| cac<br>His<br>225 | 675 |

<210> SEQ ID NO 94
<211> LENGTH: 225
<212> TYPE: PRT
<213> ORGANISM: Homo sapiens
<220> FEATURE:
<223> OTHER INFORMATION: M2-12H

<400> SEQUENCE: 94

```
Asp Val Gln Leu Val Glu Ser Gly Gly Val Val His Pro Gly Arg
 1               5                  10                 15

Ser Leu Arg Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Met
         35                  40                  45

Thr Leu Ile Ser Tyr Asp Gly Asp Asn Lys Tyr Tyr Ala Asp Ser Val
     50                  55                  60

Lys Gly Arg Phe Thr Ile Ser Arg Glu Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
     130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
             165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Ser
             195                 200                 205

Thr Lys Val Asp Lys Lys Ala Glu Pro Lys Ser His His His His
     210                 215                 220

His
225
```

<210> SEQ ID NO 95
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-16H

<400> SEQUENCE: 95

```
cag gtg cag ctg gtg cag tct ggg gga ggc gtg gtc cag cct ggg aag        48
Gln Val Gln Leu Val Gln Ser Gly Gly Gly Val Val Gln Pro Gly Lys
 1               5                  10                  15 tcc ctg aga ctc tcc tgt gca gcg tct gga ttc agc ttg agt tac tat       96
Ser Leu Arg Leu Ser Cys Ala Ala Ser Gly Phe Ser Leu Ser Tyr Tyr
             20                  25                  30 ggc atg cac tgg gtc cgc cag gtt cca ggc aag ggg ctg gag tgg gtg      144
Gly Met His Trp Val Arg Gln Val Pro Gly Lys Gly Leu Glu Trp Val
         35                  40                  45 gca gct gtc tgg tat gat gga agt act aga tat tct cca gac tcc gtg      192
Ala Ala Val Trp Tyr Asp Gly Ser Thr Arg Tyr Ser Pro Asp Ser Val
     50                  55                  60 aag ggc cga ttc acc atc tcc aga gac gat tcc aag aac acg ctg tat      240
Lys Gly Arg Phe Thr Ile Ser Arg Asp Asp Ser Lys Asn Thr Leu Tyr
 65                  70                  75                  80
```

```
ctg caa atg aac agc ctg aga gcc gag gac acg gct gtg tat tac tgt    288
Leu Gln Met Asn Ser Leu Arg Ala Glu Asp Thr Ala Val Tyr Tyr Cys
            85                  90                  95 gcg aga gat agg gtg ggc ctc ttt gac tac tgg ggc cag gga acc ctg    336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg    384
Val Thr Val Ser Ser Ala Ser Thr Lys Gly Pro Ser Val Phe Pro Leu
            115                 120                 125 gca ccc tcc tcc aag agc acc tct ggg ggc aca gcg gcc ctg ggc tgc    432
Ala Pro Ser Ser Lys Ser Thr Ser Gly Gly Thr Ala Ala Leu Gly Cys
        130                 135                 140 ctg gtc aag gac tac ttc ccc gaa ccg gtg acg gtg tcg tgg aac tca    480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc    528
Gly Ala Leu Thr Ser Gly Val His Thr Phe Pro Ala Val Leu Gln Ser
            165                 170                 175 tca gga ctc tac tcc ctc agc agc gtg gtg acc gtg ccc tcc agc agc    576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
            195                 200                 205 acc aag gtg gac aag aaa gca gag ccc aaa tct cat cac cat cac cat    672
Thr Lys Val Asp Lys Lys Ala Glu Pro Lys Ser His His His His His
            210                 215                 220 cac                                                                675
His
225

<210> SEQ ID NO 96
<211> LENGTH: 225
<212> TYPE: PRT
<213> ORGANISM: Homo sapiens
<220> FEATURE:
<223> OTHER INFORMATION: M2-16H

<400> SEQUENCE: 96

Gln Val Gln Leu Val Gln Ser Gly Gly Val Val Gln Pro Gly Lys
 1               5                  10                  15

Ser Leu Arg Leu Ser Cys Ala Ala Ser Gly Phe Ser Leu Ser Tyr Tyr
                20                  25                  30

Gly Met His Trp Val Arg Gln Val Pro Gly Lys Gly Leu Glu Trp Val
            35                  40                  45

Ala Ala Val Trp Tyr Asp Gly Ser Thr Arg Tyr Ser Pro Asp Ser Val
        50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser His His His His
    210                 215                 220

His
225

<210> SEQ ID NO 97
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-18H

<400> SEQUENCE: 97 cag gtg cag ctg gtg cag tct ggg gga ggc gtg gtc cag cct ggg aag       48
Gln Val Gln Leu Val Gln Ser Gly Gly Gly Val Val Gln Pro Gly Lys
 1               5                  10                  15 tcc ctg aga ctc tcc tgt gca gcg tct gga ttc agc ttc agt tac tat       96
Ser Leu Arg Leu Ser Cys Ala Ala Ser Gly Phe Ser Phe Ser Tyr Tyr
            20                  25                  30 ggc atg cac tgg gtc cgc cag gtt cca ggc aag ggg ctg gag tgg gtg      144
Gly Met His Trp Val Arg Gln Val Pro Gly Lys Gly Leu Glu Trp Val
        35                  40                  45 gca gct gtc tgg tat gat gga agt act aca tat tct cca gac tcc gtg      192
Ala Ala Val Trp Tyr Asp Gly Ser Thr Thr Tyr Ser Pro Asp Ser Val
    50                  55                  60 aag ggc cga ttc acc atc tcc aga gac gat tcc aag aac acg ctg tat      240
Lys Gly Arg Phe Thr Ile Ser Arg Asp Asp Ser Lys Asn Thr Leu Tyr
65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95 gcg aga gat agg gtg ggc ctc ttt gac tac tgg ggc cag gga acc ctg      336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc      432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca      480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc      528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc      576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac      624
Leu Gly Thr Gln Thr Tyr Ile Cys Asn Val Asn His Lys Pro Ser Asn
        195                 200                 205
```

|   |   |   |   |   |   |   |   |   |   |   |   |   |   |   |
|---|---|---|---|---|---|---|---|---|---|---|---|---|---|---|
|   |   |   | 195 |   |   | 200 |   |   |   | 205 |   |   |   |   |
| acc | aag | gtg | gac | aag | aaa | gca | gag | ccc | aaa | tct | cat | cac | cat | cac cat | 672 |
| Thr | Lys | Val | Asp | Lys | Lys | Ala | Glu | Pro | Lys | Ser | His | His | His | His His |
|   |   |   | 210 |   |   | 215 |   |   |   | 220 |   |   |   |   |

| cac | 675 |
|-----|-----|
| His |     |
| 225 |     |

<210> SEQ ID NO 98
<211> LENGTH: 225
<212> TYPE: PRT
<213> ORGANISM: Homo sapiens
<220> FEATURE:
<223> OTHER INFORMATION: M2-18H

<400> SEQUENCE: 98

Gln Val Gln Leu Val Gln Ser Gly Gly Gly Val Val Gln Pro Gly Lys
 1               5                  10                  15

Ser Leu Arg Leu Ser Cys Ala Ala Ser Gly Phe Ser Phe Ser Tyr Tyr
            20                  25                  30

Gly Met His Trp Val Arg Gln Val Pro Gly Lys Gly Leu Glu Trp Val
        35                  40                  45

Ala Ala Val Trp Tyr Asp Gly Ser Thr Thr Tyr Ser Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
225

<210> SEQ ID NO 99
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-20H

<400> SEQUENCE: 99

| cag | gtg | cag | ctg | gtg | cag | tct | ggg | gga | ggc | gtg | gtc | cag | cct | ggg | agg | 48 |

| | | |
|---|---|---|
| Gln Val Gln Leu Val Gln Ser Gly Gly Gly Val Val Gln Pro Gly Arg<br>1                             5                        10                     15 | |
| tcc ctg agg ctc tcc tgt gca gcc tct gga ttc act ttc agt tac tat<br>Ser Leu Arg Leu Ser Cys Ala Ala Ser Gly Phe Thr Phe Ser Tyr Tyr<br>                  20                       25                       30 | 96 |
| ggt atg cac tgg gtc cgc cag gct cca ggc aag ggg ctg gag tgg gtg<br>Gly Met His Trp Val Arg Gln Ala Pro Gly Lys Gly Leu Glu Trp Val<br>        35                       40                     45 | 144 |
| tca ctt ata aca tat gat gga agg aat aaa tac tac gcc gac tcc gtg<br>Ser Leu Ile Thr Tyr Asp Gly Arg Asn Lys Tyr Tyr Ala Asp Ser Val<br>50                             55                       60 | 192 |
| aag ggc cga ttc acc atc tcc aga gag aat tcc aag aac acg ctg tat<br>Lys Gly Arg Phe Thr Ile Ser Arg Glu Asn Ser Lys Asn Thr Leu Tyr<br>65                             70                       75                     80 | 240 |
| ctg caa atg aac agc ctg aga act gag gac acg gct gag tat tac tgt<br>Leu Gln Met Asn Ser Leu Arg Thr Glu Asp Thr Ala Glu Tyr Tyr Cys<br>                  85                       90                       95 | 288 |
| gcg aga gac ggg atc gga tac ttt gac tac tgg ggc cag gga atc ctg<br>Ala Arg Asp Gly Ile Gly Tyr Phe Asp Tyr Trp Gly Gln Gly Ile Leu<br>              100                     105                     110 | 336 |
| gtc acc gtc tcc tca gcc tcc acc aag ggc cca tcg gtc ttc ccc ctg<br>Val Thr Val Ser Ser Ala Ser Thr Lys Gly Pro Ser Val Phe Pro Leu<br>      115                     120                     125 | 384 |
| gca ccc tcc tcc aag agc acc tct ggg ggc aca gcg gcc ctg ggc tgc<br>Ala Pro Ser Ser Lys Ser Thr Ser Gly Gly Thr Ala Ala Leu Gly Cys<br>130                           135                     140 | 432 |
| ctg gtg aag gac tac ttc ccc gaa ccg gtg acg gtg tcg tgg aag tca<br>Leu Val Lys Asp Tyr Phe Pro Glu Pro Val Thr Val Ser Trp Lys Ser<br>145                        150                     155                   160 | 480 |
| ggc gcc ctg acc agc ggc gtg cac acc ttc ccg gct gtc cta cag tcc<br>Gly Ala Leu Thr Ser Gly Val His Thr Phe Pro Ala Val Leu Gln Ser<br>                  165                     170                     175 | 528 |
| tca gga ctc tac tcc ctc agc agc gtg gtg acc gtg ccc tcc agc agc<br>Ser Gly Leu Tyr Ser Leu Ser Ser Val Val Thr Val Pro Ser Ser Ser<br>180                           185                     190 | 576 |
| ttg ggc acc cag acc tac atc tgc aac gtg aat cac aag ccc agc aac<br>Leu Gly Thr Gln Thr Tyr Ile Cys Asn Val Asn His Lys Pro Ser Asn<br>      195                     200                     205 | 624 |
| acc aag gtg gac aag aaa gca gag ccc aaa tct cat cac cat cac cat<br>Thr Lys Val Asp Lys Lys Ala Glu Pro Lys Ser His His His His His<br>      210                     215                     220 | 672 |
| cac<br>His<br>225 | 675 |

```
<210> SEQ ID NO 100
<211> LENGTH: 225
<212> TYPE: PRT
<213> ORGANISM: Homo sapiens
<220> FEATURE:
<223> OTHER INFORMATION: M2-20H

<400> SEQUENCE: 100
```

Gln Val Gln Leu Val Gln Ser Gly Gly Gly Val Val Gln Pro Gly Arg
1                     5                      10                    15

Ser Leu Arg Leu Ser Cys Ala Ala Ser Gly Phe Thr Phe Ser Tyr Tyr
               20                    25                    30

Gly Met His Trp Val Arg Gln Ala Pro Gly Lys Gly Leu Glu Trp Val
        35                    40                    45

Ser Leu Ile Thr Tyr Asp Gly Arg Asn Lys Tyr Tyr Ala Asp Ser Val

```
                50                      55                      60
Lys Gly Arg Phe Thr Ile Ser Arg Glu Asn Ser Lys Asn Thr Leu Tyr
 65                      70                      75                      80

Leu Gln Met Asn Ser Leu Arg Thr Glu Asp Thr Ala Glu Tyr Tyr Cys
                    85                      90                      95

Ala Arg Asp Gly Ile Gly Tyr Phe Asp Tyr Trp Gly Gln Gly Ile Leu
                100                     105                     110

Val Thr Val Ser Ser Ala Ser Thr Lys Gly Pro Ser Val Phe Pro Leu
                115                     120                     125

Ala Pro Ser Ser Lys Ser Thr Ser Gly Gly Thr Ala Ala Leu Gly Cys
                130                     135                     140

Leu Val Lys Asp Tyr Phe Pro Glu Pro Val Thr Val Ser Trp Lys Ser
145                     150                     155                     160

Gly Ala Leu Thr Ser Gly Val His Thr Phe Pro Ala Val Leu Gln Ser
                    165                     170                     175

Ser Gly Leu Tyr Ser Leu Ser Ser Val Val Thr Val Pro Ser Ser Ser
                180                     185                     190

Leu Gly Thr Gln Thr Tyr Ile Cys Asn Val Asn His Lys Pro Ser Asn
                    195                     200                     205

Thr Lys Val Asp Lys Lys Ala Glu Pro Lys Ser His His His His
                210                     215                     220

His
225
```

<210> SEQ ID NO 101
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-31H

<400> SEQUENCE: 101

```
cag gtg cag ctg gtg gag tct ggg gga gtc gtg gtc cag cct ggg agg        48
Gln Val Gln Leu Val Glu Ser Gly Gly Val Val Val Gln Pro Gly Arg
  1               5                  10                  15 tcc ctg aga ctc tcc tgt gca gcc tct gga ttc acg ttc agt tac tat        96
Ser Leu Arg Leu Ser Cys Ala Ala Ser Gly Phe Thr Phe Ser Tyr Tyr
             20                  25                  30 ggt ata cac tgg gtc cgc cag gtt cca ggc aag gga cta gag tgg gtg      144
Gly Ile His Trp Val Arg Gln Val Pro Gly Lys Gly Leu Glu Trp Val
         35                  40                  45 gca ctt ata tca tac gat gga agc aat aaa tac tac gca gac tcc gtg      192
Ala Leu Ile Ser Tyr Asp Gly Ser Asn Lys Tyr Tyr Ala Asp Ser Val
     50                  55                  60 aag ggc cga ttc acc atc tcc aga gac aat tcc aag aac act ctg tat      240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                 85                  90                  95 gcg aga gac tgg atc ggg tac ttt gac tac tgg ggc cag gga acc ctg      336
Ala Arg Asp Trp Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
        115                 120                 125
```

-continued

| | | |
|---|---|---|
| gca ccc tcc tcc aag agc acc tct ggg ggc aca gcg gcc ctg ggc tgc<br>Ala Pro Ser Ser Lys Ser Thr Ser Gly Gly Thr Ala Ala Leu Gly Cys<br>130                               135                      140 | 432 |
| ctg gtc aag gac tac ttc ccc gaa ccg gtg acg gtg tcg tgg aac tca<br>Leu Val Lys Asp Tyr Phe Pro Glu Pro Val Thr Val Ser Trp Asn Ser<br>145                         150                        155                    160 | 480 |
| ggc gcc ctg acc agc ggc gtg cac acc ttc ccg gct gtc cta cag tcc<br>Gly Ala Leu Thr Ser Gly Val His Thr Phe Pro Ala Val Leu Gln Ser<br>                          165                      170                      175 | 528 |
| tca gga ctc tac tcc ctc agc agc gtg gtg acc gtg ccc tcc agc agc<br>Ser Gly Leu Tyr Ser Leu Ser Ser Val Val Thr Val Pro Ser Ser Ser<br>                180                      185                      190 | 576 |
| ctg ggc acc cag acc tac atc tgc aac gtg aat cac aag ccc agc aac<br>Leu Gly Thr Gln Thr Tyr Ile Cys Asn Val Asn His Lys Pro Ser Asn<br>                        195                      200                    205 | 624 |
| acc aag gtg gac aag aaa gca gag ccc aaa tct cat cac cat cac cat<br>Thr Lys Val Asp Lys Lys Ala Glu Pro Lys Ser His His His His His<br>210                               215                        220 | 672 |
| cac<br>His<br>225 | 675 |

<210> SEQ ID NO 102
<211> LENGTH: 225
<212> TYPE: PRT
<213> ORGANISM: Homo sapiens
<220> FEATURE:
<223> OTHER INFORMATION: M2-31H

<400> SEQUENCE: 102

Gln Val Gln Leu Val Glu Ser Gly Gly Val Val Gln Pro Gly Arg
1                  5                      10                     15

Ser Leu Arg Leu Ser Cys Ala Ala Ser Gly Phe Thr Phe Ser Tyr Tyr
                20                      25                      30

Gly Ile His Trp Val Arg Gln Val Pro Gly Lys Gly Leu Glu Trp Val
                35                      40                      45

Ala Leu Ile Ser Tyr Asp Gly Ser Asn Lys Tyr Tyr Ala Asp Ser Val
     50                      55                      60

Lys Gly Arg Phe Thr Ile Ser Arg Asp Asn Ser Lys Asn Thr Leu Tyr
65                           70                      75                    80

Leu Gln Met Asn Ser Leu Arg Ala Glu Asp Thr Ala Val Tyr Tyr Cys
                85                      90                      95

Ala Arg Asp Trp Ile Gly Tyr Phe Asp Tyr Trp Gly Gln Gly Thr Leu
                100                    105                    110

Val Thr Val Ser Ser Ala Ser Thr Lys Gly Pro Ser Val Phe Pro Leu
              115                    120                    125

Ala Pro Ser Ser Lys Ser Thr Ser Gly Gly Thr Ala Ala Leu Gly Cys
     130                      135                    140

Leu Val Lys Asp Tyr Phe Pro Glu Pro Val Thr Val Ser Trp Asn Ser
145                         150                        155                    160

Gly Ala Leu Thr Ser Gly Val His Thr Phe Pro Ala Val Leu Gln Ser
                165                    170                    175

Ser Gly Leu Tyr Ser Leu Ser Ser Val Val Thr Val Pro Ser Ser Ser
              180                    185                    190

Leu Gly Thr Gln Thr Tyr Ile Cys Asn Val Asn His Lys Pro Ser Asn
            195                    200                    205

Thr Lys Val Asp Lys Lys Ala Glu Pro Lys Ser His His His His His

His
225

<210> SEQ ID NO 103
<211> LENGTH: 708
<212> TYPE: DNA
<213> ORGANISM: Homo sapiens
<220> FEATURE:
<221> NAME/KEY: CDS
<222> LOCATION: (1)..(708)
<220> FEATURE:
<223> OTHER INFORMATION: M2-32H

<400> SEQUENCE: 103

| | | | | | | | | | | | | | | | | |
|---|---|---|---|---|---|---|---|---|---|---|---|---|---|---|---|---|
| cag | gtg | cag | ctg | gtg | cag | tct | ggg | gga | ggc | ttg | gta | cat | cct | ggg | ggg | 48 |
| Gln | Val | Gln | Leu | Val | Gln | Ser | Gly | Gly | Gly | Leu | Val | His | Pro | Gly | Gly | |
| 1 | | | | 5 | | | | | 10 | | | | | 15 | | |
| tcc | ctg | aga | ctc | tcc | tgt | gaa | ggc | tct | gga | ttc | atc | ttc | agg | aac | cat | 96 |
| Ser | Leu | Arg | Leu | Ser | Cys | Glu | Gly | Ser | Gly | Phe | Ile | Phe | Arg | Asn | His | |
| | | | 20 | | | | | 25 | | | | | 30 | | | |
| cct | ata | cac | tgg | gtt | cgc | cag | gct | cca | gga | aaa | ggt | ctg | gag | tgg | gta | 144 |
| Pro | Ile | His | Trp | Val | Arg | Gln | Ala | Pro | Gly | Lys | Gly | Leu | Glu | Trp | Val | |
| | | 35 | | | | | 40 | | | | | 45 | | | | |
| tca | gtt | agt | ggt | att | ggt | ggt | gac | aca | tac | tat | gca | gac | tcc | gtg | aag | 192 |
| Ser | Val | Ser | Gly | Ile | Gly | Gly | Asp | Thr | Tyr | Tyr | Ala | Asp | Ser | Val | Lys | |
| 50 | | | | | 55 | | | | | 60 | | | | | | |
| ggc | cga | ttc | tcc | atc | tcc | aga | gac | aat | gcc | aag | aac | tcc | ttg | tat | ctt | 240 |
| Gly | Arg | Phe | Ser | Ile | Ser | Arg | Asp | Asn | Ala | Lys | Asn | Ser | Leu | Tyr | Leu | |
| 65 | | | | | 70 | | | | | 75 | | | | | 80 | |
| caa | atg | aac | agc | ctg | aga | gcc | gag | gac | atg | gct | gtg | tat | tac | tgt | gca | 288 |
| Gln | Met | Asn | Ser | Leu | Arg | Ala | Glu | Asp | Met | Ala | Val | Tyr | Tyr | Cys | Ala | |
| | | | 85 | | | | | 90 | | | | | 95 | | | |
| aga | gaa | tat | tac | tat | ggt | tcg | ggg | agt | tat | cgc | gtt | gac | tac | tac | tac | 336 |
| Arg | Glu | Tyr | Tyr | Tyr | Gly | Ser | Gly | Ser | Tyr | Arg | Val | Asp | Tyr | Tyr | Tyr | |
| | | | 100 | | | | | 105 | | | | | 110 | | | |
| tac | ggt | atg | gac | gtc | tgg | ggc | caa | ggg | acc | acg | gtc | acc | gtc | tcc | tca | 384 |
| Tyr | Gly | Met | Asp | Val | Trp | Gly | Gln | Gly | Thr | Thr | Val | Thr | Val | Ser | Ser | |
| | | 115 | | | | | 120 | | | | | 125 | | | | |
| gcc | tcc | acc | aag | ggc | cca | tcg | gtc | ttc | ccc | ctg | gca | ccc | tcc | tcc | aag | 432 |
| Ala | Ser | Thr | Lys | Gly | Pro | Ser | Val | Phe | Pro | Leu | Ala | Pro | Ser | Ser | Lys | |
| 130 | | | | | 135 | | | | | 140 | | | | | | |
| agc | acc | tct | ggg | ggc | aca | gcg | gcc | ctg | ggc | tgc | ctg | gtc | aag | gac | tac | 480 |
| Ser | Thr | Ser | Gly | Gly | Thr | Ala | Ala | Leu | Gly | Cys | Leu | Val | Lys | Asp | Tyr | |
| 145 | | | | | 150 | | | | | 155 | | | | | 160 | |
| ttc | ccc | gaa | ccg | gtg | acg | gtg | tcg | tgg | aac | tca | ggc | gcc | ctg | acc | agc | 528 |
| Phe | Pro | Glu | Pro | Val | Thr | Val | Ser | Trp | Asn | Ser | Gly | Ala | Leu | Thr | Ser | |
| | | | 165 | | | | | 170 | | | | | 175 | | | |
| ggc | gtg | cac | acc | ttc | ccg | gct | gtc | cta | cag | tcc | tca | gga | ctc | tac | tcc | 576 |
| Gly | Val | His | Thr | Phe | Pro | Ala | Val | Leu | Gln | Ser | Ser | Gly | Leu | Tyr | Ser | |
| | | 180 | | | | | 185 | | | | | 190 | | | | |
| ctc | agc | agc | gtg | gtg | acc | gtg | ccc | tcc | agc | agc | ttg | ggc | acc | cag | acc | 624 |
| Leu | Ser | Ser | Val | Val | Thr | Val | Pro | Ser | Ser | Ser | Leu | Gly | Thr | Gln | Thr | |
| | | 195 | | | | | 200 | | | | | 205 | | | | |
| tac | atc | tgc | aac | gtg | aat | cac | aag | ccc | agc | aac | acc | aag | gtg | gac | aag | 672 |
| Tyr | Ile | Cys | Asn | Val | Asn | His | Lys | Pro | Ser | Asn | Thr | Lys | Val | Asp | Lys | |
| | 210 | | | | | 215 | | | | | 220 | | | | | |
| aaa | gca | gag | ccc | aaa | tct | cat | cac | cat | cac | cat | cac | | | | | 708 |
| Lys | Ala | Glu | Pro | Lys | Ser | His | His | His | His | His | His | | | | | |
| 225 | | | | | 230 | | | | | 235 | | | | | | |

<210> SEQ ID NO 104
<211> LENGTH: 236
<212> TYPE: PRT
<213> ORGANISM: Homo sapiens
<220> FEATURE:
<223> OTHER INFORMATION: M2-32H

<400> SEQUENCE: 104

```
Gln Val Gln Leu Val Gln Ser Gly Gly Gly Leu Val His Pro Gly Gly
 1               5                  10                  15

Ser Leu Arg Leu Ser Cys Glu Gly Ser Gly Phe Ile Phe Arg Asn His
             20                  25                  30

Pro Ile His Trp Val Arg Gln Ala Pro Gly Lys Gly Leu Glu Trp Val
         35                  40                  45

Ser Val Ser Gly Ile Gly Gly Asp Thr Tyr Tyr Ala Asp Ser Val Lys
     50                  55                  60

Gly Arg Phe Ser Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                 85                  90                  95

Arg Glu Tyr Tyr Tyr Gly Ser Gly Ser Tyr Arg Val Asp Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Ala Glu Pro Lys Ser His His His His His His
225                 230                 235
```

<210> SEQ ID NO 105
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-33H

<400> SEQUENCE: 105

```
cag gtg cag ctg gtg cag tct ggg gga ggc gtg gtc cag cct ggg agg      48
Gln Val Gln Leu Val Gln Ser Gly Gly Gly Val Val Gln Pro Gly Arg
 1               5                  10                  15 tcc ctg aga ctc tcc tgt gca gcg tct gga ttt acc ttc agt tac tat      96
Ser Leu Arg Leu Ser Cys Ala Ala Ser Gly Phe Thr Phe Ser Tyr Tyr
             20                  25                  30 ggc atg cac tgg gtc cgc cag gct cca ggc aag ggg ctg gaa tgg atg     144
Gly Met His Trp Val Arg Gln Ala Pro Gly Lys Gly Leu Glu Trp Met
         35                  40                  45
```

-continued

| | | |
|---|---|---|
| aca ctt ata acc tat gat gga gat aat aaa tac tat gca gac tcc gtg<br>Thr Leu Ile Thr Tyr Asp Gly Asp Asn Lys Tyr Tyr Ala Asp Ser Val<br>50              55                  60 | | 192 |
| aag ggc cga ttc acc atc tcc aga gac aat tcc aag aac acg ctg tat<br>Lys Gly Arg Phe Thr Ile Ser Arg Asp Asn Ser Lys Asn Thr Leu Tyr<br>65                  70                  75                  80 | | 240 |
| ctg caa atg aac agt ctg aga gcc gag gac acg gct gtg tat tac tgt<br>Leu Gln Met Asn Ser Leu Arg Ala Glu Asp Thr Ala Val Tyr Tyr Cys<br>                85                  90                  95 | | 288 |
| gcg aga gac ggg atc ggg tac ttt gac tat tgg ggc cag gga acc ctg<br>Ala Arg Asp Gly Ile Gly Tyr Phe Asp Tyr Trp Gly Gln Gly Thr Leu<br>            100                 105                 110 | | 336 |
| gtc acc gtc tcc tca gcc tcc acc aag ggc cca tcg gtc ttc ccc ctg<br>Val Thr Val Ser Ser Ala Ser Thr Lys Gly Pro Ser Val Phe Pro Leu<br>        115                 120                 125 | | 384 |
| gca ccc tcc tcc aag agc acc tct ggg ggc aca gcg gcc ctg ggc tgc<br>Ala Pro Ser Ser Lys Ser Thr Ser Gly Gly Thr Ala Ala Leu Gly Cys<br>130                 135                 140 | | 432 |
| ctg gtc aag gac tac ttc ccc gaa ccg gtg acg gtg tcg tgg aac tca<br>Leu Val Lys Asp Tyr Phe Pro Glu Pro Val Thr Val Ser Trp Asn Ser<br>145                 150                 155                 160 | | 480 |
| ggc gcc ctg acc agc ggc gtg cac acc ttc ccg gct gtc cta cag tcc<br>Gly Ala Leu Thr Ser Gly Val His Thr Phe Pro Ala Val Leu Gln Ser<br>                165                 170                 175 | | 528 |
| tca gga ctc tac tcc ctc agc agc gtg gtg acc gtg ccc tcc agc agc<br>Ser Gly Leu Tyr Ser Leu Ser Ser Val Val Thr Val Pro Ser Ser Ser<br>            180                 185                 190 | | 576 |
| ttg ggc acc cag acc tac atc tgc aac gtg aat cac aag ccc agc aac<br>Leu Gly Thr Gln Thr Tyr Ile Cys Asn Val Asn His Lys Pro Ser Asn<br>        195                 200                 205 | | 624 |
| acc aag gtg gac aag aaa gca gag ccc aaa tct cat cac cat cac cat<br>Thr Lys Val Asp Lys Lys Ala Glu Pro Lys Ser His His His His His<br>210                 215                 220 | | 672 |
| cac<br>His<br>225 | | 675 |

<210> SEQ ID NO 106
<211> LENGTH: 225
<212> TYPE: PRT
<213> ORGANISM: Homo sapiens
<220> FEATURE:
<223> OTHER INFORMATION: M2-33H

<400> SEQUENCE: 106

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Met
        35                  40                  45

Thr Leu Ile Thr Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Gly Tyr Phe Asp Tyr Trp Gly Gln Gly Thr Leu
            100                 105                 110

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 107
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: M2-34H

<400> SEQUENCE: 107 cag gtg cag ctg gtg gag tct ggg gga ggc gtg gtc cag cct ggg agg        48
Gln Val Gln Leu Val Glu Ser Gly Gly Gly Val Val Gln Pro Gly Arg
  1               5                  10                  15 tcc ctg aga ctc tcc tgt gca gcc tct gga ttc acg ttc agt tac tat       96
Ser Leu Arg Leu Ser Cys Ala Ala Ser Gly Phe Thr Phe Ser Tyr Tyr
             20                  25                  30 ggt ata cac tgg gtc cgc cag gtt cca ggc aag gga cta gag tgg gtg      144
Gly Ile His Trp Val Arg Gln Val Pro Gly Lys Gly Leu Glu Trp Val
         35                  40                  45 gta ctt ata tca tac gat gga agc aat aaa tac tac gca gac tcc gtg      192
Val Leu Ile Ser Tyr Asp Gly Ser Asn Lys Tyr Tyr Ala Asp Ser Val
     50                  55                  60 aag ggc cga ttc acc atc tcc aga gac aat tcc aag aac act ctg tat      240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                 85                  90                  95 gcg aga gac tgg atc ggg tac ttt gac tac tgg ggc cag gga acc ctg      336
Ala Arg Asp Trp Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc      432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca      480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc      528
Gly Ala Leu Thr Ser Gly Val His Thr Phe Pro Ala Val Leu Gln Ser
```

```
                       165                 170                 175
tca gga ctc tac tcc ctc agc agc gtg gtg acc gtg ccc tcc agc agc    576
Ser Gly Leu Tyr Ser Leu Ser Ser Val Val Thr Val Pro Ser Ser
            180                 185                 190 ctg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat    672
Thr Lys Val Asp Lys Lys Ala Glu Pro Lys Ser His His His His His
    210                 215                 220 cac                                                                675
His
225

<210> SEQ ID NO 108
<211> LENGTH: 225
<212> TYPE: PRT
<213> ORGANISM: Homo sapiens
<220> FEATURE:
<223> OTHER INFORMATION: M2-34H

<400> SEQUENCE: 108

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Tyr Tyr
            20                  25                  30

Gly Ile His Trp Val Arg Gln Val Pro Gly Lys Gly Leu Glu Trp Val
        35                  40                  45

Val Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 109
<211> LENGTH: 675
<212> TYPE: DNA
<213> ORGANISM: Homo sapiens
<220> FEATURE:
```

```
<221> NAME/KEY: CDS
<222> LOCATION: (1)..(675)
<220> FEATURE:
<223> OTHER INFORMATION: M2-35H

<400> SEQUENCE: 109
```

| | | | | | | | | | | | | | | | | |
|---|---|---|---|---|---|---|---|---|---|---|---|---|---|---|---|---|
| cag | gtg | cag | ctg | gtg | gag | tct | ggg | gga | ggc | gtg | gtc | cag | cct | ggg | agg | 48 |
| Gln | Val | Gln | Leu | Val | Glu | Ser | Gly | Gly | Gly | Val | Val | Gln | Pro | Gly | Arg | |
| 1 | | | | 5 | | | | | 10 | | | | | 15 | | |
| tcc | ctg | aga | ctc | tcc | tgt | gca | gcc | tct | gga | ttc | acg | atc | agt | tac | tat | 96 |
| Ser | Leu | Arg | Leu | Ser | Cys | Ala | Ala | Ser | Gly | Phe | Thr | Ile | Ser | Tyr | Tyr | |
| | | | 20 | | | | | 25 | | | | | 30 | | | |
| ggt | ata | cac | tgg | gtc | cgc | cag | gtt | cca | ggc | aag | gga | cta | gag | tgg | gtg | 144 |
| Gly | Ile | His | Trp | Val | Arg | Gln | Val | Pro | Gly | Lys | Gly | Leu | Glu | Trp | Val | |
| | 35 | | | | | 40 | | | | | 45 | | | | | |
| gaa | ctt | ata | tca | tac | gat | gga | agc | aat | aaa | tac | tac | gca | gac | tcc | gtg | 192 |
| Glu | Leu | Ile | Ser | Tyr | Asp | Gly | Ser | Asn | Lys | Tyr | Tyr | Ala | Asp | Ser | Val | |
| 50 | | | | | 55 | | | | | 60 | | | | | | |
| aag | ggc | cga | ttc | acc | atc | tcc | aga | gac | aat | tcc | aag | aac | act | ctg | tat | 240 |
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |
| ctg | caa | atg | aac | agc | ctg | aga | gct | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gcg | aga | gac | tgg | atc | ggg | tac | ttt | gac | tac | tgg | ggc | cag | gga | acc | ctg | 336 |
| Ala | Arg | Asp | Trp | Ile | Gly | Tyr | Phe | Asp | Tyr | Trp | Gly | Gln | Gly | Thr | Leu | |
| | | | 100 | | | | | 105 | | | | | 110 | | | |
| gtc | acc | gtc | tcc | tca | gcc | tcc | acc | aag | ggc | cca | tcg | gtc | ttc | ccc | ctg | 384 |
| Val | Thr | Val | Ser | Ser | Ala | Ser | Thr | Lys | Gly | Pro | Ser | Val | Phe | Pro | Leu | |
| | 115 | | | | | 120 | | | | | 125 | | | | | |
| gca | ccc | tcc | tcc | aag | agc | acc | tct | ggg | ggc | aca | gcg | gcc | ctg | ggc | tgc | 432 |
| Ala | Pro | Ser | Ser | Lys | Ser | Thr | Ser | Gly | Gly | Thr | Ala | Ala | Leu | Gly | Cys | |
| 130 | | | | | 135 | | | | | 140 | | | | | | |
| ctg | gtc | aag | gac | tac | ttc | ccc | gaa | ccg | gtg | acg | gtg | tcg | tgg | aac | tca | 480 |
| Leu | Val | Lys | Asp | Tyr | Phe | Pro | Glu | Pro | Val | Thr | Val | Ser | Trp | Asn | Ser | |
| 145 | | | | | 150 | | | | | 155 | | | | | 160 | |
| ggc | gcc | ctg | acc | agc | ggc | gtg | cac | acc | ttc | ccg | gct | gtc | cta | cag | tcc | 528 |
| Gly | Ala | Leu | Thr | Ser | Gly | Val | His | Thr | Phe | Pro | Ala | Val | Leu | Gln | Ser | |
| | | | 165 | | | | | 170 | | | | | 175 | | | |
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | | 180 | | | | | 185 | | | | | 190 | | | |
| ctg | ggc | acc | cag | acc | tac | atc | tgc | aac | gtg | aat | cac | aag | ccc | agc | aac | 624 |
| Leu | Gly | Thr | Gln | Thr | Tyr | Ile | Cys | Asn | Val | Asn | His | Lys | Pro | Ser | Asn | |
| | 195 | | | | | 200 | | | | | 205 | | | | | |
| acc | aag | gtg | gac | aag | aaa | gca | gag | ccc | aaa | tct | cat | cac | cat | cac | cat | 672 |
| Thr | Lys | Val | Asp | Lys | Lys | Ala | Glu | Pro | Lys | Ser | His | His | His | His | His | |
| | 210 | | | | | 215 | | | | | 220 | | | | | |
| cac | | | | | | | | | | | | | | | | 675 |
| His | | | | | | | | | | | | | | | | |
| 225 | | | | | | | | | | | | | | | | |

```
<210> SEQ ID NO 110
<211> LENGTH: 225
<212> TYPE: PRT
<213> ORGANISM: Homo sapiens
<220> FEATURE:
<223> OTHER INFORMATION: M2-35H

<400> SEQUENCE: 110
```

| | | | | | | | | | | | | | | | |
|---|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |

Ser Leu Arg Leu Ser Cys Ala Ala Ser Gly Phe Thr Ile Ser Tyr Tyr
            20                  25                  30

Gly Ile His Trp Val Arg Gln Val Pro Gly Lys Gly Leu Glu Trp Val
        35                  40                  45

Glu Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
225

<210> SEQ ID NO 111
<211> LENGTH: 47
<212> TYPE: DNA
<213> ORGANISM: Artificial Sequence
<220> FEATURE:
<223> OTHER INFORMATION: Description of Artificial Sequence: Example 23
      Primer A

<400> SEQUENCE: 111
tagtccagtg tggtggaatt cgccaccatg acttccaagc tggccgt            47

<210> SEQ ID NO 112
<211> LENGTH: 48
<212> TYPE: DNA
<213> ORGANISM: Artificial Sequence
<220> FEATURE:
<223> OTHER INFORMATION: Description of Artificial Sequence: Example 23
      Primer B

<400> SEQUENCE: 112
cgaggctgat cagcgggttt aaacttatga attctcagcc ctcttcaa           48

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Example 23
      Primer C

<400> SEQUENCE: 113
cattctcaag cctcagacag tgg                                          23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Example 23
      Primer D

<400> SEQUENCE: 114
cagacaatgc gatgcaattt cc                                           22

<210> SEQ ID NO 115
<211> LENGTH: 49
<212> TYPE: DNA
<213> ORGANISM: Artificial Sequence
<220> FEATURE:
<223> OTHER INFORMATION: Description of Artificial Sequence: Example 24
      Primer A

<400> SEQUENCE: 115
tagtccagtg tggtggaatt cgccaccatg ggcttgttag agtgctgtg              49

<210> SEQ ID NO 116
<211> LENGTH: 48
<212> TYPE: DNA
<213> ORGANISM: Artificial Sequence
<220> FEATURE:
<223> OTHER INFORMATION: Description of Artificial Sequence: Example 24
      Primer B

<400> SEQUENCE: 116
cgaggctgat cagcgggttt aaactcagaa cttggtgcct cggcccat               48

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Example 24
      Primer C

<400> SEQUENCE: 117
cattctcaag cctcagacag tgg                                          23

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Example 24
      Primer D

<400> SEQUENCE: 118
cagacaatgc gatgcaattt cc                                           22

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Oligo 1008

<400> SEQUENCE: 119
caccgtcacc ggttcgggga                                              20

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Primer 1161

<400> SEQUENCE: 120
tcgctgccca accagccatg gcc                                          23

<210> SEQ ID NO 121
<211> LENGTH: 73
<212> TYPE: DNA
<213> ORGANISM: Artificial Sequence
<220> FEATURE:
<223> OTHER INFORMATION: Description of Artificial Sequence: Primer 1178

<400> SEQUENCE: 121
gtgataaact accgcattaa agcttatcga tgataagctg tcaattagtg atggtgatgg    60
tgatgagatt tgg                                                      73

<210> SEQ ID NO 122
<211> LENGTH: 73
<212> TYPE: DNA
<213> ORGANISM: Artificial Sequence
<220> FEATURE:
<223> OTHER INFORMATION: Description of Artificial Sequence: Primer 1182

<400> SEQUENCE: 122
gtgataaact accgcattaa agcttatcga tgataagctg tcaattagtg atggtgatgg    60
tgatgacatt tgg                                                      73

<210> SEQ ID NO 123
<211> LENGTH: 673
<212> TYPE: DNA
<213> ORGANISM: Homo sapiens
<220> FEATURE:
<221> NAME/KEY: CDS
<222> LOCATION: (2)..(673)
<220> FEATURE:
<223> OTHER INFORMATION: 1C.B1 Kappa Chain

<400> SEQUENCE: 123

```
c gaa ata gtg atg acg cag tct cca gcc acc ctg tct ttg tct cca ggg    49
  Glu Ile Val Met Thr Gln Ser Pro Ala Thr Leu Ser Leu Ser Pro Gly
   1               5                  10                  15 gaa aga gcc acc ctc tcc tgc agg gcc agt cag agt gtt tac agc tac      97
Glu Arg Ala Thr Leu Ser Cys Arg Ala Ser Gln Ser Val Tyr Ser Tyr
             20                  25                  30 tta gtc tgg tac caa cag aaa cct ggc cag gct ccc agg ctc ctc atc     145
Leu Val Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc     193
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct     241
Ser Gly Ser Gly Thr Asp Phe Thr Leu Thr Ile Ser Ser Leu Glu Pro
 65                  70                  75                  80 gaa gat ttt gca ttt tat tac tgt cag cag cgt acg aac cgg ccg tac     289
Glu Asp Phe Ala Phe Tyr Tyr Cys Gln Gln Arg Thr Asn Arg Pro Tyr
                 85                  90                  95 act ttt ggc cag ggg acc aag ctg gag atc aaa cga act gtg gct gca     337
```

-continued

```
                Thr Phe Gly Gln Gly Thr Lys Leu Glu Ile Lys Arg Thr Val Ala Ala
                                100                 105                 110
cca tct gtc ttc atc ttc ccg cca tct gat gag cag ttg aaa tct gga        385
Pro Ser Val Phe Ile Phe Pro Pro Ser Asp Glu Gln Leu Lys Ser Gly
            115                 120                 125
act gcc tct gtt gtg tgc ctg ctg aat aac ttc tat ccc aga gag gcc        433
Thr Ala Ser Val Val Cys Leu Leu Asn Asn Phe Tyr Pro Arg Glu Ala
130                 135                 140
aaa gta cag tgg aag gtg gat aac gcc ctc caa tcg ggt aac tcc cag        481
Lys Val Gln Trp Lys Val Asp Asn Ala Leu Gln Ser Gly Asn Ser Gln
145                 150                 155                 160
gag agt gtc aca gag cag gac agc aag gac agc acc tac agc ctc agc        529
Glu Ser Val Thr Glu Gln Asp Ser Lys Asp Ser Thr Tyr Ser Leu Ser
                165                 170                 175
agc acc ctg acg ctg agc aaa gca gac tac gag aaa cac aaa gtc tac        577
Ser Thr Leu Thr Leu Ser Lys Ala Asp Tyr Glu Lys His Lys Val Tyr
            180                 185                 190
gcc tgc gaa gtc acc cat cag ggc ctg agc tcg ccc gtc aca aag agc        625
Ala Cys Glu Val Thr His Gln Gly Leu Ser Ser Pro Val Thr Lys Ser
        195                 200                 205
ttc aac agg gga gag tct tat cca tat gat gtg cca gat tat gcg agc        673
Phe Asn Arg Gly Glu Ser Tyr Pro Tyr Asp Val Pro Asp Tyr Ala Ser
    210                 215                 220
```

<210> SEQ ID NO 124
<211> LENGTH: 224
<212> TYPE: PRT
<213> ORGANISM: Homo sapiens
<220> FEATURE:
<223> OTHER INFORMATION: 1C.B1 Kappa Chain

<400> SEQUENCE: 124

```
Glu Ile Val Met Thr Gln Ser Pro Ala Thr Leu Ser Leu Ser Pro Gly
  1               5                  10                  15
Glu Arg Ala Thr Leu Ser Cys Arg Ala Ser Gln Ser Val Tyr Ser Tyr
                20                  25                  30
Leu Val Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Phe Tyr Tyr Cys Gln Gln Arg Thr Asn Arg Pro Tyr
                85                  90                  95
Thr Phe Gly Gln Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
```

Phe Asn Arg Gly Glu Ser Tyr Pro Tyr Asp Val Pro Asp Tyr Ala Ser
    210                 215                 220

<210> SEQ ID NO 125
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 1C.C2 Kappa Chain

<400> SEQUENCE: 125

```
gag ctc gtg atg aca cag tct cca gcc acc ctg tct ttg tct cca ggg      48
Glu Leu Val Met Thr Gln Ser Pro Ala Thr Leu Ser Leu Ser Pro Gly
  1               5                  10                  15 gaa aga gcc acc ctc tcc tgc agg gcc agt cag agt gtt tac agc tac      96
Glu Arg Ala Thr Leu Ser Cys Arg Ala Ser Gln Ser Val Tyr Ser Tyr
             20                  25                  30 tta gtc tgg tac caa cag aaa cct ggc cag gct ccc agg ctc ctc atc     144
Leu Val Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acg aac tgg ccg tgg     288
Glu Asp Phe Ala Val Tyr Tyr Cys Gln Gln Arg Thr Asn Trp Pro Trp
                 85                  90                  95 acg ttc ggc caa ggg acc aag gtg gaa atc aaa cga act gtg gct gca     336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tct tat cca tat ggt gtg cca gat tat gcg agc     672
Phe Asn Arg Gly Glu Ser Tyr Pro Tyr Gly Val Pro Asp Tyr Ala Ser
    210                 215                 220
```

<210> SEQ ID NO 126
<211> LENGTH: 224
<212> TYPE: PRT
<213> ORGANISM: Homo sapiens
<220> FEATURE:

<223> OTHER INFORMATION: 1C.C2 Kappa Chain

<400> SEQUENCE: 126

```
Glu Leu Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Tyr Ser Tyr
             20                  25                  30

Leu Val Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Ser Tyr Pro Tyr Gly Val Pro Asp Tyr Ala Ser
210                 215                 220
```

<210> SEQ ID NO 127
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 1C.C6 Kappa Chain

<400> SEQUENCE: 127

```
gag ctc gtg atg acc cag act cca ctc tcc ctg tct ttg tct cca ggg      48
Glu Leu Val Met Thr Gln Thr Pro Leu Ser Leu Ser Leu Ser Pro Gly
  1               5                  10                  15 gaa aga gcc acc ctc tcc tgc agg gcc agt cag agt att tac aac tac      96
Glu Arg Ala Thr Leu Ser Cys Arg Ala Ser Gln Ser Ile Tyr Asn Tyr
             20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80
```

```
gaa gat ttt gca gtt tat tac tgt cag cag cgt acg aac tgg ccg tgg    288
Glu Asp Phe Ala Val Tyr Tyr Cys Gln Gln Arg Thr Asn Trp Pro Trp
                85                  90                  95 acg ttc ggc caa ggg acc aag gtg gaa atc aaa cga acc gtg gct gca    336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
        130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc    672
Phe Asn Arg Gly Glu Ser Tyr Pro Tyr Asp Val Pro Asp Tyr Ala Ser
    210                 215                 220
```

<210> SEQ ID NO 128
<211> LENGTH: 224
<212> TYPE: PRT
<213> ORGANISM: Homo sapiens
<220> FEATURE:
<223> OTHER INFORMATION: 1C.C6 Kappa Chain

<400> SEQUENCE: 128

```
Glu Leu Val Met Thr Gln Thr Pro Leu Ser Leu Ser Leu Ser Pro Gly
  1               5                  10                  15

Glu Arg Ala Thr Leu Ser Cys Arg Ala Ser Gln Ser Ile Tyr Asn Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 129
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 1C.C8 Kappa Chain

<400> SEQUENCE: 129 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt att tac aac tac      96
Glu Arg Ala Thr Leu Ser Cys Arg Ala Ser Gln Ser Ile Tyr Asn Tyr
             20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acg aac tgg ccg tgg     288
Glu Asp Phe Ala Val Tyr Tyr Cys Gln Gln Arg Thr Asn Trp Pro Trp
                 85                  90                  95 acg ttc ggc caa ggg acc aag gtg gaa atc aaa cga act gtg gct gca     336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc     672
Phe Asn Arg Gly Glu Ser Tyr Pro Tyr Asp Val Pro Asp Tyr Ala Ser
    210                 215                 220
```

<210> SEQ ID NO 130
<211> LENGTH: 224
<212> TYPE: PRT
<213> ORGANISM: Homo sapiens
<220> FEATURE:
<223> OTHER INFORMATION: 1C.C8 Kappa Chain

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Tyr Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 131
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 1C.D7 Kappa Chain

<400> SEQUENCE: 131 gag ctc gtg atg acc cag tct cca gcc acc ctg tct ttg tct cca ggg     48
Glu Leu Val Met Thr Gln Ser Pro Ala Thr Leu Ser Leu Ser Pro Gly
1               5                   10                  15 gaa aga gcc acc ctc tcc tgc agg gcc agt cag agt att tac aac tac     96
Glu Arg Ala Thr Leu Ser Cys Arg Ala Ser Gln Ser Ile Tyr Asn Tyr
            20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
    50                  55                  60

```
agt ggg tct ggg aca gac ttc act ctc acc atc agc agc cta gag cct    240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acg aac tgg ccg tgg    288
Glu Asp Phe Ala Val Tyr Tyr Cys Gln Gln Arg Thr Asn Trp Pro Trp
                 85                  90                  95 acg ttc ggc caa ggg acc aag gtg gaa atc aaa cga act gtg gct gca    336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc    672
Phe Asn Arg Gly Glu Ser Tyr Pro Tyr Asp Val Pro Asp Tyr Ala Ser
210                 215                 220
```

<210> SEQ ID NO 132
<211> LENGTH: 224
<212> TYPE: PRT
<213> ORGANISM: Homo sapiens
<220> FEATURE:
<223> OTHER INFORMATION: 1C.D7 Kappa Chain

<400> SEQUENCE: 132

```
Glu Leu Val Met Thr Gln Ser Pro Ala Thr Leu Ser Leu Ser Pro Gly
  1               5                  10                  15

Glu Arg Ala Thr Leu Ser Cys Arg Ala Ser Gln Ser Ile Tyr Asn Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Ser Tyr Pro Tyr Asp Val Pro Asp Tyr Ala Ser
        210                 215                 220

<210> SEQ ID NO 133
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 1C.E8 Kappa Chain

<400> SEQUENCE: 133
```

| | | | | | | | | | | | | | | | | |
|---|---|---|---|---|---|---|---|---|---|---|---|---|---|---|---|---|
| gag | ctc | gtg | atg | acc | cag | act | cca | ctc | tcc | ctg | tct | ttg | tct | cca | ggg | 48 |
| Glu | Leu | Val | Met | Thr | Gln | Thr | Pro | Leu | Ser | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | aat | gtt | tac | agc | tac | 96 |
| Glu | Arg | Ala | Thr | Leu | Ser | Cys | Arg | Ala | Ser | Gln | Asn | Val | Tyr | Ser | Tyr | |
| | | | 20 | | | | | 25 | | | | | 30 | | | |
| tta | gcc | tgg | tac | caa | cag | aaa | cct | ggc | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
| | | 35 | | | | | 40 | | | | | 45 | | | | |
| tat | gat | gca | tcc | aac | agg | gcc | cct | ggc | atc | cca | gcc | agg | ttc | agt | ggc | 192 |
| Tyr | Asp | Ala | Ser | Asn | Arg | Ala | Pro | Gly | Ile | Pro | Ala | Arg | Phe | Ser | Gly | |
| | 50 | | | | | 55 | | | | | 60 | | | | | |
| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65 | | | | | 70 | | | | | 75 | | | | | 80 | |
| gaa | gat | ttt | gca | gtt | tat | tac | tgt | cag | cag | cgt | acg | aac | tgg | ccg | tgg | 288 |
| Glu | Asp | Phe | Ala | Val | Tyr | Tyr | Cys | Gln | Gln | Arg | Thr | Asn | Trp | Pro | Trp | |
| | | | | 85 | | | | | 90 | | | | | 95 | | |
| acg | ttc | ggc | caa | ggg | acc | aag | gtg | gaa | atc | aaa | cga | act | gtg | gct | gca | 336 |
| Thr | Phe | Gly | Gln | Gly | Thr | Lys | Val | Glu | Ile | Lys | Arg | Thr | Val | Ala | Ala | |
| | | | 100 | | | | | 105 | | | | | 110 | | | |
| cca | tct | gtc | ttc | atc | ttc | ccg | cca | tct | gat | gag | cag | ttg | aaa | tct | gga | 384 |
| Pro | Ser | Val | Phe | Ile | Phe | Pro | Pro | Ser | Asp | Glu | Gln | Leu | Lys | Ser | Gly | |
| | | | 115 | | | | | 120 | | | | | 125 | | | |
| act | gcc | tct | gtt | gtg | tgc | ctg | ctg | aat | aac | ttc | tat | ccc | aga | gag | gcc | 432 |
| Thr | Ala | Ser | Val | Val | Cys | Leu | Leu | Asn | Asn | Phe | Tyr | Pro | Arg | Glu | Ala | |
| | | 130 | | | | | 135 | | | | | 140 | | | | |
| aaa | gta | cag | tgg | aag | gtg | gat | aac | gcc | ctc | caa | tcg | ggt | aac | tcc | cag | 480 |
| Lys | Val | Gln | Trp | Lys | Val | Asp | Asn | Ala | Leu | Gln | Ser | Gly | Asn | Ser | Gln | |
| 145 | | | | | 150 | | | | | 155 | | | | | 160 | |
| gag | agt | gtc | aca | gag | cag | gac | agc | aag | gac | agc | acc | tac | agc | ctc | agc | 528 |
| Glu | Ser | Val | Thr | Glu | Gln | Asp | Ser | Lys | Asp | Ser | Thr | Tyr | Ser | Leu | Ser | |
| | | | | 165 | | | | | 170 | | | | | 175 | | |
| agc | acc | ctg | acg | ctg | agc | aaa | gca | gac | tac | gag | aaa | cac | aaa | gtc | tac | 576 |
| Ser | Thr | Leu | Thr | Leu | Ser | Lys | Ala | Asp | Tyr | Glu | Lys | His | Lys | Val | Tyr | |
| | | | 180 | | | | | 185 | | | | | 190 | | | |
| gcc | tgc | gaa | gtc | acc | cat | cag | ggc | ctg | agc | tcg | ccc | gtc | aca | aag | agc | 624 |
| Ala | Cys | Glu | Val | Thr | His | Gln | Gly | Leu | Ser | Ser | Pro | Val | Thr | Lys | Ser | |
| | | | | 195 | | | | | 200 | | | | | 205 | | |

```
ttc aac agg gga gag tct tat cca tat gat gtg cca gat tat gcg agc    672
Phe Asn Arg Gly Glu Ser Tyr Pro Tyr Asp Val Pro Asp Tyr Ala Ser
    210                 215                 220
```

<210> SEQ ID NO 134
<211> LENGTH: 224
<212> TYPE: PRT
<213> ORGANISM: Homo sapiens
<220> FEATURE:
<223> OTHER INFORMATION: 1C.E8 Kappa Chain

<400> SEQUENCE: 134

```
Glu Leu Val Met Thr Gln Thr Pro Leu Ser Leu Ser Leu Ser Pro Gly
1               5                   10                  15

Glu Arg Ala Thr Leu Ser Cys Arg Ala Ser Gln Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 135
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 3E.1 Kappa Chain

<400> SEQUENCE: 135

```
gaa ata gtg atg acg cag tct cca ggc acc ctg tct ttg tct cca ggg     48
Glu Ile Val Met Thr Gln Ser Pro Gly Thr Leu Ser Leu Ser Pro Gly
1               5                   10                  15 gaa aga gcc acc ctc tcc tgc agg gcc agt cag agt gtt agc agc cgc     96
Glu Arg Ala Thr Leu Ser Cys Arg Ala Ser Gln Ser Val Ser Ser Arg
            20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
```

```
                   35                  40                  45
atc tat ggt gca tcc agc agg gcc act ggc atc cca gac agg ttc agt       192
Ile Tyr Gly Ala Ser Ser Arg Ala Thr Gly Ile Pro Asp Arg Phe Ser
     50                  55                  60 ggc agt ggg tct ggg aca gac ttc act ctc gcc atc agc aga ctg gag       240
Gly Ser Gly Ser Gly Thr Asp Phe Thr Leu Ala Ile Ser Arg Leu Glu
 65                  70                  75                  80 cct gaa gat ttt gca gtg tat ttc tgt cag cag tat ggt agc tca atc       288
Pro Glu Asp Phe Ala Val Tyr Phe Cys Gln Gln Tyr Gly Ser Ser Ile
                 85                  90                  95 acc ttc ggc caa ggg aca cga ctg gag att aaa cga act gtg gct gca       336
Thr Phe Gly Gln Gly Thr Arg Leu Glu Ile Lys Arg Thr Val Ala Ala
            100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc       624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc       672
Phe Asn Arg Gly Glu Ser Tyr Pro Tyr Asp Val Pro Asp Tyr Ala Ser
    210                 215                 220
```

<210> SEQ ID NO 136
<211> LENGTH: 224
<212> TYPE: PRT
<213> ORGANISM: Homo sapiens
<220> FEATURE:
<223> OTHER INFORMATION: 3E.1 Kappa Chain

<400> SEQUENCE: 136

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ala Ile Ser Arg Leu Glu
 65                  70                  75                  80

Pro Glu Asp Phe Ala Val Tyr Phe Cys Gln Gln Tyr Gly Ser Ser Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Ser Tyr Pro Tyr Asp Val Pro Asp Tyr Ala Ser
210                 215                 220

<210> SEQ ID NO 137
<211> LENGTH: 684
<212> TYPE: DNA
<213> ORGANISM: Homo sapiens
<220> FEATURE:
<221> NAME/KEY: CDS
<222> LOCATION: (13)..(684)
<220> FEATURE:
<223> OTHER INFORMATION: 3E.2 Kappa Chain

<400> SEQUENCE: 137
ccagccatgg cc aac atc cag atg acc cag tct cca tcc tca ctg tct gca        51
              Asn Ile Gln Met Thr Gln Ser Pro Ser Ser Leu Ser Ala
                1               5                  10 tct gta gga gac aga gtc acc atc act tgt cgg gcg agt cag ggt att         99
Ser Val Gly Asp Arg Val Thr Ile Thr Cys Arg Ala Ser Gln Gly Ile
 15                  20                  25 agc agc tgg tta gcc tgg tat cag cag aaa cca gag aaa gcc cct aag        147
Ser Ser Trp Leu Ala Trp Tyr Gln Gln Lys Pro Glu Lys Ala Pro Lys
 30                  35                  40                  45 tcc ctg atc tat gct gca tcc agt ttg caa agt ggg gtc cca tca agg        195
Ser Leu Ile Tyr Ala Ala Ser Ser Leu Gln Ser Gly Val Pro Ser Arg
                 50                  55                  60 ttc agc ggc agt gga tct ggg aca gat ttc act ctc acc atc agc agc        243
Phe Ser Gly Ser Gly Ser Gly Thr Asp Phe Thr Leu Thr Ile Ser Ser
             65                  70                  75 ctg cag cct gaa gat ttt gca act tat tac tgc caa cag tat aat agt        291
Leu Gln Pro Glu Asp Phe Ala Thr Tyr Tyr Cys Gln Gln Tyr Asn Ser
         80                  85                  90 tac cca ttc act ttc ggc cct ggg acc aaa gtg gat atc aaa cga act        339
Tyr Pro Phe Thr Phe Gly Pro Gly Thr Lys Val Asp Ile Lys Arg Thr
     95                 100                 105 gtg gct gca cca tct gtc ttc atc ttc ccg cca tct gat gag cag ttg        387
Val Ala Ala Pro Ser Val Phe Ile Phe Pro Pro Ser Asp Glu Gln Leu
110                 115                 120                 125 aaa tct gga act gcc tct gtt gtg tgc ctg ctg aat aac ttc tat ccc        435
Lys Ser Gly Thr Ala Ser Val Val Cys Leu Leu Asn Asn Phe Tyr Pro
                130                 135                 140 aga gag gcc aaa gta cag tgg aag gtg gat aac gcc ctc caa tcg ggt        483
Arg Glu Ala Lys Val Gln Trp Lys Val Asp Asn Ala Leu Gln Ser Gly
            145                 150                 155 aac tcc cag gag agt gtc aca gag cag gac agc aag gac agc acc tac        531
Asn Ser Gln Glu Ser Val Thr Glu Gln Asp Ser Lys Asp Ser Thr Tyr
        160                 165                 170 agc ctc agc agc acc ctg acg ctg agc aaa gca gac tac gag aaa cac        579
Ser Leu Ser Ser Thr Leu Thr Leu Ser Lys Ala Asp Tyr Glu Lys His
    175                 180                 185
```

```
aaa gtc tac gcc tgc gaa gtc acc cat cag ggc ctg agc tcg ccc gtc       627
Lys Val Tyr Ala Cys Glu Val Thr His Gln Gly Leu Ser Ser Pro Val
190             195                 200                 205 aca aag agc ttc aac agg gga gag tct tat cca tat gat gtg cca gat       675
Thr Lys Ser Phe Asn Arg Gly Glu Ser Tyr Pro Tyr Asp Val Pro Asp
            210                 215                 220 tat gcg agc                                                            684
Tyr Ala Ser <210> SEQ ID NO 138
<211> LENGTH: 224
<212> TYPE: PRT
<213> ORGANISM: Homo sapiens
<220> FEATURE:
<223> OTHER INFORMATION: 3E.2 Kappa Chain

<400> SEQUENCE: 138

Asn Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 139
<211> LENGTH: 672
<212> TYPE: DNA
<213> ORGANISM: Homo sapiens
<220> FEATURE:
<221> NAME/KEY: CDS
<222> LOCATION: (1)..(672)
<220> FEATURE:
<223> OTHER INFORMATION: 3E.3 Kappa Chain

<400> SEQUENCE: 139 gac atc cag atg atc cag tct cca tcc tcc ccg tct gca tct gta gga        48
Asp Ile Gln Met Ile Gln Ser Pro Ser Ser Pro Ser Ala Ser Val Gly
```

```
                1               5                   10                  15
gac aga gtc acc atc act tgc cgg gca agt cag ggc att agc agt gct       96
Asp Arg Val Thr Ile Thr Cys Arg Ala Ser Gln Gly Ile Ser Ser Ala
             20                  25                  30 tta gcc tgg tat cag cag aaa cca ggg aaa gct cct aag ctc ctg atc      144
Leu Ala Trp Tyr Gln Gln Lys Pro Gly Lys Ala Pro Lys Leu Leu Ile
         35                  40                  45 tat gat gcc tcc agt ttg gaa agt ggg gtc cca tca agg ttc agc ggc      192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac ccg ctc      288
Glu Asp Phe Ala Thr Tyr Tyr Cys Gln Gln Tyr Asn Ser Tyr Pro Leu
                 85                  90                  95 act ttc ggc gga ggg acc aag gtg gag atc aaa cga act gtg gct gca      336
Thr Phe Gly Gly Gly Thr Lys Val Glu Ile Lys Arg Thr Val Ala Ala
             100                 105                 110 cca tct gtc ttc atc ttc ccg cca tct gat gag cag ttg aaa tct gga      384
Pro Ser Val Phe Ile Phe Pro Pro Ser Asp Glu Gln Leu Lys Ser Gly
         115                 120                 125 act gcc tct gtt gtg tgc ctg ctg aat aac ttc tat ccc aga gag gcc      432
Thr Ala Ser Val Val Cys Leu Leu Asn Asn Phe Tyr Pro Arg Glu Ala
     130                 135                 140 aaa gta cag tgg aag gtg gat aac gcc ctc caa tcg ggt aac tcc cag      480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc      528
Glu Ser Val Thr Glu Gln Asp Ser Lys Asp Ser Thr Tyr Ser Leu Ser
                 165                 170                 175 agc acc ctg acg ctg agc aaa gca gac tac gag aaa cac aaa gtc tac      576
Ser Thr Leu Thr Leu Ser Lys Ala Asp Tyr Glu Lys His Lys Val Tyr
             180                 185                 190 gcc tgc gaa gtc acc cat cag ggc ctg agc tcg ccc gtc aca aag agc      624
Ala Cys Glu Val Thr His Gln Gly Leu Ser Ser Pro Val Thr Lys Ser
         195                 200                 205 ttc aac agg gga gag tct tat cca tat gat gtg cca gat tat gcg agc      672
Phe Asn Arg Gly Glu Ser Tyr Pro Tyr Asp Val Pro Asp Tyr Ala Ser
     210                 215                 220
```

<210> SEQ ID NO 140
<211> LENGTH: 224
<212> TYPE: PRT
<213> ORGANISM: Homo sapiens
<220> FEATURE:
<223> OTHER INFORMATION: 3E.3 Kappa Chain

<400> SEQUENCE: 140

```
Asp Ile Gln Met Ile Gln Ser Pro Ser Pro Ser Ala Ser Val Gly
 1               5                   10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80
```

-continued

```
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Ser Tyr Pro Tyr Asp Val Pro Asp Tyr Ala Ser
    210                 215                 220
```

<210> SEQ ID NO 141
<211> LENGTH: 669
<212> TYPE: DNA
<213> ORGANISM: Homo sapiens
<220> FEATURE:
<223> OTHER INFORMATION: 3e.4 Kappa Chain

<400> SEQUENCE: 141

```
gaaatagtga tgacgcagcc aggcaccctg tctttgtctc caggggaaag agccaccctc    60
tcctgcaggg ccagtcagag tgttagcagc cgctacttag cctggtacca gcagaaacct   120
ggccaggctc ccaggctcct catctatggt gcatccagca gggccactgg catcccagac   180
aggttcagtg gcagtgggtc tgggacagac ttcactctcg ccatcagcag actggagcct   240
gaggattttg cagtgtattt ctgtcagcag tatggtagct caatcacctt cggccaaggg   300
acacgactgg agattaaacg aactgtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtctt atccatatga tgtgccagat   660
tatgcgagc                                                           669
```

<210> SEQ ID NO 142
<211> LENGTH: 224
<212> TYPE: PRT
<213> ORGANISM: Homo sapiens
<220> FEATURE:
<223> OTHER INFORMATION: 3E4 Kappa Chain

<400> SEQUENCE: 142

```
Glu Ile Val Met Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Arg
             20                  25                  30
Tyr Leu Ala Trp Tyr Gln Gln Lys Pro Gly Gln Ala Pro Arg Leu Leu
         35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Phe Cys Gln Gln Tyr Gly Ser Ser Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 143
<211> LENGTH: 684
<212> TYPE: DNA
<213> ORGANISM: Homo sapiens
<220> FEATURE:
<221> NAME/KEY: CDS
<222> LOCATION: (13)..(684)
<220> FEATURE:
<223> OTHER INFORMATION: 3E.8 Kappa Chain

<400> SEQUENCE: 143
ccagccatgg cc gcc atc cag ttg acc cag tct cca tcc tcc ctg tct gca        51
               Ala Ile Gln Leu Thr Gln Ser Pro Ser Ser Leu Ser Ala
                1               5                   10 tct gta gga gac aga gtc acc atc act tgc cgg gca agt cag ggc att         99
Ser Val Gly Asp Arg Val Thr Ile Thr Cys Arg Ala Ser Gln Gly Ile
        15                  20                  25 agc agt gct tta gcc tgg tat cag cag aaa cca gag aaa gct cct aag        147
Ser Ser Ala Leu Ala Trp Tyr Gln Gln Lys Pro Glu Lys Ala Pro Lys
30                  35                  40                  45 ctc ctg atc tat gat gcc tcc agt ttg gaa agt ggg gtc cca tca agg        195
Leu Leu Ile Tyr Asp Ala Ser Ser Leu Glu Ser Gly Val Pro Ser Arg
                50                  55                  60 ttc agc ggc agt gga tct ggg aca gat ttc act ctc acc atc agc agc        243
Phe Ser Gly Ser Gly Ser Gly Thr Asp Phe Thr Leu Thr Ile Ser Ser
            65                  70                  75 ctg cag cct gaa gat ttt gca act tat tac tgc caa cag tat aat agt        291
Leu Gln Pro Glu Asp Phe Ala Thr Tyr Tyr Cys Gln Gln Tyr Asn Ser
        80                  85                  90 tac ccg tgg acg ttc ggc caa ggg acc aag gtg gaa atc aaa cga act        339
Tyr Pro Trp Thr Phe Gly Gln Gly Thr Lys Val Glu Ile Lys Arg Thr
    95                  100                 105 gtg gct gca cca tct gtc ttc atc ttc ccg cca tct gat gag cag ttg        387
Val Ala Ala Pro Ser Val Phe Ile Phe Pro Pro Ser Asp Glu Gln Leu
110                 115                 120                 125
```

```
                                                           -continued aaa tct gga act gcc tct gtt gtg tgc ctg ctg aat aac ttc tat ccc      435
Lys Ser Gly Thr Ala Ser Val Val Cys Leu Leu Asn Asn Phe Tyr Pro
            130                 135                 140 aga gag gcc aaa gta cag tgg aag gtg gat aac gcc ctc caa tcg ggt      483
Arg Glu Ala Lys Val Gln Trp Lys Val Asp Asn Ala Leu Gln Ser Gly
        145                 150                 155 aac tcc cag gag agt gtc aca gag cag gac agc aag gac agc acc tac      531
Asn Ser Gln Glu Ser Val Thr Glu Gln Asp Ser Lys Asp Ser Thr Tyr
    160                 165                 170 agc ctc agc agc acc ctg acg ctg agc aaa gca gac tac gag aaa cac      579
Ser Leu Ser Ser Thr Leu Thr Leu Ser Lys Ala Asp Tyr Glu Lys His
175                 180                 185 aaa gtc tac gcc tgc gaa gtc acc cat cag ggc ctg agc tcg ccc gtc      627
Lys Val Tyr Ala Cys Glu Val Thr His Gln Gly Leu Ser Ser Pro Val
190                 195                 200                 205 aca aag agc ttc aac agg gga gag tct tat cca tat gat gtg cca gat      675
Thr Lys Ser Phe Asn Arg Gly Glu Ser Tyr Pro Tyr Asp Val Pro Asp
                210                 215                 220 tat gcg agc                                                          684
Tyr Ala Ser <210> SEQ ID NO 144
<211> LENGTH: 224
<212> TYPE: PRT
<213> ORGANISM: Homo sapiens
<220> FEATURE:
<223> OTHER INFORMATION: 3E.8 Kappa Chain

<400> SEQUENCE: 144

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Glu Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

```
<210> SEQ ID NO 145
<211> LENGTH: 684
<212> TYPE: DNA
<213> ORGANISM: Homo sapiens
<220> FEATURE:
<221> NAME/KEY: CDS
<222> LOCATION: (13)..(684)
<220> FEATURE:
<223> OTHER INFORMATION: 3E.9 Kappa Chain

<400> SEQUENCE: 145
ccagccatgg cc gag ctc gtg atg acc cag tct cca tcc tca ctg tct gca        51
              Glu Leu Val Met Thr Gln Ser Pro Ser Ser Leu Ser Ala
              1               5                  10 tct gta gga gac aga gtc acc atc act tgt cgg gcg agt cag ggt att          99
Ser Val Gly Asp Arg Val Thr Ile Thr Cys Arg Ala Ser Gln Gly Ile
 15                  20                  25 agc agc tgg tta gcc tgg tat cag cag aaa cca gag aaa gcc cct aag          147
Ser Ser Trp Leu Ala Trp Tyr Gln Gln Lys Pro Glu Lys Ala Pro Lys
         30                  35                  40                  45 tcc ctg atc tat gct gca tcc agt ttg caa agt ggg gtc cca tca agg          195
Ser Leu Ile Tyr Ala Ala Ser Ser Leu Gln Ser Gly Val Pro Ser Arg
                 50                  55                  60 ttc agc ggc agt gga tct ggg aca gat ttc act ctc acc atc agc agc          243
Phe Ser Gly Ser Gly Ser Gly Thr Asp Phe Thr Leu Thr Ile Ser Ser
             65                  70                  75 ctg cag cct gaa gat ttt gca act tat tac tgc caa cag tat aat agt          291
Leu Gln Pro Glu Asp Phe Ala Thr Tyr Tyr Cys Gln Gln Tyr Asn Ser
         80                  85                  90 tac ccg atc acc ttc ggc caa ggg aca cga ctg gag att aaa cga act          339
Tyr Pro Ile Thr Phe Gly Gln Gly Thr Arg Leu Glu Ile Lys Arg Thr
     95                  100                 105 gtg gct gca cca tct gtc ttc atc ttc ccg cca tct gat gag cag ttg          387
Val Ala Ala Pro Ser Val Phe Ile Phe Pro Pro Ser Asp Glu Gln Leu
110                 115                 120                 125 aaa tct gga act gcc tct gtt gtg tgc ctg ctg gat aac ttc tat ccc          435
Lys Ser Gly Thr Ala Ser Val Val Cys Leu Leu Asp Asn Phe Tyr Pro
                 130                 135                 140 aga gag gcc aaa gta cag tgg aag gtg gat aac gcc ctc caa tcg ggt          483
Arg Glu Ala Lys Val Gln Trp Lys Val Asp Asn Ala Leu Gln Ser Gly
             145                 150                 155 aac tcc cag gag agt gtc aca gag cag gac agc aag gac agc acc tac          531
Asn Ser Gln Glu Ser Val Thr Glu Gln Asp Ser Lys Asp Ser Thr Tyr
         160                 165                 170 agc ctc agc agc acc ctg acg ctg agc aaa gca gac tac gag aaa cac          579
Ser Leu Ser Ser Thr Leu Thr Leu Ser Lys Ala Asp Tyr Glu Lys His
     175                 180                 185 aaa gtc tac gcc tgc gaa gtc acc cat cag ggc ctg agc tcg ccc gtc          627
Lys Val Tyr Ala Cys Glu Val Thr His Gln Gly Leu Ser Ser Pro Val
190                 195                 200                 205 aca aag agc ttc aac agg gga gag tct tat cca tat gat gtg cca gat          675
Thr Lys Ser Phe Asn Arg Gly Glu Ser Tyr Pro Tyr Asp Val Pro Asp
                 210                 215                 220 tat gcg agc                                                              684
Tyr Ala Ser <210> SEQ ID NO 146
<211> LENGTH: 224
<212> TYPE: PRT
<213> ORGANISM: Homo sapiens
<220> FEATURE:
<223> OTHER INFORMATION: 3E.9 Kappa Chain
```

<400> SEQUENCE: 146

| | | | | | | | | | | | | | | | |
|---|---|---|---|---|---|---|---|---|---|---|---|---|---|---|---|
|Glu|Leu|Val|Met|Thr|Gln|Ser|Pro|Ser|Ser|Leu|Ser|Ala|Ser|Val|Gly|
|1| | | |5| | | | |10| | | | |15| |

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 147
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.B1 Heavy Chain

<400> SEQUENCE: 147

```
cag gtg cag ctg gtg gag tct ggg gga ggc gtg gtc cag cct ggg agg     48
Gln Val Gln Leu Val Glu Ser Gly Gly Gly Val Val Gln Pro Gly Arg
1               5                   10                  15 tcc ctg aga ctc tcc tgt gca gcc tct gga ttc acc ctc aga agc tat     96
Ser Leu Arg Leu Ser Cys Ala Ala Ser Gly Phe Thr Leu Arg Ser Tyr
            20                  25                  30 gct atg cac tgg gtc cgc cag gct cca ggc aag ggg ctg gag tgg gtg    144
Ala Met His Trp Val Arg Gln Ala Pro Gly Lys Gly Leu Glu Trp Val
        35                  40                  45 gca gtt ata tca tat gat gga agc tat aag tcc tac gca gac tcc gtg    192
Ala Val Ile Ser Tyr Asp Gly Ser Tyr Lys Ser Tyr Ala Asp Ser Val
    50                  55                  60 aag ggc cga ttc atc agc tcc aga gac aat tcc aag aac acg ctg tct    240
Lys Gly Arg Phe Ile Ser Ser Arg Asp Asn Ser Lys Asn Thr Leu Ser
65                  70                  75                  80 ctg caa atg aac agc ctg aga gct gag gac acg gct gtg tat ttc tgt    288
Leu Gln Met Asn Ser Leu Arg Ala Glu Asp Thr Ala Val Tyr Phe Cys
```

```
Leu Gln Met Asn Ser Leu Arg Ala Glu Asp Thr Ala Val Tyr Phe Cys
                85                  90                  95 gcg agg gct atg gtt cgg gga gtt atc ttt gac tac tgg ggc cag gga    336
Ala Arg Ala Met Val Arg Gly Val Ile Phe Asp Tyr Trp Gly Gln Gly
               100                 105                 110 acc ctt gtc acc gtc tcc tca gcc tcc acc aag ggc cca tcg gtc ttc    384
Thr Leu Val Thr Val Ser Ser Ala Ser Thr Lys Gly Pro Ser Val Phe
            115                 120                 125 ccc ctg gca ccc tcc tcc aag agc acc tct ggg ggc aca gcg gcc ctg    432
Pro Leu Ala Pro Ser Ser Lys Ser Thr Ser Gly Gly Thr Ala Ala Leu
130                 135                 140 ggc tgc ctg gtc aag gac tac ttc ccc gaa ccg gtg acg gtg tcg tgg    480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta    528
Asn Ser Gly Ala Leu Thr Ser Gly Val His Thr Phe Pro Ala Val Leu
                165                 170                 175 cag tcc tca gga ctc tac tcc ctc agc agc gtg gtg acc gtg ccc tcc    576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc    624
Ser Ser Leu Gly Thr Gln Thr Tyr Ile Cys Asn Val Asn His Lys Pro
        195                 200                 205 agc aac acc aag gtg gac aag aaa gca gag ccc aaa tct cat cac cat    672
Ser Asn Thr Lys Val Asp Lys Lys Ala Glu Pro Lys Ser His His His
210                 215                 220 cac cat cac                                                        681
His His His
225
```

<210> SEQ ID NO 148
<211> LENGTH: 227
<212> TYPE: PRT
<213> ORGANISM: Homo sapiens
<220> FEATURE:
<223> OTHER INFORMATION: 1C.B1 Heavy Chain

<400> SEQUENCE: 148

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Leu Arg Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Ser Tyr Ala Asp Ser Val
    50                  55                  60

Lys Gly Arg Phe Ile Ser Ser Arg Asp Asn Ser Lys Asn Thr Leu Ser
65                  70                  75                  80

Leu Gln Met Asn Ser Leu Arg Ala Glu Asp Thr Ala Val Tyr Phe Cys
                85                  90                  95

Ala Arg Ala Met Val Arg Gly Val Ile Phe Asp Tyr Trp Gly Gln Gly
               100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
            195                 200                 205

Ser Asn Thr Lys Val Asp Lys Lys Ala Glu Pro Lys Ser His His His
    210                 215                 220

His His His
225

<210> SEQ ID NO 149
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.C2 Heavy Chain

<400> SEQUENCE: 149 gag gtg cag ctg gtg cag tct ggg gga ggc gtg gtc cag cct ggg agg      48
Glu Val Gln Leu Val Gln Ser Gly Gly Gly Val Val Gln Pro Gly Arg
1               5                   10                  15 tcc ctg aga ctc tcc tgt gca gcc tct gaa ttc acc ttc agt aac tat      96
Ser Leu Arg Leu Ser Cys Ala Ala Ser Glu Phe Thr Phe Ser Asn Tyr
            20                  25                  30 gct ttt cac tgg gtc cgc cag gct cca ggc aag ggg ctg gag tgg gtg     144
Ala Phe His Trp Val Arg Gln Ala Pro Gly Lys Gly Leu Glu Trp Val
        35                  40                  45 gca att ata tca tat gat gga agc cat aaa tac tac gca gac tcc gtg     192
Ala Ile Ile Ser Tyr Asp Gly Ser His Lys Tyr Tyr Ala Asp Ser Val
    50                  55                  60 acg ggc cga ttc acc atc tcc aga gac aat tcc aag aac acg ctg tat     240
Thr Gly Arg Phe Thr Ile Ser Arg Asp Asn Ser Lys Asn Thr Leu Tyr
65                  70                  75                  80 ctg caa atg aac agc ctg aga gct gag gac acg gct gtg tac tac tgt     288
Leu Gln Met Asn Ser Leu Arg Ala Glu Asp Thr Ala Val Tyr Tyr Cys
            85                  90                  95 gcg agg gcg atg gtt cgg gga gtt atc ttt gac tac tgg ggc cag gga     336
Ala Arg Ala Met Val Arg Gly Val Ile Phe Asp Tyr Trp Gly Gln Gly
        100                 105                 110 acc ctg gtc acc gtc tcc tca gcc tcc acc aag ggc cca tcg gtc ttc     384
Thr Leu Val Thr Val Ser Ser Ala Ser Thr Lys Gly Pro Ser Val Phe
    115                 120                 125 ccc ctg gca ccc tcc tcc aag agc acc tct ggg ggc aca gcg gcc ctg     432
Pro Leu Ala Pro Ser Ser Lys Ser Thr Ser Gly Gly Thr Ala Ala Leu
130                 135                 140 ggc tgc ctg gtc aag gac tac ttc ccc gaa ccg gtg acg gtg tcg tgg     480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta     528
Asn Ser Gly Ala Leu Thr Ser Gly Val His Thr Phe Pro Ala Val Leu
            165                 170                 175 cag tcc tca gga ctc tac tcc ctc agc agc gtg gtg acc gtg ccc tcc     576
Gln Ser Ser Gly Leu Tyr Ser Leu Ser Ser Val Val Thr Val Pro Ser
        180                 185                 190 agc agc ttg ggc acc cag acc tac atc tgc aac gtg aat cac aag ccc     624
Ser Ser Leu Gly Thr Gln Thr Tyr Ile Cys Asn Val Asn His Lys Pro
    195                 200                 205
```

```
agc aac acc aag gtg gac aag aaa gca gag ccc aaa tct cat cac cat      672
Ser Asn Thr Lys Val Asp Lys Lys Ala Glu Pro Lys Ser His His His
    210                 215                 220 cac cat cac                                                          681
His His His
225
```

<210> SEQ ID NO 150
<211> LENGTH: 227
<212> TYPE: PRT
<213> ORGANISM: Homo sapiens
<220> FEATURE:
<223> OTHER INFORMATION: 1C.C2 Heavy Chain

<400> SEQUENCE: 150

```
Glu Val Gln Leu Val Gln Ser Gly Gly Gly Val Val Gln Pro Gly Arg
 1               5                  10                  15

Ser Leu Arg Leu Ser Cys Ala Ala Ser Glu Phe Thr Phe Ser Asn Tyr
             20                  25                  30

Ala Phe His Trp Val Arg Gln Ala Pro Gly Lys Gly Leu Glu Trp Val
         35                  40                  45

Ala Ile Ile Ser Tyr Asp Gly Ser His Lys Tyr Tyr Ala Asp Ser Val
     50                  55                  60

Thr Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Met Val Arg Gly Val Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser His His His
    210                 215                 220

His His His
225
```

<210> SEQ ID NO 151
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.C6 Heavy Chain

<400> SEQUENCE: 151

```
gag gtg cag ctg gtg cag tct ggg gga ggc ttg gta cag cct ggg ggg       48
Glu Val Gln Leu Val Gln Ser Gly Gly Gly Leu Val Gln Pro Gly Gly
```

```
                1               5              10              15
            tcc ctg aga ctc tcc tgt gca gcc tct gga ttc acc ttt agc aac tat      96
            Ser Leu Arg Leu Ser Cys Ala Ala Ser Gly Phe Thr Phe Ser Asn Tyr
                         20                  25                  30 gcc atg agc tgg gtc cgc cag gct cca ggg aag ggg ctg gag tgg gtc     144
            Ala Met Ser Trp Val Arg Gln Ala Pro Gly Lys Gly Leu Glu Trp Val
                         35                  40                  45 tca gct att aat tat ggt ggt ggt agc aca tac tac gca gac tcc gtg     192
            Ser Ala Ile Asn Tyr Gly Gly Gly Ser Thr Tyr Tyr Ala Asp Ser Val
                 50                  55                  60 aag ggc cgg ttc acc atc tcc aga gac aat tcc aag aac acg ctg tat     240
            Lys Gly Arg Phe Thr Ile Ser Arg Asp Asn Ser Lys Asn Thr Leu Tyr
             65                  70                  75                  80 ctg caa atg aac agc ctg aga gcc gag gac acg gcc gta tat tac tgt     288
            Leu Gln Met Asn Ser Leu Arg Ala Glu Asp Thr Ala Val Tyr Tyr Cys
                             85                  90                  95 gcg aaa cat atg gtt cgg gga gtc ctc ttt gac tac tgg ggc cag gga     336
            Ala Lys His Met Val Arg Gly Val Leu Phe Asp Tyr Trp Gly Gln Gly
                            100                 105                 110 acc ctg gtc acc gtc tcc tca gcc tcc acc aag ggc cca tcg gtc ttc     384
            Thr Leu Val Thr Val Ser Ser Ala Ser Thr Lys Gly Pro Ser Val Phe
                        115                 120                 125 ccc ctg gca ccc tcc tcc aag agc acc tct ggg ggc aca gcg gcc ctg     432
            Pro Leu Ala Pro Ser Ser Lys Ser Thr Ser Gly Gly Thr Ala Ala Leu
                    130                 135                 140 ggc tgc ctg gtc aag gac tac ttc ccc gaa ccg gtg acg gtg tcg tgg     480
            Gly Cys Leu Val Lys Asp Tyr Phe Pro Glu Pro Val Thr Val Ser Trp
            145                 150                 155                 160 aac tca ggc gcc ctg acc agc ggc gtg cac acc ttc ccg gct gtc cta     528
            Asn Ser Gly Ala Leu Thr Ser Gly Val His Thr Phe Pro Ala Val Leu
                            165                 170                 175 cag tcc tca gga ctc tac tcc ctc agc agc gtg gtg acc gtg ccc tcc     576
            Gln Ser Ser Gly Leu Tyr Ser Leu Ser Ser Val Val Thr Val Pro Ser
                        180                 185                 190 agc agc ttg ggc acc cag acc tac atc tgc aac gtg aat cac aag ccc     624
            Ser Ser Leu Gly Thr Gln Thr Tyr Ile Cys Asn Val Asn His Lys Pro
                    195                 200                 205 agc aac acc aag gtg gac aag aaa gca gag ccc aaa tct cat cac cat     672
            Ser Asn Thr Lys Val Asp Lys Lys Ala Glu Pro Lys Ser His His His
            210                 215                 220 cac cat cac                                                         681
            His His His
            225
```

<210> SEQ ID NO 152
<211> LENGTH: 227
<212> TYPE: PRT
<213> ORGANISM: Homo sapiens
<220> FEATURE:
<223> OTHER INFORMATION: 1C.C6 Heavy Chain

<400> SEQUENCE: 152

```
Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ser Ala Ile Asn Tyr Gly Gly Gly Ser Thr Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Met Val Arg Gly Val Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser His His His
    210                 215                 220

His His His
225

<210> SEQ ID NO 153
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.C8 Heavy Chain

<400> SEQUENCE: 153 cag gtg cag ctg gtg cag tct ggg gga ggc gtg gtc cag cct ggg agg      48
Gln Val Gln Leu Val Gln Ser Gly Gly Gly Val Val Gln Pro Gly Arg
  1               5                  10                  15 tcc ctg aga ctc tcc tgt gca gcc tct gga ttc acc ttc agt aac tat      96
Ser Leu Arg Leu Ser Cys Ala Ala Ser Gly Phe Thr Phe Ser Asn Tyr
                 20                  25                  30 gct ttt cac tgg gtc cgc cag gct cca ggc aag ggg ctg gag tgg gtg     144
Ala Phe His Trp Val Arg Gln Ala Pro Gly Lys Gly Leu Glu Trp Val
            35                  40                  45 gca att ata tca tat gat gga agc cat aaa tac tac gca gac tcc gtg     192
Ala Ile Ile Ser Tyr Asp Gly Ser His Lys Tyr Tyr Ala Asp Ser Val
        50                  55                  60 acg ggc cga ttc acc atc tcc aga gac aat tcc aag aac acg ctg tat     240
Thr Gly Arg Phe Thr Ile Ser Arg Asp Asn Ser Lys Asn Thr Leu Tyr
 65                  70                  75                  80 ctg caa atg aac agc ctg aga gct gag gac acg gct gtg tac tac tgt     288
Leu Gln Met Asn Ser Leu Arg Ala Glu Asp Thr Ala Val Tyr Tyr Cys
                 85                  90                  95 gcg agg gcg atg gtt cgg gga gtt atc ttt gac tac tgg ggc cag gga     336
Ala Arg Ala Met Val Arg Gly Val Ile Phe Asp Tyr Trp Gly Gln Gly
            100                 105                 110 acc ctg gtc acc gtc tcc tca gcc tcc acc aag ggc cca tcg gtc ttc     384
Thr Leu Val Thr Val Ser Ser Ala Ser Thr Lys Gly Pro Ser Val Phe
        115                 120                 125
```

```
ccc ctg gca ccc tcc tcc aag agc acc tct ggg ggc ata gcg gcc ctg         432
Pro Leu Ala Pro Ser Ser Lys Ser Thr Ser Gly Gly Ile Ala Ala Leu
            130                 135                 140 ggc tgc ctg gtc aag gac tac ttc ccc gaa ccg gtg acg gtg tcg tgg         480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta         528
Asn Ser Gly Ala Leu Thr Ser Gly Val His Thr Phe Pro Ala Val Leu
                165                 170                 175 cag tcc tca gga ctc tac tcc ctc agc agc gtg gtg acc gtg ccc tcc         576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc         624
Ser Ser Leu Gly Thr Gln Thr Tyr Ile Cys Asn Val Asn His Lys Pro
        195                 200                 205 agc aac acc aag gtg gac aag aaa gca gag ccc aaa tct cat cac cat         672
Ser Asn Thr Lys Val Asp Lys Lys Ala Glu Pro Lys Ser His His His
    210                 215                 220 cac cat cac                                                             681
His His His
225
```

<210> SEQ ID NO 154
<211> LENGTH: 227
<212> TYPE: PRT
<213> ORGANISM: Homo sapiens
<220> FEATURE:
<223> OTHER INFORMATION: 1C.C8 Heavy Chain

<400> SEQUENCE: 154

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Phe His Trp Val Arg Gln Ala Pro Gly Lys Gly Leu Glu Trp Val
        35                  40                  45

Ala Ile Ile Ser Tyr Asp Gly Ser His Lys Tyr Tyr Ala Asp Ser Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Met Val Arg Gly Val Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Ile Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser His His His
    210                 215                 220
```

His His His
225

<210> SEQ ID NO 155
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.D7 Heavy Chain

<400> SEQUENCE: 155

| cag | gtg | cag | ctg | gtg | gag | tct | ggg | gga | ggc | gtg | gtc | cag | cct | ggg | agg | 48 |
|---|---|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg | |
| 1 | | | | 5 | | | | | 10 | | | | | 15 | | |

| tcc | ctg | aga | ctg | tcc | tgt | gca | gcc | tct | gga | ttc | acc | ttc | agt | aac | tat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Asn | Tyr | |
| | | | 20 | | | | | 25 | | | | | 30 | | | |

| gct | atg | cac | tgg | gtc | cgc | cag | gct | cca | ggc | aag | ggg | ctg | gag | tgg | gtg | 144 |
|---|---|---|---|---|---|---|---|---|---|---|---|---|---|---|---|---|
| Ala | Met | His | Trp | Val | Arg | Gln | Ala | Pro | Gly | Lys | Gly | Leu | Glu | Trp | Val | |
| | | 35 | | | | | 40 | | | | | 45 | | | | |

| gca | att | atc | tca | tat | gat | gga | acc | tat | aaa | tat | tac | gca | gac | tcc | gtg | 192 |
|---|---|---|---|---|---|---|---|---|---|---|---|---|---|---|---|---|
| Ala | Ile | Ile | Ser | Tyr | Asp | Gly | Thr | Tyr | Lys | Tyr | Tyr | Ala | Asp | Ser | Val | |
| 50 | | | | | 55 | | | | | 60 | | | | | | |

| aag | ggc | cga | ttc | acc | atc | tcc | aga | gac | aat | tcc | aag | aac | acg | ctg | tat | 240 |
|---|---|---|---|---|---|---|---|---|---|---|---|---|---|---|---|---|
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |

| ctg | caa | atg | aac | agc | ctg | aga | gct | gag | gac | acg | gct | gtg | tat | tac | tgt | 288 |
|---|---|---|---|---|---|---|---|---|---|---|---|---|---|---|---|---|
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| gcg | agg | gct | atg | gtt | cgg | gga | gtt | atc | ttt | gac | tac | tgg | ggc | cag | gga | 336 |
|---|---|---|---|---|---|---|---|---|---|---|---|---|---|---|---|---|
| Ala | Arg | Ala | Met | Val | Arg | Gly | Val | Ile | Phe | Asp | Tyr | Trp | Gly | Gln | Gly | |
| | | | 100 | | | | | 105 | | | | | 110 | | | |

| gcc | ctg | gtc | acc | gtc | tcc | tca | gcc | tcc | acc | aag | ggc | cca | tcg | gtc | ttc | 384 |
|---|---|---|---|---|---|---|---|---|---|---|---|---|---|---|---|---|
| Ala | Leu | Val | Thr | Val | Ser | Ser | Ala | Ser | Thr | Lys | Gly | Pro | Ser | Val | Phe | |
| | | 115 | | | | | 120 | | | | | 125 | | | | |

| ccc | ctg | gca | ccc | tcc | tcc | aag | agc | acc | tct | ggg | ggc | aca | gcg | gcc | ctg | 432 |
|---|---|---|---|---|---|---|---|---|---|---|---|---|---|---|---|---|
| Pro | Leu | Ala | Pro | Ser | Ser | Lys | Ser | Thr | Ser | Gly | Gly | Thr | Ala | Ala | Leu | |
| | 130 | | | | | 135 | | | | | 140 | | | | | |

| ggc | tgc | ctg | gtc | aag | gac | tac | ttc | ccc | gaa | ccg | gtg | acg | gtg | tcg | tgg | 480 |
|---|---|---|---|---|---|---|---|---|---|---|---|---|---|---|---|---|
| Gly | Cys | Leu | Val | Lys | Asp | Tyr | Phe | Pro | Glu | Pro | Val | Thr | Val | Ser | Trp | |
| 145 | | | | | 150 | | | | | 155 | | | | | 160 | |

| aac | tca | ggc | gcc | ctg | acc | agc | ggc | gtg | cac | acc | ttc | ccg | gct | gtc | cta | 528 |
|---|---|---|---|---|---|---|---|---|---|---|---|---|---|---|---|---|
| Asn | Ser | Gly | Ala | Leu | Thr | Ser | Gly | Val | His | Thr | Phe | Pro | Ala | Val | Leu | |
| | | | | 165 | | | | | 170 | | | | | 175 | | |

| cag | tcc | tca | gga | ctc | tac | tcc | ctc | agc | agc | gtg | gtg | acc | gtg | ccc | tcc | 576 |
|---|---|---|---|---|---|---|---|---|---|---|---|---|---|---|---|---|
| Gln | Ser | Ser | Gly | Leu | Tyr | Ser | Leu | Ser | Ser | Val | Val | Thr | Val | Pro | Ser | |
| | | | 180 | | | | | 185 | | | | | 190 | | | |

| agc | agc | ttg | ggc | gcc | cag | acc | tac | atc | tgc | aac | gtg | aat | cac | aag | ccc | 624 |
|---|---|---|---|---|---|---|---|---|---|---|---|---|---|---|---|---|
| Ser | Ser | Leu | Gly | Ala | Gln | Thr | Tyr | Ile | Cys | Asn | Val | Asn | His | Lys | Pro | |
| | | 195 | | | | | 200 | | | | | 205 | | | | |

| agc | aac | acc | aag | gtg | gac | aag | aaa | gca | gag | ccc | aaa | tct | cat | cac | cat | 672 |
|---|---|---|---|---|---|---|---|---|---|---|---|---|---|---|---|---|
| Ser | Asn | Thr | Lys | Val | Asp | Lys | Lys | Ala | Glu | Pro | Lys | Ser | His | His | His | |
| | 210 | | | | | 215 | | | | | 220 | | | | | |

| cac | cat | cac | | | | | | | | | | | | | | 681 |
|---|---|---|---|---|---|---|---|---|---|---|---|---|---|---|---|---|
| His | His | His | | | | | | | | | | | | | | |
| 225 | | | | | | | | | | | | | | | | |

<210> SEQ ID NO 156

```
<211> LENGTH: 227
<212> TYPE: PRT
<213> ORGANISM: Homo sapiens
<220> FEATURE:
<223> OTHER INFORMATION: 1C.D7 Heavy Chain

<400> SEQUENCE: 156

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Ala Met His Trp Val Arg Gln Ala Pro Gly Lys Gly Leu Glu Trp Val
         35                  40                  45

Ala Ile Ile Ser Tyr Asp Gly Thr Tyr Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Met Val Arg Gly Val Ile Phe Asp Tyr Trp Gly Gln Gly
            100                 105                 110

Ala Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Ala Gln Thr Tyr Ile Cys Asn Val Asn His Lys Pro
        195                 200                 205

Ser Asn Thr Lys Val Asp Lys Lys Ala Glu Pro Lys Ser His His His
    210                 215                 220

His His His
225

<210> SEQ ID NO 157
<211> LENGTH: 681
<212> TYPE: DNA
<213> ORGANISM: Homo sapiens
<220> FEATURE:
<221> NAME/KEY: CDS
<222> LOCATION: (1)..(681)
<220> FEATURE:
<223> OTHER INFORMATION: 1C.E8 Heavy Chain

<400> SEQUENCE: 157 cag gtg cag ctg gtg cag tct ggg gga ggc gtg gtc cag cct ggg agg      48
Gln Val Gln Leu Val Gln Ser Gly Gly Gly Val Val Gln Pro Gly Arg
 1               5                  10                  15 tcc ctg aga ctc tcc tgt gca gcc tct gga ttc acc ttc agt aac tat      96
Ser Leu Arg Leu Ser Cys Ala Ala Ser Gly Phe Thr Phe Ser Asn Tyr
             20                  25                  30 gct ttt cac tgg gtc cgc cag gct cca ggc aag ggg ctg gag tgg gtg     144
Ala Phe His Trp Val Arg Gln Ala Pro Gly Lys Gly Leu Glu Trp Val
         35                  40                  45 gca att ata tca tat gat gga agc cat aaa tac tac gca gac tcc gtg     192
```

```
Ala Ile Ile Ser Tyr Asp Gly Ser His Lys Tyr Tyr Ala Asp Ser Val
     50                  55                  60 acg ggc cga ttc acc acc tcc aga gac aat tcc aag aac acg ctg tat       240
Thr Gly Arg Phe Thr Thr Ser Arg Asp Asn Ser Lys Asn Thr Leu Tyr
 65                  70                  75                  80 ctg caa atg aac agc ctg aga gct gag gac acg gct gtg tac tac tgt       288
Leu Gln Met Asn Ser Leu Arg Ala Glu Asp Thr Ala Val Tyr Tyr Cys
                 85                  90                  95 gcg agg gcg atg gtt cgg gga gtt atc ttt gac tac tgg ggc cag gga       336
Ala Arg Ala Met Val Arg Gly Val Ile Phe Asp Tyr Trp Gly Gln Gly
                 100                 105                 110 acc ctg gtc acc gtc tcc tca gcc tcc acc aag ggc cca tcg gtc ttc       384
Thr Leu Val Thr Val Ser Ser Ala Ser Thr Lys Gly Pro Ser Val Phe
            115                 120                 125 ccc ctg gca ccc tcc tcc aag agc acc tct ggg ggc aca gcg gcc ctg       432
Pro Leu Ala Pro Ser Ser Lys Ser Thr Ser Gly Gly Thr Ala Ala Leu
        130                 135                 140 ggc tgc ctg gtc aag gac tac ttc ccc gaa ccg gtg acg gtg tcg tgg       480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta       528
Asn Ser Gly Ala Leu Thr Ser Gly Val His Thr Phe Pro Ala Val Leu
                165                 170                 175 cag tcc tca gga ctc tac tcc ctc agc agc gtg gtg acc gtg ccc tcc       576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc       624
Ser Ser Leu Gly Thr Gln Thr Tyr Ile Cys Asn Val Asn His Lys Pro
        195                 200                 205 agc aac acc aag gtg gac aag aaa gca gag ccc aaa tct cat cac cat       672
Ser Asn Thr Lys Val Asp Lys Lys Ala Glu Pro Lys Ser His His His
    210                 215                 220 cac cat cac                                                           681
His His His
225

<210> SEQ ID NO 158
<211> LENGTH: 227
<212> TYPE: PRT
<213> ORGANISM: Homo sapiens
<220> FEATURE:
<223> OTHER INFORMATION: 1C.E8 Heavy Chain

<400> SEQUENCE: 158

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Ala Phe His Trp Val Arg Gln Ala Pro Gly Lys Gly Leu Glu Trp Val
            35                  40                  45

Ala Ile Ile Ser Tyr Asp Gly Ser His Lys Tyr Tyr Ala Asp Ser Val
     50                  55                  60

Thr Gly Arg Phe Thr Thr Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Met Val Arg Gly Val Ile Phe Asp Tyr Trp Gly Gln Gly
                 100                 105                 110

Thr Leu Val Thr Val Ser Ser Ala Ser Thr Lys Gly Pro Ser Val Phe
```

-continued

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser His His His
    210                 215                 220

His His His
225
```

<210> SEQ ID NO 159
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.1 Heavy Chain

<400> SEQUENCE: 159

```
cag gtg cag ctg gtg cag tct ggg gga ggc gtg gtc cag tct ggg agg      48
Gln Val Gln Leu Val Gln Ser Gly Gly Gly Val Val Gln Ser Gly Arg
  1               5                  10                  15 tcc ctg aga ctc tcc tgt gca gcc tct gga atc acc gtc agg aac tat      96
Ser Leu Arg Leu Ser Cys Ala Ala Ser Gly Ile Thr Val Arg Asn Tyr
             20                  25                  30 gct atg cac tgg gtc cgc cag gtt cca ggc aag ggg ctg gag tgg gtg     144
Ala Met His Trp Val Arg Gln Val Pro Gly Lys Gly Leu Glu Trp Val
         35                  40                  45 gca gtt ata tca tat gat gga agc aat aaa tac tac gca gac tcc gtg     192
Ala Val Ile Ser Tyr Asp Gly Ser Asn Lys Tyr Tyr Ala Asp Ser Val
     50                  55                  60 aag ggc cga ttc acc ctc tcc aga gac aat tcc aag aac acg ctg tat     240
Lys Gly Arg Phe Thr Leu Ser Arg Asp Asn Ser Lys Asn Thr Leu Tyr
 65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                 85                  90                  95 gcg aga gag gac tac tac ggt atg gac gtc tgg ggc caa ggg acc acg     336
Ala Arg Glu Asp Tyr Tyr Gly Met Asp Val Trp Gly Gln Gly Thr Thr
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175
```

| | | | | | | | | | | | | |
|---|---|---|---|---|---|---|---|---|---|---|---|---|
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | 180 | | | | | 185 | | | | | 190 | | | | |
| ttg | ggc | acc | cag | acc | tac | atc | tgc | aac | gtg | aat | cac | aag | ccc | agc | aac | 624 |
| Leu | Gly | Thr | Gln | Thr | Tyr | Ile | Cys | Asn | Val | Asn | His | Lys | Pro | Ser | Asn | |
| | | 195 | | | | | 200 | | | | | 205 | | | | |
| acc | aag | gtg | gac | aag | aaa | gca | gag | ccc | aaa | tgt | cat | cac | cat | cac | cat | 672 |
| Thr | Lys | Val | Asp | Lys | Lys | Ala | Glu | Pro | Lys | Cys | His | His | His | His | His | |
| | | 210 | | | | | 215 | | | | | 220 | | | | |

| | |
|---|---|
| cac | 675 |
| His | |
| 225 | |

<210> SEQ ID NO 160
<211> LENGTH: 225
<212> TYPE: PRT
<213> ORGANISM: Homo sapiens
<220> FEATURE:
<223> OTHER INFORMATION: 3E.1 Heavy Chain

<400> SEQUENCE: 160

Gln Val Gln Leu Val Gln Ser Gly Gly Gly Val Val Gln Ser Gly Arg
 1               5                  10                  15

Ser Leu Arg Leu Ser Cys Ala Ala Ser Gly Ile Thr Val Arg Asn Tyr
             20                  25                  30

Ala Met His Trp Val Arg Gln Val Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Leu Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Cys His His His His His
    210                 215                 220

His
225

<210> SEQ ID NO 161
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.2 Heavy Chain

<400> SEQUENCE: 161

| cag gtg cag ctg gtg cag tct ggg gca gag gtg aaa aag ccc ggg gag | 48 |
|---|---|
| Gln Val Gln Leu Val Gln Ser Gly Ala Glu Val Lys Lys Pro Gly Glu | |
| 1               5                   10                  15 | |

| tct ctg aag atc tcc tgt aag ggt tct gga tac agc ttt acc aac tac | 96 |
|---|---|
| Ser Leu Lys Ile Ser Cys Lys Gly Ser Gly Tyr Ser Phe Thr Asn Tyr | |
|         20                  25                  30 | |

| tgg atc ggc tgg gtg cgc cag atg ccc ggg aaa ggc ctg gag tgg atg | 144 |
|---|---|
| Trp Ile Gly Trp Val Arg Gln Met Pro Gly Lys Gly Leu Glu Trp Met | |
|     35                  40                  45 | |

| ggg ttc atc tat tct gat gac tct gtt acc aga tac agc ccg tcc ttc | 192 |
|---|---|
| Gly Phe Ile Tyr Ser Asp Asp Ser Val Thr Arg Tyr Ser Pro Ser Phe | |
| 50                  55                  60 | |

| caa ggc cag gtc acc atc tca gcc gac aag tcc atc agt acc gcc tac | 240 |
|---|---|
| Gln Gly Gln Val Thr Ile Ser Ala Asp Lys Ser Ile Ser Thr Ala Tyr | |
| 65                  70                  75                  80 | |

| ctg cag tgg agc agc ctg aag gcc tcg gac acc gcc atg tat tac tgt | 288 |
|---|---|
| Leu Gln Trp Ser Ser Leu Lys Ala Ser Asp Thr Ala Met Tyr Tyr Cys | |
|             85                  90                  95 | |

| acg aga gat ggt ccc gaa gct ttt gat atc tgg ggc caa ggg aca atg | 336 |
|---|---|
| Thr Arg Asp Gly Pro Glu Ala Phe Asp Ile Trp Gly Gln Gly Thr Met | |
|             100                 105                 110 | |

| gtc acc gtc tct tca gcc tcc acc aag ggc cca tcg gtc ttc ccc ctg | 384 |
|---|---|
| Val Thr Val Ser Ser Ala Ser Thr Lys Gly Pro Ser Val Phe Pro Leu | |
|         115                 120                 125 | |

| gca ccc tcc tcc aag agc acc tct ggg ggc aca gcg gcc ctg ggc tgc | 432 |
|---|---|
| Ala Pro Ser Ser Lys Ser Thr Ser Gly Gly Thr Ala Ala Leu Gly Cys | |
| 130                 135                 140 | |

| ctg gtc aag gac tac ttc ccc gaa ccg gtg acg gtg tcg tgg aac tca | 480 |
|---|---|
| Leu Val Lys Asp Tyr Phe Pro Glu Pro Val Thr Val Ser Trp Asn Ser | |
| 145                 150                 155                 160 | |

| ggc gcc ctg acc agc ggc gtg cac acc ttc ccg gct gtc cta cag tcc | 528 |
|---|---|
| Gly Ala Leu Thr Ser Gly Val His Thr Phe Pro Ala Val Leu Gln Ser | |
|             165                 170                 175 | |

| tca gga ctc tac tcc ctc agc agc gtg gtg acc gtg ccc tcc agc agc | 576 |
|---|---|
| Ser Gly Leu Tyr Ser Leu Ser Ser Val Val Thr Val Pro Ser Ser Ser | |
|             180                 185                 190 | |

| ttg ggc acc cag acc tac atc tgc aac gtg aat cac aag ccc agc aac | 624 |
|---|---|
| Leu Gly Thr Gln Thr Tyr Ile Cys Asn Val Asn His Lys Pro Ser Asn | |
|         195                 200                 205 | |

| acc aag gtg gac aag aaa gca gag ccc aaa tgt cat cac cat cac cat | 672 |
|---|---|
| Thr Lys Val Asp Lys Lys Ala Glu Pro Lys Cys His His His His His | |
|     210                 215                 220 | |

| cac | 675 |
|---|---|
| His | |
| 225 | |

<210> SEQ ID NO 162
<211> LENGTH: 225
<212> TYPE: PRT
<213> ORGANISM: Homo sapiens
<220> FEATURE:
<223> OTHER INFORMATION: 3E.2 Heavy Chain

<400> SEQUENCE: 162

Gln Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ser Phe Thr Asn Tyr
             20                  25                  30

Trp Ile Gly Trp Val Arg Gln Met Pro Gly Lys Gly Leu Glu Trp Met
         35                  40                  45

Gly Phe Ile Tyr Ser Asp Asp Ser Val Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Thr Arg Asp Gly Pro Glu Ala Phe Asp Ile Trp Gly Gln Gly Thr Met
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Lys Ala Glu Pro Lys Cys His His His His
 210                 215                 220

His
225

<210> SEQ ID NO 163
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.3 Heavy Chain

<400> SEQUENCE: 163 cag gtg cag ctg gtg cag tct ggg gca gag gtg aaa aag ccc ggg gag      48
Gln Val Gln Leu Val Gln Ser Gly Ala Glu Val Lys Lys Pro Gly Glu
 1               5                  10                  15 tct ctg aag atc tcc tgt aag ggt tct gga tac agc ttt acc aac tac      96
Ser Leu Lys Ile Ser Cys Lys Gly Ser Gly Tyr Ser Phe Thr Asn Tyr
             20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
         35                  40                  45 ggg ttc atc tat tct gat gac tct gtt acc aga tac agc ccg tcc ttc     192
Gly Phe Ile Tyr Ser Asp Asp Ser Val Thr Arg Tyr Ser Pro Ser Phe
     50                  55                  60 caa ggc cag gtc acc atc tca gcc gac aag tcc atc agt acc gcc tac     240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                 85                  90                  95
```

```
acg aga gat ggt ccc gaa gct ttt gat atc tgg ggc caa ggg aca atg     336
Thr Arg Asp Gly Pro Glu Ala Phe Asp Ile Trp Gly Gln Gly Thr Met
        100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
            115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc     576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac     624
Leu Gly Thr Gln Thr Tyr Ile Cys Asn Val Asn His Lys Pro Ser Asn
        195                 200                 205 acc aag gtg gac aag aaa gca gag ccc aaa tgt cat cac cat cac cat     672
Thr Lys Val Asp Lys Lys Ala Glu Pro Lys Cys His His His His His
    210                 215                 220 cac                                                                 675
His
225

<210> SEQ ID NO 164
<211> LENGTH: 225
<212> TYPE: PRT
<213> ORGANISM: Homo sapiens
<220> FEATURE:
<223> OTHER INFORMATION: 3E.3 Heavy Chain

<400> SEQUENCE: 164

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Phe Ile Tyr Ser Asp Asp Ser Val Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Asp Gly Pro Glu Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Cys His His His His
    210                 215                 220

His
225

<210> SEQ ID NO 165
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.4 Heavy Chain

<400> SEQUENCE: 165 cag gtg cag ctg gtg cag tct ggg gga ggc gtg gtc cag tct ggg agg        48
Gln Val Gln Leu Val Gln Ser Gly Gly Gly Val Val Gln Ser Gly Arg
1               5                   10                  15 tcc ctg aga ctc tcc tgt gca gcc tct gga atc acc gtc agg aac tat        96
Ser Leu Arg Leu Ser Cys Ala Ala Ser Gly Ile Thr Val Arg Asn Tyr
                20                  25                  30 gct atg cac tgg gtc cgc cag gtt cca ggc aag ggg ctg gag tgg gtg       144
Ala Met His Trp Val Arg Gln Val Pro Gly Lys Gly Leu Glu Trp Val
            35                  40                  45 gca gtt ata tca tat gat gga agc aat aaa tac tac gca gac tcc gtg       192
Ala Val Ile Ser Tyr Asp Gly Ser Asn Lys Tyr Tyr Ala Asp Ser Val
        50                  55                  60 aag ggc cga ttc acc ctc tcc aga gac aat tcc aag aac acg ctg tat       240
Lys Gly Arg Phe Thr Leu Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aga gag gac tac tac ggt atg gac gtc tgg ggc caa ggg acc acg       336
Ala Arg Glu Asp Tyr Tyr Gly Met Asp Val Trp Gly Gln Gly Thr Thr
            100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc       432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205 acc aag gtg gac aag aaa gca gag ccc aaa tgt cat cac cat cac cat       672
Thr Lys Val Asp Lys Lys Ala Glu Pro Lys Cys His His His His His
    210                 215                 220
```

```
              210                 215                 220
cac                                                               675
His
225

<210> SEQ ID NO 166
<211> LENGTH: 225
<212> TYPE: PRT
<213> ORGANISM: Homo sapiens
<220> FEATURE:
<223> OTHER INFORMATION: 3E.4 Heavy Chain

<400> SEQUENCE: 166

Gln Val Gln Leu Val Gln Ser Gly Gly Gly Val Val Gln Ser Gly Arg
  1               5                  10                  15

Ser Leu Arg Leu Ser Cys Ala Ala Ser Gly Ile Thr Val Arg Asn Tyr
             20                  25                  30

Ala Met His Trp Val Arg Gln Val Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Leu Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Cys His His His His
    210                 215                 220

His
225

<210> SEQ ID NO 167
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.8 Heavy Chain

<400> SEQUENCE: 167 cag gtg cag ctg gtg gag tct ggg gga ggc gtg gtc cag cct ggg agg      48
Gln Val Gln Leu Val Glu Ser Gly Gly Gly Val Val Gln Pro Gly Arg
  1               5                  10                  15 tcc ctg aga ctc tcc tgt gca gcg tct gga ttc acc ttc agg aga tat      96
```

```

Ser Leu Arg Leu Ser Cys Ala Ala Ser Gly Phe Thr Phe Arg Arg Tyr
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
        35                  40                  45 gca gtt ata tca tat gat gga agc aat aaa tac tac gca gac tcc gtg    192
Ala Val Ile Ser Tyr Asp Gly Ser Asn Lys Tyr Tyr Ala Asp Ser Val
 50                  55                  60 aag ggc cga ttc acc ctc ccc aga gac aat tcc aag aac acg ctg tat    240
Lys Gly Arg Phe Thr Leu Pro Arg Asp Asn Ser Lys Asn Thr Leu Tyr
 65                  70                  75                  80 ctg caa atg aac agc ctg aga gct gag gac acg gct gtg tat tac tgt    288
Leu Gln Met Asn Ser Leu Arg Ala Glu Asp Thr Ala Val Tyr Tyr Cys
                85                  90                  95 gcg aga gag gac tac tac ggt atg gac gtc tgg ggc caa ggg acc acg    336
Ala Arg Glu Asp Tyr Tyr Gly Met Asp Val Trp Gly Gln Gly Thr Thr
            100                 105                 110 gtc acc gtc tcc tca gcc tcc acg aag ggc cca tcg gtc ttc ccc ctg    384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc    432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aag tca    480
Leu Val Lys Asp Tyr Phe Pro Glu Pro Val Thr Val Ser Trp Lys Ser
145                 150                 155                 160 ggc gcc ctg acc agc ggc gtg cac acc ttc ccg gct gtc cta cag tcc    528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc    576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tgt cat cac cat cac cat    672
Thr Lys Val Asp Lys Lys Ala Glu Pro Lys Cys His His His His His
    210                 215                 220 cac                                                                675
His
225

<210> SEQ ID NO 168
<211> LENGTH: 225
<212> TYPE: PRT
<213> ORGANISM: Homo sapiens
<220> FEATURE:
<223> OTHER INFORMATION: 3E.8 Heavy Chain

<400> SEQUENCE: 168

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Arg Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Leu Pro Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Asp Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Lys Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Cys His His His His
    210                 215                 220

His
225

<210> SEQ ID NO 169
<211> LENGTH: 675
<212> TYPE: DNA
<213> ORGANISM: Homo sapiens
<220> FEATURE:
<221> NAME/KEY: CDS
<222> LOCATION: (1)..(675)
<220> FEATURE:
<223> OTHER INFORMATION: 3E.9 Heavy Chain

<400> SEQUENCE: 169 cag gtg cag ctg gtg cag tct ggg gca gag gtg aaa aag ccc ggg gag      48
Gln Val Gln Leu Val Gln Ser Gly Ala Glu Val Lys Lys Pro Gly Glu
  1               5                  10                  15 tct ctg aag atc tcc tgt aag ggt tct gga tac agc ttt acc aac tac      96
Ser Leu Lys Ile Ser Cys Lys Gly Ser Gly Tyr Ser Phe Thr Asn Tyr
             20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
         35                  40                  45 ggg atc atc tat tct gat gac tct gtt acc aga tac agc ccg tcc ttc     192
Gly Ile Ile Tyr Ser Asp Asp Ser Val Thr Arg Tyr Ser Pro Ser Phe
     50                  55                  60 caa ggc cag gtc acc atc tca gcc gac aag tcc atc agt acc gcc tac     240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                 85                  90                  95 acg aga gat ggt ccc gaa gct ttt gat atc tgg ggc caa ggg aca atg     336
Thr Arg Asp Gly Pro Glu Ala Phe Asp Ile Trp Gly Gln Gly Thr Met
            100                 105                 110 gtc acc gtc tct tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
    130                 135                 140
```

```
ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
            165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
        180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
    195                 200                 205 acc aag gtg gac aag aaa gca gag ccc aaa tgt cat cac cat cac cat       672
Thr Lys Val Asp Lys Lys Ala Glu Pro Lys Cys His His His His His
210                 215                 220 cac                                                                    675
His
225

<210> SEQ ID NO 170
<211> LENGTH: 225
<212> TYPE: PRT
<213> ORGANISM: Homo sapiens
<220> FEATURE:
<223> OTHER INFORMATION: 3E.9 Heavy Chain

<400> SEQUENCE: 170

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Ser Asp Asp Ser Val Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Asp Gly Pro Glu Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Cys His His His His
    210                 215                 220

His
225
```

-continued

```
<210> SEQ ID NO 171
<211> LENGTH: 70
<212> TYPE: DNA
<213> ORGANISM: Artificial Sequence
<220> FEATURE:
<223> OTHER INFORMATION: Description of Artificial Sequence: Primer 1 of
      Figure 2

<400> SEQUENCE: 171
tatttccagc ttggtccctc tagagttaac gatatcaacg tttatctaat cagcaagaga      60
tggaggcttg                                                            70

<210> SEQ ID NO 172
<211> LENGTH: 70
<212> TYPE: DNA
<213> ORGANISM: Artificial Sequence
<220> FEATURE:
<223> OTHER INFORMATION: Description of Artificial Sequence: Primer 2 of
      Figure 2

<400> SEQUENCE: 172
tgaggttcct tgaccccact gcagagtact aggcctctga gctactcagt taggtgattg      60
agtagccagt                                                            70
```

HUMAN ANTIBODIES

CROSS-REFERENCES TO RELATED APPLICATION

The present application is a US national phase of PCT US00/27237 filed Oct. 2, 2000, which is a continuation-in-part of Ser. No. 09/453,234, filed Dec. 1, 1999, now U.S. Pat. No. 6,794,132, which derives priority from U.S. Ser. No. 60/157,414, filed Oct. 2, 1999, both of which are incorporated by reference in their entirety for all purposes.

BACKGROUND

Over recent years, it has become apparent that mouse antibodies are not ideal reagents for in vivo use due to induction of human anti-mouse responses in recipient patients. A number of solutions have been proposed including the production of chimeric and humanized antibodies (Queen et al., *Proc. Natl. Acad. Sci. USA* 86:10029–10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539).

Human monoclonals antibodies are advantageous compared with those from mouse or other species, because, inter alia, they exhibit little or no immunogenicity in a human host. However, conventional technology for producing murine monoclonals cannot be applied unmodified to production of human antibodies for several reasons. First, mouse procedures typically involve sacrificing the mouse, a procedure that is obviously unacceptable to humans. Second, humans cannot be immunized with many types of antigens, including human antigens, due to the risk of inducing an undesired immune response. Third, forming immortalized derivatives of human B cells has proved more difficult than for mouse B cells.

Early techniques for producing human antibodies met with only limited success. For example, immortalization of immunized human lymphocytes with Epstein-Barr virus, while successful in forming monoclonal-antibody secreting cultures, has often failed to produce cells having sufficiently long lifespans to provide a reliable source of the desired antibody. Kozbor et al. (1982), *Hybridoma* 1:323. In another approach, hybridomas generated by fusion of immunized human lymphoid cell lines with mouse myelomas, were found to exhibit chromosomal instability. Nowinski et al. (1980), *Science* 210:537; Lane et al. (1982), *J. Exp. Med.* 155:133 (1982).

Another approach has been described by Ostberg et al. (1983), *Hybridoma* 2:361–367 and Engelman et al., U.S. Pat. No. 4,634,666. This method entails fusing a mouse myeloma cell with a nonimmunized human B-lymphocyte to form a xenogenic fusion cell. The fusion cell is then fused with an immunized human B-lymphocyte to produce a trioma cell. A number of human monoclonal antibodies to viral pathogens have been isolated using this approach.

A further approach has used the phage display technique to screen libraries of immunoglobulin genes obtained directly from human lymphatic cells from a naïve human. A basic concept of phage display methods is the establishment of a physical association between DNA encoding an antibody to be screened and the antibody chain. This physical association is provided by the phage particle, which displays an antibody as part of a capsid enclosing the phage genome which encodes the antibody. The establishment of a physical association between antibodies and their genetic material allows simultaneous mass screening of very large numbers of phage bearing different antibodies. Phage displaying an antibody with affinity to a target bind to the target and these phage are enriched by affinity screening to the target. The identity of antibodies displayed from these phage can be determined from their respective genomes. Using these methods an antibody identified as having a binding affinity for a desired target can then be synthesized in bulk by conventional means. Although the phage display method provides a powerful means of selection, the number of potential antibodies to be analyzed in a naïve human library is very large, about $10^{12}$. Further, many of the antibodies in such a library are nonnaturally occurring combinations of heavy and light chain resulting from the random manner in which populations of these chains are combined when being cloned into the phage display vector. Such nonnaturally occurring combinations often lack capacity for strong binding. Thus, desired human antibodies with strong affinity for a human antibody are typically rare and consequently difficult to isolate from such libraries.

Human antibodies can also be produced from non-human transgenic mammals having transgenes encoding human immunoglobulin genes and having an inactivated endogenous immunoglobulin locus. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are reported by, e.g., Lonberg et al., WO93/12227 (1993); U.S. Pat. No. 5,877,397, U.S. Pat. No. 5,874,299, U.S. Pat. No. 5,814,318, U.S. Pat. No. 5,489,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547–1553 (1994), *Nature Biotechnology* 14, 826 (1996), Kucherlapati, WO 91/10741 (1991) (each of which is incorporated by reference in its entirety for all purposes). Antibodies are obtained by immunizing a transgenic nonhuman mammal, such as described by Lonberg or Kucherlapati, supra, with antigen Monoclonal antibodies are prepared by fusing B-cells from such mammals to suitable myeloma cell lines using conventional Kohler-Milstein technology.

SUMMARY OF THE INVENTION

The invention provides methods of producing a human antibody display library. Such methods entail providing a nonhuman transgenic animal whose genome comprises a plurality of human immunoglobulin genes that can be expressed to produce a plurality of human antibodies. A population of nucleic acids encoding human antibody chains is isolated from lymphatic cells of the nonhuman transgenic animal. The nucleic acids are then introduced into a display vector to provide a library of display packages, in which a library member comprises a nucleic acid encoding an antibody chain, and the antibody chain is displayed from the package.

In some methods, library members are contacted with a target. Library members displaying an antibody chain and binding partner (if present) with specific affinity for the target bind to the target, to produce a subpopulation of display packages. The resulting subpopulation of display packages typically comprises at least ten different display packages comprising at least ten nucleic acids encoding at least ten antibody chains. At least 50% of the nucleic acids typically encode human antibody chains, which with the binding partner (if present) show at least $10^8$ $M^{-1}$ affinity for the target and no library member constitutes more than 50% of the library.

Some methods entails a step of preenriching lymphatic cells before cloning antibody sequences. The subpopulation is enriched for lymphatic cells expressing an IgG antibody before the isolating step. The subpopulation can be prepared by contacting the isolated lymphatic cells with a reagent that binds to the Fc region of an IgG antibody. In addition, nucleic acids can be cloned from the lymphatic cells using a pair of primers one of which is specific for DNA encoding IgG heavy chains. In some methods, at least 90% of the human antibody chains cloned into a display vector have IgG isotype.

In some methods, nucleic acids having affinity for a target have a median of at least 2 somatic mutations per antibody chain encoded by the nucleic acids. In some methods, the nucleic acids having affinity for the target have a median of at least 5 somatic mutations per antibody chain encoded by the nucleic acids.

In some methods, the lymphatic cells are obtained from bone marrow.

In some methods, the lymphatic cells are from a nonhuman transgenic animal that has been immunized with an immunogen without developing a titer to the immunogen greater than ten fold of a negative control. In some methods, the lymphatic cells are from a nonhuman transgenic animal that has been immunized with an immunogen without developing a detectable titer against the immunogen.

In some methods, the display members are screened with a target is expressed on the surface of a cell. In some methods, the target is a protein within a phospholipid membrane or particle.

The invention also provides methods of producing a human Fab phage display library. Such methods entail providing a nonhuman transgenic animal whose genome comprises a plurality of human immunoglobulin genes that can be expressed to produced a plurality of human antibodies. Populations of nucleic acids respectively encoding human antibody heavy chains and human antibody light chains are isolated from lymphatic cells of the nonhuman transgenic animal. The populations are cloned into multiple copies of a phage display vector to produce a display library, in which a library member comprises a phage capable of displaying from its outersurface a fusion protein comprising a phage coat protein, a human antibody light chain or human antibody heavy chain. In at least some members, the human antibody heavy or light chain is complexed with a partner human antibody heavy or light chain, the complex forming a Fab fragment to be screened.

Library members are typically contacted with a target. Library members displaying a complex of a human heavy and light chain with specific affinity for the target bind to the target, to produce a subpopulation of display packages. The resulting subpopulation of display packages typically comprises at least ten different display packages comprising at least ten pairs of nucleic acids encoding at least ten pairs of heavy and light chains. Typically at least 50% of the pairs of nucleic acids encoding pairs of heavy and light chains forming complexes showing at least $10^8$ $M^{-1}$ affinity for the target and no library member constitutes more than 50% of the library.

In some methods, lymphatic cells re preenriched to prepare a subpopulation of lymphatic cells expressing an IgG antibody. In some methods, the subpopulation is prepared by contacting the isolated lymphatic cells with a reagent that binds to the Fc region of an IgG antibody. In some methods, DNA is isolated from lymphatic cells using a pair of primers one of which is specific for DNA encoding IgG heavy chains.

In some methods, pairs of nucleic acids encoding antibodies with specific affinity for the target have a median of at least 10 mutations in the nucleic acids encoding heavy chains and a median of at least two somatic mutations in the nucleic acids encoding light chains. In some methods, the pairs of nucleic acids have a median of at least 10 somatic mutations in the nucleic acids encoding the heavy chains and at least five somatic mutations in the nucleic acids encoding the light chains. In some methods, the pairs of nucleic acids have a median of at least ten somatic mutations in the nucleic acids encoding the heavy chains and a median of at least ten somatic mutations in the nucleic acids encoding the light chains.

In some methods, the lymphatic cells are obtained from bone marrow.

In some methods, the lymphatic cells are from a nonhuman transgenic mammal that has been immunized with an immunogen without developing a significant titer to the immunogen.

In some methods, the target is expressed on the surface of a cell.

In some methods at least 90% of the human antibody heavy chains encoded by a display vector have IgG isotype.

In some methods, the populations of nucleic acids respectively encode populations of human heavy and light chain variable regions, and the phage display vector encodes human heavy and light chain constant regions expressed in frame with human heavy and light chains inserted into the vector.

In some methods, the fusion protein encoded by the phage display vector further comprises a tag that is the same in different library members. Library members are screened for binding to a receptor with specific affinity for the tag.

In some methods, a mixed population of nucleic acids encoding human antibody heavy chains and human antibody light chains from the further subpopulation of library members is cloned into multiple copies of an expression vector to produce modified expression vectors.

The invention further provides libraries of at least ten different nucleic segments encoding human antibody chains. At least 50% of segments in the library encode human antibody chains showing at least $10^8$ $M^{-1}$ affinity for the same target and no library member constitutes more than 50% of the library. In some libraries, at least 90% of the pairs of different nucleic acid segments encode heavy and light chains that form complexes having at least $10^9$ $M^{-1}$ affinity of the target.

Some libraries comprise at least ten pairs of different nucleic acid segments, the members of a pair respectively encoding heavy and light human antibody chains, wherein at least 50% of the pairs encode heavy and light human antibody chains that form complexes showing specific affinity for the same target, and no pair of nucleic acid segments constitutes more than 50% of the library. Some libraries comprise at least 100 or 1000 pairs of different nucleic acid segments.

In some libraries, at least 50% of the pairs encode heavy and light chains that form complexes having affinity of at least $10^9$ $M^{-1}$ for the target. In some libraries, at least 50 or 90% of the pairs encode heavy and light chains that form complexes having affinity of at least $10^{10}$ $M^{-1}$ for the target. In some libraries, at least the pairs of different nucleic acid segments encoding antibodies with specific affinity for the target have a median of at least 10 somatic mutations in the nucleic acids encoding the heavy chains and a median of at least 2 somatic mutations in the nucleic acids encoding the light chains. In some libraries, the pairs of different nucleic acid segments encoding antibodies with affinity for the target have a median of at least 10 somatic mutations in the nucleic acids encoding the heavy chains and a median of at least 10 somatic mutations in the nucleic acids encoding the light chains. In some libraries, at least 90% of pairs of different nucleic acids segments have a nucleic acid segment encoding a heavy chain of IgG isotype.

The invention further provides libraries of at least 1000 different nucleic segments encoding human antibody chains, wherein at least 90% of segments in the library encode human antibody chains for the same target and no library member constitutes more than 50% of the library, wherein each segment comprises subsequence(s) from a human VH and/or a human VL gene, and no more than 40 human VH genes and no more than 40 human VL genes are represented in the library.

The invention further provides a method of producing a human antibody display library in which an immunogen is introduced into a nonhuman transgenic animal whose genome comprises a plurality of human immunoglobulin genes that can be expressed to produce a plurality of human antibodies. A population of nucleic acids encoding human antibody chains is isolated from lymphatic cells of the nonhuman transgenic animal, the nonhuman transgenic animal lacking a detectable titer or having a titer to the immunogen less than ten fold the background titer before immunization. A library of display packages is formed displaying the antibody chains, in which a library member comprises a nucleic acid encoding an antibody chain, and the antibody chain is displayed from the package. In some methods, the immunogen is a nucleic acid. In some methods, the nucleic acid encodes a membrane bound receptor.

The invention further provides a method of producing a human antibody display library in which a nonhuman transgenic animal whose genome comprises a plurality of human immunoglobulin genes that can be expressed to produce a plurality of human antibodies is provided. Lymphatic cells are obtained from the nonhuman mammal and the cells are enriched to produce a subpopulation or cells expressing antibodies of IgG isotype. Populations of nucleic acids encoding human heavy and light antibody chains are then isolated from the subpopulation. A library of display packages is formed displaying the human heavy and light antibody chains, in which a library member comprises nucleic acids encoding human antibody heavy and light chains, and a complex of the heavy and light chains is displayed from the library member. In some such methods, the nucleic acids encoding the human antibody heavy chains and the nucleic acids encoding the human antibody light chains both have a median of at least 5 somatic mutations per nucleic acid.

The invention further provides a method of producing a human antibody display library. Such methods entail introducing a nucleic acid encoding a protein immunogen into a nonhuman transgenic animal whose genome comprises a plurality of human immunoglobulin genes that can be expressed to produce a plurality of human antibodies. A population of nucleic acids encoding human antibody chains is isolated from lymphatic cells of the nonhuman transgenic animal. A library of display packages displaying the antibody chains is formed in which a library member comprises a nucleic acid encoding an antibody chain, and the antibody chain is displayed from the package. In some methods, the immunogen is a natural protein. In some the nucleic acid encodes a membrane bound protein or an EST. In some such methods, library members are contacted with a target so that library members displaying an antibody chain and binding partner (if present) with specific affinity for the target bind to the target, to produce a subpopulation of display packages. This screening can result in a subpopulation of display packages comprises at least ten different display packages comprising at least ten nucleic acids encoding at least ten antibody chains, and at least 50% of the nucleic acids encode human antibody chains, which in combination with a binding partner (if present) show at least $10^{10}$ $M^{-1}$ affinity for the target and no library member constitutes more than 50% of the library The invention further provides a method of preparing a population of antibodies. Such methods employ a first library of display packages displaying antibody chains, in which a library member comprises a nucleic acid encoding an antibody chain, and the antibody chain is displayed from the package. Such a library is screened for binding to a target to isolate a first population of display packages displaying antibody chains that specifically bind to the target. One then screens a second library of similar display packages displaying antibody chains for binding to the target, the screening being conducted in the presence of antibodies displayed from the first population of display packages to generate a second population of display packages displaying antibody chains that specifically bind to the target. The antibody chains in the second population of chains and the antibody chains in the first population of chain have different epitope binding profiles in the target.

BRIEF DESCRIPTION OF THE DRAWINGS

FIG. 2: Oligonucleotides used in vector construction (SEQ ID NOS:171–172).

FIG. 6 Targeted insertion of a neo cassette into the SmaI site of the mu1 exon. A. Schematic diagram of the genomic structure of the mu locus. The filled boxes represent the mu exons. B. Schematic diagram of the CmuD targeting vector. The dotted lines denote those genomic mu sequences included in the construct. Plasmid sequences are not shown. C. Schematic diagram of the targeted mu locus in which the neo cassette has been inserted into mu1. The box at the right shows those RFLP's diagnostic of homologous recombination between the targeting construct and the *mus* locus. The FGLP's were detected by Southern blot hybridization using probe A, the 915 SaI fragment shown in C.

Definitions

Figure 1:
FIG. 1: shows a vector obtained from Ixsys, Inc. and described in Huse, WO 92/06204, which provides the starting material for producing phage display vectors. The following abbreviations are used:
    A. Nonessential DNA sequence later deleted.
    B. Lac promoter and ribosome binding site.
    C. Pectate lyase signal sequence.
    D. Kappa chain variable region.
    E. Kappa chain constant region.
    F. DNA sequence separating kappa and heavy chain, includes ribosome binding site for heavy chain.
    G. Alkaline phosphatase signal sequence.
    H. Heavy chain variable region.
    I. Heavy chain constant region including 5 amino acids of the hinge region.
    J. Decapeptide DNA sequence.
    K. Pseudo gene VIII sequence with amber stop codon at 5' end.
    L. Nonessential DNA sequence that was later deleted.

Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$, $10^{10}$ $M^{-1}$, $10^{11}$ $M^{-1}$, $10^{12}$ $M^{-1}$ or $10^{13}$ $M^{-1}$. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxyl-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989, 4th edition (1999), Paul William E., ed. Raven Press, N.Y., (incorporated by reference in its entirety for all purposes). The genes encoding variable regions of heavy and light immunoglobulin chains are referred to as $V_H$ and $V_L$ respectively. Although the amino acid sequence of an immunoglobulin chain is not exactly the same as would be predicted from the $V_H$ or $V_L$ gene that encoded it due to somatic mutations (see FIG. 7), there is sufficient similarity between predicted and actual sequences of immunoglobulins that the actual sequence is characteristic and allows recognition of a corresponding $V_H$ or $V_L$ gene. The term constant region is used to refer to both full-length natural constant regions and segments thereof, such as $C_H1$, hinge, $C_H2$ and $C_H3$ or fragments thereof. Typically, segments of light and heavy chain constant regions in antibodies have sufficient length to contribute to interchain bonding between heavy and light chain.

The variable regions of each light/heavy chain pair form the antibody binding site. Thus, an intact antibody has two binding sites. Except in bifunctional or bispecific antibodies, the two binding sites are the same. The chains all exhibit the same general structure of four relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat, et al., supra. An alternative structural definition has been proposed by Chothia, et al., *J. Mol. Biol.* 196:901–917 (1987); *Nature* 342:878–883 (1989); and *J. Mol. Biol.* 186:651–663 (1989).

The term antibody is used to mean whole antibodies and binding fragments thereof. Binding fragments include single chain fragments, Fv fragments and Fab fragments The term Fab fragment is sometimes used in the art to mean the binding fragment resulting from papain cleavage of an intact antibody. The terms Fab' and F(ab')2 are sometimes used in the art to refer to binding fragments of intact antibodies generated by pepsin cleavage. Here, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the $C_H1$ domain of the constant region.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods). A target is any molecule for which it is desired to isolate partners with specific binding affinity for the target.

Targets of interest include antibodies, including anti-idiotypic antibodies and autoantibodies present in autoimmune diseases, such as diabetes, multiple sclerosis and rheumatoid arthritis. Other targets of interest are growth factor receptors (e.g., FGFR, PDGFR, EFG, NGFR, and VEGF) and their ligands. Other targets are G-protein receptors and include substance K receptor, the angiotensin receptor, the - and -adrenergic receptors, the serotonin receptors, and PAF receptor. See, e.g., Gilman, *Ann. Rev. Biochem.* 56:625–649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selectins, and immunoglobulin superfamily members (see Springer, *Nature* 346:425–433 (1990). Osborn, *Cell* 62:3 (1990); Hynes, *Cell* 69:11 (1992)). Other targets are cytokines, such as interleukins IL-1 through IL-13, tumor necrosis factors &, interferons, and, tumor growth factor Beta (TGF-), colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241. Some agents screened by the target merely bind to a target. Other agents agonize or antagonize the target.

Display library members having full-length polypeptide coding sequences have coding sequences the same length as that of the coding sequences originally inserted into a display vector before propagation of the vector.

The term phage is used to refer to both phage containing infective genomes and phage containing defective genomes that can be packaged only with a helper phage. Such phage are sometimes referred to as phagemids.

The term "human antibody" includes antibodies having variable and constant regions (if present) derived from human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies).

A rearranged heavy chain or light chain immunoglobulin locus has a V segment positioned immediately adjacent to a D-J or J segment in a conformation encoding essentially a complete $V_H$ or $V_L$ domain, respectively. A rearranged immunoglobulin gene locus can be identified by comparison to germline DNA; the rearranged locus having at least one recombined heptamer/nonamer homology element. Conversely, an unrearranged or germline configuration refers to a configuration in which the V segment is not recombined so as to be immediately adjacent to a D or J segment.

"Isotype switching" refers to the phenomenon by which the class, or isotype, of an antibody changes from one Ig class to one of the other Ig classes.

"Nonswitched isotype" refers to the isotypic class of heavy chain that is produced when no isotype switching has taken place; the $C_H$ gene encoding the nonswitched isotype is typically the first CH gene immediately downstream from the functionally rearranged VDJ gene. Isotype switching has been classified as classical or non-classical isotype switching. Classical isotype switching occurs by recombination events that involve at least one switch sequence region in the transgene. Non-classical isotype switching may occur by, for example, homologous recombination between human $\sigma_\mu$ and human $\Sigma_\mu$, (δ-associated deletion). Alternative non-classical switching mechanisms, such as intertransgene and/or interchromosomal recombination, among others, may occur and effectuate isotype switching.

The term "switch sequence" refers to those DNA sequences responsible for switch recombination. A "switch donor" sequence, typically a µ switch region, are 5' (i.e., upstream) of the construct region to be deleted during the switch recombination. The "switch acceptor" region are between the construct region to be deleted and the replacement constant region (e.g., γ, ε, etc.). As there is no specific site where recombination always occurs, the final gene sequence is not typically predictable from the construct.

Somatic mutation and affinity maturation of antibody genes allows for the evolutionary selection of variable regions of antibodies based on binding affinity. However, this process differs from evolutionary natural selection of individuals from sexually reproducing species because there is no mechanism to allow for the combination of separately selected beneficial mutations. The absence of recombination between individual B cells requires that beneficial mutations be selected for sequentially. Theoretically, combinatorial libraries allow for such combinations (at least in the case where the two mutations are on heavy and light chains respectively). However, combinatorial libraries derived from natural sources include such a wide diversity of different heavy/light chain pairs that the majority of the clones are not derived from the same B cell bone marrow precursor cell. Such pairings are less likely to form stable antibody molecules that recognize the target antigen.

DETAILED DESCRIPTION

I. General

The present invention uses display methods to screen libraries of antibodies originally expressed in nonhuman transgenic animals to produce populations of human antibodies having unexpected characteristics. These characteristics include unusually high binding affinities (e.g., pM dissociation constants in some instances), virtually unlimited numbers of such antibodies, and a high degree of enrichment for such antibodies in the population. The methods of the invention typically work by immunizing a nonhuman transgenic animal having human immunoglobulin genes. The animal expresses a diverse range of human antibodies that bind to the antigen. Nucleic acids encoding the antibody chain components of such antibodies are then cloned from the animal into a display vector. Typically, separate populations of nucleic acids encoding heavy and light chain sequences are cloned, and the separate populations then recombined on insertion into the vector, such that any given copy of the vector receives a random combination of a heavy and light chains. The vector is designed to express antibody chains so that they can be assembled and displayed on the outersurface of a display package containing the vector. For example, antibody chains can be expressed as fusion proteins with a phage coat protein from the outersurface of the phage. Thereafter, display packages can be screened for display of antibodies binding to a target.

In some methods, display packages are subject to a prescreening step. In such methods, the display package encode a tag expressed as a fusion protein with an antibody chain displayed from the package. Display packages are prescreened for binding to a receptor to the tag. The prescreening step serves to enrich for display packages displaying multiple copies of an antibody chain linked to the tag. It is believed that it is this subset of display packages that binds to target in the subsequent screening step to a target. After prescreening with receptor (if any) and screening with target, display packages binding to the target are isolated, and optionally, subject to further rounds screening to target, with each such round optionally being preceded by prescreening to receptor. By including one or more rounds of prescreening with a tag, the extent of enrichment can increase to approaching or even beyond 99% in contrast with conventional procedures in which the extent of enrichment typically plateaus after a few rounds of screening at around 10–20%. Display packages are typically amplified between rounds of screening to target but not between prescreening and screening steps. After one or a few rounds of screening to target, the remaining display packages are highly enriched for high affinity binders to the target. Furthermore, the conditions of screening can be controlled to select antibodies having affinity in excess of a chosen threshold.

In some methods, nucleic acids encoding human antibody chains are subcloned en masse from display vectors surviving selection to an expression vector. Typically, a nucleic acid encoding both heavy and light chains of an antibody displayed from a display package is subcloned to an expression vector thereby preserving the same combinations of heavy and light chains in expression vectors as were present in the display packages surviving selection. The expression vector can be designed to express inserted antibody chains as Fab fragments, intact antibodies or other fragments. Cloning en masse of nucleic acids encoding antibody chains into an expression vector and subsequent expression of the vector in host cells results in a polyclonal population of intact human antibodies or fragments thereof. Such a population contains a diverse mixture of different antibody types, the majority of which types show very high affinity for the same target, albeit usually to different epitopes within the target.

It is believed that the success of the invention in providing virtually unlimited numbers of unusually high affinity human antibodies to any desired target (see Example 21) results in part from reducing the total number of combinations of heavy and light chains that might form by random combination of the respective repertoires of these chains in the human repertoire. Display methods provide a means for screening vast numbers of antibodies for desired properties. However, the random association of light and heavy chains that occurs on cloning into a display vector results in unnatural combinations of heavy and light chains that may be nonfunctional. When heavy and light chains are cloned from a natural human, the number of permutations of heavy and light chains is very high, and probably a very large proportion of these are nonnaturally occurring and not capable of high affinity binding. Thus, high affinity antibodies constitute a very small proportion of such libraries and are difficult to isolate. Nonhuman transgenic animals with human immunoglobulin genes typically do not include the full complement of human immunoglobulin genes present in a natural human. It is believed that the more limited complement of human immunoglobulin genes present in such animals results in a reduced proportion of unnatural random permutations of heavy and light chains incapable of high affinity binding. Thus, when the vast power of display selection is applied free of the burden of very large numbers of unnatural combinations inherent in previous methods, indefinitely large numbers of human immunoglobulins having very high affinities result.

The enrichment for productive combinations of heavy and light chains afforded by use of transgenic animals with less than a full complement of human genes can be supplemented or substituted by preenrichment for lymphatic cells expressing IgG heavy chains and their binding partners. IgG heavy chains typically show strongest affinity for a target antigen. By enriching for cells expressing such chains and their natural light chain partners before random combination of nucleic acids attendant to introduction into a display vector, one produces a display library containing a higher proportion of heavy and light chain combinations with potential for tight binding to a target. Although random association between heavy and light chains still produces nonnaturally occurring combinations of heavy and light chains, these combinations are formed from component chains of the tightest binding natural antibodies, are more likely therefore to be themselves tight binding antibodies. Enrichment for IgG increases the proportion of IgG antibodies in selected display libraries, and increases the median number of somatic mutations in nucleic acids encoding antibody chains in selected display libraries. By preenriching for both IgG chains and their binding partners, the median number of somatic mutations increases in both heavy and light chains. The increase is particular notable for the light chain because no this chain is not subjected to further enrichment at the PCR stage by use of iostype specific primers. Thus, in methods employing IgG enrichment of B cells, the number of somatic mutations per light chain approaches or equals that per heavy chain. Although the mechanisms discussed above are believed to explain in part the results achieved using the invention, practice of the invention is not dependent on the correctness of this belief.

II. Production of Antibodies in Transgenic Animals with Human Immune Systems

A. Transgenic Animals

The transgenic animals used in the invention bear a heterologous human immune system and typically a knocked out endogenous immune systems. Mice are a preferred species of nonhuman animal. Such transgenic mice sometimes referred to as HuMAb mice contain a human immunoglobulin gene miniloci that encodes unrearranged human heavy (μ and γ) and κ light chain immunoglobulin sequences, together with targeted mutations that inactivate the endogenous μ and κ chain loci (Lonberg et al. (1994) *Nature* 368(6474):856–859 and U.S. Pat. No. 5,770, 429). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al. (1994), supra; reviewed in Lonberg, N. (1994) *Handbook of Experimental Pharmacology* 113:49–101; Lonberg and Huszar. (1995) *Intern. Rev. Immunol. Vol.* 13: 65–93, and Harding and Lonberg (1995) *Ann. N.Y. Acad. Sci* 764:536–546); Taylor, L. et al. (1992) *Nucleic Acids Research* 20:6287–6295; Chen, J. et al. (1993) *International Immunology* 5: 647–656; Tuaillon et al. (1993) *Proc. Natl. Acad. Sci USA* 90:3720–3724; Choi et al. (1993) *Nature Genetics* 4:117–123; Chen, J. et al. (1993) EMBO J. 12: 821–830; Tuaillon et al. (1994) *J. Immunol.* 152:2912–2920; Lonberg et al, (1994) *Nature* 368(6474):856–859; Lonberg, N. (1994) *Handbook of Experimental Pharmacology* 113:49–101; Taylor, L. et al. (1994) *International Immunology* 6: 579–591; Lonberg, N. and Huszar, D. (1995) *Intern. Rev. Immunol. Vol.* 13: 65–93; Harding, F. and Lonberg, N. (1995) *Ann. N.Y. Acad. Sci* 764:536–546; Fishwild, D. et al. (1996) *Nature Biotechnology* 14: 845–851; U.S. Pat. Nos. 5,625,126 and 5,770,429 U.S. Pat. No. 5,545,807, U.S. Pat. No. 5,939,598, WO 98/24884, WO 94/25585, WO 93/1227, WO 92/22645, WO 92/03918, the disclosures of all of which are hereby incorporated by reference in their entity.

Some transgenic non-human animals are capable of producing multiple isotypes of human monoclonal antibodies to an antigen (e.g., IgG, IgA and/or IgE) by undergoing V-D-J recombination and isotype switching. Isotype switching may occur by, e.g., classical or non-classical isotype switching.

Transgenic non-human animal are designed so that human immunoglobulin transgenes contained within the transgenic animal function correctly throughout the pathway of B-cell development. In some mice, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

In transgenic animals in which the endogenous immunoglobulin loci of the transgenic animals are functionally disrupted, the transgene need not activate allelic exclusion. Further, in transgenic animals in which the transgene comprises a functionally rearranged heavy and/or light chain immunoglobulin gene, the second criteria of functional gene rearrangement is unnecessary, at least for transgenes that are already rearranged.

Some transgenic non-human animals used to generate the human monoclonal antibodies contain rearranged, unrearranged or a combination of rearranged and unrearranged heterologous immunoglobulin heavy and light chain transgenes in the germline of the transgenic animal. In addition, the heavy chain transgene can contain functional isotype switch sequences, which are capable of supporting isotype switching of a heterologous transgene encoding multiple CH genes in the B-cells of the transgenic animal. Such switch sequences can be those which occur naturally in the germline immunoglobulin locus from the species that serves as the source of the transgene CH genes, or such switch sequences can be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences can be isolated and cloned by conventional cloning methods, or can be synthesized de novo from overlapping synthetic oligonucleotides designed on the basis of published sequence information relating to immunoglobulin switch region sequences (Mills et al., *Nucl. Acids Res.* 15:7305–7316 (1991); Sideras et al., *Intl. Immunol.* 1:631–642 (1989) incorporated by reference). Typically, functionally rearranged heterologous heavy and light chain immunoglobulin transgenes are found in a significant fraction of the B-cells of the above transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species other than the transgenic non-human animal, typically the human species.

Typically transgenes are constructed so that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen. Such transgenes typically comprise a substantial portion of the C, D, and J segments as well as a subset of the V gene segments.

In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences can be incorporated into the transgene from the same or a related species of the non-human animal used in the invention. For example, human immunoglobulin gene segments can be combined in a transgene with a rodent immunoglobulin enhancer sequence for use in a transgenic mouse. Alternatively, synthetic regulatory sequences can be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. The transgene can comprise a minilocus.

Some transgenic animals used to generate human antibodies contain at least one, typically 2–10, and sometimes 25–50 or more copies of the transgene described in Example 37 of U.S. Pat. No. 5,770,429, or the transgene described in Example 24 (e.g., HCo12), at least one copy of a light chain transgene described in Examples 38 of U.S. Pat. No. 5,770, 429, two copies of the Cmu deletion described in Example 23, and two copies of the Jkappa deletion described in Example 9 of U.S. Pat. No. 5,770,429, each incorporated by reference in its entirety for all purposes.

Some transgenic, animals exhibit immunoglobulin production with a significant repertoire. Thus, for example, animals in which the endogenous Ig genes have been inactivated, the total immunoglobulin levels range from about 0.1 to 10 mg/ml of serum, preferably 0.5 to 5 mg/ml. The immunoglobulins expressed by the transgenic mice typically recognize about one-half or more of highly antigenic proteins, e.g., *staphylococcus* protein A.

The transgenic nonhuman animals can be immunized with a purified or enriched preparation of antigen and/or cells expressing antigen. The animals produce B cells that undergo class-switching via intratransgene switch recombination (cis-switching) and express immunoglobulins reactive with the antigen with which they are immunized. The immunoglobulins can be human sequence antibodies, in which the heavy and light chain polypeptides are encoded by human transgene sequences, which can include sequences derived by somatic mutation and V region recombinatorial joints, as well as germline-encoded sequences. These human sequence immunoglobulins can be referred to as being substantially identical to a polypeptide sequence encoded by a human $V_L$ or $V_H$ gene segment and a human JL or JL segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies frequently have some variable region sequences (and less frequently constant region sequences) which are not encoded by human V, D, or J gene segments as found in the human transgene(s) in the germline of the mice. Typically, such non-germline sequences (or individual nucleotide positions) cluster in or near CDRs, or in regions where somatic mutations are known to cluster.

Figure 7:
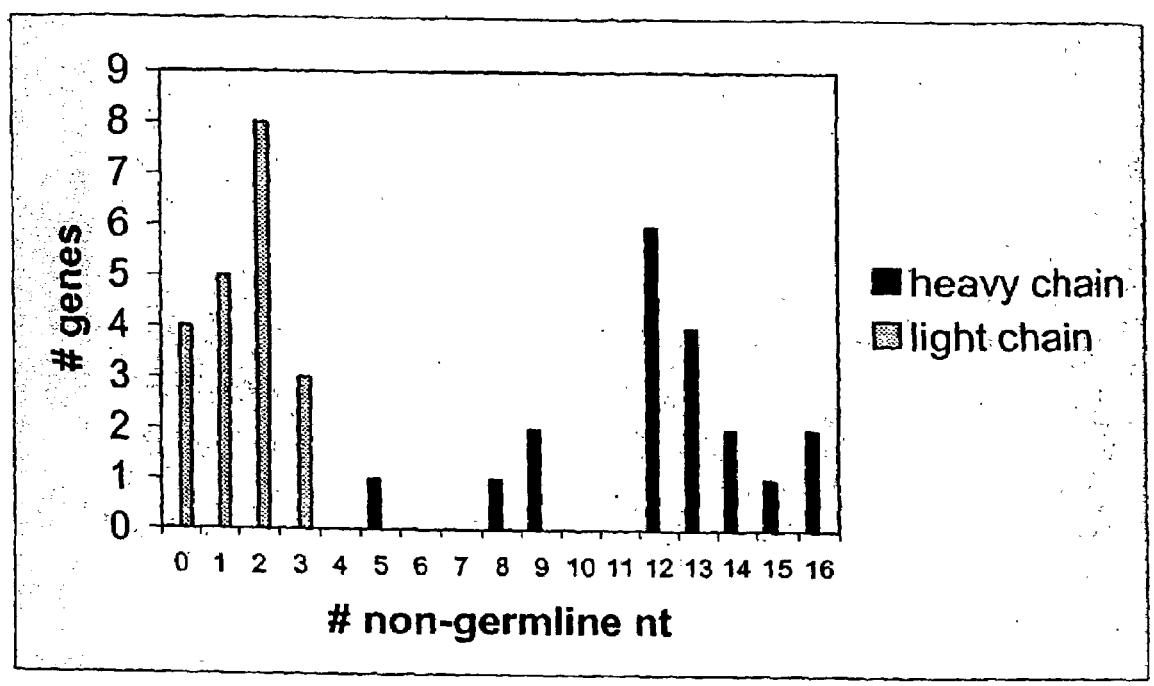
FIG. 7 Nongermline encoded nucleotides in heavy and light chain V genes. Heavy chain V genes were found to be heavily somatically mutated. Light chain V genes comprised fewer non-germline encoded nucleotides.

The human sequence antibodies which bind to the predetermined antigen can result from isotype switching, such that human antibodies comprising a human sequence γ chain (such as γ1, γ2, γ3, or γ4) and a human sequence light chain (such as kappa or lambda) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. FIG. 7 shows the frequency of somatic mutations in various immunoglobulins of the invention (without the benefit of enrichment for IgG B cells before cloning nucleic acids encoding antibody chains).

B. Immunization

1. Immunization with Antigen

HuMAb transgenic animals can be immunized intraperitoneally (IP) with antigen in complete Freund's adjuvant, followed by IP immunizations with antigen in incomplete Freund's adjuvant every two weeks or month for a few months. Adjuvants other than Freund's are also effective. In addition, whole cells in the absence of adjuvant are found to be highly immunogenic. The immune response can be monitored over the course of the immunization protocol with plasma samples being obtained by retroorbital bleeds. Mice can be boosted intravenously with antigen 3 days before sacrifice and removal of the spleen.

In some methods, antibody libraries can be generated from immunized transgenic animals notwithstanding the absence of a significant titer to the antigen in serum from the animal. It is believed that such animals express mRNA without secreting significant amounts of antibody encoded by the mRNA. mRNA from such cells can thus be converted to cDNA and cloned into a display vector notwithstanding the absence of a detectable titer in the animal from which the mRNA was obtained. The insight that an antibody titer is not required shortens the number of immunizations and period following the immunization that would be required according to conventional wisdom whereby the number of tight binding antibodies correlates with the extent of immune response. Accordingly, one or two immunizations with antigen, and a total period following the first immunization of one or two weeks are often sufficient for mRNA to be expressed and give rise to satisfactory antibody libraries by the display screening procedures described below. Additionally, the insight that antibody titer is not required extends the range of antigens that can be used to generate antibodies. Antigens that might previously have been rejected as immunogens through lack of measurable antibody titer in serum can now be used to produce mRNA libraries, and thus antibodies libraries according to the present methods.

In some methods of the invention, nucleic acids encoding mRNAs are harvested from transgenic animals immunized with an antigen but lacking any detectable titer. This means that the immune response of sera to the antigen is not significantly different (i.e., within experimental error) of a negative control. If serum is titered by binding to antigen immobilized to a solid phase, a suitable negative control is the solid phase without the antigen. Alternatively, serum from the animal before immunization can be used as a negative control. In some methods, nucleic acids are harvested from a transgenic animal showing a titer that is above the background level of a negative control but not to an extent that would by conventional wisdom be considered sufficient for production of tight binding antibodies. For example, the titer can be 2-fold, 5-fold, 10-fold, 50 fold or 100-fold above a negative control.

2. Immunization with DNA

In some methods, DNA is used as an immunogen. It is believed that the DNA is transcribed and translated in situ, and the translation product generates an immune response. Although there have been a few previous attempt at DNA immunization reported in the literature (see WO 99/28471, Chowdhury et al., *PNAS* 95, 669–674 (1998) and *J. Immunol. Methods* 231, 83–91 (1999)), this technique has been little used due to the lack of detectable titer generally observed, and the perception that such a strong titer is necessary to prepare antibodies. The present invention shows that mRNA encoding antibodies specific to the antigen encoded by the DNA is routinely produced in B-cells of such animals notwithstanding a lack of detectable titer. The DNA can be cloned and used to produce antibody libraries according to the methods of the invention. Example 36 shows that a population of antibodies having very tight binding affinities of the order of $10^{12}$ $M^{-1}$ affinity can be produced notwithstanding lack of detectable titer to the antigen in the transgenic animal from which mRNA was harvested.

Use of DNA as an immunogen has a number of advantages, particularly for generating an immune response to antigens that are difficult to purify, are available only in small amounts, if at all, or which lose their secondary structure on purification. Use of DNA as an immunogen is also useful for producing antibodies to proteins that have not yet been isolated or characterized, for example, the expression products of expressed sequence tags (ESTs). Because DNA immunization can produce antigens in a more native format than immunization with the antigen per se tighter binding antibodies can also be routinely produced. For example, affinities of at least $10^{10}$, $10^{11}$, $10^{12}$ or $10^{13}$ $M^{-1}$ are possible. DNA immunization can be performed with or without an adjuvant. The adjuvant, if present, can be one that is typically used with a protein antigen, such as complete or incomplete Freund's adjuvant, or SDS, or it can be an adjuvant that is specifically chosen to associate with DNA, such as the positively charged detergent CTAB. The DNA to be used as an immunogen is typically operably linked to a promoter and other regulatory sequences required for its expression and translation. Optionally, the DNA is present as a component of a vector. In some instances, the vector encodes proinflammatory cytokines to attract immune cells to the site of injection. In some instances, the DNA encodes a fusion protein, comprising an antigenic component to which antibodies are desired and a T-cell antigen, such as tetanus toxoid, or other adjuvant such as C3d (see Dempsey et al., *Science* 271, 348–50 (1996)). The DNA can encode a full length protein or a desired epitopic fragment thereof. Typically, the DNA encodes a protein other than a random peptide, for example, a random peptide showing no more than chance resemblance to a natural protein. In some methods, the DNA encodes a natural protein, and in some methods, the natural protein is a human protein. Natural proteins include naturally occurring allelic variants.

C. Harvesting B Cells

In conventional methods of antibody production using cell fusion, the spleen is usually used as a source of B-cells because B-cells from this source can readily be activated and thereby rendered amenable to fusion. In the present methods, in which no fusion is required, B-cells can be harvested from any tissue source irrespective whether the B-cells from that source are subjectable to activation and cell fusion. Sources of B-cells other than the spleen can be advantageous in some circumstances. For example B-cells from the bone marrow contain potentially interesting populations of B cells that are refractory to this activation. The bone marrow is a source of circulating high affinity antibodies long after germinal center formation of secondary repertoire B cells (Slifka et al. 1995, *J. Virol.* 69, 1895–1902; Takahashi et al, 1998, *J. Exp. Med.* 187, 885–895). Fusion of bone marrow cells does not efficiently access the memory B and plasma cells that encode these high affinity antibodies. Display systems provide a method for recovering the V region sequences of these useful, but otherwise unavailable antibodies. Use of bone marrow as a source of B-cells can also be advantageous in that bone marrow contains a smaller number of B-cell types and random combination of heavy and light chains from this reduced repertoire can lead to more productive combinations.

D. Enrichment for B-Cells

In some methods, B-cells from spleen, bone marrow or other tissue source are subject to an enrichment procedure to select a subpopulation of cells that is enriched for heavy chains of IgG isotype and their natural binding partners. This subpopulation constitutes a secondary repertoire of B cells in which both heavy and light antibody chains have been subject to extensive affinity maturation. Enrichment can be accomplished by antibody mediated panning using anti-IgG antibodies to positively select for secondary repertoire B cells; or using anti-IgM and/or anti-IgD antibodies to negatively select against primary repertoire B cells. Negative selection can also be carried out using antibody mediated compliment lysis (Mishell and Shiigi, *Selected Methods in Cellular Immunology*, W.H. Freeman and Co., New York). Optionally, negative selection can be followed by addition of RNAse-free DNAse to the compliment lysis reaction mixture to prevent bystander killing and cross contamination by primary repertoire DNA released from lysed cells. Flow cytometric sorting can also be used to separate IgG positive B cells from IgM/IgD positive B cells using fluorescently tagged antibodies. These methods select for B-cells bearing IgG heavy chains and their natural partner light chains, both of which have a higher median number of somatic mutations per cell that antibody chains from the total B-cell repertoire.

E. Cloning Nucleic Acids Encoding Antibodies from B Cells

Nucleic acids encoding at least the variable regions of heavy and light chains can be cloned from either immunized or naïve transgenic animals. Nucleic acids can be cloned as genomic or cDNA from lymphatic cells of such animals. No immortalization of such cells is required prior to cloning of immunoglobulin sequences. Usually, mRNA is isolated and amplified by reverse transcription with polydT primers. The cDNA is then amplified using primers to conserved regions of human immunoglobulins. The libraries can be easily enriched for non-mu isotypes using a 3' primer specific for non-mu sequences (e.g., IgG) Typically, the amplified population of light chains comprises at least 100, 1000, 10,000, 100,000 or 1,000,000 different light chains. Likewise, the amplified population of heavy chains comprises at least 100, 1000, 10,000, 100,000 or 1,000,000 different heavy chains. Using IgG primers, typically at least 90, 95 or 99% of amplified heavy chains are of IgG isotype. If B-cell enrichment is performed, typically, at least 50%, 60%, 75%, 90%, 95% or 99% of light chains are the natural partners of IgG heavy chains.

III. Display Libraries

A. Display Packages

A display package, sometimes referred to as a replicable genetic package, is a screenable unit comprising a polypeptide to be screened linked to a nucleic acid encoding the polypeptide. The nucleic acid should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Cells, spores or viruses are examples of display packages. The replicable genetic package can be eukaryotic or prokaryotic. A display library is formed by introducing nucleic acids encoding exogenous polypeptides to be displayed into the genome of the display package to form a fusion protein with an endogenous protein that is normally expressed from the outer surface of the display package. Expression of the fusion protein, transport to the outer surface and assembly results in display of exogenous polypeptides from the outer surface of the genetic package.

A further type of display package comprises a polypeptide bound to a nucleic acid encoding the polypeptide. Such an arrangement can be achieved in several ways. U.S. Pat. No. 5,733,731 describe a method in which a plasmid is engineered to expression a fusion protein comprising a DNA binding polypeptide and a polypeptide to be screened. After expression the fusion protein binds to the vector encoding it though the DNA binding polypeptide component. Vectors displaying fusion proteins are screened for binding to a target, and vectors recovered for further rounds of screening or characterization. In another method, polypeptides are screened as components of display package comprising a polypeptide being screened, and mRNA encoding the polypeptide, and a ribosome holding together the mRNA and polypeptide (see Hanes & Pluckthun, *PNAS* 94, 4937–4942 (1997); Hanes et al., *PNAS* 95, 14130–14135 (1998); Hanes et al, *FEBS Let.* 450, 105–110 (1999); U.S. Pat. No. 5,922,545). mRNA of selected complexes is amplified by reverse transcription and PCR and in vitro transcription, and subject to further screening linked to a ribosome and protein translated from the mRNA. In another method, RNA is fused to a polypeptide encoded by the RNA for screening (Roberts & Szostak, *PNAS* 94, 12297–12302 (1997), Nemoto et al., *FEBS Letters* 414, 405–408 (1997). RNA from complexes surviving screening is amplified by reverse transcription PCR and in vitro transcription. In another methods, antibodies are displayed from the outersurface of yeast (see Boder et al., *PNAS* 97, 10701–10705 (2000); Foote et al., id. at 10679–10681).

The genetic packages most frequently used for display libraries are bacteriophage, particularly filamentous phage, and especially phage M13, Fd and Fl. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wild type copies of coat protein expressed from the helper phage. See, e.g., Garrard, WO 92/09690.

Eukaryotic viruses can be used to display polypeptides in an analogous manner. For example, display of human heregulin fused to gp70 of Moloney murine leukemia virus has been reported by Han, et al., *Proc. Natl. Acad. Sci. USA* 92:9747–9751 (1995). Spores can also be used as display packages. In this case, polypeptides are displayed from the outer surface of the spore. For example, spores from *B. subtilis* have been reported to be suitable. Sequences of coat proteins of these spores are provided by Donovan, et al., *J. Mol. Biol.* 196:1–10 (1987). Cells can also be used as display packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by Ladner, et al., U.S. Pat. No. 5,571,698, and Georgiou, et al., *Nature Biotechnology* 15:29–34 (1997) and references cited therein. For example, the lamB protein of *E. coli* is suitable.

B. Displayed Antibodies

Antibody chains can be displayed in single or double chain form. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner, et al., WO 88/06630; McCafferty, et al., WO 92/01047. Double-chain antibodies are formed by noncovalent association of heavy and light chains or binding fragments thereof. Double chain antibodies can also form by association of two single chain antibodies, each single chain antibody comprising a heavy chain variable domain, a linker and a light chain variable domain. In such antibodies, known as diabodies, the heavy chain of one single-chain antibody binds to the light chain of the other and vice versa, thus forming two identical antigen binding sites (see Hollinger et al., *Proc. Natl. Acad. Sci. USA* 90, 6444–6448 (1993) and Carter & Merchan, *Curr. Op. Biotech.* 8, 449–454 (1997). Thus, phage displaying single chain antibodies can form diabodies by association of two single chain antibodies as a diabody.

The diversity of antibody libraries can arise from obtaining antibody-encoding sequences from a natural source, such as a nonclonal population of immunized or unimmunized B cells. Alternatively, or additionally, diversity can be introduced by artificial mutagenesis of nucleic acids encoding antibody chains before or after introduction into a display vector. Such mutagenesis can occur in the course of PCR or can be induced before or after PCR.

Nucleic acids encoding antibody chains to be displayed optionally flanked by spacers are inserted into the genome of a display package as discussed above by standard recombinant DNA techniques (see generally, Sambrook, et al., *Molecular Cloning, A Laboratory Manual*, 2d ed., Cold Spring Harbor Laboratory Press, Cold Spring Harbor, N.Y., 1989, incorporated by reference herein). The nucleic acids are ultimately expressed as antibody chains (with or without spacer or framework residues). In phage, bacterial and spore vectors, antibody chains are fused to all or part of the an outer surface protein of the replicable package. Libraries often have sizes of about $10^3$, $10^4$, $10^6$, $10^7$, $10^8$ or more members.

Double-chain antibody display libraries represent a species of the display libraries discussed above. Production of such libraries is described by, e.g., Dower, U.S. Pat. No. 5,427,908; U.S. Pat. No. 5,580,717, Huse WO 92/06204; Huse, in Antibody Engineering, (Freeman 1992), Ch. 5; Kang, WO 92/18619; Winter, WO 92/20791; McCafferty, WO 92/01047; Hoogenboom WO 93/06213; Winter, et al., *Annu. Rev. Immunol.* 12:433–455 (1994); Hoogenboom, et al., *Immunological Reviews* 130:41–68 (1992); Soderlind, et al., *Immunological Reviews* 130:109–124 (1992). For example, in double-chain antibody phage display libraries, one antibody chain is fused to a phage coat protein, as is the case in single chain libraries. The partner antibody chain is complexed with the first antibody chain, but the partner is not directly linked to a phage coat protein. Either the heavy or light chain can be the chain fused to the coat protein. Whichever chain is not fused to the coat protein is the partner chain. This arrangement is typically achieved by incorporating nucleic acid segments encoding one antibody chain gene into either gIII or gVIII of a phage display vector to form a fusion protein comprising a signal sequence, an antibody chain, and a phage coat protein. Nucleic acid segments encoding the partner antibody chain can be inserted into the same vector as those encoding the first antibody chain. Optionally, heavy and light chains can be inserted into the same display vector linked to the same promoter and transcribed as a polycistronic message. Alternatively, nucleic acids encoding the partner antibody chain can be inserted into a separate vector (which may or may not be a phage vector). In this case, the two vectors are expressed in the same cell (see WO 92/20791). The sequences encoding the partner chain are inserted such that the partner chain is linked to a signal sequence, but is not fused to a phage coat protein. Both antibody chains are expressed and exported to the periplasm of the cell where they assemble and are incorporated into phage particles.

Typically, only the variable region of human light and heavy chains are cloned from a nonhuman transgenic animal. In such instances, the display vector can be designed to express heavy and light chain constant regions or fragments thereof in-frame with heavy and light chain variable regions expressed from inserted sequences. Typically, the constant regions are naturally occurring human constant regions; a few conservative substitutions can be tolerated but are not preferred. In a Fab fragment, the heavy chain constant region usually comprises a $C_H1$ region, and optionally, part or all of a hinge region, and the light chain constant region is an intact light chain constant region, such as $C_\kappa$ or $C_\lambda$. Choice of constant region isotype depends in part on whether complement-dependent cytotoxicity is ultimately required. For example, human isotypes IgG1 and IgG4 support such cytotoxicity whereas IgG2 and IgG3 do not. Alternatively, the display vector can provide nonhuman constant regions. In such situations, typically, only the variable regions of antibody chains are subsequently subcloned from display vectors and human constant regions are provided by an expression vector in frame with inserted antibody sequences.

In a further variation, both constant and variable regions can be cloned from the transgenic animal. For example, heavy chain variable regions can be cloned linked to the $C_H1$ constant region and light chain variable regions linked to an intact light chain constant region for expression of Fab fragments. In this situation, display vectors need not encode constant regions.

Antibody encoding sequences can be obtained from lymphatic cells of a nonhuman transgenic animal. Typically, the cells have been immunized, in which case immunization can be performed in vivo before harvesting cells, or in vitro after harvesting cells, or both. Spleen cells of an immunized animal are a preferred source material. Immunization can be performed with any type of antigen. Antigens are often human proteins.

Rearranged immunoglobulin genes can be cloned from genomic DNA or mRNA. For the latter, mRNA is extracted from the cells and cDNA is prepared using reverse transcriptase and poly dT oligonucleotide primers. Primers for cloning antibody encoding sequences are discussed by Larrick, et al., *Bio/Technology* 7:934 (1989), Danielsson & Borrebaceick, in Antibody Engineering: A Practical Guide (Freeman, N.Y., 1992), p. 89 and Huse, id. at Ch. 5.

Repertoires of antibody fragments have been constructed by combining amplified $V_H$ and $V_L$ sequences together in several ways. Light and heavy chains can be inserted into different vectors and the vectors combined in vitro (Hogrefe, et al., *Gene* 128:119–126 (1993)) or in vivo (Waterhouse, et at, *Nucl. Acids. Res.* :2265–66 (1993)). Alternatively, the light and heavy chains can be cloned sequentially into the same vector (Barbas, et al., *Proc. Natl. Acad. Sci. USA* 88: 7987–82 (1991)) or assembled together by PCR and then inserted into a vector (Clackson, et al, *Nature* 352:624–28 (1991)). Repertoires of heavy chains can be also be combined with a single light chain or vice versa. Hoogenboom, et al., *J. Mol. Biol.* 227: 381–88 (1992).

Typically, segments encoding heavy and light antibody chains are subcloned from separate populations of heavy and light chains resulting in random association of a pair of heavy and light chains from the populations in each vector. Thus, modified vectors typically contain combinations of heavy and light chain variable region not found in naturally occurring antibodies. Some of these combinations typically survive the selection process and also exist in the polyclonal libraries described below.

Some exemplary vectors and procedures for cloning populations of heavy chain and light chain encoding sequences have been described by Huse, WO 92/06204. Diverse populations of sequences encoding $H_c$ polypeptides are cloned into M13IX30 and sequences encoding $L_c$ polypeptides are cloned into M13IX11. The populations are inserted between the XhoI-SeeI or StuI restriction enzyme sites in M13IX30 and between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the $H_c$ and $L_c$ encoding sequences and their associated vector sequences. The two pairs are symmetrically orientated about the cloning site so that only the vector proteins containing the sequences to be expressed are exactly combined into a single vector.

Optionally, antibody-encoding sequences can be subjected to artificial mutagenesis before screening to augment the effect of natural somatic mutations. Mutagenesis can be performed by amplifying nucleic acids encoding antibody chains under conditions of mutagenic PCR, or by using mutagenic primers or using uracil templates. Optionally, nucleic acids encoding antibodies can be shuffled with each other, and/or random oligonucleotides as described by Stemmer, U.S. Pat. No. 6,117,679.

Others exemplary vectors and procedures for cloning antibody chains into filamentous phage are described in the present Examples.

IV. Enrichment for Polyvalent Display Members

A. Theory of the Method

That a display library should preferably be enriched for members displaying multiple copies of a polypeptide is a finding apparently at variance with some early reports in the field. See, e.g., Cwirla et al., supra. Most work on display libraries has been done by inserting nucleic acid libraries into pIII or pVIII of filamentous phage. Because pIII is present in 4 or 5 copies per phage and pVIII is present in several hundred copies per phage, some early reports assumed that foreign polypeptides would be displayed in corresponding numbers per phage. However, more recent work has made clear that the actual number of copies of polypeptide displayed per phage is well below theoretical expectations, perhaps due to proteolytic cleavage of polypeptides. Winter, et al., *Ann. Rev. Immunol.* 12:433–55 (1994). Further, vector systems used for phage display often encode two copies of a phage coat protein, one of which is a wild type protein and the other of which forms a fusion protein with exogenous polypeptides to be displayed. Both copies are expressed and the wild type coat protein effectively dilutes the representation of the fusion protein in the phage coat.

A typical ratio of displayed Fabs per phage, when Fabs are expressed from pVIII of a filamentous phage is about 0.2. The probability, Pr(y), of y Fabs being expressed on a phage particle if the average frequency of expression per phage is n is given by the Poisson probability distribution $$Pr(y)=e^{-n}n^y/y!$$

For a frequency of 0.2 Fabs per phage, the probabilities for the expression of 0, 1, 2, and 3 Fabs per phage are 0.82, 0.16, 0.016, and 0.0011. The proportion of phage particle displaying two or more Fabs is therefore only 0.017.

The low representation of members displaying more than one Fab fragment in a phage display library can be related to the result that only a small percentage of such library members are capable of surviving affinity selection to immobilized binding partners. A library was constructed in which all members encoded the same Fab fragment which was known to have a high binding affinity for a particular target. It was found that even under the mildest separation conditions for removal of free from bound phage, it was not possible to bind more than about 0.004 of the total phage. This proportion is the same order of magnitude as the proportion of phage displaying at least two Fab fragments, suggesting that phage must display at least two Fab fragments to bind to immobilized target. Probably shear forces dissociate phage displaying only a single Fab fragment from the solid phase. Therefore, at least two binding events are necessary for a phage-Fab library member to be bound to immobilized target with sufficient avidity to enable separation of the bound from the free phage. It is expected that similar constraints apply in other forms of display library.

Therefore, a preferred strategy of the present invention is to enrich for library members binding to a receptor fused to displayed antibody chains before the library is contacted with a screening target. It is believed that the prescreening enriches for library members displaying at least two copies of a tag and therefore at least two copies of an antibody chain linked to the tag. Library members lacking two or more antibody chains, which are incapable of surviving affinity selection via binding through displayed antibody chain to any immobilized screening target, but which nevertheless can survive affinity selection by formation of multiple nonspecific bonds to such a target or its support, are thus substantially eliminated before screening of the library to the target is performed (see WO98/47343).

B. Tags and Receptors

The above strategy is effected by the use of paired tags and receptors. A tag can any peptide sequence that is common to different members of the library, heterologous to the display package, and fused to a polypeptide displayed from the display package. For example, a tag can be a synthetic peptide sequence, a constant region of an antibody. In some methods, single chain antibodies are displayed in which only the light or heavy chain variable region but not both varies between members. In such situations, among others, the variable region that is the same in different members can be used as a tag. Suitable tag-receptor combinations include epitope and antibody; for example, many high affinity hexapeptide ligands are known for the anti-dynorphin mAb 32.39, (see Barrett et al, *Neuropeptides* 6:113–120 (1985) and Cull et al., *Proc. Nat'l Acad. Sci. USA* 89:1865–1869 (1992)) and a variety of short peptides are known to bind the MAb 3E7 (Schatz, *Biotechnology* 11:1138–43 (1993)). Another combination of tag and antibody is described by Blanar & Rutter, *Science* 256:1014–1018 (1992).

Another example of a tag-receptor pair is the FLAG™ system (Kodak). The FLAG™ molecular tag consists of an eight amino acid FLAG peptide marker that is linked to the target binding moiety. A 24 base pair segment containing a FLAG coding sequence can be inserted adjacent to a nucleotide sequence that codes for the displayed polypeptide. The FLAG peptide includes an enterokinase recognition site that corresponds to the carboxyl-terminal five amino acids. Capture moieties suitable for use with the FLAG peptide marker include antibodies Anti-FLAG M1, M2 and M5, which are commercially available.

Still other combinations of peptides and antibodies can be identified by conventional phage display methods. Further suitable combinations of peptide sequence and receptor include polyhistidine and metal chelate ligands containing $Ni^{2+}$ immobilized on agarose (see Hochuli in Genetic Engineering: Principles and Methods (ed. J K Setlow, Plenum Press, NY), Ch. 18, pp. 87–96 and maltose binding protein (Maina, et al., *Gene* 74:365–373 (1988)).

Receptors are often labeled with biotin allowing the receptors to be immobilized to an avidin-coated support. Biotin labeling can be performed using the biotinylating enzyme, BirA (see, e.g., Schatz, *Biotechnology* 11:1138–43 (1993)).

A nucleic acid sequence encoding a tag is inserted into a display vector in such a manner that the tag is expressed as part of the fusion protein containing the polypeptide to be displayed and an outer surface protein of the display package. The relative ordering of these components is not critical provided that the tag and polypeptide to be displayed are both exposed on the outer surface of the package. For example, the tag can be placed between the outer surface protein and the displayed polypeptide or at or near the exposed end of the fusion protein.

In display packages displaying Fabs, a tag can be fused to either the heavy or the light Fab chain, irrespective which chain is linked to a phage coat protein. Optionally, two different tags can used one fused to each of the heavy and light chains. One tag is usually positioned between the phage coat protein and antibody chain linked thereto, and the other tag is positioned at either the N- or C-terminus of the partner chain.

C. Selection of Polyvalent Library Members Members

Selection of polyvalent library members is performed by contacting the library with the receptor for the tag component of library members. Usually, the library is contacted with the receptor immobilized to a solid phase and binding of library members through their tag to the receptor is allowed to reach equilibrium. The complexed receptor and library members are then brought out of solution by addition of a solid phase to which the receptor bears affinity (e.g., an avidin-labeled solid phase can be used to immobilize biotin-labeled receptors). Alternatively, the library can be contacted with receptor in solution and the receptor subsequently immobilized. The concentration of receptor should usually be at or above the Kd of the tag/receptor during solution phase binding so that most displayed tags bind to a receptor at equilibrium. When the receptor-library members are contacted with the solid phase only the library members linked to receptor through at least two displayed tags remain bound to the solid phase following separation of the solid phase from library members in solution. Library members linked to receptor through a single tag are presumably sheared from the solid phase during separation and washing of the solid phase. After removal of unbound library members, bound library members can be dissociated from the receptor and solid phase by a change in ionic strength or pH, or addition of a substance that competes with the tag for binding to the receptor. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The average number of polypeptides per library member selected by this method is affected by a number of factors. Decreasing the concentration of receptor during solution-phase binding has the effect of increasing the average number of polypeptides in selected library members. An increase in the stringency of the washing conditions also increases the average number of polypeptides per selected library member. The physical relationship between library members and the solid phase can also be manipulated to increase the average number of polypeptides per library member. For example, if discrete particles are used as the solid phase, decreasing the size of the particles increases the steric constraints of binding and should require a higher density of polypeptides displayed per library member.

For Fab libraries having two tags, one linked to each antibody chain, two similar rounds of selection can be performed, with the products of one round becoming the starting materials for the second round. The first round of selection is performed with a receptor to the first tag, and the second round with a receptor to the second tag. Selecting for both tags enriches for library members displaying two copies of both heavy and light antibody chains (i.e., two Fab fragments).

Although the theory underlying the above methods of polyvalent enrichment is believed to be correct, the practice of the invention is in no way dependent on the correctness of this theory. Prescreening a display library for members binding to a tag, followed by screening those members for binding to a target results in a higher degree of enrichment for members with affinity for a target than if the method is performed without the prescreening step. Thus, the method can be practiced as described, and achieve the desired result of highly enriched libraries without any understanding of the underlying mechanism.

D. Selection For Affinity to Target

Library members displaying antibody chains, with or without prescreening to a tag receptor, are screened for binding to a target. The target can be any molecule of interest for which it is desired to identify binding partners. The target should lack specific binding affinity for the tag(s) (if used), because in this step it is the displayed polypeptides being screened, and not the tags that bind to the target. The screening procedure at this step is closely analogous to the prescreening step except that the affinity reagent is a target of interest rather than a receptor to a tag. The enriched library members are contacted with the target which is usually labeled (e.g., with biotin) in such a manner that allows its immobilization. Binding is allowed to proceed to equilibrium and then target is brought out of solution by contacting with the solid phase in a process known as panning (Parmley & Smith, *Gene* 73:305–318 (1988)). Library members that remain bound to the solid phase throughout the selection process do so by virtue of polyvalent bonds between them and immobilized target molecules. Unbound library members are washed away from the solid phase. In some methods, library members are screened by binding to cells displaying a receptor of interest. Thereafter, the entire cell population can be recovered by centrifugation or fractions bound to phage can be isolated by labelling with a phage specific antibody and separating labelled phage bound to cells using magnetic beads or FACS™. Screening can also be performed for membrane bound proteins using a preparation of phospholipid bearing the antigen. Complexes between the phospholipid and phage can be precipitated using wheat germ agluttin to bind lectins in the phospholipid. Alternatively, phospholipids can be labelled with biotin, and complexes precipitated using avidin-labelled beads.

Usually, library members are subject to amplification before performing a subsequent round of screening. Often, bound library members can be amplified without dissociating them from the support. For example, gene VIII phage library members immobilized to beads, can be amplified by immersing the beads in a culture of *E. coli*. Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members are now enriched for antibody chains having specific affinity for the target of interest (and for polyvalent display members if a prescreening step has been performed). After subsequent amplification, to produce a secondary library, the secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been achieved. In some methods, some but not all cycles of affinity screening are preceded by polyvalent enrichment. For example, a first cycle can be performed with affinity enrichment for a target alone, second and third cycles with both polyvalent enrichment and affinity enrichment, and a fourth cycle with just enrichment to the target. Two cycles of polyvalent enrichment are often sufficient.

In a variation, affinity screening to a target is performed in competition with a compound that resembles but is not identical to the target. Such screening preferentially selects for library members that bind to a target epitope not present on the compound. In a further variation, bound library members can be dissociated from the solid phase in competition with a compound having known crossreactivity with a target for an antigen. Library members having the same or similar binding specificity as the known compound relative to the target are preferentially eluted. Library members with affinity for the target through an epitope distinct from that recognized by the compound remain bound to the solid phase.

Discrimination in selecting between antibody chains of different monovalent affinities for the target is affected by the valency of library members and the concentration of target during the solution phase binding. Assuming a minimum of i labeled target molecules must be bound to a library member to immobilize it on a solid phase, then the probability of immobilization can be calculated for a library member displaying n polypeptides. From the law of mass action, the bound/total antibody chain fraction, F, is K[targ]/(1+K[targ]), where [targ] is the total target concentration in solution. Thus, the probability that i or more displayed antibody chains per library member are bound by the labeled target is given by the binomial probability distribution:

$$\sum_{n}^{y=i} (n!/[y!(n-y)!]F^y(1-F)^{n-y}$$

As the probability is a function of K and [target], multivalent display members each having a monovalent affinity, K, for the target can be selected by varying the concentration of target. The probabilities of solid-phase immobilization for i=1, 2, or 3, with library members exhibiting monovalent affinities of 0.1/[Ag], 1/[Ag], and 10/[Ag], and displaying n polypeptides per member are:

| n | K = 0.1/[targ] | K = 1/[targ] | K = 10/[targ] |
|---|---|---|---|
| Probability of Immobilization (i = 1) | | | |
| 1 | 0.09 | 0.5 | 0.91 |
| 2 | 0.17 | 0.75 | 0.99 |
| 3 | 0.25 | 0.875 | |
| 4 | 0.32 | 0.94 | |
| 5 | 0.38 | 0.97 | |
| 6 | 0.44 | 0.98 | |
| 7 | 0.49 | 0.99 | |
| 8 | 0.53 | | |
| 9 | 0.58 | | |
| 10 | 0.61 | | |
| 20 | 0.85 | | |
| 50 | 0.99 | | |
| Probability of Immobilization (i = 2) | | | |
| 2 | 0.008 | 0.25 | 0.83 |
| 3 | 0.023 | 0.50 | 0.977 |
| 4 | 0.043 | 0.69 | 0.997 |
| 5 | 0.069 | 0.81 | |
| 6 | 0.097 | 0.89 | |
| 7 | 0.128 | 0.94 | |

-continued

| n | K = 0.1/[targ] | K = 1/[targ] | K = 10/[targ] |
|---|---|---|---|
| 8 | 0.160 | 0.965 | |
| 9 | 0.194 | 0.98 | |
| 20 | 0.55 | | |
| 50 | 0.95 | | |
| Probability of Immobilization (i = 3) | | | |
| 3 | 0.00075 | 0.125 | 0.75 |
| 4 | 0.0028 | 0.31 | 0.96 |
| 5 | 0.0065 | 0.50 | 0.99 |
| 6 | 0.012 | 0.66 | |
| 7 | 0.02 | 0.77 | |
| 8 | 0.03 | 0.855 | |
| 9 | 0.0415 | 0.91 | |
| 10 | 0.055 | 0.945 | |
| 12 | 0.089 | 0.98 | |
| 14 | 0.128 | 0.99 | |
| 20 | 0.27 | | |
| 50 | 0.84 | | |

The above tables show that the discrimination between immobilizing polypeptides of different monovalent binding affinities is affected by the valency of library members (n) and by the concentration of target for the solution binding phase. Discrimination is maximized when n (number of polypeptides displayed per phage) is equal to i (minimum valency required for solid phase binding). Discrimination is also increased by lowering the concentration of target during the solution phase binding. Usually, the target concentration is around the Kd of the polypeptides sought to be isolated. Target concentration of $10^{-8}$–$10^{-10}$ M are typical.

Enriched libraries produced by the above methods are characterized by a high proportion of members encoding polypeptides having specific affinity for the target. For example, at least 10, 25, 50, 75, 80, 90, 95, or 99% of members encode antibody chains having specific affinity for the target. In some libraries, at least 10, 25, 50, 75, 80, 90, 95, or 99% of members have affinities of at least $10^8$ $M^{-1}$, $10^9$ $M^{-1}$ or $10^{10}$ $M^{-1}$, $10^{11}$ $M^{-1}$, $10^{12}$ $M^{-1}$, $10^{-13}$ $M^{-1}$. In some libraries, at least 90, 95 or 99% of nucleic acids encoding antibody heavy chains encode heavy chains of IgG isotype. In some libraries, the nucleic acids encoding heavy chains of members having specific affinity for the target have a median of at least 5, 10, 14, 15, 20 or 25 somatic nucleotide mutations per chain. In some libraries, the nucleic acids encoding light chains of members having specific affinity for the target have a median of a least of 2, 3, 5, 10, 15, 20 or 25 somatic nucleotide mutations per chain. In libraries of double chain antibodies, a pair of segments encoding heavy and light chains of an antibody is considered a library member. The exact percentage of members having affinity for the target depends whether the library has been amplified following selection, because amplification increases the representation of genetic deletions. However, among members with full-length polypeptide coding sequences, the proportion encoding polypeptides with specific affinity for the target is very high (e.g., at least 50, 75, 80, 90, 95 or 99% having affinity of $10^8$ $M^{-1}$, $10^9$ $M^{-1}$, $10^{10}$ $M^{-1}$, $10^{11}$ $M^{-1}$, $10^{12}$ $M^{-12}$, $10^{-13}$ $M^{-1}$ Not all of the library members that encode an antibody chain with specific affinity for the target necessarily display the antibody chain. For example, in a library in which 95% of members with full-length coding sequences encode antibody chains with specific affinity for the target, usually fewer than half actually display the antibody chain. Usually, such libraries have at least 4, 10, 20, 50, 100, 1000, 10,000 or 100,000 different coding sequences. Usually, the representation of any one such coding sequences is no more than 50%, 25% or 10% of the total coding sequences in the library.

E. Variations

1. Generation of Normalized Display Libraries

A complex antigen, such as a protein molecule, comprises multiple distinct non-overlapping epitopes. However, the individual epitopes of a given antigen are not accessed with equal frequency by the humoral immune system. Instead, particular epitopes can dominate an antibody response. This can result in biased display libraries and biased polyclonal reagents. However, the selection process described above can be manipulated so as to normalize the display library and correct for this natural bias.

Normalized libraries are generated in an iterative process whereby a first non-normalized library is generated, and a non-normalized polyclonal reagent is produced. This non-normalized polyclonal reagent is then mixed with derivatized (e.g. biotinylated) antigen at near stoichiometric concentrations to produce a treated antigen preparation. The non-normalized polyclonal reagent comprises a high concentration of antibody binding species that recognize (and mask) dominant epitopes. Antibody binding species recognizing rare epitopes are found at lower concentrations in the non-normalized polyclonal reagent. For this reason, the treated antigen preparation is depleted of unmasked dominant epitopes relative to an untreated antigen preparation. If this treated antigen preparation is then used to select a new display library; the new library is relatively enriched for antibodies that are not blocked by antibodies that recognize dominant epitopes. Thus the new library, and polyclonal reagents generated from the new library, are normalized. These normalized reagents are useful for characterization of novel antigens in immunohistochemical and functional assays where epitope dominance could otherwise lead to the generation of reagents that missed particular interesting epitopes. Such rare epitopes in some instances represent neutralizing or agonist epitopes that reveal the biological role of the antigen and the usefulness of antibody reagents for intervening in disease processes mediated by the antigen. Rare epitopes in some instances also reveal otherwise hidden patterns of gene expression due to cell type specific splicing or processing of transcripts or gene products.

The concentration of non-normalized polyclonal reagent used to treat the antigen preparation can be selected using a model antigen. The model antigen can be, for example, an equimolar mixture of four different antigens with different immunogenicities (e.g. keyhole limpet hemocyanin, tetanus toxoid, ovalbumin, and hen eggwhite lysozyme). Mice are immunized with this mixture and an initial non-normalized display library is made from spleen RNA and selected using an equimolar mixture of the same four antigens at a concentration of 1 to 10 nM. Prior to use, the selecting antigens are biotinylated to allow for selection on avidin coated magnetic beads (Binding pairs other than biotin and avidin can be used to derivative the antigen and magnetic beads respectively. Antibody antigen pairs are suitable, particularly antibodies to small molecule hatpins that can be readily used to derivative the antigen. Antibodies to the antigen itself can also be used, and if these antibodies themselves are biotinylated directly, avidin coated magnetic beads can be used for selection. Because monoclonal antibodies bias the selection against cross-blocking epitopes, it is in some cases desirable to use a polyclonal reagent for this purpose). This initial library is then used to generate a non-normalized polyclonal reagent. The non-normalized polyclonal reagent is then used to treat the biotinylated antigen mixture. Five different preparations of treated antigen are prepared at molar ratios of antigen to polyclonal of 1:10, 1:3, 1:1, 3:1, and 1:10. Each of these five treated antigen preparations is then used to select new display libraries made from the original immunized spleen RNA. Individual clones from the original non-normalized library and the five new normalized libraries are then tested in microtiter, or western dot blot formats for reactivity with each of four individual molecules used in the antigen mixture. The frequency of clonal reactivity to each of the four different antigens will be skewed towards the more immunogenic antigens such as keyhole limpet hemocyanin, and away from less immunogenic antigens such as ovalbumin, in the non-normalized libraries. In optimally normalized libraries the frequencies of clonal reactivity for each of the four antigens will be closer to each other. Thus, the resulting data can be used to select the optimal ratio of antigen to polyclonal for depleting clones recognizing dominant epitopes, and enriching for biding species recognizing rare epitopes.

2. Selection of Display Libraries for Binding to Cell Surface Antigens

It is sometimes desirable to select display libraries for recognition of cell surface antigens that cannot be easily isolated and purified. Often, purified antigen is either unavailable, or the purification process alters the antigen so as to mask or destroy the desired epitope found on natural cells. It is then useful to be able to select phage libraries directly for recognition of antigen on whole cells. Phage display particles from libraries generated from mice immunized with whole cells can be mixed directly with the same, or different whole cells, and the bound phage separated from unbound phage by precipitation or filtration. Non-specific binding can be reduced by prior clearing with a cell preparation that does not express the desired antigen target or epitope target. For example, mice are immunized with whole cells that have been transfected with a gene encoding an antigen target expressed on the cell surface. The RNA from the immunized mouse is then used to generate a display library, which is first exposed to the parent un-transfected cell line, precleared, then exposed to the transfected cell line, and bound phage particles recovered. Alternatively, the mouse is immunized with whole human cells from tissue affected by a particular disease such as cancer or rheumatoid arthritis. The resulting display library could then be precleared using cells from unaffected tissue to obtain a library enriched for antigens associated with the diseased cells.

The library can also be enriched for desired binding species by simultaneous cross-blocking followed by differential selection. For example, mice are immunized with whole human peripheral blood lymphocytes (PBL), and the immunized spleen RNA used to generate a library. The library is then selected by exposure to whole human PBL that is treated with a biotinylated antibody to a specific desired PBL subset such as the T cell antigen CD4. Phage particles binding to the CD4 positive subset are then selected with avidin coated magnetic beads. Alternatively, other separation techniques, such as flow cytometric sorting, can be used to enrich for binding to specific cell subsets. In this case the antibody to the specific cell subset would either be directly conjugated to a fluorescent dye, or avidin conjugated fluorescent dye would be used as a second step reagent to mark the cells.

Solubilized unpurified antigen preparations can also be used to select display libraries for binding to cell surface antigens. Whole intact cells are first chemically modified to attach biotin (or some other derivative) specifically to proteins accessible on the cell surface. The cells are then disrupted with a mild detergent and/or mild proteolysis to solubilize the bound proteins. The crude solubilized protein preparation can then be used directly to select a display library using avidin (or other binding molecule recognizing the derivatized antigens) coated magnetic beads. The crude preparation can also be further purified prior to the selection step. This method may be advantageous because it provides for selection of the library based on monovalent affinity, as described above.

V. Subcloning Antibody Chains into an Expression Vector

Screening of display library members typically results in a subpopulation of library members having specific affinity for a target. There are a number of options at this point. In some methods, clonal isolates of library members are obtained, and these isolates used directly. In other methods, clonal isolates of library member are obtained, and DNA encoding antibody chains amplified from each isolate. Typically, heavy and light chains are amplified as components of the same DNA molecule before transfer to an expression vector, such that combinations of heavy and light chain existing in the display vector are preserved in the expression vector. For displayed antibody chains that include both human variable regions and human constant regions, typically nucleic acids encoding both the variable region and constant region are subcloned. In other methods, nucleic acids encoding antibody chains are amplified and subcloned en masse from a pool of library members into multiple copies of an expression vector without clonal isolation of individual members.

The subcloning process is now described in detail for transfer of a mixed population of nucleic acids from a display vector to an expression vector. Essentially the same process can be used on nucleic acids obtained from a clonal isolate of an individual display vector.

Nucleic acids encoding antibody chains to be subcloned can be excised by restriction digestion of flanking sequences or can be amplified by PCR using primers to sites flanking the coding sequences. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila, et al., *Nucleic Acids Res.* 19:967 (1991); Eckert, et al., *PCR Methods and Applications* 1:17 (1991); PCR (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. For Fab libraries, if heavy and light chains are inserted adjacent or proximate to each other in a display vector, the two chains can be amplified or excised together. For some Fab libraries, only the variable domains of antibody chain(s) are excised or amplified. If the heavy or light chains of a Fab library are excised or amplified separately, they can subsequently be inserted into the same or different expression vectors.

Having excised or amplified fragments encoding displayed antibody chains, the fragments are usually size-purified on an agarose gel or sucrose gradient. Typically, the fragments run as a single sharp full-length band with a smear at lower molecular corresponding to various deleted forms of coding sequence. The band corresponding to full-length coding sequences is removed from the gel or gradient and these sequences are used in subsequent steps.

The next step is to join the nucleic acids encoding full-length coding sequences to an expression vector thereby creating a population of modified forms of the expression vector bearing different inserts. This can be done by conventional ligation of cleaved expression vector with a mixture of inserts cleaved to have compatible ends. Alternatively, the use of restriction enzymes on insert DNA can be avoided. This method of cloning is beneficial because naturally encoded restriction enzyme sites may be present within insert sequences, thus, causing destruction of the sequence when treated with a restriction enzyme. For cloning without restricting, a mixed population of inserts and linearized vector sequences are treated briefly with a 3' to 5' exonuclease such as T4 DNA polymerase or exonuclease III. See Sambrook, et al., Molecular Cloning, A Laboratory Manual (2nd Ed., CSHP, New York 1989). The protruding 5' termini of the insert generated by digestion are complementary to single-stranded overhangs generated by digestion of the vector. The overhangs are annealed, and the re-annealed vector transfected into recipient host cells. The same result can be accomplished using 5' to 3' exonucleases rather than a 3' to 5' exonuclease.

Preferably, ligation of inserts to expression vector is performed under conditions that allow selection against re-annealed vector and uncut vector. A number of vectors containing conditional lethal genes that allow selection against re-annealed vector under nonpermissive conditions are known. See, e.g., Conley & Saunders, *Mol. Gen. Genet.* 194:211–218 (1984). These vectors effectively allow positive selection for vectors having received inserts. Selection can also be accomplished by cleaving an expression vector in such a way that a portion of a positive selection marker (e.g., antibiotic resistance) is deleted. The missing portion is then supplied by full-length inserts. The portion can be introduced at the 3' end of polypeptide coding sequences in the display vector, or can be included in a primer used for amplification of the insert. An exemplary selection scheme, in which inserts supply a portion of a tetracycline-resistance gene promoter deleted by HindIII cleavage of a pBR-derivative vector, is described in Example 14.

The choice of expression vector depends on the intended host cells in which the vector is to be expressed. Typically, the vector includes a promoter and other regulatory sequences in operable linkage to the inserted coding sequences that ensure the expression of the latter. Use of an inducible promoter is advantageous to prevent expression of inserted sequences except under inducing conditions. Inducible promoters include arabinose, lacZ, metallothionein promoter or a heat shock promoter. Cultures of transformed organisms can be expanded under noninducing conditions without biasing the population for coding sequences whose expression products are better tolerated by the host cells. The vector may also provide a secretion signal sequence position to form a fusion protein with polypeptides encoded by inserted sequences, although often inserted polypeptides are linked to a signal sequences before inclusion in the vector. Vectors to be used to receive sequences encoding antibody light and heavy chain variable domains sometimes encode constant regions or parts thereof that can be expressed as fusion proteins with inserted chains thereby leading to production of intact antibodies or fragments thereof. Typically, such constant regions are human. Conservative mutations although not preferred can be tolerated. For example, if display packages display a heavy chain variable region linked to a $C_H1$ constant region and a light chain variable region linked to an intact light chain constant region, and the complete antibody chains are transferred from the display vector to the expression vector, then the expression vector can be designed to encode human heavy chain constant region hinge, $C_H2$ and $C_H3$ regions in-frame with the $C_H1$ region of the inserted heavy chain nucleic acid thereby resulting in expression of an intact antibody. Of course, many minor variations are possible as to precisely which segment of the human heavy chain constant region is supplied by the display package and which by the expression vector. For example, the display package can be designed to include a $C_H1$ region, and some or all of the hinge region. In this case, the expression vector is designed to supply the residual portion of the hinge region (if any) and the $C_H2$ and $C_H3$ regions for expression of intact antibodies.

*E. coli* is one prokaryotic host useful particularly for cloning the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e g, an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, are also used for expression. *Saccharomyces* is a preferred host, with suitable vectors having expression control sequences, such as promoters, including 3-phosphoglycerate kinase or other glycolytic enzymes, and an origin of replication, termination sequences and the like as desired. Insect cells in combination with baculovirus vectors can also be used.

Mammalian tissue cell culture can also be used to express and produce the polypeptides of the present invention (see Winnacker, From Genes to Clones (VCH Publishers, N.Y., N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include expression control sequences, such as an origin of replication, a promoter, and an enhancer (Queen, et al., *Immunol. Rev.* 89:49–68 (1986), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra).

Once expressed, collections of antibodies are purified from culture media and host cells. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like (see generally Scopes, Protein Purification (Springer-Verlag, N.Y., 1982)).

The above methods result in novel libraries of nucleic acid sequences encoding antibody chains having specific affinity for a chosen target. The libraries of nucleic acids typically have at least 5, 10, 20, 50, 100, 1000, $10^4$ or $10^5$ different members. Usually, no single member constitutes more than 25 or 50% of the total sequences in the library. Typically, at least 25, 50%, 75, 90, 95, 99 or 99.9% of library members encode antibody chains with specific affinity for the target molecules. In the case of double chain antibody libraries, a pair of nucleic acid segments encoding heavy and light chains respectively is considered a library member. The nucleic acid libraries can exist in free form, as components of any vector or transfected as a component of a vector into host cells. In some libraries, at least 90, 95 or 99% of nucleic acids encoding antibody heavy chains encode heavy chains of IgG isotype. In some libraries, the nucleic acids encoding heavy chains of members having specific affinity for the target have a median of at least 5, 10, 14, 15, 20 or 25 somatic nucleotide mutations per chain. In some libraries, the nucleic acids encoding light chains of members having specific affinity for the target have a median of a least 2, 3, 5, 10, 15, 20 or 25 somatic nucleotide mutations per chain.

The nucleic acid libraries can be expressed to generate polyclonal libraries of antibodies having specific affinity for a target. The composition of such libraries is determined from the composition of the nucleotide libraries. Thus, such libraries typically have at least 5, 10, 20, 50, 100, 1000, $10^4$ or $10^5$ members with different amino acid composition. Usually, no single member constitutes more than 25 or 50% of the total polypeptides in the library. The percentage of antibody chains in an antibody chain library having specific affinity for a target is typically lower than the percentage of corresponding nucleic acids encoding the antibody chains. The difference is due to the fact that not all polypeptides fold into a structure appropriate for binding despite having the appropriate primary amino acid sequence to support appropriate folding. In some libraries, at least 25, 50, 75, 90, 95, 99 or 99.9% of antibody chains have specific affinity for the target molecules. Again, in libraries of multi-chain antibodies, each antibody (such as a Fab or intact antibody) is considered a library member. In some libraries, at least 90, 95 or 99% of heavy chains are of IgG isotype. In some libraries, the heavy chains having specific affinity for the target have a median of at least 1, 2, 3, 4, 5, 7, 10, 12, 15, or 20 somatic amino acid mutations per chain. In some libraries, the light chains having specific affinity for the target have a median of a least of 1, 2, 3, 5, 10, 12, 15, 20 somatic amino acid mutations per chain. The different antibody chains differ from each other in terms of fine binding specificity and affinity for the target. Some such libraries comprise members binding to different epitopes on the same antigen. Some such libraries comprises at least two members that bind to the same antigen without competing with each other.

Polyclonal libraries of human antibodies resulting from the above methods are distinguished from natural populations of human antibodies both by the high percentages of high affinity binders in the present libraries, and in that the present libraries typically do not show the same diversity of antibodies present in natural populations. The reduced diversity in the present libraries is due to the nonhuman transgenic animals that provide the source materials not including all human immunoglobulin genes. For example, some polyclonal antibody libraries are free of antibodies having lambda light chains. Some polyclonal antibody libraries of the invention have antibody heavy chains encoded by fewer than 10, 20, 30 or 40 $V_H$ genes. Some polyclonal antibody libraries of the invention have antibody light chains encoded by fewer than 10, 20, 30 or 40 $V_L$ genes.

VI. Diagnostic and Therapeutics Uses

Human antibodies produced by the invention have a number of treatment (both therapeutic and prophylactic), diagnostic and research uses. For example, human antibodies to pathogenic microorganisms can be used for treatment of infections by the organisms. Such antibodies can also be used for diagnosis, either in vivo or in vitro. Antibodies directed against cellular receptors can be used to agonize or antagonize receptor function. For example, antibodies directed against adhesion molecules can be used to reduced undesired immune response. Such antibodies can also be used for in vivo imaging of inflammation. Other antibodies are directed against tumor antigens, and can be used either directly or in combination with an effector molecule for elimination of tumor cells. Antibodies can also be used for diagnosis, either in vitro or in vivo.

Use of polyclonal human antibodies of the invention in diagnostics and therapeutics is particularly advantageous. Use of polyclonals hitherto has been limited by the inability to generate preparations that have a well-defined affinity and specificity. Monoclonal antibodies developed using hybridoma technology do have well-defined specificity and affinity, but the selection process is often long and tedious. Further, a single monoclonal antibody often does not meet all of the desired specificity requirements. Formation of polyclonal mixtures by isolation, and characterization of individual monoclonal antibodies, which are then mixed would be time consuming process which would increase in proportion to the number of monoclonals included in the mixture and become prohibitive for substantial numbers of monoclonal antibodies. The polyclonal libraries of antibodies and other polypeptides having specificity for a given target produced by the present methods avoid these difficulties, and provide reagents that are useful in many therapeutic and diagnostic applications.

The use of polyclonal mixtures has a number of advantages with respect to compositions made of one monoclonal antibody. By binding to multiple sites on a target, polyclonal antibodies or other polypeptides can generate a stronger signal (for diagnostics) or greater blocking/inhibition/cytotoxicity (for therapeutics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto.

Polyclonal mixture are also particularly useful as reagents for analyzing the function of individual gene products. A single protein can comprise multiple epitopes; and binding of antibody molecules to these different epitopes can have different effects on the ability of the protein to function. For example, a cytokine molecule can have antigenic epitopes within or near the normal receptor binding site. Antibodies that recognize these epitopes may therefore be considered neutralizing because they block receptor binding. These antibodies may therefore be particularly useful for elucidating the normal function of this cytokine. The antibodies can be used in in vivo or in vitro assays to discover the consequences of loss of function for this particular cytokine. However, the same cytokine may comprise additional epitopes that are distant from the normal receptor binding site. Antibodies that bind to these epitopes may fail to neutralize the cytokine. These individual antibodies may then be less useful for determining the normal function of this particular cytokine. It is therefore desirable to perform such assays using polyclonal mixtures of different antibodies to the target molecule. Such mixtures are preferred over monoclonal antibody reagents because they have a higher probability of including neutralizing antibodies. Thus, polyclonal reagents have a higher probability of being informative in assays for determining the normal function of an individual gene product.

Cytokines are not the only class of molecules for which polyclonal reagents are useful for determining normal function. Many different biological molecules are involved in receptor-ligand type binding interactions. Many of these also comprise multiple epitopes, only a fraction of which are within or adjacent to the sites of intermolecular interaction. Polyclonal reagents have a higher probability of blocking these intermolecular interactions than monoclonal reagents. Enzymes will also show different degrees of perturbation from their normal function on binding to different antibodies with different epitope specificities. Thus polyclonal mixtures of antibodies, comprising individual molecules with different epitope specificities, are useful for determining the normal function of biomolecules that comprise multiple epitopes.

Polyclonal mixtures are also important for determining the tissue distribution of individual proteins. Differential RNA splicing, glycosylation and post-translational modifications can mask or eliminate individual epitopes in particular tissues or cell types. Polyclonal mixtures will thus have a higher probability of including antibodies that recognize target molecules in a broad variety of tissues and cell types than monoclonal reagents which recognize only a single epitope.

In addition, polyclonal reagents are useful for determining the correlation between particular genetic backgrounds, pathologies, or disease states, and the expression of a particular gene product. In this case, the polyclonal reagent can be used to detect the presence of the gene product in samples from a variety of different individuals, each of which could express allelic variants of the gene product that might eliminate particular epitopes.

After a polyclonal reagent has been used either to determine the function of a given target, or to associate the expression of that particular target with a particular pathology. A monoclonal reagent that also recognizes the target can be generated. Particular epitopes are sometimes desired. Epitopes resulting in broad recognition across a population, or epitopes resulting in neutralizing or blocking antibodies, or epitopes resulting in agonist or antagonist antibody molecules. If the desired characteristic was detected in the polyclonal reagent, it may be possible to identify monoclonal antibodies from with the polyclonal pool. This is a particular advantage of using expression libraries to generate the polyclonal reagent. It is relatively simple to isolate and test individual expression clones from the library used to generate the polyclonal reagent. These clones can then be tested individually, or in smaller pools, to find monoclonal antibodies having the desired characteristics. Such monoclonal Fabs can then be expressed in mammalian expression vectors as intact whole human IgG, IgA, IgM, IgD, or IgE antibodies. These whole antibodies may be useful as therapeutic reagents for the treatment of pathologies associated with the target molecule. It is thus desirable to use human immunoglobulin transgenic mice for the construction of the original phage display library. Monoclonal antibodies derived from such animals can be expressed as completely human molecules, and will exhibit reduced immunogenicity.

Individual antibodies or polyclonal preparations of antibodies can be incorporated into compositions for diagnostic or therapeutic use. The preferred form depends on the intended mode of administration and diagnostic or therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. See Remington's Pharmaceutical Science, (15th ed., Mack Publishing Company, Easton, Pa., 1980). Compositions intended for in vivo use are usually sterile. Compositions for parental administration are sterile, substantially isotonic and made under GMP condition.

It is apparent from the foregoing that the invention provides for a variety of uses. The invention provides the use of a display method to screen nucleic acids encoding antibody chains obtained from an immunized nonhuman transgenic animal whose genome comprises a plurality of human immunoglobulin genes to produce a highly enriched polyclonal population of human antibodies with high affinity for the immunogen. The above use does not require screening phage displaying antibodies with a random peptide library to select random peptide sequences, and the random peptides are in turn being used to immunize an animal such that further antibodies are generated. The invention further provides for the use of a nucleic acid to immunize a nonhuman transgenic animal whose genome comprises a plurality of human immunoglobulin genes that can be expressed to produce a human antibody to the protein encoded by the nucleic acid. The invention further provides for use of an immunized animal that lacks a detectable titer to the immunogen for the production of antibodies to the immunogen. The invention further provides for the use of enrichment of a population of B cells for a subpopulation expressing antibodies of IgG isotype for the production of a display library containing random combinations of heavy and light chains.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. Cell lines producing antibodies CD.TXA.1.PC (ATCC 98388, Apr. 3, 1997), CD.43.9 (ATCC 98390, Apr. 3, 1997), CD.43.5.PC (ATCC 98389, Apr. 3, 1997) and 7F11 (HB-12443, Dec. 5, 1997) have been deposited at the American Type Culture Collection, Rockville, Md. under the Budapest Treaty on the dates indicated and given the accession numbers indicated. The deposits will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EXAMPLE 1

Purification of RNA from Mouse Spleens

Mice having 3 different sets of human heavy chain genes were used to make the antibody phage libraries to interleukin 8. Production of mice is described in Examples 23 and 24. The mice were immunized with interleukin 8 (Example 1). Mice were immunized with 25 microgram of antigen at 0.713 mg/ml. In a first procedure, mice were immunized once a month beginning with CFA followed by IFA until a high human gamma titer was reached (ca 6500) after a further six weeks, mice were boosted ip on days −7, −6, −5, and sacrificed 5 days later. In an alternative procedure, mice were immunized every two weeks beginning with CFA and followed by IFA. After a high human gamma titer was reached, mice were boosted on days −3, and −2 and sacrificed two days later.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Roche Molecular Biochemicals, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 µl of solution D to recover any remaining spleen, and this was transferred to the tube. The suspension was then pulled through a 22 gauge needle an additional 5–10 times. The sample was divided evenly between two microcentrifuge tubes and the following added in order, with mixing by inversion after each addition: 100 µl 2 M sodium acetate (pH 4.0), 1.0 ml water-saturated phenol (Fisher Scientific, Pittsburgh, Pa.), 200 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14,000 rpm for 20 min at 4° C., the supernatant was aspirated away, the tubes briefly spun and all traces of liquid removed. The RNA pellets were each dissolved in 300 µl of solution D, combined, and precipitated with an equal volume of isopropanol at −20° C. for a minimum of 30 min. The sample was centrifuged 14,000 rpm for 20 min at 4° C., the supernatant aspirated as before, and the sample rinsed with 100 µl of ice-cold 70% ethanol. The sample was again centrifuged 14,000 rpm for 20 min at 4° C., the 70% ethanol solution aspirated, and the RNA pellet dried in vacuo. The pellet was resuspended in 100 µl of sterile distilled water. The concentration was determined by $A_{260}$ using an absorbance of 1.0 for a concentration of 40 µg/ml. The RNA was stored at −80° C.

EXAMPLE 2

Preparation of Complementary DNA (cDNA)

The total RNA purified as described above was used directly as template for cDNA. RNA (50 µg) was diluted to 100 µL with sterile water, and 10 µL-130 ng/µL oligo dT12 (synthesized on Applied Biosystems Model 392 DNA synthesizer at Biosite Diagnostics) was added. The sample was heated for 10 min at 70° C., then cooled on ice. 40 µL 5×first strand buffer was added (Gibco/BRL, Gaithersburg, Md.), 20 µL 0.1 M dithiothreitol (Gibco/BRL, Gaithersburg, Md.), 10 µL 20 mM deoxynucleoside triphosphates (dNTP's, Roche Molecular Biochemicals, Indianapolis, Ind.), and 10 µL water on ice. The sample was then incubated at 37° C. for 2 min. 10 µL reverse transcriptase (Superscript™ II, Gibco/BRL, Gaithersburg, Md.) was added and incubation was continued at 37° C. for 1 hr. The cDNA products were used directly for polymerase chain reaction (PCR).

EXAMPLE 3

Amplification of Human Antibody Sequence cDNA by PCR

The cDNA of four mice having the genotype HCo7 was amplified using 3-5' oligonucleotides and 1-3' oligonucleotide for heavy chain sequences (Table A), and 10-5' oligonucleotides and 1-3' oligonucleotide for the kappa chain sequences (Table B). The cDNA of one mouse having the genotype HCo12 was amplified using 5-5' oligonucleotides and 1-3' oligonucleotide for heavy chain sequences (Table C), and the oligonucleotides shown in Table B for the kappa chain sequences. The cDNA of two mice having the genotype HCo7/Co12 was amplified using the oligonucleotide sequences shown in Tables A and C for the heavy chain sequences and oligonucleotides shown in Table B for the kappa chain sequences. The 5' primers were made so that a 20 nucleotide sequence complementary to the M13 uracil template was synthesized on the 5' side of each primer. This sequence is different between the H and L chain primers, corresponding to 20 nucleotides on the 3' side of the pelB signal sequence for L chain primers and the alkaline phosphatase signal sequence for H chain primers. The constant region nucleotide sequences required only one 3' primer each to the H chains and the kappa L chains (Tables A and B). Amplification by PCR was performed separately for each pair of 5' and 3' primers. A 50 µL reaction was performed for each primer pair with 50 pmol of 5' primer, 50 pmol of 3' primer, 0.25 µL Taq DNA Polymerase (5 units/µL, Roche Molecular Biochemicals, Indianapolis, Ind.), 3 µL cDNA (described in Example 2), 5 µL 2 mM dNTP's, 5 µL 10×Taq DNA polymerase buffer with $MgCl_2$ (Roche Molecular Biochemicals, Indianapolis, Ind.), and $H_2O$ to 50 µL. Amplification was done using a GeneAmp® 9600 thermal cycler (Perkin Elmer, Foster City, Calif.) with the following program: 94° C. for 1 min; 30 cycles of 94° C. for 20 sec, 55° C. for 30 see, and 72° C. for 30 sec; 72° C. for 6 min; 4° C.

TABLE A

Heavy chain oligonucleotides used to amplify cDNA for Hco7 mice. Oligonucleotides 188, 944 and 948 are 5' primers and oligonucleotide 952 is the 3' primer.

| OLIGO # | 5' TO 3' SEQUENCE | |
|---|---|---|
| 188 | TT ACC CCT GTG GCA AAA GCC GAA GTG CAG CTG GTG GAG TCT GG | (SEQ ID NO:1) |
| 944 | TT ACC CCT GTG GCA AAA GCC CAG GTG GAG CTG GTG CAG TCT GG | (SEQ ID NO:2) |
| 948 | TT ACC CCT GTG GCA AAA GCC CAG GTG CAG CTG GTG GAG TCT GG | (SEQ ID NO:3) |
| 952 | GA TGG GCC CTT GGT GGA GGC | (SEQ ID NO:4) |

TABLE B

Kappa chain oligonucleotides used to amplify cDNA from Hco7 mice, Hco12 mice, and Hco7/Co12 mice. Oligonucleotide 973 is the 3' primer and the rest are 5' primers.

| OLIGO # | 5' TO 3' SEQUENCE | |
|---|---|---|
| 189 | CT GCC CAA CCA GCC ATG GCC GAA ATT GTG CTC ACC CAG TCT CC | (SEQ ID NO:5) |
| 931 | TC GCT GCC CAA CCA GCC ATG GCC GTC ATC TGG ATG ACC CAG TCT CC | (SEQ ID NO:6) |
| 932 | TC GCT GCC CAA CCA GCC ATG GCC AAC ATC CAG ATG ACC CAG TCT CC | (SEQ ID NO:7) |
| 933 | TC GCT GCC CAA CCA GCC ATG GCC GCC ATC CGG ATG ACC CAG TCT CC | (SEQ ID NO:8) |
| 934 | TC GCT GCC CAA CCA GCC ATG GCC GCC ATC CAG TTG ACC CAG TCT CC | (SEQ ID NO:9) |
| 935 | TC GCT GCC CAA CCA GCC ATG GCC GAA ATA GTG ATG ACG CAG TCT CC | (SEQ ID NO:10) |
| 936 | TC GCT GCC CAA CCA GCC ATG GCC GAT GTT GTG ATG ACA CAG TCT CC | (SEQ ID NO:11) |
| 937 | TC GCT GCC CAA CCA GCC ATG GCC GAA ATT GTG TTG ACG CAG TCT CC | (SEQ ID NO:12) |
| 955 | TC GCT GCC CAA CCA GCC ATG GCC GAC ATC CAG ATG ATC CAG TCT CC | (SEQ ID NO:13) |
| 956 | TC GCT GCC CAA CCA GCC ATG GCC GAT ATT GTG ATG ACC CAG ACT CC | (SEQ ID NO:14) |
| 973 | CAG CAG GCA CAC AAC AGA GGC | (SEQ ID NO:15) |

TABLE C

Heavy chain oligonucleotides used to amplify cDNA for Hco12 mice. Oligonucleotides 944, 945, 946, 947 and 948 are 5' primers and oligonucleotide 952 is the 3' primer. The sequences of 944, 948 and 952 are shown in Table A.

| OLIGO # | 5' TO 3' SEQUENCE | |
|---|---|---|
| 945 | TT ACC CCT GTG GCA AAA GCC GAG GTG CAG CTG TTG GAG TCT GG | (SEQ ID NO:16) |
| 946 | TT ACC CCT GTG GCA AAA GCC GAG GTG CAG CTG GTG CAG TCT GG | (SEQ ID NO:17) |
| 947 | TT ACC CCT GTG GCA AAA GCC CAG GTG CAG CTA CAG CAG TGG GG | (SEQ ID NO:18) |

The dsDNA products of the PCR process were then subjected to asymmetric PCR using only 3' primer to generate substantially only the anti-sense strand of the target genes. Oligonucleotide 953 was used as the 3' primer for kappa chain asymmetric PCR (Table D) and oligonucleotide 952 was used as the 3' primer for heavy chain asymmetric PCR (Table A). For each spleen, two asymmetric reactions were run for the kappa chain PCR products to primer 189, 931, 932, 933, 934, 936, 955, and 956, four asymmetric reactions were run for the kappa chain PCR product to primer 935, and eight asymmetric reactions were run for the kappa chain PCR product to primer 937. The number of asymmetric reactions used for each heavy chain PCR product was dependent on the mouse genotype. For Co7 mice, eight asymmetric reactions were run for each PCR product. For Co12 mice, eight asymmetric reactions were run for the PCR product from primer 944, and four asymmetric reactions were run for the PCR products from the other primers. For Co7/Co12 mice, six asymmetric reactions were run for the PCR products from primers 944 and 948, and three asymmetric reactions were run for the PCR products from the other primers Each reaction described above is 100 µL total volume with 200 pmol of 3' primer, 2 µL of ds-DNA product, 0.5 µL Taq DNA Polymerase, 10 µL 2 mM dNTP's, 10 µL 10×Taq DNA polymerase buffer with $MgCl_2$, and $H_2O$ to 100 µL. Heavy chain reactions were amplified using the thermal profile described above, while kappa chain reactions were amplified with the same thermal profile but 25 cycles were used instead of 30 cycles.

TABLE D

Oligonucleotide sequences used for asymmetric PCR of kappa chains.

| OLIGO # | 5' TO 3' SEQUENCE |
|---|---|
| 953 | GAC AGA TGG TGC AGC CAC AGT (SEQ ID NO:19) |

EXAMPLE 4

Purification of ss-DNA by High Performance Liquid Chromatography and Kinasing ss-DNA The H chain ss-PCR products and the L chain ss-PCR products were separately pooled and ethanol precipitated by adding 2.5 volumes ethanol and 0.2 volumes 7.5 M ammonium acetate and incubating at −20° C. for at least 30 min. The DNA was pelleted by centrifuging at 15,000 rpm for 15 min at 2–8° C. The supernatant was carefully aspirated, and the tubes were briefly spun a 2nd time. The last drop of supernatant was removed with a pipet. The DNA was dried in vacuo for 10 min on medium heat. The H chain products were dissolved in 210 µL water and the L chain products were dissolved separately in 210 µL water. The ss-DNA was purified by high performance liquid chromatography (HPLC) using a Hewlett Packard 1090 HPLC and a GenPak™ FAX anion exchange column (Millipore Corp., Milford, Mass.). The gradient used to purify the ss-DNA is shown in Table 1, and the oven temperature was at 60° C. Absorbance was monitored at 260 nm. The ss-DNA eluted from the HPLC was collected in 0.5 min fractions. Fractions containing ss-DNA were pooled, ethanol precipitated, pelleted and dried as described above. The dried DNA pellets were resuspended in 200 µL sterile water.

TABLE 1

HPLC gradient for purification of ss-DNA

| Time (min) | % A | % B | % C | Flow (mL/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |

TABLE 1-continued

HPLC gradient for purification of ss-DNA

| Time (min) | % A | % B | % C | Flow (mL/min) |
|---|---|---|---|---|
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The ss-DNA was kinased on the 5' end in preparation for mutagenesis (Example 7). 24 µL 10×kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio)-chloroform-isoamyl alcohol (50:49:1) and one extraction with chloroform:isoamyl alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/mL for an absorbance of 1.0. Samples were stored at −20° C.

EXAMPLE 5

Construction of Antibody Phage Display Vector Having Human Antibody Constant Region Sequences The antibody phage display vector for cloning antibodies was derived from an M13 vector supplied by Ixsys, designated 668-4. The vector 668-4 contained the DNA sequences encoding the heavy and light chains of a mouse monoclonal Fab fragment inserted into a vector described by Huse, WO 92/06024. The vector had a Lac promoter, a pelB signal sequence fused to the 5' side of the L chain variable region of the mouse antibody, the entire kappa chain of the mouse antibody, an alkaline phosphatase signal sequence at the 5' end of the H chain variable region of the mouse antibody, the entire variable region and the first constant region of the H chain, and 5 codons of the hinge region of an IgG1 H chain. A decapeptide sequence was at the 3' end of the H chain hinge region and an amber stop codon separated the decapeptide sequence from the pseudo-gene VIII sequence.

The amber stop allowed expression of H chain fusion proteins with the gene VIII protein in E. coli suppressor strains such as XL1 blue (Stratagene, San Diego, Calif.), but not in nonsuppressor cell strains such as MK30 (Boehringer Mannheim, Indianapolis, Ind.) (see FIG. 1).

To make the first derivative cloning vector, deletions were made in the variable regions of the H chain and the L chain by oligonucleotide directed mutagenesis of a uracil template (Kunkel, Proc. Natl. Acad. Sci. USA 82:488 (1985); Kunkel, et al., Methods. Enzymol. 154:367 (1987)). These mutations deleted the region of each chain from the 5' end of CDR1 to the 3' end of CDR3, and the mutations added a DNA sequence where protein translation would stop (see FIG. 2 for mutagenesis oligonucleotides). This prevented the expression of H or L chain constant regions in clones without an insert, thereby allowing plaques to be screened for the presence of insert. The resulting cloning vector was called BSI 1.

Many changes were made to BS11 to generate the cloning vector used in the present screening methods. The amber stop codon between the heavy chain and the pseudo gene VIII sequence was removed so that every heavy chain was expressed as a fusion protein with the gene VIII protein. This increased the copy number of the antibodies on the phage relative to BS11. A HindIII restriction enzyme site in the sequence between the 3' end of the L chain and the 5' end of the alkaline phosphatase signal sequence was deleted so antibodies could be subcloned into a pBR322 derivative (Example 14). The interchain cysteine residues at the carboxyl-terminus of the L and H chains were changed to serine residues. This increased the level of expression of the antibodies and the copy number of the antibodies on the phage without affecting antibody stability. Nonessential DNA sequences on the 5' side of the lac promoter and on the 3' side of the pseudo gene VIII sequence were deleted to reduce the size of the M13 vector and the potential for rearrangement. A transcriptional stop DNA sequence was added to the vector at the L chain cloning site to replace the translational stop so that phage with only heavy chain proteins on their surface, which might be nonspecifically in panning, could not be made. Finally, DNA sequences for protein tags were added to different vectors to allow enrichment for polyvalent phage by metal chelate chromatography (polyhistidine sequence) or by affinity purification using a decapeptide tag and a magnetic latex having an immobilized antibody that binds the decapeptide tag. BS45 had a polyhistidine sequence between the end of the heavy chain constant region and the pseudo-gene VIII sequence, and a decapeptide sequence at the 3' end of the kappa chain constant region.

The mouse heavy and kappa constant region sequences were deleted from BS45 by oligonucleotide directed mutagenesis. Oligonucleotide 864 was used to delete the mouse kappa chain and oligonucleotide 862 was used to delete the mouse heavy chain.

```
Oligonucleotide 864
5' ATC TGG CAC ATC ATA TGG ATA AGT TTC GTG TAC AAA ATG CCA GAC CTA GAG
GAA TTT TAT TTC CAG CTT GGT CCC
(SEQ ID NO:20)

Oligonucleotide 862
5' GTG ATG GTG ATG GTG ATG GAT CGG AGT ACC AGG TTA TCG AGC CCT CGA TAT
TGA GGA GAC GGT GAC TGA
(SEQ ID NO:21)
```

Deletion of both constant region sequences was determined by amplifying the DNA sequence containing both constant regions by PCR using oligonucleotides 5 and 197, followed by sizing the PCR products on DNA agarose gel. The PCR was accomplished as described in Example 3 for the double-stranded DNA, except 1 µL of phage was template instead of cDNA. Phage with the desired deletion had a shorter PCR product than one deletion or no deletion. Uracil template was made from one phage stock having both deletions, as described in Example 6. This template, BS46, was used to insert the human constant region sequences for the kappa chain and IgG1.

```
Primer 5
5' GCA ACT GTT GGG AAG GG (SEQ ID NO:22)

Primer 197

5' TC GCT GCC CAA CCA GCC ATG (SEQ ID NO:23)
```

The human constant region DNA sequences were amplified from human spleen cDNA (Clontech, Palo Alto, Calif.). Oligonucleotides 869 and 870 were used to amplify the kappa constant region sequence, and oligonucleotides 867 and 876 were used to amplify the IgG1 constant region sequence and the codons for 6 amino acids of the hinge region (Kabat et al., Sequences of Proteins of Immunological Interest, 1991).

5' PCR primer (869)-
GGG ACC AAG CTG GAA ATA AAA CGG GCT GTG GCT GCA CCA TCT GTC T
(SEQ ID NO:24)

3' PCR primer (870)-
ATC TGG CAC ATC ATA TGG ATA AGA CTC TCC CCT GTT GAA GCT CTT
(SEQ ID NO:25)

5' PCR primer (867)-
TCA GTC ACC GTC TCC TCA GCC TCC ACC AAG GGC CCA TC
(SEQ ID NO:26)

3' PCR primer (876)-
GTG ATG GTG ATG GTG ATG AGA TTT GGG CTC TGC TTT CTT GTG C
(SEQ ID NO:27)

PCR (1–50 μL reaction for each chain) was performed using Expand high-fidelity PCR system (Roche Molecular Biochemicals, Indianapolis, Ind.). Each 50 μL reaction contained 50 pmol of 5' primer, 50 pmol of 3' primer, 0.35 units of Expand DNA polymerase, 5 μL 2 mM dNTP's, 5 μL 10×Expand reaction buffer, 1 μL cDNA as template, and water to 50 μL. The reaction was carried out in a Perkin-Elmer thermal cycler (Model 9600) using the following thermal profile for the kappa chain: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The thermal profile used for the heavy chain reaction had twenty cycles instead of fifteen in the second part of the thermal profile.

The dsDNA products of the PCR process were then subjected to asymmetric PCR using only 3' primer to generate substantially only the anti-sense strand of the human constant region genes, as described in Example 3. Five reactions were done for the kappa chain and ten reactions were done for the heavy chain (100 μL per reaction). The thermal profile for both constant region genes is the same as that described in Example 3, including the heavy chain asymmetric PCR was done with 30 cycles and the kappa chain asymmetric PCR was done with 25 cycles. The single stranded DNA was purified by HPLC as described in Example 4. The HPLC purified kappa chain DNA was dissolved in 55 μL of water and the HPLC purified heavy chain was dissolved in 100 μL of water. The DNA was quantified by absorbance at 260 nm, as described in Example 4, then the DNA was kinased as described in Example 4 except added 6 μL 10× kinase buffer, 2.6 μL 10 mM ATP, and 0.5 μL of polynucleotide kinase to 50 μL of kappa chain DNA. Twice those volumes of kinase reagents were added to 100 μL of heavy chain DNA.

The kinased DNA was used to mutate BS46 without purifying the DNA by extractions. The mutagenesis was performed on a 2 μg scale by mixing the following in a 0.2 mL PCR reaction tube: 8 μl of (250 ng/μl) BS46 uracil template, 8 μl of 10× annealing buffer (200 mM Tris pH 7.0, 20 mM MgCl$_2$, 500 mM NaCl), 2.85 μl of kinased single-stranded heavy chain insert (94 ng/μl), 6.6 μl of kinased single-stranded kappa chain insert (43.5 ng/μl), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10×synthesis buffer (5 mM each dNTP, 10 mM ATP, 100 mM Tris pH 7.4, 50 mM MgCl$_2$, 20 mM DTT), 8 μl T4 DNA ligase (1 U/μl, Roche Molecular Biochemicals, Indianapolis, Ind.), 8 μl diluted T7 DNA polymerase (1 U/μl, New England BioLabs, Beverly, Mass.) and incubating at 37° C. for 30 min. The reaction was stopped with 296 μl of mutagenesis stop buffer (10 mM Tris pH 8.0, 10 mM EDTA). The mutagenesis DNA was extracted once with equilibrated phenol (pH>8):chloroform: isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water. 1 μl mutagenesis DNA was (500 ng) was transferred into 40 μl electrocompetent E. coli DH12S (Gibco/BRL, Gaithersburg, Md.) using the electroporation conditions in Example 8. The transformed cells were mixed with 1.0 mL 2×YT broth (Sambrook, et al, supra) and transferred to a 15 mL sterile culture tube. Aliquots (10 μL of 10$^{-3}$ and 10$^{-4}$ dilutions) of the transformed cells were plated on 100 mm LB agar plates as described in Example 11. After 6 hr of growth at 37° C., 20 individual plaques were picked from a plate into 2.75 mL 2×YT and 0.25 ml overnight XL1 blue cells. The cultures were grown at 37° C., 300 rpm overnight to amplify the phage from the individual plaques. The phage samples were analyzed for insertion of both constant regions by PCR using oligonucleotides 197 and 5 (see above in BS46 analysis), followed by sizing of the PCR products by agarose gel electrophoresis. The sequence of two clones having what appeared to be two inserts by agarose gel electrophoresis was verified at MacConnell Research (San Diego, Calif.) by the dideoxy chain termination method using a Sequatherm sequencing kit (Epicenter Technologies, Madison, Wis.) and a LI-COR 4000 L automated sequencer (LI-COR, Lincoln, Nebr.). Oligonucleotide primers 885 and 5, that bind on the 3' side of the kappa chain and heavy chain respectively, were used. Both clones had the correct sequence. The uracil template having human constant region sequences, called BS47, was prepared as described in Example 6.

Primer 885
5' TAA GAG CGG TAA GAG TGC CAG (SEQ ID NO:28)

EXAMPLE 6

Preparation of Uracil Templates used in Generation of Spleen Antibody Phage Libraries 1 mL of *E. coli* CJ236 (BioRAD, Hercules, Calif.) overnight culture and 10 μL of a 1/100 dilution of vector phage stock was added to 50 ml 2×YT in a 250 mL baffled shake flask. The culture was grown at 37° C. for 6 hr. Approximately 40 mL of the culture was centrifuged at 12,000 rpm for 15 minutes at 4° C. The supernatant (30 mL) was transferred to a fresh centrifuge tube and incubated at room temperature for 15 minutes after the addition of 15 μl of 10 mg/ml RnaseA (Boehringer Mannheim, Indianapolis, Ind.). The phage were precipitated by the addition of 7.5 ml of 20% polyethylene glycol 8000 (Fisher Scientific, Pittsburgh, Pa.)/ 3.5 M ammonium acetate (Sigma Chemical Co., St. Louis, Mo.) and incubation on ice for 30 min. The sample was centrifuged at 12,000 rpm for 15 min at 2–8° C. The supernatant was carefully discarded, and the tube was briefly spun to remove all traces of supernatant. The pellet was resuspended in 400 μl of high salt buffer (300 mM NaCl, 100 mM Tris pH 8.0, 1 mM EDTA), and transferred to a 1.5 mL tube. The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at –20° C. The DNA was centrifuged at 14,000 rpm for 10 min at 4° C., the pellet washed once with cold 70% ethanol, and dried in vacuo. The uracil template DNA was dissolved in 100 μl sterile water and the concentration determined by $A_{260}$ using an absorbance of 1.0 for a concentration of 40 μg/ml. The template was diluted to 250 ng/μl with sterile water, aliquoted, and stored at –20° C.

EXAMPLE 7

Mutagenesis of Uracil Template with ss-DNA and Electroporation into *E. coli* to Generate Antibody Phage Libraries Antibody phage-display libraries were generated by simultaneously introducing single-stranded heavy and light chain genes onto a phage-display vector uracil template. A typical mutagenesis was performed on a 2 μg scale by mixing the following in a 0.2 mL PCR reaction tube: 8 μl of (250 ng/μl) BS47 uracil template (examples 5 and 6), 8 μl of 10× annealing buffer (200 mM Tris pH 7.0, 20 mM $MgCl_2$, 500 mM NaCl), 3.33 μl of kinased single-stranded heavy chain insert (100 ng/μl), 3.1 μl of kinased single-stranded light chain insert (100 ng/ml), and sterile water to 80 μL. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10×synthesis buffer (5 mM each dNTP, 10 mM ATP, 100 mM Tris pH 7.4, 50 mM $MgCl_2$, 20 mM DTT), 8 μl T4 DNA ligase (1 U/μl), 8 ill diluted T7 DNA polymerase (1 U/μl) and incubating at 37° C. for 30 min. The reaction was stopped with 300 μl of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform: isoamyl alcohol (49:1), and the DNA was ethanol precipitated at –20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water. 1 μl mutagenesis DNA was (500 ng) was transferred into 40 μl electrocompetent *E. coli* DH 12S (Gibco/BRL, Gaithersburg, Md.) using the electroporation conditions in Example 8. The transformed cells were mixed with 0.4 mL 2×YT broth (Sambrook, et al., supra) and 0.6 mL overnight XL1 Blue cells, and transferred to 15 mL sterile culture tubes. The first round antibody phage samples were generated by plating the electroporated samples on 150 mm LB plates as described in Example 11. The plates were incubated at 37° C. for 4 hr, then 20° C. overnight. The first round antibody phage was eluted from the 150 mm plates by pipeting 10 mL 2YT media onto the lawn and gently shaking the plate at room temperature for 20 min. The phage were transferred to 15 mL disposable sterile centrifuge tubes with plug seal cap and the debris from the LB plate was pelleted by centrifuging for 15 min at 3500 rpm. The $1^{st}$ round antibody phage was then transferred to a new tube.

The efficiency of the electroporation was measured by plating 10 μl of $10^{-3}$ and $10^{-4}$ dilutions of the cultures on LB agar plates (see Example 11). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$.

EXAMPLE 8

Transformation of *E. coli* by Electroporation

The electrocompetent *E. coli* cells were thawed on ice. DNA was mixed with 20–40 μL electrocompetant cells by gently pipetting the cells up and down 2–3 times, being careful not to introduce air-bubble. The cells were transferred to a Gene Pulser cuvette (0.2 cm gap, BioRAD, Hercules, Calif.) that had been cooled on ice, again being careful not to introduce an air-bubble in the transfer. The cuvette was placed in the *E. coli* Pulser (BioRAD, Hercules, Calif.) and electroporated with the voltage set at 1.88 kV according to the manufacturer's recommendation. The transformed sample was immediately diluted to 1 ml with 2×YT broth or 1 ml of a mixture of 400 μL 2×YT/600 μL overnight XL1 Blue cells and processed as procedures dictate.

EXAMPLE 9

Preparation of Biotinylated Interleukin 8 (IL8)

IL8 was dialyzed against a minimum of 100 volumes of 20 mM borate, 150 mM NaCl, pH 8 (BBS) at 2–8° C. for at least 4 hr. The buffer was changed at least once prior to biotinylation. IL8 was reacted with biotin-XX-NHS ester (Molecular Probes, Eugene, Oreg., stock solution at 40 mM in dimethylformamide) at a final concentration of 1 mM for 1 hr at room temperature. After 1 hr, the IL8 was extensively dialyzed into BBS to remove unreacted small molecules.

EXAMPLE 10

Preparation of Avidin Magnetic Latex

The magnetic latex (superparamagnetic microparticles, 0.96 μm, Estapor, 10% solids, Bangs Laboratories, Carmel, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

EXAMPLE 11

Plating M13 Phage or Cells Transformed with Antibody Phage-Display Vector Mutagenesis Reaction The phage samples were added to 200 μL of an overnight culture of *E. coli* XL1-Blue when plating on 100 mm LB agar plates or to 600 μL of overnight cells when plating on 150 mm plates in sterile 15 ml culture tubes. The electroporated phage samples were in 1 mL 2×YT/overnight XL1 cells, as described in Example 8, prior to plating on 150 mm plates. After adding LB top agar (3 mL for 100 mm plates or 9 mL for 150 mm plates, top agar stored at 55° C., Appendix A1, Molecular Cloning, A Laboratory Manual, (1989) Sambrook. J), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

EXAMPLE 12

Develop Nitrocellulose Filters with Alkaline Phosphatase (AP) Conjugates

After overnight incubation of the nitrocellulose filters on LB agar plates, the filters were carefully removed from the plates with membrane forceps and incubated for 2 hr in block (1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0).

After 2 hr, the filters were incubated with goat anti-human kappa AP (Southern Biotechnology Associates, Inc, Birmingham, Ala.) for 2–4 hr. The AP conjugate was diluted into block at a final concentration of 1 μg/mL. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

EXAMPLE 13

Enrichment of Polyclonal Phage to Human Interleukin-8 Using a Decapeptide Tag on the Kappa Chain The first round antibody phage was prepared as described in Example 7 using BS47 uracil template, which has a decapeptide tag for polyvalent enrichment fused to the kappa chain. Fourteen electroporations of mutagenesis DNA were done from 7 different spleens (2 electroporations from each spleen) yielding 14 different phage samples. Prior to functional panning, the antibody phage samples were enriched for polyvalent display using the decapeptide tag on the kappa chain and the 7F11 magnetic latex. Binding studies had previously shown that the decapeptide could be eluted from the monoclonal antibody 7F11 (see Example 17) at a relatively mild pH of 10.5–11. The 7F11 magnetic latex (2.9 mL) was equilibrated with panning buffer as described above for the avidin magnetic latex (Example 10). Each first round phage stock (1 mL) was aliquoted into a 15 mL tube. The 7F11 magnetic latex (200 μL per phage sample) was incubated with phage for 10 min at room temperature. After 10 min, 9 mL of panning buffer was added, and the magnetic latex was separated from unbound phage by placing the tubes in a magnet for 10 min. After 10 min in the magnet, the unbound phage was carefully removed with a 10 mL sterile pipet. The magnetic latex was then resuspended in 1 mL panning buffer and transferred to 1.5 mL tubes. The magnetic latex was separated from unbound phage by placing the tubes in a smaller magnet for 5 min, then the supernatant was carefully removed with a sterile pipet. The latexes were washed with 1 additional 1 mL panning buffer wash. Each latex was resuspended in 1 mL elution buffer (20 mM 3-(cyclohexylamino)propanesulfonic acid (United States Biochemical, Cleveland, Ohio), 150 mM NaCl, 20 mg/mL BSA, pH 10.5) and incubated at room temperature for 10 min. After 10 min, tubes were placed in the small magnet again for 5 min and the eluted phage was transferred to a new 1.5 mL tube. The phage samples were again placed in the magnet for 5 min to remove the last bit of latex that was transferred. Eluted phage was carefully removed into a new tube and 25 μL 3 M Tris, pH 6.8 was added to neutralize the phage. Panning with IL8-biotin was set up for each sample by mixing 900 μL 7F11/decapeptide enriched phage, 100 μL panning buffer, and 10 μL $10^{-7}$ M IL8-biotin and incubating overnight at 2–8° C.

The antibody phage samples were panned with avidin magnetic latex. The equilibrated avidin magnetic latex (see Example 10), 200 µL latex per sample, was incubated with the phage for 10 min at room temperature. After 10 min, approximately 9 mL of panning buffer was added to each phage sample, and the magnetic latex was washed as described above for the 7F11 magnetic latex. A total of one 9 mL and three 1 mL panning buffer washes were done. After the last wash, each latex was resuspended in 200 µL 2×YT, then the entire latex of each sample was plated on 150 mm LB plates to generate the 2nd round antibody phage. The 150 mm plates were incubated at 37° C. for 4 hr, then overnight at 20° C.

The resulting $2^{nd}$ round antibody phage samples were set up for the second round of functional panning in separate 15 mL disposable sterile centrifuge tubes with plug seal cap by mixing 900 µL panning buffer, 100 µL $2^{nd}$ round antibody phage, and 10 µL $10^{-7}$ M interleukin-8-biotin. After overnight incubation at 2–8° C., the phage samples were panned with avidin magnetic latex as described above. Aliquots of one sample from each spleen were plated on 100 mm LB agar plates to determine the percentage of kappa positives (Example 12). The percentage of kappa positives for the 2nd round of panning was between 83–92% for 13 samples. One sample was discarded because it was 63% kappa positive.

The remaining thirteen samples were set up for a third round of functional panning as described above using 950 µL panning buffer, 50 µL $3^{rd}$ round antibody phage, and 10 µL $10^{-6}$ M interleukin-8-biotin. After incubation for 1.5 hours at 2–8° C., the phage samples were panned with avidin magnetic latex, and nitrocellulose filters were placed on each phage sample, as described above. The percentage of kappa positives for the 4th round antibody phage samples was estimated to be greater than 80%.

The 4th round antibody phage samples were titered by plating 50 µL $10^{-8}$ dilutions on 100 mm LB plates. After 6 hr at 37° C., the number of plaques on each plate were counted, and the titers were calculated by multiplying the number of plaques by $2\times10^9$. A pool of 13—4th round phage was made by mixing an equal number of phage from each phage stock so that high titer phage stocks would not bias the pool. The pooled antibody phage was set up in duplicate for a $4^{th}$ round of functional panning as described above using 950 µL panning buffer, 50 µL $4^{th}$ round pooled-antibody phage. One sample (foreground) received 10 µL $10^{-6}$ M interleukin-8-biotin and the other sample (background) did not receive interleukin-8-biotin and served as a blank to monitor non-specific binding of phage to the magnetic latex. After incubation for 1.5 hours at 2–8° C., the phage samples were panned with avidin magnetic latex as described above. The next day, the $5^{th}$ round antibody phage was eluted and the number of plaques was counted on the foreground and background plates. The foreground:background ratio was 58:1.

The $5^{th}$ round antibody phage was set up in triplicate as described above using 950 µL panning buffer, 50 µL 5th round antibody phage per sample with the experimental (foreground) tubes receiving 10 µL $10^{-7}$ M interleukin-8-biotin or 10 µL $10^{-8}$ M interleukin-8-biotin, respectively. The third tube did not receive any interleukin-8-biotin. This round of panning or affinity selection preferentially selects for antibodies of $\geq 10^9$ affinity and $\geq 10^{10}$ affinity by including the interleukin-8-biotin at a final concentration of $10^{-9}$ M and $10^{-10}$ M, respectively. After greater than 24 hours at 2–8° C., the phage samples were panned with avidin magnetic latex and processed as described above. The $6^{th}$ round antibody phage sample $10^{-9}$ M cut had a foreground:background ratio 1018:1 and the $10^{-10}$ M cut had a foreground:background ratio 225:1.

An additional round of panning was done on the $6^{th}$ round $10^{-10}$ M cut antibody phage to increase the number of antibodies with affinity of $10^{10}$. The $6^{th}$ round phage were set up as described above using 975 µL panning buffer, 25 µL 6th round antibody phage per sample with the experimental (foreground) tube receiving 10 µL $10^{-8}$ M interleukin-8-biotin. The blank did not receive any interleukin-8-biotin. After overnight incubation at 2–8° C., the phage samples were panned with avidin magnetic latex and processed as described above. The $7^{th}$ round antibody phage sample $10^{-10}$ M cut had a foreground:background ratio 276:1. The antibody phage populations were subcloned into the expression vector and electroporated as described in Example 15.

EXAMPLE 14

Construction of the pBR Expression Vector

Figure 3:
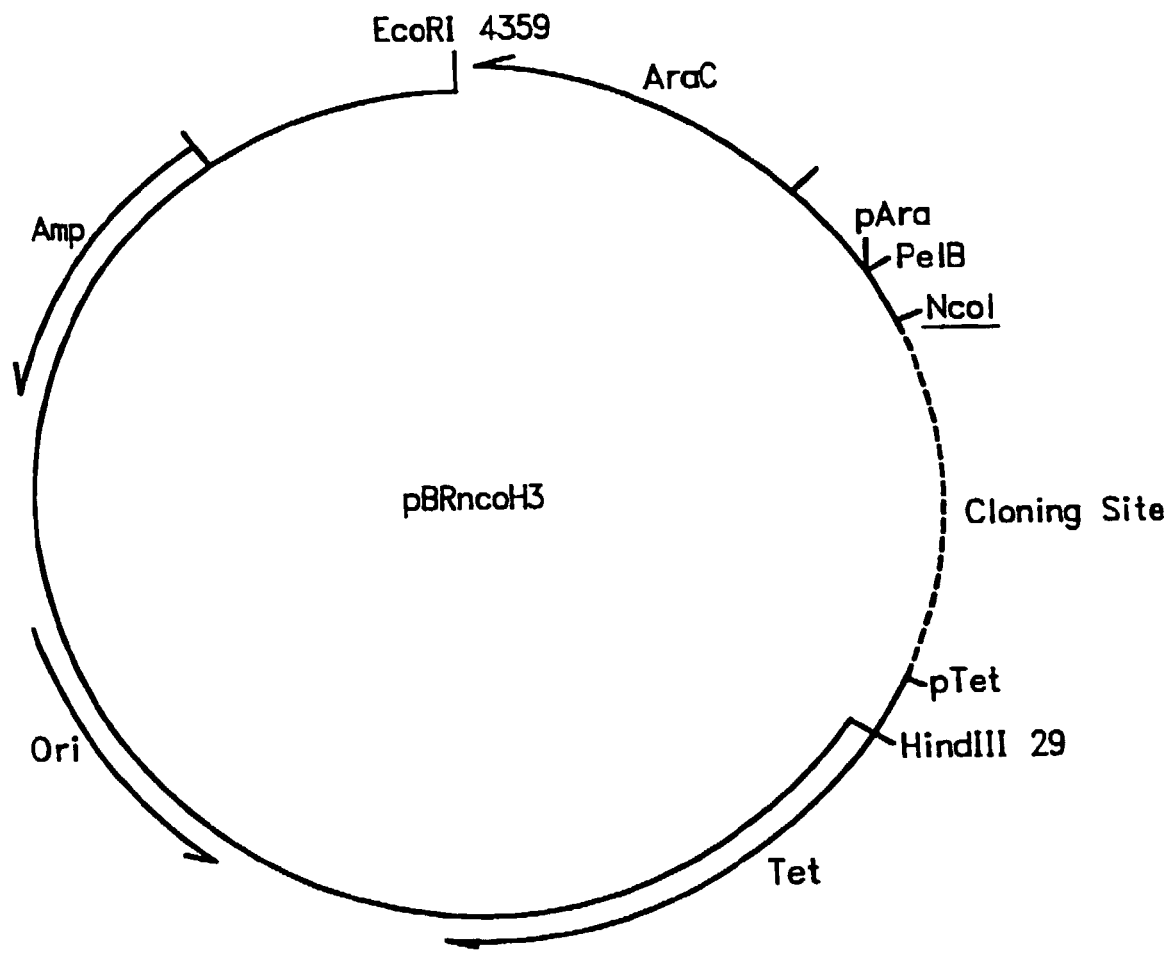
FIG. 3: Map of the vector pBRncoH3.

An expression vector and a process for the subcloning of monoclonal and polyclonal antibody genes from a phage-display vector has been developed that is efficient, does not substantially bias the polyclonal population, and can select for vector containing an insert capable of restoring antibiotic resistance. The vector is a modified pBR322 plasmid, designated pBRncoH3, that contains an arabinose promoter, ampicillin resistance (beta-lactamase) gene, a partial tetracycline resistance gene, a pelB (pectate lyase) signal sequence, and NcoI and HindIII restriction sites. (FIG. 3). The pBRncoH3 vector can also be used to clone proteins other than Fabs with a signal sequence. A second vector, pBRnsiH3, has been developed for cloning proteins with or without signal sequences, identical to the vector described above except that the pelB signal sequence is deleted and the NcoI restriction site has been replaced with an NsiI site.

The araC regulatory gene (including the araBAD promoter) was amplified from *E. coli* K-12 strain NL31-001 (a gift from Dr. Nancy Lee at UCSB) by PCR (Example 3) using Taq DNA polymerase (Boehringer Mannheim, Indianapolis, Ind.) with primers A and B (Table 3). Primers A and B contain 20 base-pairs of the BS39 vector sequence at their 5'-ends complementary to the 5' side of the lac promoter and the 5' side of the pelB signal sequence, respectively. Primer A includes an EcoRI restriction site at its 5'-end used later for ligating the ara insert into the pBR vector. The araCpa-raBAD PCR product was verified by agarose gel electrophoresis and used as template for an asymmetric PCR reaction with primer 'B' in order to generate the anti-sense strand of the insert. The single-stranded product was run on agarose gel electrophoresis, excised, purified with GeneClean (Bio101, San Diego, Calif.), and resuspended in water as per manufacturers recommendations. The insert was kinased with T4 polynucleotide kinase for 45 min at 37° C. The T4 polynucleotide kinase was heat inactivated at 70° C. for 10 min and the insert extracted with an equal volume of phenol/chloroform, followed by chloroform. The DNA was precipitated with ethanol at −20° C. for 30 min. The DNA was pelleted by centrifugation at 14 krpm for 15 min at 4° C., washed with ice-cold 70% ethanol, and dried in vacuo.

The insert was resuspended in water and the concentration determined by $A_{260}$ using an absorbance of 1.0 for a concentration of 40 g/ml. The insert was cloned into the phage-display vector BS39 for sequence verification and to introduce the pelB signal sequence in frame with the arabinose promoter (the pelB signal sequence also contains a NcoI restriction site at its 3'-end used later for ligating the ara insert into the pBR vector). The cloning was accomplished by mixing 250 ng of BS39 uracil template (Example 5), 150 ng of kinased araCpBAD insert, and 1.0 l of 10× annealing buffer in a final volume of 10 l. The sample was heated to 70 C for 2 min and cooled over 20 min to room temperature to allow the insert and vector to anneal. The insert and vector were ligated together by adding 1 l of 10×synthesis buffer, 1 l T4 DNA ligase (1 U/l), 1 l T7 DNA polymerase (1 U/l) and incubating at 37° C. for 30 min. The reaction was stopped with 90 l of stop buffer (10 mM Tris pH 8.0, 10 mM EDTA) and 1 l electroporated (Example 8) into electrocompetent E. coli strain, DH10B, (Life Technologies, Gaithersburg, Md.).

The transformed cells were diluted to 1.0 ml with 2×YT broth and 1 l, 10 l, 100 l plated as described in Example 12. Following incubation overnight at 37° C., individual plaques were picked, amplified by PCR with primers A and B, and checked for full-length insert by agarose gel electrophoresis. Clones with full-length insert were sequenced with primers D, E, F, G (Table 3) and checked against the literature. An insert with the correct DNA sequence was amplified by PCR (Example 3) from BS39 with primers A and C (FIG. 4A) and the products run on agarose gel electrophoresis.

Figure 4A:
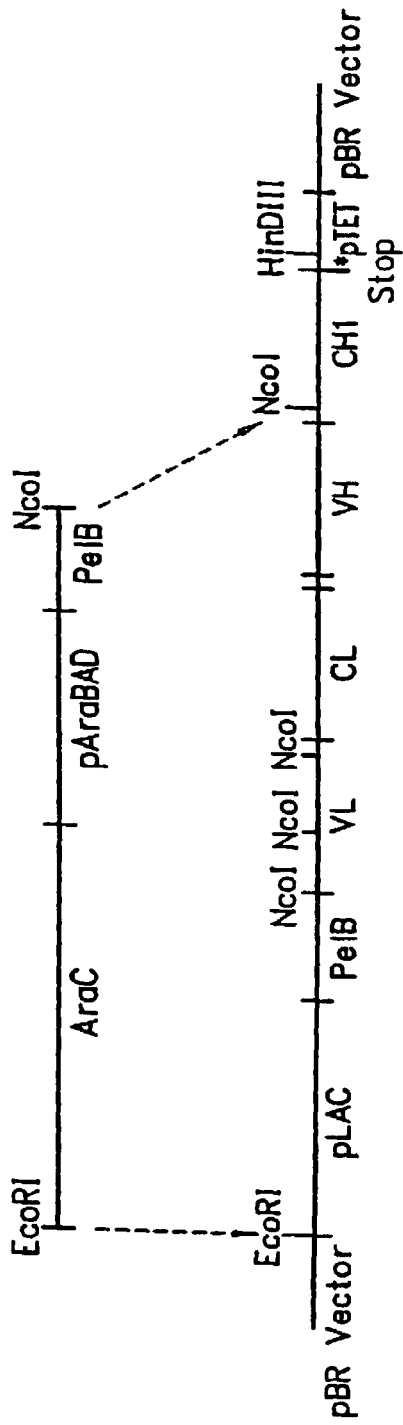
FIG. 4: Insertion of araC into pBR-based vector (FIG. 4A) and the resulting vector pBRnco (FIG. 4B).

Full-length products were excised from the gel and purified as described previously and prepared for cloning by digestion with EcoRI and NcoI. A pBR lac-based expression vector that expressed a murine Fab was prepared to receive this insert by EcoRI and NcoI digestion. This digestion excised the lac promoter and the entire coding sequence up to the 5'-end of the heavy chain ($C_H1$) constant region (FIG. 4A).

The insert and vector were mixed (2:1 molar ratio) together with 1 l 10 mM ATP, 1 l (1 U/l) T4 DNA ligase, 1 l 10×ligase buffer in a final volume of 10 l and ligated overnight at 15° C. The ligation reaction was diluted to 20 l, and 1 l electroporated into electrocompetent E. coli strain, DH10B (Example 8), plated on LB tetracycline (10 g/ml) plates and grown overnight at 37° C.

Figure 4B:
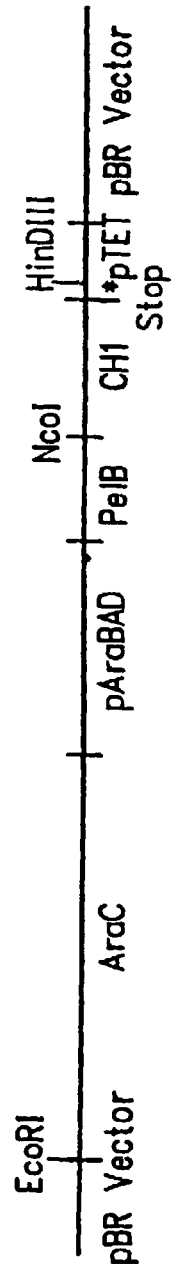

Clones were picked and grown overnight in 3 ml LB broth supplemented with tetracycline at 20 g/ml. These clones were tested for the correct insert by PCR amplification (Example 3) with primers A and C, using 1 l of overnight culture as template. Agarose gel electrophoresis of the PCR reactions demonstrated that all clones had the araCparaB insert. The vector (plasmid) was purified from each culture by Wizard miniprep columns (Promega, Madison, Wis.) following manufacturers recommendations. The new vector contained the araC gene, the araB promoter, the pelB signal sequence, and essentially the entire $C_H1$ region of the heavy chain (FIG. 4B).

The vector was tested for expression by re-introducing the region of the Fab that was removed by EcoRI and NcoI digestion. The region was amplified by PCR, (Example 3) from a plasmid (20 ng) expressing 14F8 with primers H and I (Table 3). The primers, in addition to having sequence specific to 14F8, contain 20 base-pairs of vector sequence at their 5'-end corresponding to the 3'-end of the pelB signal sequence and the 5'-end of the $C_H1$ region for cloning purposes. The PCR products were run on agarose gel electrophoresis and full-length products excised from the gel and purified as described previously.

Figure 5:
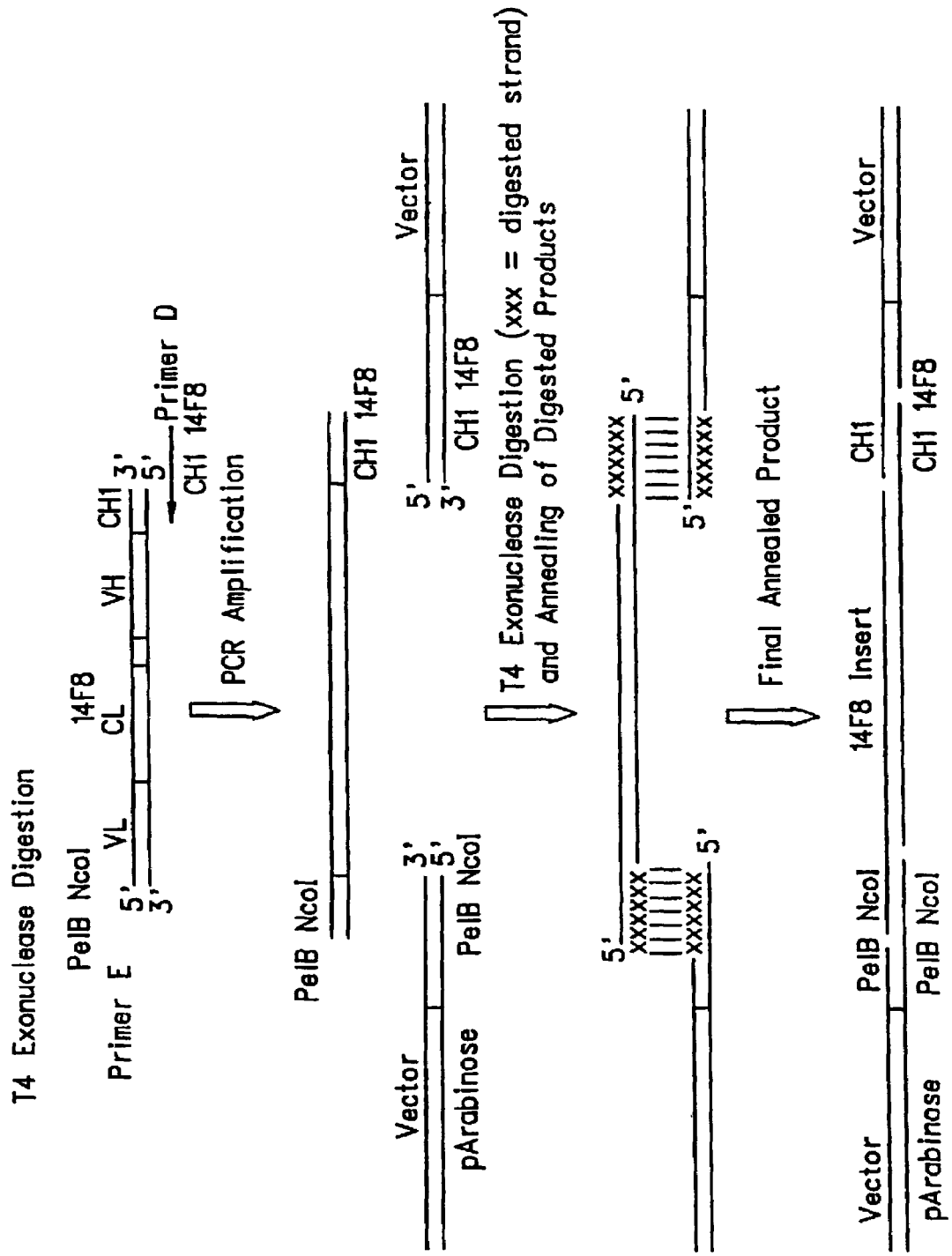
FIG. 5: Subcloning of a DNA segment encoding a Fab by T4 exonuclease digestion.

The vector was linearized with NcoI and together with the insert, prepared for cloning through the 3' 5' exonuclease activity of T4 DNA polymerase. The insert and NcoI digested vector were prepared for T4 exonuclease digestion by aliquoting 1.0 g of each in separate tubes, adding 1.0 l of 10×restriction endonuclease Buffer A (Boehringer Mannheim, Indianapolis, Ind.) and bringing the volume to 9.0 l with water. The samples were digested for 5 min at 30° C. with 1 l (1 U/l) of T4 DNA polymerase. The T4 DNA polymerase was heat inactivated by incubation at 70° C. for 15 min. The samples were cooled, briefly spun, and the digested insert (35 ng) and vector (100 ng) mixed together and the volume brought to 10 l with 1 mM $MgCl_2$. The sample was heated to 70° C. for 2 min and cooled over 20 min to room temperature to allow the complementary 5' single-stranded overhangs of the insert and vector resulting from the exonuclease digestion to anneal together (FIG. 5). The annealed DNA (1.5 l) was electroporated (Example 8) into 30 l of electrocompetent E. coli strain DH10B.

The transformed cells were diluted to 1.0 ml with 2×YT broth and 1 l, 10 l, and 100 l plated on LB agar plates supplemented with tetracycline (10 g/ml) and grown overnight at 37° C. The following day, two clones were picked and grown overnight in 2×YT (10 g/ml tetracycline) at 37° C. To test protein expression driven from the ara promoter, these cultures were diluted 1/50 in 2×YT(tet) and grown to $OD_{600}=1.0$ at which point they were each split into two cultures, one of which was induced by the addition of arabinose to a final concentration of 0.2% (W/V). The cultures were grown overnight at room temperature, and assayed for Fab production by ELISA. Both of the induced cultures were producing approximately 20 g/ml Fab. There was no detectable Fab in the uninduced cultures.

Initial efforts to clone polyclonal populations of Fab were hindered by backgrounds of undigested vector ranging from 3–13%. This undigested vector resulted in loss of Fab expressing clones due to the selective advantage non-expressing clones have over Fab expressing clones. A variety of means were tried to eliminate undigested vector from the vector preparations with only partial success; examples including: digesting the vector overnight 37° C. with NcoI, extracting, and redigesting the preparation a second time; including spermidine in the NcoI digest; including single-stranded binding protein (United States Biochemical, Cleveland, Ohio) in the NcoI digest; preparative gel electrophoresis. It was then noted that there is a HindIII restriction site in pBR, 19 base-pairs from the 5'-end of the tetracycline promoter. A vector missing these 19 base-pairs is incapable of supporting growth in the presence of tetracycline, eliminating background due to undigested vector.

The ara-based expression vector was modified to make it tetracycline sensitive in the absence of insert. This was done by digesting the pBRnco vector with NcoI and HindIII (Boehringer Mannheim, Indianapolis, Ind.), which removed the entire antibody gene cassette and a portion of the tet promoter (FIG. 4B). The region excised by NcoI/HindIII digestion was replaced with a stuffer fragment of unrelated DNA by ligation as described above. The ligation reaction was diluted to 20 l, and 1 l electroporated (Example 8) into electrocompetent E. coli strain DH10B, plated on LB ampicillin (100 g/ml) and incubated at 37° C.

After overnight incubation, transformants were picked and grown overnight in LB broth supplemented with ampicillin (100 g/ml). The vector (plasmid) was purified from each culture by Wizard miniprep columns following manufacturers recommendations. This modified vector, pBRncoH3, is tet sensitive, but still retains ampicillin resistance for growing preparations of the vector.

The antibody gene inserts were amplified by PCR with primers I and J (Table 3) as described in Example 3; primer J containing the 19 base-pairs of the tet promoter removed by HindIII digestion, in addition to 20 base-pairs of vector sequence 3' to the HindIII site for annealing. This modified vector was digested with NcoI/HindIII and, together with the insert, exonuclease digested and annealed as described previously. The tet resistance is restored only in clones that contain an insert capable of completing the tet promoter. The annealed Fab/vector (1 1) was transformed (Example 8) into 30 1 of electrocompetent E. coli strain, DH10B.

The transformed cells were diluted to 1.0 ml with 2×YT broth and 10 1 of $10^{-2}$ and $10^{-3}$ dilutions plated on LB agar plates supplemented with tetracycline at 10 g/ml to determine the size of the subcloned polyclonal population. This plating also provides and opportunity to pick individual clones from the polyclonal if necessary. The remaining cells were incubated at 37° C. for 1 hr and then diluted ¹⁄₁₀₀ into 30 ml 2×YT supplemented with 1% glycerol and 20 g/ml tetracycline and grown overnight at 37° C. The overnight culture was diluted ¹⁄₁₀₀ into the same media and grown 8 hr at which time glycerol freezer stocks were made for long term storage at −80° C.

The new vector eliminates growth bias of clones containing vector only, as compared to clones with insert. This, together with the arabinose promoter which is completely repressed in the absence of arabinose, allows cultures of transformed organisms to be expanded without biasing the polyclonal antibody population for antibodies that are better tolerated by E. coli until induction.

A variant of this vector was also constructed to clone any protein with or without a signal sequence. The modified vector has the NcoI restriction site and all of the pelB signal-sequence removed. In its place a NsiI restriction site was incorporated such that upon NsiI digestion and then T4 digestion, there is single base added, in frame, to the araBAD promoter that becomes the adenosine residue (A) of the ATG initiation codon. The HindIII site and restoration of the tetracycline promoter with primer J (Table 3) remains the same as described for the pBRncoH3 vector. Additionally, the T4 exonuclease cloning process is identical to that described above, except that the 5' PCR primer used to amplify the insert contains 20 bp of vector sequence at its 5'-end corresponding to 3'-end of the araBAD promoter rather than the 3'-end of the PelB signal sequence.

Three PCR primers, K, L, and M (Table 3) were used for amplifying the araC regulatory gene (including the araBAD promoter). The 5'-primer, primer K, includes an EcoRI restriction site at its 5'-end for ligating the ara insert into the pBR vector. The 3'-end of the insert was amplified using two primers because a single primer would have been too large to synthesize. The inner 3'-primer (L) introduces the NsiI restriction site, in frame, with the araBAD promoter, with the outer 3' primer (M) introducing the HindIII restriction site that will be used for ligating the insert into the vector.

The PCR reaction was performed as in Example 3 on a 4×100 1 scale; the reactions containing 100 pmol of 5' primer (K), 1 pmol of the inner 3' primer (L), and 100 pmol of outer 3' primer (M), 10 1 2 mM dNTPs, 0.5 L Taq DNA Polymerase, 10 1 10×Taq DNA polymerase buffer with $MgCl_2$, and $H_{20}$ to 100 L. The araCparaBAD PCR product was precipitated and fractionated by agarose gel electrophoresis and full-length products excised from the gel, purified, resuspended in water, and prepared for cloning by digestion with EcoRI and HindIII as described earlier. The pBR vector (Life Technologies, Gaithersburg, Md.) was prepared to receive this insert by digestion with EcoRI and HindIII and purification by agarose gel electrophoresis as described above.

The insert and vector were mixed (2:1 molar ratio) together with 1 1 10 mM ATP, 1 1 (1 U/1) T4 DNA ligase, 1 1 10×ligase buffer in a final volume of 10 1 and ligated overnight at 15° C. The ligation reaction was diluted to 20 1, and 1 1 electroporated into electrocompetent E. coli strain, DH 10B (Example 8), plated on LB tetracycline (10 g/ml) plates and grown overnight at 37° C. Clones were picked and grown overnight in 3 ml LB broth supplemented with tetracycline.

These clones were tested for the correct insert by PCR amplification (Example 3) with primers K and M, using 1 1 of overnight culture as template. Agarose gel electrophoresis of the PCR reactions demonstrated that all clones had the araCparaB insert. The vector (plasmid) was purified from each culture by Wizard miniprep columns following manufacturers recommendations. The new vector, pBRnsi contained the araC gene, the araBAD promoter, and a NsiI restriction site.

The vector was tested for expression by introducing a murine Fab. The region was amplified by PCR (Example 3) from a plasmid (20 ng) containing a murine Fab with primers O and N (Table 3). The primers, in addition to having sequence specific to the Fab, contain 20 bp of vector sequence at their 5'-end corresponding to the 3'-end araBAD promoter and the 5'-end of the $C_H 1$ region for cloning purposes. The pBRnsi vector was linearized with NsiI and HindIII. The vector and the PCR product were run on an agarose gel, and full-length products were excised from the gel and purified as described previously. The vector and insert were digested with T4 DNA polymerase and annealed as described earlier. The annealed DNA (1 1) was electroporated (Example 8) into 30 1 of electrocompetent E. coli strain DH10B. The transformed cells were diluted to 1.0 ml with 2×YT broth and 11, 10 1, and 100 1 plated on LB agar plates supplemented with tetracycline (10 g/ml) and grown overnight at 37° C.

Nitrocellulose lifts were placed on the placed on the surface of the agar plates for 1 min and processed as described (Section 12.24, Molecular Cloning, A laboratory Manual, (1989) Sambrook. J.). The filters were developed with goat anti-kappa-AP, and a positive (kappa expressing) clone was picked and grown overnight in 2×YT (10 g/ml tetracycline) at 37° C. The vector (plasmid) was purified from the culture by Wizard miniprep columns (Promega, Madison, Wis.) following manufacturers recommendations. The Fab region was excised by NcoI/HindIII digestion and replaced with a stuffer fragment of unrelated DNA by ligation as described above. The ligation reaction was diluted to 20 1, and 1 1 electroporated (Example 8) into electrocompetent E. coli strain DH10B, plated on LB ampicillin (100 g/ml) and incubated at 37° C. After overnight incubation, transformants were picked and grown overnight in LB broth supplemented with ampicillin (100 g/ml). The vector (plasmid) was purified from each culture by Wizard miniprep columns following manufacturers recommendations. This modified vector, pBRnsiH3, is tet sensitive, but still retains ampicillin resistance for growing preparations of the vector.

EXAMPLE 15

Subcloning Polyclonal Fab Populations into Expression Vectors and Electroporation into *Escherichia coli*

The polyclonal IL8 antibody phage form both the $10^9$ and $10^{10}$ affinity cuts (see Example 13) were diluted ¹⁄₃₀ in 2×YT and 1 μl used as template for PCR amplification of the antibody gene inserts with primers 197 (Example 5) and 970 (see below). PCR (3–100 μL reactions) was performed using a high-fidelity PCR system, Expand (Roche Molecular Biochemicals, Indianapolis, Ind.) to minimize errors incorporated into the DNA product. Each 100 µl reaction contained 100 pmol of 5' primer 197, 100 pmol of 3' primer 970, 0.7 units of Expand DNA polymerase, 10 µl 2 mM dNTPs, 10 µl 10×Expand reaction buffer, 1 µl diluted phage stock as template, and water to 100 µl. The reaction was carried out in a Perkin-Elmer thermal cycler (Model 9600) using the following thermal profile: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The PCR products were ethanol precipitated, pelleted and dried as described above. The DNA was dissolved in water and fractionated by agarose gel electrophoresis. Only full-length products were excised from the gel, purified, and resuspended in water as described earlier.

```
Primer 970-5' GT GAT AAA CTA CCG TA AAG CTT ATC
GAT GAT AAG CTG TCA A TTA GTG ATG GTG ATG GTG ATG
AGA TTT G (SEQ ID NO:29)
```

The insert and NcoI/HindIII digested pBRncoH3 vector were prepared for T4 exonuclease digestion by adding 1.0 µl of 10× Buffer A to 1.0 µg of DNA and bringing the final volume to 9 µl with water. The samples were digested for 4 min at 30° C. with 1 µl (1 U/µl) of T4 DNA polymerase. The T4 DNA polymerase was heat inactivated by incubation at 70° C. for 10 min. The samples were cooled, briefly spun, and 100 ng of the digested antibody gene insert and 1 µl of 10× annealing buffer were mixed with 100 ng of digested vector in a 1.5 mL tube. The volume was brought to 10 µl with water, heated to 70° C. for 2 min and cooled over 20 min to room temperature to allow the insert and vector to anneal. The insert and vector were ligated together by adding 1 µl of 10×synthesis buffer, 1 µl T4 DNA ligase (1 U/µl), 1 µl diluted T7 DNA polymerase (1 U/µl) and incubating at 37° C. for 15 min.

The ligated DNA (1 µl) was diluted into 2 µL of water, then 1 µL of the diluted DNA was electroporated (Example 8) into 40 µl of electrocompetent E. coli strain, DH10B. The transformed cells were diluted to 1.0 ml with 2×YT broth and 10 µl of $10^{-1}$, $10^{-2}$ and $10^{-3}$ dilutions plated on LB agar plates supplemented with tetracycline at 10 µg/ml to determine the size of the subcloned polyclonal population. The $10^9$ affinity polyclonal had approximately 6000 different clones, and the $10^{10}$ affinity polyclonal had approximately 10,000 different clones. The remaining cells were incubated at 37° C., 300 rpm for 1 hr, and then the entire culture was transferred into 50 ml 2×YT supplemented with 1% glycerol and 20 µg/ml tetracycline and grown overnight at 37° C. The overnight culture was diluted 1/100 into the same media, grown 8 hr, and glycerol freezer stocks made for long term storage at −80° C.

Monoclonal antibodies were obtained by picking individual colonies off the LB agar plates supplemented with tetracycline used to measure the subcloning efficiency or from plates streaked with cells from the glycerol freezer stocks. The picks were incubated overnight at 37° C., 300 rpm in a shake flask containing 2×YT media and 10 µg/mL tetracyclin. Glycerol freezer stocks were made for each monoclonal for long term storage at −80° C. A total of 15 different colonies were picked off of the $10^9$ affinity cut and analyzed for binding to IL8. Of those 15 clones, two expressed a very low amount of antibody, one expressed antibody but did not bind IL8, two expressed functional antibody but the DNA sequence was ambiguous most likely due to sequence template quality, and one expressed functional protein but was not sequenced. Nine clones were sequenced as described in Example 22. A total of 21 different colonies were picked off of the $10^{10}$ affinity cut and analyzed for binding to IL8. Of those 21 clones, four expressed a very low amount of antibody, three expressed antibody but did not bind IL8, and four expressed functional protein but were not sequenced. Ten clones were sequenced as described in Example 22.

EXAMPLE 16

Expression of IL8 or Antibodies in Shake Flasks and Purification

A shake flask inoculum is generated overnight from a −80° C. cell bank or from a colony (Example 15) in an incubator shaker set at 37° C., 300 rpm. The cells are cultured in a defined medium described above. The inoculum is used to seed a 2 L Tunair shake flask (Shelton Scientific, Shelton, Conn.) which is grown at 37° C., 300 rpm. Expression is induced by addition of L(+)-arabinose to 2 g/L during the logarithmic growth phase, following which, the flask is maintained at 23° C., 300 rpm. Following batch termination, the culture is passed through an M-110Y Microfluidizer (Microfluidics, Newton, Mass.) at 17000 psi.

Purification employs immobilized metal affinity chromatography. Chelating Sepharose FastFlow resin (Pharmacia, Piscataway, N.J.) is charged with 0.1 M $NiCl_2$ and equilibrated in 20 mM borate, 150 mM NaCl, 10 mM imidazole, 0.01% $NaN_3$, pH 8.0 buffer. A stock solution is used to bring the culture to 10 mM imidazole. The supernatant is then mixed with the resin and incubated for at least 1 hour in the incubator shaker set at room temperature, 150–200 rpm. IL8 or antibody is captured by means of the high affinity interaction between nickel and the hexahistidine tag on the protein. After the batch binding is complete, the resin is allowed to settle to the bottom of the bottle for at least 10 min. The culture is carefully poured out of the bottle, making sure that the resin is not lost. The remaining culture and resin mixture is poured into a chromatography column. After washing, the protein is eluted with 20 mM borate, 150 mM NaCl, 200 mM imidazole, 0.01% $NaN_3$, pH 8.0 buffer. If needed, the protein pool is concentrated in a Centriprep-10 concentrator (Amicon, Beverly, Mass.) at 3500 rpm. It is then dialyzed overnight into 20 mM borate, 150 mM NaCl, 0.01% $NaN_3$, pH 8.0 for storage, using 12–14,000 MWCO dialysis tubing.

IL8 was further purified by the following procedure. The protein was dialyzed exhaustively against 10 mM sodium phosphate, 150 mM sodium chloride, pH 7.35, and diluted 1:3 with 10 mM sodium phosphate, pH 7.35. This material was loaded onto a Q-Sepharose column (Amersham Pharmacia Biotech, Piscataway, N.J.) equilibrated in 10 mM sodium phosphate, 40 mM NaCl. The IL8 was contained in the flow through fraction. By SDS-polyacrylamide gel analysis, the IL8 was greater than 95% pure. The IL8 was brought to 120 mM NaCl and 0.01% $NaN_3$ and stored at −80° C.

EXAMPLE 17

Preparation of 7F11 Monoclonal Antibody

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 min, under argon, a solution of 1-acetylimidazole (9.6 g, 0.087 moles) in THF (100 ml). The solution was allowed to stir a further 3 hr at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

Decapeptide Derivatives

The decapeptide, YPYDVPDYAS (SEQ ID NO:30), (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 min at room temperature. This solution was added to the decapeptide solution and the reaction mixture was stirred for at least six hr at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 M potassium hydroxide was added to a final concentration of 0.2 M while mixing vigorously. The derivative solution was allowed to stand for 5 min at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 µL of the solution into 990 µL of a solution containing 0.25 mM 5,5'-dithiobis (2-nitrobenzoic acid) (DTNB, Aldrich Chemical Co., Milwaukee Wis.) and 0.2 M potassium borate, pH 8.0. The thiol concentration in mM units was equal to the A412(100/13.76).

Preparation of Conjugates of Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hr at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed decapeptide derivative was separately added to portions of the KLH-maleimide in substantial molar excess over the estimated maleimide amounts present and the solution was stirred for 4 hr at 4° C. and then each was dialyzed against 3 volumes of one liter of pyrogen-free phosphate-buffered saline, pH7.4, prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed decapeptide derivative was separately added to portions of the BSA-maleimide in substantial molar excess over the estimated maleimide amounts present and the solution was stirred for 4 hr at 4° C. The solutions were used to coat microtiter plates for the detection of antibodies that bound to the decapeptide derivative by standard techniques.

Production and Primary Selection of Monoclonal Antibodies

Immunization of Balb/c mice was performed according to the method of Liu, et al. *Clin Chem* 25:527–538 (1987). Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with a BSA conjugate of decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to the decapeptide derivative identified which of the positive clones that bound the BSA conjugates were actually binding the SMCC-BSA. The antibodies specific for SMCC-BSA may be eliminated at this step. Monoclonal antibody 7F11, specific for the decapeptide derivative, was produced and selected by this process.

EXAMPLE 18

Preparation of 7F11 Magnetic Latex
MAG/CM-BSA

To 6 mL of 5% magnetic latex (MAG/CM, 740 m 5.0%, Seradyn, Indianapolis, 1N) was added 21 mL of water followed by 3 mL of 600 mM 2-(4-morpholino)-ethane sulfonic acid, pH 5.9 (MES, Fisher Scientific, Pittsburgh, Pa.). Homocysteine thiolactone hydrochloride (HCTL, 480 mg, Aldrich Chemical Co., Milwaukee, Wis.) and 1-(3-Dimethylaminopropyl)-3-ethylcarbodiimide (EDAC, 660 mg, Aldrich Chemical Co., Milwaukee, Wis.) were added in succession, and the reaction mixture was rocked at room temperature for 2 h. The derivatized magnetic latex was washed 3 times with 30 mL of water (with magnet as in Example 14) using probe sonication to resuspend the particles. The washed particles were resuspended in 30 mL of water. Three mL of a solution containing sodium hydroxide (2M) and EDTA (1 mM) was added to the magnetic latex-HCTL suspension, and the reaction proceeded at room temperature for 5 min. The pH was adjusted to 6.9 with 6.45 mL of 1 M hydrochloric acid in 500 mM sodium phosphate, 100 mM sodium borate. The hydrolyzed magnetic latex-HCTL was separated from the supernate with the aid of a magnet, and then resuspended in 33 mL of 50 mM sodium phosphate, 10 mM sodium borate, 0.1 mM EDTA, pH 7.0. The magnetic latex suspension was then added to 2 mL of 36 mg mL-1 BSA-SMCC (made as described in Example 21 with a 5-fold molar excess of SMCC over BSA), and the reaction mixture was rocked overnight at room temperature. N-Hydroxyethylmaleimide (NHEM, 0.42 mL of 500 mM, Organix Inc., Woburn, Mass.) was added to cap any remaining thiols for 30 min. After 30 min, the magnetic latex-BSA was washed twice with 30 mL of 50 mM potassium phosphate, 10 mM potassium borate, 150 mM sodium chloride, pH 7.0 (50/10/150) and twice with 30 mL of 10 mM potassium phosphate, 2 mM potassium borate, 200 mM sodium thiocyanate, pH 7.0 (10/2/200). The magnetic latex-BSA was resuspended in 30 mL of 10/2/200.

7F11-SH (1:5)

To a solution of 7F11 (3.8 mL of 5.85 mg mL$^{-1}$) was added 18 L of SPDP (40 mM in acetonitrile). The reaction proceeded at room temperature for 90 min after which taurine (Aldrich Chemical Co., Milwaukee, Wis.) was added to a final concentration of 20 mM. Fifteen min later DTT was added to a final concentration of 2 mM, and the reduction reaction proceeded at room temperature for 30 min. The 7F11-SH was purified on G-50 (40 mL) that was eluted with 50/10/150 plus 0.1 mM EDTA. The pool of purified 7F11-SH was reserved for coupling to the MAG/CM-BSA-SMCC.

MAG/CM-BSA-7F11

SMCC (10 mg) was dissolved in 0.5 mL of dry dimethylformamide (Aldrich Chemical Co., Milwaukee, Wis.), and this solution was added to the magnetic latex-BSA suspension. The reaction proceeded at room temperature with gentle rocking for 2 h. Taurine was added to a final concentration of 20 mM. After 20 min the magnetic latex-BSA-SMCC was separated from the supernate with the aid of a magnet and then resuspended in 10/2/200 (20 mL) with probe sonication. The magnetic latex was purified on a column of Superflow-6 (240 mL, Sterogene Bioseparations Inc., Carlsbad, Calif.) that was eluted with 10/2/200. The buffer was removed, and to the magnetic latex cake was added 30 mL of 0.7 mg mL$^{-1}$ 7F11-SH. The reaction mixture was rocked overnight at room temperature. After 20 hr the reaction was quenched with mercaptoethanol (2 mM, Aldrich Chemical Co., Milwaukee, Wis.) followed by NHEM (6 mM). The MAG/CM-7F11 was washed with 10/2/200 followed by 50/10/150. The magnetic latex was then resuspended in 30 mL of 50/10/150.

EXAMPLE 19

Cloning of the Mature Human Interleukin-8 Antigen

PCR primers A and B (5' and 3' respectively, Table 3) were made corresponding to the coding sequence at the 5'-end of the mature human interleukin-8 antigen and the coding sequence at the 3'-end of human interleukin-8 (Genbank accession number M28130). The 5' primer contains 20 base pairs of vector sequence at its 5'-end corresponding to the 3'-end of the pBRncoH3 vector (Example 14). The 3' primer has six histidine codons inserted between the end of the coding sequence and the stop codon to assist in purification of the recombinant protein by metal-chelate chromatography. The 3' primer also has 19 base-pairs of tet promoter removed from the tet resistance gene in pBRncoH3 by HindIII digestion, and 20 base-pairs of vector sequence 3' to the HindIII site at its 5' end (Example 14).

The PCR amplification of the mature interleukin-8 gene insert was done on a 3×100 µl reaction scale each containing 100 pmol of 5' primer (A), 100 pmol of 3' primer (B), 2.5 units of Expand polymerase, 10 µl 2 mM dNTPs, 10 µl 10× Expand reaction buffer, 1 µl of Clontech Quick-clone human liver cDNA (Clontech Laboratories, Palo Alto, Calif.) as template, and water to 100 µl. The reaction was carried out in a Perkin-thermal cycler as described in Example 15. The PCR products were precipitated and fractionated by agarose gel electrophoresis and full-length products excised from the gel, purified, and resuspended in water (Example 14). The insert and NcoI/HindIII digested pBRncoH3 vector were prepared for T4 exonuclease digestion by adding 10 µl of 10× Buffer A to 10 µg of DNA and bringing the final volume to 9 µl with water. The samples were digested for 4 minutes at 30° C. with 1 µl (1 U/µl) of T4 DNA polymerase. The T4 DNA polymerase was heat inactivated by incubation at 70° C. for 10 minutes. The samples were cooled, briefly spun, and 15 ng of the digested insert added to 100 ng of digested pBRncoH3 vector in a fresh microfuge tube. After the addition of 1.0 µl of 10× annealing buffer, the volume was brought to 10 µl with water. The mixture was heated to 7$^{0o}$ C. for 2 minutes and cooled over 20 minutes to room temperature, allowing the insert and vector to anneal. The annealed DNA was diluted one to four with distilled water and electroporated (example 8) into 30 µl of electrocompetent E. coli strain, DH10B. The transformed cells were diluted to 1.0 ml with 2×YT broth and 10 µl 100 µl, 300 µl plated on LB agar plates supplemented with tetracycline (10 µg/ml) and grown overnight at 37° C. Colonies were picked and grown overnight in 2×YT (20 µg/ml tetracycline at 37° C. The following day glycerol freezer stocks were made for long term storage at −80° C. The sequence of these clones was verified at MacConnell Research (San Diego, Calif.) by the dideoxy chain termination method using a Sequatherm sequencing kit (Epicenter Technologies, Madison, Wis.), oligonucleotide primers C and D (Table 3) that bind on the 5' and 3' side of the insert in the pBR vector, respectively, and a LI-COR 4000L automated sequencer (LI-COR, Lincoln, Nebr.).

TABLE 3

PCR and Sequencing Primer Sequences

A- 5' (TCGCTGCCCAACCAGCCATGGCCAGTGCTAAAGAACTTAGATCTCAG)
(SEQ ID NO:31)

B- 5' (GTGATAAACTACCGCATTAAAGCTTATCGATGATAAGCTGTCAATTAGTGAT
GGTGATGGTGATGTGAATTCTCAGCCCTCTTCAA)

TABLE 3-continued

PCR and Sequencing Primer Sequences (SEQ ID NO:32)

C- 5' (GCAACTCTCTACTGTTTCTCC)
(SEQ ID NO:33)

D- 5' (GAGGATGACGATGAGCGC)
(SEQ ID NO:34)

EXAMPLE 20

Estimation of Library Diversity

Upon the completion of library selection for a given target antigen, the library contains members encoding antibodies exhibiting an affinity determined by the criteria used during the selection process. Preferably, the selection process is repeated until the majority of the members in the library encode antibodies exhibiting the desired characteristics. Most preferably, the selection process is repeated until substantially all of the members of the library encode antibodies that exhibit the desired affinity for the target antigen. In order to estimate the number of different antibodies in the selected library, individual members are randomly chosen and sequenced to determine if their amino acid sequences are different. Antibodies exhibiting at least one amino acid difference in either the heavy or light chain variable domain (preferably in the CDRs) are considered different antibodies. A random sampling of the library in such a manner provides an estimate of the frequency antibody copies in the library. If ten antibodies are randomly sampled and each antibody amino acid sequence is distinct from the other sampled antibodies, then an estimate of 1/10 can be applied to the frequency that one might expect to observe for repeated antibodies in the library. A library with hundreds or thousands of total members will exhibit a probability distribution for the frequency of antibody copies that closely approximates the Poisson distribution, $Pr(y)=e^{-\eta}\eta^y/y!$, where the probability of a particular value y of the frequency is dependent only on the mean frequency $\eta$. If no antibody replicates are observed in a random sampling of ten antibodies, then an estimate for $\eta$ is 0.1 and the probability of not observing a copy of a library member when randomly sampling the library is estimated by $Pr(0)=e^{-0.1}=0.9$. Multiplying this probability by the total number of members in the library provides an estimate of the total number of different antibodies in the library.

EXAMPLE 21

Determination of Antibody Affinity for IL-8 Labeled with Biotin

The equilibrium binding constants of individual monoclonal antibodies were determined by analysis of the total and free antibody concentrations after a binding equilibrium was established in the presence of biotinylated IL-8 at $10^{-10}$ M in a 1% solution of bovine serum albumin buffered at pH 8.0. In all experiments the antibody was mixed with IL-8 and incubated overnight at room temperature before the biotin-labeled IL-8 was removed from the solution by adding superparamagnetic microparticles (0.96 µm, Bangs Laboratories, Carmel, Ind.) coated with NeutrAvidin™ (deglycosylated avidin, Pierce, Rockford, Ill.) incubating for 10 minutes, and separating the particles from the solution using a permanent magnet. The supernatant solution was removed from the microtiter wells containing the magnetic particles and the antibody concentration was determined. The concentration of total antibody added to the individual wells was determined by quantifying the antibody in a sample that was not mixed with IL-8. The concentration of immunoreactive antibody (the fraction of the antibody protein that was capable of binding to IL-8) was determined by incubating a large excess of biotin-labeled IL-8 with a known concentration of antibody for a sufficient time to reach equilibrium, removing the IL-8 using magnetic latex as described above, and quantifying the concentration of antibody left in the solution using the assay described below. The fraction of antibody that bound to the excess of IL-8 is the immunoreactive fraction and the fraction that did not bind to IL-8 is the non-immunoreactive fraction. When determining the concentration of total antibody in an equilibrium mixture, the antibody concentration is the amount of total antibody in the mixture determined from the assay described below multiplied by the immunoreactive fraction. Similarly, when calculating the free antibody in an equilibrium mixture after the removal of IL-8, the non-immunoreactive fraction of antibody is subtracted from the free antibody concentration determined by the assay described below. The bound fraction, B, is determined by subtracting the free immunoreactive antibody concentration in the mixture, F, from the total immunoreactive antibody concentration in the mixture. From the Law of Mass Action, $B/F=-KB+KT$ where T is the total antigen concentration. A plot of B/F vs. B yields a slope of $-K$ and a y-intercept of KT.

To determine the antibody concentrations in samples a sandwich assay was constructed using immobilized monoclonal antibody 7F11 to bind the decapeptide tag present a the C-terminus of the kappa chain and affinity-purified goat-anti-human kappa antibody conjugated to alkaline phosphatase (Southern Biotechnology Associates, Birmingham, Ala.) to bind the kappa chain of each human antibody. A purified antibody of known concentration with the same kappa chain construction as the assayed antibodies was used to calibrate the assay. The 7F11 antibody was labeled with biotin and immobilized on microtiter plates coated with streptavidin using standard methods. The assay was performed by adding 50 µl of sample from the equilibrium mixtures to each well and incubating for four hours at room temperature. The conjugate was added at a final concentration of approximately 0.125 µg/ml to each well and incubated overnight at room temperature. The wells were washed using an automatic plate washer with borate buffered saline containing 0.02% polyoxyethylene 20-sorbitan monolaurate at pH 8.2 and the ELISA Amplification System (Life Technologies, Gaithersburg, Md.) was employed to develop the assay. The absorbance at 490 nm was measured using a microtiter plate reader and the unknown antibody concentrations were determined from the standard curve.

TABLE 4

Affinities of anti-IL-8 antibodies

| Monoclonal Antibody | % Immunoreactive Protein | Affinity ($10^{10}$ $M^{-1}$) |
|---|---|---|
| M1-3 | 93 | 6.1 |
| M1-4 | 93 | 22 |
| M1-5 | 90 | 11 |
| M1-8 | 91 | 10 |
| M1-10 | 90 | 6.1 |
| M1-21 | 67 | 6.6 |
| M1-23 | 91 | 8.9 |
| M1-25 | 90 | 6.4 |
| M2-11 | 93 | 10 |
| M2-12 | 93 | 28 |
| M2-16 | 90 | 1.9 |
| M2-18 | 80 | 5.4 |
| M2-20 | 94 | 37 |
| M2-34 | 94 | 27 |

EXAMPLE 22

DNA Sequence Analysis of Random Clones

The glycerol freezer stocks (Example 5) corresponding to each monoclonal Fab to be analyzed were used to inoculate 50 ml cultures for plasmid isolation and subsequent DNA sequencing of the interleukin-8 insert. After overnight growth in 2×YT (10 µg/ml tetracycline) at 37° C., the recombinant plasmid was purified using a Qiagen Plasmid Midi kit (Qiagen, Valencia, Calif.) following manufacturer's recommendations. The sequence corresponding to the kappa and heavy chain variable and constant regions for each monoclonal was determined at MacConnell Research (San Diego, Calif.). The nomenclature used for antibodies is the same as that in Example 21. Sequencing was done by the dideoxy chain termination method using a Sequatherm sequencing kit (Epicenter Technologies, Madison, Wis.), oligonucleotide primers C and D (Table 3) that bind on the 5' and 3' side of the Fab cassette in the pBR vector, respectively, and a LI-COR 4000L automated sequencer (LI-COR, Lincoln, Nebr.).

M1-1L (SEQ ID NO:35)

AAATTGTGTTGACGCATTCCAGCCAC CCTGTCTTTGTCTCCAGGGGAAAGAGCCACCCTCTCCTGCAGG GCCAGTCAGGGTGTTAGCAGCTACTTAGCCTGGTACCAACAGAAACCTGGC CAGGCTCCCAGGCTCCTC ATCTATGATGCATCCAACAGGGCCACTGGCATCCCAGCCAGGT TCAGTGGCAGTGGGTCTGGGACAGAC TTCACTCTCACCATCAGCAGCCTAGAGCCTGAAGATTTTGCA GTTTATT ACTGTCAGCAGCGTAGAACT GGCCTCGGACGTTCGGCCAAGGGACCAAGGTGGAAATCAAACGAACTGTGGCTGCACCATCTGTCTTCA TCTTCCCGCCATCTGATGAGCAGTTGAAATCTGGAAC TGCCTCTGTTGTGT GCCTGCTGAATAACTTCT ATCCAGAGAGGCCAAAGTACAGTGGAAGGTGGATAACGCCCTCCAATCGGTA ACTCCCAGGAGAGTG TCACAGAGCAGGACAGCAAGGACAGCACCTACAGCCTC AGCAGCACCCTG ACGCTGAGCAAAGCAGACT ACGAGAAACACAAAGTCTACGCCTGCGAAGTCACCCATCAGGGCCTGAGCTCGCCC GTCACAAAGAGCT TCAACAGGGGAGAGTCTTATCCATATGATGTGCCAGATTATGCGAGC

M1-3L (SEQ ID NO:37)

GAAATAGTGATGACGCAGTCTCCAGCCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGACTGGAGCCTGAAGATTTTGCA GTGTATTACTGTCAGCAGTAT GGTAGCTCACCTCCATTCACTTTCGGCCCTGGGACCAAAGTGGATATCAAACGAACTGTGGCTGCACCA TCTGTCTTCATCTTCCCGCCATCTGATGAGCAGTTGAAATCTGGAACTG CCTCTGTTGTGTGCCTGCTG AATAACTTCTATCCCAGAGAGGCCAAAGTACAGTGGAAGGTGGATAACGCCCTCCAATCGGGTAACTCC CAGGAGAGTGTCACAGAGCAGGACAGCAAGGACAGCACCTACAGCCTCAGCAGCACCCTGACGCTGAGC AAAGCAGACTACGAGAAACACAAAGTCTACGCCTGCGAAGTCACCCATCAGGGC CTGAGCTCGCCCGTC ACAAAGAGCTTCAACAGGGGAGAGTCTTATCCATATGATGTGCCAGATTATGCG AGC

M1-4L (SEQ ID NO:39)

GAAATTGTGTTGACGCAGTCTCCAGGCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAGG CTCCACATCTATGGTGCATCCAGAAGGGCCACTGGCATCCCAGACAGGTTCAGTGGCAGTGGGTCTGGG ACAGACTCACTCTCACCATCAGCAGACTGGAGCCTGAAGAT TTTGCA GTGTATTACTGTCAGCAGTTT GGTAGCTCATTCACTTTCGGCCCTGGGACCAAAGTGGATATCAAACGAACTGTGGCTGCACCATCTGTC TTCATCTTCCCGCCATCTGATGAGCAGTTGAAATCTGGAACTGCCTCTGTTGTGT GCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAG CAGCACCCTGACGCTGAGCAAAGCA GACTACGAGAAACACAAAGTCTACGCCTGCGAAGTCACCCATCAGGGCCTGAGCT CGCCGTCACAAAG CAGGGGAGAGTCTTATCCATATGATGTGCCAGATTATGCGAGC

M1–5L (SEQ ID NO:41)

GAAATAGTGATGACGCAGTCTCCAGGCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGACTGGAGCCTGAAGATTTTGCA GTGTATTACTGTCAGCAGTAT GGTAGCTCACCTATATTCACTTTCGGCCCTGGGACCAAAGTGGATATCAAACGAACTGTGGCTGCACCA TCTGTCTTCATCTTCCCGCCATCTGATGAGCAGTTGAAATCTGGAACTG CCTCTGTTGTGTGCCTGCTG AATAACTTCTATCCCAGAGAGGCCAAAGTACAGTGGAAGGTGGATAACGCCCTCCAA

TCGGGTAACTCC CAGGAGAGTGTCACAGAGCAG-
GACAGCAAGGACAGCACCTACAGCCTCAGC
AGCACCCTGACGCTGAGC AAAGCAGACTAC-
GAGAAACACAAAGTCTACGCCTGC-
GAAGTCACCCATCAGGGC CTGAGCTCGCCCGTC
ACAAAGAGCTTCAACAGGGGAGAGTCT-
TATCCATATGATGTGCCAGATTATGCG AGC

M1-8L (SEQ ID NO:43)

GAAATAGTGATGACGCAGTCTCCAG-
GCACCCTGTCTTTGTCTCCAGGGGAAA-
GAGCCACCCTCTCCTGC AGGGCCAGTCAGAGTGT-
TAGCAGCACCTACTTAGCCTGGTACCAGCAGAAA
CCTGGCCAGGCTCCCAGG CTCCTCATCTATGGTG-
CATCCAGCAGGGCCACTGGCATCCCAGA-
CAGGTTCAGTGGCAGTGGGTCTGGG ACAGACT-
TCACTCTCACCATCAGCAGACTGGAGCCTGAAGA
TTTTGCA GTGTATTACTGTCAGCAGTAT GTTAGCT-
CATTCACTTTCGGCCCTGGGAC-
CAAAGTGGATATCAAACGAACTGTGGCT-
GCACCATCTGTC
TTCATCTTCCCGCCATCTGATGAGCAGT-
TGAAATCTGGAACTGCCTCTGTTGTGT GCCTGCT-
GAATAAC TTCTATCCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGC AGCACCCT-
GACGCTGAGCAAAGCA GACTACGAGAAACA-
CAAAGTCTACGCCTGCGAAGTCACCCATCAGGGC
CTGAGCT CGCCCGTCACAAAG AGCTTCAA-
CAGGGGAGAGTCTTATCCATATGATGT-
GCCAGATTATGC GAGC

M1-10L (SEQ ID NO:45)

GATGTTGTGATGACACAGTCTCCAGC-
CACCCTGTCTTTGTCTCCAGGGGAAA-
GAGCCACCCTCTCCTGC AGGGCCAGTCAGAGTGT-
TAGCAGCTACTTAGCCTGGTACCAACAGAAACC
TGGCCAGGCTCCCAGGCTC CTCATCTATGATG-
CATCCAACAGGGCCACTGGCATCCCAGC-
CAGGTTCAGTGGCAGTGGGTCTGGGACA GACT-
TCACTCTCACCATCAGCAGCCTAGAGCCTGAAGAT
TTTGCAGTTTATT ACTGTCAGCAGCGTAGC AACTG-
GCCTCCCACTTTCGGCGGAGGGACCAAG-
GTGGAGATCAAACGAACTGTGGCTGCAC-
CATCTGTC
TTCATCTTCCCGCCATCTGATGAGCAGT-
TGAAATCTGGAACTGCCTCTGTTGTGT GCCTGCT
GAATAAC TTCTATCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGCA GCACCCT-
GACGCTGAGCAAAGCA GACTACGAGAAACA-
CAAAGTCTACGCCTGCGAAGTCACCCATCAGGGC
CTGAGCTCGCCCGTCACAAAG AGCTTCAACAGGG-
GAGAGTCTTATCCATATGATGTGCCA-
GATTATGCGAGC

M1-21L (SEQ ID NO:47)

GCCATCCGGATGACCCAGTCTCCATCCT-
TCCTGTCTGCATCTGTAGGAGACAGAGT-
CACCATCACTTGC CGGGCAAGTCAGAGCATTAG-
CAGCTATTTAAATTGGTATCAGCAGAAACCAGGG
AAAGCCCCTAAGCTC CTGATCTATGCTGCATC-
CAGTTTGCAAAGTGGGGTCCCATCAAG-
GTTCAGTGTCAGTGGATCTGGGACA GATCT-
CACTCTCACCATCAGCAGTCTGCAACCTGAAGAT
TTTGCAACTTATT ACTGTCAGTGTGGTTAC AGTA-

CACCATTCACTTTCGGCCCTGGGAC-
CAAAGTGGATATCAAACGAACTGTGGCT-
GCACCATCTGTC
TTCATCTTCCCGCCATCTGATGAGCAGT-
TGAAATCTGGAACTGCCTCTGTTGTGT GCCTGCT-
GAATAAC TTCTATCCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGC AGCACCCT-
GACGCTGAGCAAAGCA GACTACGAGAAACA-
CAAAGTCTACGCCTGCGAAGTCACCCATCAGGGC
CTGAGCT GCCCGTCACAAAG AGCTTCAACAGGG-
GAGAGTCTTATCCATATGATGTGCCAGATTATGCG
AGC

M1-23L (SEQ ID NO:49)

GAAATTGTGTTGACGCAGTCTCCAG-
GCACCCTGTCTTTGTCTCCAGGGGAAA-
GAGCCACCCTCTCCTGC AGGGCCAGTCAGAGTGT-
TAGCAGCAGCTACTTAGCCTGGTACCAGCAGAAA
CCTGGCCAGGCTCCCAGG CTCCTCATCTATGGTG-
CATCCAGCAGGGCCACTGGCATCCCAGA-
CAGGTTCAGTGGCAGTGGGTCTGGG ACAGACT-
TCACTCTCACCATCAGCAGACTGGAGCCTGAAGA
TTTTGCA GTGTATTACTGTCAGCAGTAT GGTAGCT-
CACCTCCGTACACTTTTGGCCAGGGGAC-
CAAGCTGGAGATCAAACGAACTGTGGCTGCACCA
TCTGTCTTCATCTTCCCGCCATCTGAT-
GAGCAGTTGAAATCTGGAACTG CCTCTGTTGTGT-
GCCTGCTG AATAACTTCTATCCCAGAGAGGC-
CAAAGTACAGTGGAGGGTGGATAACGCCCTCCAA
TCGGGTAACTCC CAGGAGAGTGTCACAGAGCAG-
GACAGCAAGGACAGCACCTACAGCCTCAGC
AGCACCCTGACGCTGAGC AAAGCAGACTAC-
GAGAAACACAAAGTCTACGCCTGC-
GAAGTCACCCATCAGGGCCTGAGCTCGCCCGTC
ACAAAGAGCTTCAACAGGGGAGAGTCT-
TATCCATATGATGTGCCAGATTATGCG AGC

M1-25L (SEQ ID NO:51)

GAAATTGTGTTGACGCAGTCTCCAG-
GCACCCTGTCTTTGTCTCCAGGGGAAA-
GAGCCACCCTCTCCTGC AGGGCCAGTCAGAGTGT-
TAGCAGCAGCTACTTAGCCTGGTACCAGCAGAAA
CCTGGCCAGGCTCCCAGG CTCCTCATCTATGGTG-
CATCCAGCAGGGCCACTGGCATCCCAAA-
CAGGTTCAGTGGCAGTGGGTCTGGG ACAGACT-
TCACTCTCACCATCAGCAGACTGGAGCCTGAAGA
TTTTGCA GTGTATTACTGTCAGCAGTAT GGTAGCT-
CATTCACTTTCGGCCCTGGGAC-
CAAAGTGGATATCAAACGAACTGTGGCT-
GCACCATCTGTC
TTCATCTTCCCGCCATCTGATGAGCAGT-
TGAAATCTGGAACTGCCTCTGTTGTGT GCCTGCT-
GAATAAC TTCTATCCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGCAG-
CACCCTGACGCTGAGCAAAGCA GACTAC-
GAGAAACACAAAGTCTACGCCTGCGAAGTCACCC
ATCAGGGC CTGAGCTCGCCCGTCACAAAG AGCT-
TCAACAGGGGAGAGTCTTATCCATAT-
GATGTGCCAGATTATGCGAGC

M1-1H (SEQ ID NO:53)

CAGGTGCAGCTGGTGGAGTCTGGGGGAG-
GCGTGGTCCAGCCTGGGAAGTCCCT-
GAGACTCTCCTGTGCA GCGTCTGAATTCACCAT-

CAGTTACTATGGCATGCACTGGGTCCGCCAGGTT CCAGGCAAGGGGCTGGAG TGGGGTGGCAGCT-GTCTGGTATGATGAAAGTACTACATAT-TCTCCAGACTCCGTGAAGGGCCGATTCACC ATCTC-CAGAGACGATTCCAAGAACACGCTGTATCTGCAA ATGAACAGCC GAGAGCCGAGGACACGGCT GTG-TATTACTGTGCGAGAGATAGGGTGGGC-CTCTTTGACTACTGGGGCCAGGGAAC-CCTGGTCACCGTC TCCTCAGCCTCCACCAAGGGCCCATCG-GTCTTCCCCCT GGCACCC TCCTCCAAGAGCAC-CTCTGGGGGC ACAGCGGCCCTGGGCTGCCTGGT-CAAGGACTACTTCCCCGAACCGGTGACGGTGTCG TGGAACTCAGGC GCCCTGACCAGCGGCGTGCA-CACCTTCCCGGCTGTCCTACAGTCCTCAGGAC TCTACTCCCTCAGCAGC GTGGTGACCGTGCCCTC-CAGCAGCTTGGGCACCCAGACCTA-CATCTGCAACGTGAATCA CAAGCCCAGC AACAC-CAAGGTGGACAAGAAAGCAGAGCCCAAATCTCA TCACCATCACCAT CAC

M1-3H (SEQ ID NO:55)

CCGATGTGCAGCTGGTGCAGTCTGGGG-GAGGCGTGGTCCAGCCTGGGAGGTCCCT-GAGACTCTCCTGTG CAGCGTCTGGATTCACCT-TCAGTTACTATGGCATGCACTGGGTCCGCCAGGC TCCAGGCAAGGGGCTGG AGTGGGTGACACT-TATAACCTATGATGGAGATAATAAATAC-TATGCAGACTCCGTGAAGGGCCGATTCA CCATCTC-CAGAGACAATTCCAAGAACACGCTGTATCTGCAA ATGAACAGCCTG AGAGCCGAGGACACGG CTGTG-TATTACTGTGCGAGAGACGGGATCGGG-TACTTTGACTATTGGGGCCAGGGAAC-CCTGGTCACCG TCTCCTCAGCCTCCACCAAGGGC-CCATCGGTCTTCCCCCT GGCACCC TCCTCCAA-GAGCACCTCTGGGG GCACAGCGGCCCTGGGCTGC-CTGGTCAAGGACTACTTCCCCGAACCGGTGACGG TGTCGTGGAACTCAG GCGCCCTGACCAGCGGCGT-GCACACCTTCCCGGCTGTCCTACAGTCCTC AGGACTCTACTCCCTCAGCA GCGTGGTGACCGT-GCCCTCCAGCAGCTTGGGCACCCAGAC-CTACATCTGCAACGTG AATCACAAGCCCA GCAA-CACCAAGGTGGACAAGAAAGCAGAGCCCAAATC TCATCACCATCACCAT CAC

M1-4H (SEQ ID NO:57)

CAGGTGCAGCTGGTGGAGTCTGGGGGAG-GCGTGGTCCAGCCTGGGAAGTCCCT-GAGACTCTCCTGTGCA GCGTCTGGATTCACCT-TCAGTTACTATGGCATGCACTGGGTCCGCCAGGTT CCAGGCAAGGGGCTGGAG TGGGTGGCAGCT-GTCTGGTATGATGGAAGTACTACATAT-TCTCCAGACTCCGTGAAGGGCCGATTCAC C ATCTC-CAGAGACGATTCCAAGAACACGCTGTATCTGCAA ATGAACAGCCTG AGAGCCGAGGACACGG CT GTG-TATTACTGTGCGAGAGATAGGGTGGGC-CTCTTTGACTACTGGGGCCAGGGAAC-CCTGGTCACCGT C TCCTCAGCCTCCACCAAGGGCCCATCG-GTCTTCCCCTGGCACCCTCCTCCAA-GAGCACCTCTGGGGGC ACAGCGGCCCTGGGCTGC-CTGGTCAAGGACTACTTCCCCGAACCGGTGACGG TGTCGTGGAACTCAGGC GCCCTGACCAGCGGCGT-GCACACCTTCCCGGCTGTCCTACAGTC-CTCAGGACTCTACTCCCTCAGCAG C GTGGTGAC-CGTGCCCTCCAGCAGCTTGGGCACCCAGACCTAC ATCTGCAAC GTGAATCACAAGCCCA GC AACAC-CAAGGTGGACAAGAAAGCAGGGC-CCAAATCTCATCACCATCACCATCAC

M1-5H (SEQ ID NO:59)

CAGGTGCAGCTGGTGGAGTCTGGGGGAG-GCGTGGTCCAGCCTGGGAGGTCCCT-GAGACTCTCCTGTGCA GCGTCTGGATTTACCT-TCAGTTACTATGGCATGCACTGGGTCCGCCAGGCT CCAGGCAAGGGGCTGGAG TGGGTGACACT-TATAACCTATGATGGAGATAATAAATAC-TATGCAGACTCCGTGAAGGGCCGATTCACC ATCTC-CAGAGACAATTCCAAGAACACGCTGTATCTGCAA ATGAACAGCCTG AGAGCCGAGGACACGGC T GTG-TATTACTGTGCGAGAGACGGGATCGGG-TACTTTGACTATTGGGGCCAGGGAAC-CCTGGTCACCGT C TCCTCAGCCTCCACCAAGGGCCCATCG-GTCTTCCCCCT GGCACCC TCCTCCAAGAGCAC-CTCTGGG GGC ACAGCGGCCCTGGGCTGCCTGGT-CAAGGACTACTTCCCCGAACCGGTGACGGTGTCG TGGAACTCA GGC GCCCTGACCAGCGGCGTGCA-CACCTTCCCGGCTGTCCTACAGTCCTCAGGAC TCTACTCCCTCAGC AGC GTGGTGACCGTGCCCTC-CAGCAGCTTGGGCACCCAGACCTA-CATCTGCAACGTGAATCA CAAGCC CAGC AACAC-CAAGGTGGACAAGAAAGCAGAGCCCAAATCTCA TCACCATCACCAT CAC

M1-8H (SEQ ID NO:61)

CAGGTGCAGCTGGTGCAGTCTGGGGGAG-GCGTGGTCCAGCCTGGGAAGTCCCT-GAAACTCTCCTGTGCA GCGTCTGGATTCACCT-TCAGTTACTATGGCATGCACTGGGTCCGCCAGGCT CCAGGCAAGGGGCTGGAG TGGGTGGCAGCTG-TATGGTATGATGGAAGTAACACAT-ACTCTCCAGACTCCGTGAAGGGCCGATTCACC ATCTCCAGAGACGATTCCAAGAACACG-GTGTATCTGCAAATGAACAGCCTG AGAGCCGAG-GACACGGCT GTGTATTACTGTGCGAGAGAT-AGGGTGGGCCTCTTTGACTACTGGGGCCAGGGAA CCCTGGTCACCGTC TCCTCAGCCTCCAC-CAAGGGCCCATCGGTCTTCCCCCTGGCACCC TCCTCCAAGAGCACCTCTGGGGG C ACAGCGGC-CCTGGGCTGCCTGGTCAAGGACTACTTC-CCCGAACCGGTGACGGTGTCC TGGAACTCAGG C GCCCTGACCAGCGGCGTGCACACCTTC-CCGGCTGTCCTACAGTCCTCAGGAC TCTACTCCCT-CAGCA GC GTGGTGACCGTGCCCTCCAGCAGCT-TGGGCACCCAGACCTACATCTGCAACGTGAATCA CAAGCCCA GC AACACCAAGGTGGACAAGAAAG-CAGAGCCCAAATCTCATCACCATCACCAT CAC

M1-10H (SEQ ID NO:63)

CAGGTGCAGCTGGTGCAGTCTGGGGGAG-GCTTGGTACATCCTGGGGGGTCCCT-GAGACTCTCCTGTGAA GGCTCTGGATTCATCT-TCAGGAACCATCCTATACACTGGGTTCGCCAGGCT CCAGGAAAAGGTCTGGAG TGGGTATCAGTTAGTG-GTATTGGTGGTGACACATACTATGCA-GACTCCGTGAAGGCCGATTCTCCATC TCCA-GAGACAATGCCAAGAACTCCTTGTATCTTCAAATG AACAGCCTG AGAGCCGAGGACATGGCTGT G TAT-TACTGTGCAAGAGAATATTACTATGGT-TCGGGGAGTTATCGCGTTGACTACTAC-TACTACGGTATG GACGTCTGGGGCCAAGGGACCACGGT-CACCGTCTCCTCAGCCTCCACCAAG GGCCCATCG-GTCTTCCCC CTGGCACCCTCCTCCAAGAGCAC-

CTCTGGGGGCACAGCGGCCCTGGGCTGCCTGGTCAAGGACTACTTC CCCGAACCGGTGACGGTGTCGTGGAACTCAGGCGCCCTGACCAGCGGC GTGCACACCTTCCCGGCTGTC CTACAGTCCTCAGGACTCTACTCCCTCAGCAGCGTGGTGACCGTGCCCTCCAGCAGCTTG GGCACCCAG ACCTACATCTGCAACGTGAATCACAAGCCCAGCAACACCAAGGTGGACAA AAAGCAGAGCCCAAATCT CATCACCATCACCATCAC

M1-21H (SEQ ID NO:65)

CAGGTGCAGCTGGTGCAGTCTGGGGGAGGCGTGGTCCAGCCTGGGAAGTCCCTGAGACTCTCCTGTGCA GCGTCTGGATTCACCTTCAGTTACTATGGCATGCACTGGGTCCGCCAGGTTCCAGGCAAGGGGCTGGAG TGGGTGGCAGCTGTCTGGTATGATGGAAGTACTACATATTCTCCAGACTCCGTGAAGGGCCGATTCACC ATCTCCAGAGACGATTCCAAGAACACGCTGTATCTGCAAATGAGCAGCCTG AGAGCCGAGGACACGGCT GTGTATTACTGTGCGAGAGATAGGGTGGGCCTCTTTGACTACTGGGGCCAGGGAACCCTGGTCACCGTC TCCTCAGCCTCCACCAAGGGCCCATCGGTCTTCCCCCT GGCACCC TCCTCCAAGAGCACCTCTGGGGGC ACAGCGGCCCTGGGCTGCCTGGTCAAGGACTACTTCCCCGAACCGGTGACGGTGTCGTGGAACTCAGGC GCCCTGACCAGCGGCGTGCACACCTTCCCGGCTGTCCTACAGTCCTCAGGAC TCTACTCCCTCAGCAGC GTGGTGACCGTGCCCTCCAGCAGCTTGGGCACCCAGACCTACATCTGCAACGTGAATCA CAAGCCCAGC AACACCAAGGTGGACAAGAAAGCAGAGCCCAAATCTCAT CACCATCACCAT CAC

M1-23H (SEQ ID NO:67)

CAGGTGCAGCTGGTGCAGTCTGGGGAGGCGTGGTCCAGCCTGGGAGGTCCCTGAGACTCTCCTGTGCA GCGTCTGGATTCACCTTCAGTAACTATGGCATGCACTGGGTCCGCCAGGCTCCAGGCAAGGGGCTGGAG TGGGTGGCAGCTATATGGTATGATGGAAGTAAAACATACAATGCAGACTCCGTGAAGGGCCGATTCACC ATCTCCAGAGACAATTCCAAGAACACGCTGTATCTGCAAATGAACAGCCTG AGAGCCGAGGACACGGCT GTGTATTACTGTGCGAGAGATGGGATAGGCTACTTTGACTACTGGGGCCAGGGAACCCTGGTCACCGTC TCCTCAGCCTCCACCAAGGGCCCATCGGTCTTCCCCCTG GCACCCTCCTCCAAGA GCACCTCTGGGGGC ACAGCGGCCCTGGGCTGCCTGGTCAAGGACTACTTCCCCGAACCGGTGACGGTGTCG TGGAACTCAGGC GCCCTGACCAGCGGCGTGCACACCTTCCCGGCTGTCCTACAGTCCTCAGGAC TCTACTCCCTCAGCAGC GTGGTGACCGTGCCCTCCAGCAGCTTGGGCACCCAGACCTACATCTGCAACGTGAATCACAAGCCCAGC AACACCAAGGTGGACAAGAAAGCAGAGCCCAAATCTCA TCACCATCACCATCAC

M1-25H (SEQ ID NO:69)

CAGGTGCAGCTGGTGGAGTCTGGGGGAGGCTTGGTCCAGCCTGGGGGGTCCCTGAGACTCTCCTGTGCA GCGTCTGGATTCACCTTCAGTTACTATGGCATGCACTGGGTCCGCCAGGTTCCAGGCAAGGGGCTGGAG TGGGTGGCAGCTGTCTGGTATGATGGAAGTACTACATATCTCCAGACTCCGTGAAGGGCCGATTCACC ATCTCCAGAGACGATTCCAAGAACACGCTGTATCTGCA AATGAACAGCCTG AGAGCCGAGGACACGGCT GTTTATTACTGTGCGAGAGATAGGGTGGGCCTCTTTGACTACTGGGGCCAGGGAACCCTGGTCACCGTC TCCTCAGCCTCCACCAAGGGCCCATCGGTCTTCCCCCT GGCACCC TCCTCCAAGAGCACCTCTGGGGGC ACAGCGGCCCTGGGCTGCCTGGTCAAGGACTACTTCCCCGAACCGGTGACGGTGTCGTGGAACTCAGGC GCCCTGACCAGCGGCGTGCACACCTTCCCGGCTGTCCTACAGTCCTCAGGAC TCTACTCCCTCAGCAGC GTGGTGACCGTGCCCTCCAGCAGCTTGGGCACCCAGACCTACATCTGCAACGTGAATCA AAGCCCAGC AACACCAAGGTGGACAAGAAAGCAGAGCCCAAATCTCATCACCATCACCAT CAC

M2-11L (SEQ ID NO:71)

GAAATAGTGATGACGCAGTCTCCAGGCACCCTGTCTTTGTCTCCAGGGGAAAGAGCCACCCTCTCCTGC AGGGCCAGTCAGGGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGACTGGAGCCTGAAGA TTTTGCA GTGTATTACTGTCAGCAGTAT GGTAGCTCACCTCCATTCACTTTCGGCCCTGGGACCAAAGTGGATATCAAACGAACTGTGGCTGCACCA TCTGTCTTCATCTTCCCGCCATCTGATGAGCAGTTGAGATCTGGAACTG CCTCTGTTGTGTGCCTGCTG AATAACTTCTATCCCAGAGAGGCCAAAGTACAGTGGAAGGTGGATAACGCCCTCCAATCGGGTAACTCC CAGGAGAGTGTCACAGAGCAGGACAGCAAGGACAGCACCTACAGCCTCAGC AGCACCCTGACGCTGAGC AAAGCAGACTACGAGAAACACAAAGTCTACGCCTGCGAAGTCACCCATCAGGGC CTGAGCTCGCCCGTC ACAAAGAGCTTCAACAGGGGAGAGTCTTATCCATATGATGTGCCAGATTATGCG AGC

M2-12L (SEQ ID NO:73)

GAAATAGTGATGACGCAGTCTCCAGGCACCCTGTCTTTGTCTCCAGGGGAAAGAGCCACCCTCTCCTGC AGGGCCAGTCAGGGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGCCTAGAGCCTGAAGATTTTGCA GTGTATTACTGTCAGCAGTAT GGTAGCTCACCTCCGTACACTTTTGGCCAGGGGACCAAGCTGGAGATCAAACGAACTGTGGCTGCACCA TCTGTCTTCATCTTCCCGCCATCTGATGAGCAGTTGAAATCTGGAACTGCCTCTGTTGTGTGCCTGCTG AATAACTTCTATCCCAGAGAGGCCAAAGTACAGTGGAAGGTGGATAACG CCCTCCAATCGGGTAACTCC CAGGAGAGTGTCACAGAGCAGGACAGCAAGGACAGCACCTACAGCCTCAGCAGCACCCTGACGCTGAGC AAAGCAGACTACGAGAAACACAAAGTCTACGCCTGCGAA GTCACCC ATCAGGGCCTGAGCTCGCCCGTC ACAAAGAGCTTCAACAGGGGAGAGTCTTATCCATATGATGTGCCAGATTATGCGAGC

M1-16L (SEQ ID NO:75)

GAAATAGTGATGACGCAGTCTCCAGGCACCCTGTCTTTGTCTCCAGGGGAAAGAGCCACCCTCTCCTGC AGGGCCAGTCAGAGTGT

TAGCAGCAGCTACTTAGCCTGGTACCAGCAGAAA
CCTGGCCAGGCTCCCAGG CTCCTCATCTATGGTG-
CATCCAGCAGGGCCACTGGCATCCCAGA-
CAGGTTCAGTGTCAGTGGGTCTGGG ACAGACT-
TCACTCTCACCATCAGCAGACTGGAGCCTGAAGA
TTTTGCA GTGTATTACTGTCAGCAGTAT GGTAGCT-
CATTCACTTTCGGCCCTGGGAC-
CAAAGTGGATATCAAACGAACTGTGGCT-
GCACCATCTGTC
TTCATCTTCCCGCCATCTGATGAGCAGT-
TGAAATCTGGAACTGCCTCTGTTGTGT GCCTGCT-
GAATAAC TTCTATCCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGC GCACCCT-
GACGCTGAGCAAAGCA GACTACGAGAAACA-
CAAAGTCTACGCCTGCGAAGTCACCCATCAGGGC
CTGAGCT CGCCCGTCACAAAG AGCTTCAA-
CAGGGGAGAGTCTTATCCATATGATGT-
GCCAGATTATGCG AGC

M2-18L (SEQ ID NO:77)

GAAATAGTGATGACGCAGTCTCCAG-
GCACCCTGTCTTTGTCTCCAGGGGAAA-
GAGCCACCCTCTCCTGC AGGGCCAGTCAGAGTGT-
TAGCAGCACCTACTTAGCCTGGTACCAGCAGAAA
CCTGGCCAGGCTCCCAGG CTCCTCATCTATGGTG-
CATCCAGCAGGGCCACTGGCATCCCAGA-
CAGGTTCAGTGGCAGTGGGTCTGGG ACAGACT-
TCACTCTCACCATCAGCAGACTGGAGCCTGAAGA
TTTTGCA GTGTATTACTGTCAGCAGTAT GTTAGCT-
CATTCACTTTCGGCCCTGGGAC-
CAAAGTGGATATCAAACGAACTGTGGCT-
GCACCATCTGTC
TTCATCTTCCCGCCATCTGATGAGCAGT-
TGAAATCTGGAACTGCCTCTGTTGTGT GCCTGCT-
GAATAAC TTCTATCCCAGAGAGGCCAAAGTA-
CAGTGGAAGGTGGATAACGCCCTCCAATCGGGTA
ACTCCCAGGAG AGTGTCACAGAGCAGGACAG-
CAAGGACAGCACCTACAGCCTCAGC AGCACCCT-
GACGCTGAGCAAAGCA GACTACGAGAAACA-
CAAAGTCTACGCCTGCGAAGTCACCCATCAGGGC
CTGAGCTC GCCCGTCACAAAG AGCTTCAA-
CAGGGGAGAGTCTTATCCATATGATGT-
GCCAGATTATGCG AGC

M2-20L (SEQ ID NO:79)

GAAATAGTGATGACGCAGTCTCCAG-
GCACCCTGTCTTTGTCTCCAGGGGAAA-
GAGCCACCCTCTCCTGC AGGGCCAGTCAGAGTGT-
TAGCAGCAGCTACTTAGCCTGGTACCAGCAGAAA
CCTGGCCAGGCTCCCAGG CTCCTCATCTACGGTG-
CATCCAGGAGGGCCACTGGCATCCCAGA-
CAGGTTCAGTGGCAGTGGGTCTGGG ACAGACT-
TCACTCTCACCATCAGCAGACTGGAGCCTGAAGA
TTTTGCAGTGTATTACTGTCAGCAGTAT GGTAGCT-
CACCCATGTACACTTTTGGCCAGGGGAC-
CAAGCTGGAGATCAAACGAACTGTGGCTGCACCA
TCTGTCTTCATCTTCCCGCCATCTGAT-
GAGCAGTTGAAATCTGGAACTG CCTCTGTTGTGT-
GCCTGCTG AATAACTTCTATCCCAGAGAGGC-
CAAAGTACAGTGGAAGGTGGATAACGCCCTCCA
ATCGGGTAACTCC CAGGAGAGTGTCACAGAGCAG-
GACAGCAAGGACAGCACCTACAGCCTCAGC
AGCACCCTGACGCTGAGC AAAGCAGACTAC-
GAGAAACACAAAGTCTACGCCTGC-
GAAGTCACCCATCAGGG CCTGAGCTCGCCCGTC

ACAAAGAGCTTCAACAGGGGAGAGTCT-
TATCCATATGATGTGCCAGATTATGCG AGC

M2-31L (SEQ ID NO:81)

GAAATTGTGTTGACGCAGTCTCCAGC-
CACCCTGTCTTTGTCTCCAGGGGAAA-
GAGCCACCCTCTCCTGC AGGGCCAGTCAGAGTGT-
TAGCAGCTACTTAGCCTGGTACCAACAGAAACCT
GGCCAGGCTCCCAGGCTC CTCATCTATGATGCATC-
CAACAGGGCCACTGGCATCCCAGCCAG-
GTTCAGTGGCAGTGGGTCTGGGACA GACT-
TCACTCTCACCATCAGCAGCCTAGAGCCTGAAGA
TTTTGCAGTTTATT ACTGTCAGCAGCGTACG
AACTGGCCTCGGACGTTCGGCCAAGG-
GACCAAGGTGGAAATCAAACGAACTGTG-
GCTGCACCATCTGTC TTCATCTTCCCGCCATCTGAT-
GAGCAGTTGAAATCTGGAACT GCCTCTGTTGTGT
GCCTGCTGAATAAC TTCTATCCCAGAGAGGC-
CAAAGTACAGTGGAAGGTGGATAACGC-
CCTCCAATCGGGTAACTCCCAGGAG AGTGTCACA-
GAGCAGGACAGCAAGGACAGCACCTACAGCCTC
AGC AGCACCCTGACGCTGAGCAAAGCA GACTAC-
GAGAAACACAAAGTCTACGCCTGC-
GAAGTCACCCATCAGGGCCTGAGCTCGC-
CCGTCACAAAG
AGCTTCAACAGGGGAGAGTCTTATC-
CATATGATGTGCCAGATTATGCG AGC

M2-32L (SEQ ID NO:83)

GAAATTGTGTTGACGCAGTCTCCAGC-
CACCCTGTCTTTGTCTCCAGGGGAAA-
GAGCCACCCTCTCCTGC AGGGCCAGTCAGAGTGT-
TAGCAGCTACTTAGCCTGGTACCAACAGAAACCT
GGCCAGGCTCCCAGGCTC CTCATCTATGATGCATC-
CAACAGGGCCGCTGGCATCCCAGCCAG-
GTTCAGTGGCAGTGGGTCTGGGACA GACT-
TCACTCTCACCATCAGCAGCCTAGAGCCTGAAGA
TTTTGCAGTTTATT ACTGTCAGCAACGTAAC
AACTGGCCTCTCACTTTCGGCGGAGG-
GACCAAGGTGGAGATCAAACGAACTGTG-
GCTGCACCATCTGTC TTCATCTTCCCGCCATCTGAT-
GAGCAGTTGAAATCTGGAACTGCCTCTGTTGTGT
GCCTGCTGAATAAC TTCTATCCCAGAGAGGC-
CAAAGTACAGTGGAAGGTGGATAACGC-
CCTCCAATCGGGTA ACTCCCAGGAG AGTGTCACA-
GAGCAGGACAGCAAGGACAGCACCTACAGCCTC
AGC AGCACCCTGACGCTGAGCAAAGCA GACTAC-
GAGAAACACAAAGTCTACGCCTGC-
GAAGTCACCCATCAGGGCCTGAGCT CGCCCGTCA-
CAAAG
AGCTTCAACAGGGGAGAGTCTTATC-
CATATGATGTGCCAGATTATGCG AGC

M2-33L (SEQ ID NO:85)

GAAATTGTGTTGACGCAGTCTCCAG-
GCACCCTGTCTTTGTCTCCAGGGGAAA-
GAGCCACCCTCTCCTGC AGGGCCAGTCAGAGTGT-
TAGCAGCAGCTACTTAGCCTGGTACCAGCAGAAA
CCTGGCCAGGCTCCCAGG CTCCTCATCTATGGTG-
CATCCAGCAGGGCCACTGGCATCCCAGA-
CAGGTTCAGTGGCAGTGGGTCTGGG ACAGACT-
TCACTCTCACCATCAGCAGACTGGAGCCTGAAGA
TTTTGCA GTGTATTACTGTCAGCAGTAT GGTAGCT-
CACCTCCGTACACTTTTGGCCAGGGGAC-
CAAGCTGGAGATCAAACGAACTGTGGCTGCACCA
TCTGTCTTCATCTTCCCGCCATCTGAT-
GAGCAGTTGAAATCTGGAACTG CCTCTGTTGTGT-
GCCTGCTG AATAACTTCTATCCCAGAGAGGC-

CAAAGTACAGTGGAAGGTGGATAACGCCCTCCAA
TCGGGTAACTCC CAGGAGAGTGTCACAGAGCAG-
GACAGCAAGGACAGCACCTACAGCCTCAGC
AGCACCCTGACGCTGAGC AAAGCAGACTAC-
GAGAAACACAAAGTCTACGCCTGC-
GAAGTCACCCATCAGGGC CTGAGCTCGCCCGTC
ACAAAGAGCTTCAACAGGGGAGAGTCT-
TATCCATATGATGTGCCAGATTATGCG AGC

M2-34L (SEQ ID NO:87)

GAAATTGTGTTGACGCAGTCTCCAGC-
CACCCTGTCTTTGTCTCCAGGGGAAA-
GAGCCACCCTCTCCTGC AGGGCCAGTCAGAGTGT-
TAGCAGCTACTTAGCCTGGTACCAACAGAAACCTG
GCCAGGCTCCCAGGCTC CTCATCTATGATGCATC-
CAACAGGGCCACTGGCATCCCAGCCAG-
GTTCAGTGGCAGTGGGTCTGGGACA GACT-
TCACTCTCACCATCAGCAGCCTAGAGCCTGAAGA
TTTTGCAGTTTATT ACTGTCAGCAGCGTACG
AACTGGCCTCGGACGTTCGGCCAAGG-
GACCAAGGTGGAAATCAAACGAACTGTG-
GCTGCACCATCTGTC TTCATCTTCCCGCCATCTGAT-
GAGCAGTTGAAATCTGGAAC TGCCTCTGTTGTGT
GCCTGCTGAATAAC TTCTATCCCAGAGAGGC-
CAAAGTACAGTGGAAGGTGGATAACGC-
CCTCCAATCGGGTAACTCCCAGGAG AGTGTCACA-
GAGCAGGACAGCAAGGACAGCACCTACAGCCTC
AGC AGCACCCTGACGCTGAGCAAAGCA GACTAC-
GAGAAACACAAAGTCTACGCCTGC-
GAAGTCACCCATCAGGGCCTGAGCTCGC-
CCGTCACAAAG
AGCTTCAACAGGGGAGAGTCTTATC-
CATATGATGTGCCAGATTATGCG AGC

M2-35L (SEQ ID NO:89)

GAAATTGTGTTGACGCAGTCTCCAGC-
CACCCTGTCTTTGTCTCCAGGGGAAA-
GAGCCACCCTCTCCTGC AGGGCCAGTCAGAGTGT-
TAGCAGCTACTTAGCCTGGTACCAACAGAAACCT
GGCCAGGCTCCCAGGCTC CTCATCTATGATGCATC-
CAACAGGGCCACTGGCATCCCAGCCAG-
GTTCAGTGGCAGTGGGTCTGGGACA GACT-
TCACTCTCACCATCAGCAGCCTAGAGCCTGAAGA
TTTTGCAGTTTATT ACTGTCAGCAGCGTACG
AACTGGCCTCGGACGTTCGGCCAAGG-
GACCAAGGTGGAAATCAAACGAACTGTG-
GCTGCACCATCTGTC TTCATCTTCCCGCCATCTGAT-
GAGCAGTTGAAATCTGGAAC TGCCTCTGTTGTGT
GCCTGCTGAATAAC TTCTATCCCAGAGAGGC-
CAAAGTACAGTGGAAGGTGGATAACGC-
CCTCCAATCGGGTAACTCCCAGGAG AGTGTCACA-
GAGCAGGACAGCAAGGACAGCACCTACAGCCTC
AG CAGCACCCTGACGCTGAGCAAAGCA GACTAC-
GAGAAACACAAAGTCTACGCCTGC-
GAAGTCACCCATCAGGGCCTGAGCT CGCCCGTCA-
CAAAG
AGCTTCAACAGGGGAGAGTCTTATC-
CATATGATGTGCCAGATTATGCG AGC

M2-11H (SEQ ID NO:91)

CAGGTGCAGCTGGTGGAGTCTGGGGGAG-
GCGTGGTCCAGCCTGGGAGGTCCCT-
GAGACTCTCCTGTGCA GCGTCTGGATTTACCT-
TCAGTTACTATGGCATGCACTGGGTCCGCCAGGCT
CCAGGCAAGGGGCTGGAG TGGGTGACACT-
TATAACCTATGATGGAGATAATAAATAC-
TATGCAGACTCCGTGAAGGGCCGATTCACC ATCTC-
CAGAGACAATTCCAAGAACACGCTGTATCTGCAA

ATGAACAGCCTG AGAGCCGAGGACACGGCT GTG-
TATTACTGTGCGAGAGACGGGATCGGG-
TACTTTGACTATTGGGGCCAGGGAAC-
CCTGGTCACCGTC
TCCTCAGCCTCCACCAAGGGCCCATCG-
GTCTTCCCCCTG GCACCC TCCTCCAAGAGCAC-
CTCTGGGGGC ACAGCGGCCCTGGGCTGCCTGGT-
CAAGGACTACTTCCCCGAACCGGTGACGGTGTCG
TGGAACTCAGGC GCCCTGACCAGCGGCGTGCA-
CACCTTCCCGGCTGTCCTACAGTCCTCAGGAC
TCTACTCCCTCAGCAGC GTGGTGACCGTGCCCTC-
CAGCAGCTTGGGCACCCAGACCTA-
CATCTGCAACGTGAATCA ACAAGCCCAGC AACAC-
CAAGGTGGACAAGAAAGCAGAGCCCAAATCTCAT
CACCATCACCAT CAC

M2-12H (SEQ ID NO:93)

GATGTGCAGCTGGTGGAGTCTGGGGGAG-
GCGTGGTCCATCCTGGGAGGTCCCT-
GAGACTCTCCTGTGCA GCGTCTGGATTTACCT-
TCAGTTACTATGGCATGCACTGGGTCCGCCAGGCT
CCAGGCAAGGGGCTGGAA TGGATGACACT-
TATATCCTATGATGGAGATAATAAATAC-
TATGCAGACTCCGTGAAGGGCCGATTCACC ATCTC-
CAGAGAAAATTCCAAGAACACGCTGTATCTGCAA
ATGAACAGTCTG AGAGCCGAGGACACGGCT GTG-
TATTACTGTGCGAGAGACGGGATCGGG-
TACTTTGACTATTGGGGCCAGGGAAC-
CCTGGTCACCGTC
TCCTCAGCCTCCACCAAGGGCCCATCG-
GTCTTCCCCCT GGCACCC TCCTCCAAGAGCAC-
CTCTGGGGGC ACAGCGGCCCTGGGCTGCCTGGT-
CAAGGACTACTTCCCCGAACCGGTGACGGTGTCG
TGGAACTCAGGC GCCCTGACCAGCGGCGTGCA-
CACCTTCCCGGCTGTCCTACAGTCCTCAGGAC
TCTACTCCCTCAGCAGC GTGGTGACCGTGCCCTC-
CAGCAGCTTGGGCACCCAGACCTA-
CATCTGCAACGTGAATCA CAAGCCCAGC AGCAC-
CAAGGTGGACAAGAAAGCAGAGCCCAAATCTCAT
CACCATCACCAT CAC

M2-16H (SEQ ID NO:95)

CAGGTGCAGCTGGTGCAGTCTGGGGGAG-
GCGTGGTCCAGCCTGGGAAGTCCCT-
GAGACTCTCCTGTGCA GCGTCTGGATTCAGCT-
TGAGTTACTATGGCATGCACTGGGTCCGCCAGGTT
CCAGGCAAGGGGCTGGAG TGGGTGGCAGCT-
GTCTGGTATGATGGAAGTACTAGATAT-
TCTCCAGACTCCGTGAAGGGCCGATTCACC ATCTC-
CAGAGACGATTCCAAGAACACGCTGTATCTGCAA
ATGAACAGCCTG AGAGCCGAGGACACGGCT GTG-
TATTACTGTGCGAGAGATAGGGTGGGC-
CTCTTTGACTACTGGGGCCAGGGAAC-
CCTGGTCACCGTC
TCCTCAGCCTCCACCAAGGGCCCATCG-
GTCTTCCCCCTGGCACCCT CCTCCAAGAGCAC-
CTCTGGGGGC ACAGCGGCCCTGGGCTGCCTGGT-
CAAGGACTACTTCCCCGAACCGGTGACGGTGTCG
TGGAACTCAGGC GCCCTGACCAGCGGCGTGCA-
CACCTTCCCGGCTGTCCTACAGTCCTCAGGACT
CTACTCCCTCAGCAGC GTGGTGACCGTGCCCTC-
CAGCAGCTTGGGCACCCAGACCTA-
CATCTGCAACGTGAATCA CAAGCCCAGC AACAC-
CAAGGTGGACAAGAAAGCAGAGCCCAAATCTCA
TCACCATCACCATCAC

M2-18H (SEQ ID NO:97)

CAGGTGCAGCTGGTGCAGTCTGGGGGAG-
GCGTGGTCCAGCCTGGGAAGTCCCT-

GAGACTCTCCTGTGCA GCGTCTGGATTCAGCTTCAGTTACTATGGCATGCACTGGGTCCGCCAGGTTCCAGGCAAGGGGCTGGAG TGGGTGGCAGCTGTCTGGTATGATGGAAGTACTACATATTCTCCAGACTCCGTGAAGGGCCGATTCACC ATCTCCAGAGACGATTCCAAGAACACGCTGTATCTGCAAATGAACAGCCTG AGAGCCGAGGACACGGCT GTGTATTACTGTGCGAGAGATAGGGTGGGCCTCTTTGACTACTGGGGCCAGGGAACCCTGGTCACCGTC
TCCTCAGCCTCCACCAAGGGCCCATCGGTCTTCCCCCT GGCACCC TCCTCCAAGAGCACCTCTGGGGGC ACAGCGGCCCTGGGCTGCCTGGTCAAGGACTACTTCCCCGAACCGGTGACGGTGTCGTGGAACTCAGGC GCCCTGACCAGCGGCGTGCACACCTTCCCGGCTGTCCTACAGTCCTCAGGACTCTACTCCCTCAGCAGC GTGGTGACCGTGCCCTCCAGCAGCTTGGGCACCCAGACCTACATCTGCAACGTGAATCA CAAGCCCAGC AACACCAAGGTGGACAAGAAAGCAGAGCCCAAATCTCATCACCATCACCAT CAC

M2-20H (SEQ ID NO:99)

CAGGTGCAGCTGGTGCAGTCTGGGGGAGGCGTGGTCCAGCCTGGGAGGTCCCTGAGGCTCTCCTGTGCA GCCTCTGGATTCACTTTCAGTTACTATGGTATGCACTGGGTCCGCCAGGCTCCAGGCAAGGGGCTGGAG TGGGTGTCACTTATAACATATGATGGAAGGAATAAATACTACGCCGACTCCGTGAAGGGCCGATTCACC ATCTCCAGAGAGAATTCCAAGAACACGCTGTATCTGCAAATGAACAGCCTG AGAACTGAGGACACGGCT GAGTATTACTGTGCGAGAGACGGGATCGGATACTTTGACTACTGGGGCCAGGGAATCCTGGTCACCGTC
TCCTCAGCCTCCACCAAGGGCCCATCGGTCTTCCCCCT GGCACCCTCCT CCAAGAGCACCTCTGGGGGC ACAGCGGCCCTGGGCTGCCTGGTGAAGGACTACTTCCCCGAACCGGTGACGGTGTCGTGGAAGTCAGGC GCCCTGACCAGCGGCGTGCACACCTTCCCGGCTGTCCTACAGTCCTCAGGACTCTACTCCCTCAGCAGC GTGGTGACCGTGCCCTCCAGCAGCTTGGGCACCCAGACCTACATCTGCAACGTGAATCA CAAGCCCAGC AACACCAAGGTGGACAAGAAAGCAGAGCCCAAATCTCATCACCATCACCATC AC

M2-31H (SEQ ID NO:101)

CAGGTGCAGCTGGTGGAGTCTGGGGAGTCGTGGTCCAGCCTGGGAGGTCCCTGAGACTCTCCTGTGCA GCCTCTGGATTCACGTTCAGTTACTATGGTATACACTGGGTCCGCCAGGTTCCAGGCAAGGGACTAGAG TGGGTGGCACTTATATCATACGATGGAAGCAATAAATACTACGCAGACTCCGTGAAGGGCCGATTCACC ATCTCCAGAGACAATTCCAAGAACACTCTGTATCTGCAAATGAACAGCCTG AGAGCTGAGGACACGGCT GTGTATTACTGTGCGAGAGACTGGATCGGGTACTTTGACTACTGGGGCCAGGGAACCCTGGTCACCGTC
TCCTCAGCCTCCACCAAGGGCCCATCGGTCTTCCCCTG GCACCC TCCTCCAAGAGCACCTCTGGGGGC ACAGCGGCCCTGGGCTGCCTGGTCAAGGACTACTTCCCCGAACCGGTGACGGTGTCGTGGAACTCAGGC GCCCTGACCAGCGGCGTGCACACCTTCCCGGCTGTCCTACAGTCCTCAGGACTCTACTCCCTCAGCAGC GTGGTGACCGTGCCCTCCAGCAGCTTGGGCACCCAGACCTACATCTGCAACGTGAATCA CAAGCCCAGC AACACCAAGGTGGACAAGAAAGCAGAGCCCAAATCTCATCACCATC ACCATCAC

M2-32H (SEQ ID NO:103)

CAGGTGCAGCTGGTGCAGTCTGGGGGAGGCTTGGTACATCCTGGGGGGTCCCTGAGACTCTCCTGTGAA GGCTCTGGATTCATCTTCAGGAACCATCCTATACACTGGGTTCGCCAGGCTCCAGGAAAAGGTCTGGAG TGGGTATCAGTTAGTGGTATTGGTGGTGACACATACTATGCAGACTCCGTGAAGGGCCGATTCTCCATC TCCAGAGACAATGCCAAGAACTCCTTGTATCTTCAAATGA ACAGCCTGA GAGCCGAGGACATGGCTGTG TATTACTGTCAAGAGAATATTACTATGGTTCGGGGAGTTATCGCGTTGACTACTACTACTACGGTATG GACGTCTGGGGCCAAGGGACCACGGTCACCGTCTCCTCAGCCTCCACCAA GGGCCCATCGGTCTTCCCC CTGGCACCCTCCTCCAAGAGCACCTCTGGGGGCACAGCGGCCCTGGGCTGCCTGGTCAAGGACTACTTC CCCGAACCGGTGACGGTGTCGTGGAACTCAGGCGCCCTGACCAGCGGCG TGCACACCTTCCCGGCTGTC CTACAGTCCTCAGGACTCTACTCCCTCAGCAGCGTGGTGACCGTGCCCTCCAGCAGCTTGGGCACCCAG ACCTACATCTGCAACGTGAATCACAAGCCCAGCAACACCAAGGTGGACAA GAAAGCAGAGCCCAAATCT CATCACCATCACCATCAC

M2-33H (SEQ ID NO:105)

CAGGTGCAGCTGGTGCAGTCTGGGGGAGGCGTGGTCCAGCCTGGGAGGTCCCTGAGACTCTCCTGTGCA GCGTCTGGATTTACCTTCAGTTACTATGGCATGCACTGGGTCCGCCAGGCTCCAGGCAAGGGGCTGGAA TGGATGACACTTATAACCTATGATGGAGATAATAAATACTATGCAGACTCCGTGAAGGGCCGATTCACC ATCTCCAGAGACAATTCCAAGAACACGCTGTATCTGCAAATGAACAGTCTG AGAGCCGAGGACACGGCT GTGTATTACTGTGCGAGAGACGGGATCGGGTACTTTGACTATTGGGGCCAGGGAACCCTGGTCACCGTC
TCCTCAGCCTCCACCAAGGGCCCATCGGTCTTCCCCCT GGCACCCT CCTCCAAGAGCACCTCTGGGGGC ACAGCGGCCCTGGGCTGCCTGGTCAAGGACTACTTCCCCGAACCGGTGACGGTGTCGTGGAACTCAGGC GCCCTGACCAGCGGCGTGCACACCTTCCCGGCTGTCCTACAGTCCTCAGGACTCTACTCCCTCAGCAGC GTGGTGACCGTGCCCTCCAGCAGCTTGGGCACCCAGACCTACATCTGCAACGTGAATCA CAAGCCCAGC AACACCAAGGTGGACAAGAAAGCAGAGCCCAAATCTCATCACCATCACCAT CAC

M2-34H (SEQ ID NO:107)

CAGGTGCAGCTGGTGGAGTCTGGGGGAGGCGTGGTCCAGCCTGGGAGGTCCCTGAGACTCTCCTGTGCA GCCTCTGGATTCACGTTCAGTTACTATGGTATACACTGGGTCCGCCAGGTTCCAGGCAAGGGACTAGAG TGGGTGGCACTTATATCATACGATGGAAGCAATAAATACTACGCAGACTCCGTGAAGGGCCGATTCACC ATCTCCAGAGACAATTCCAAGAACACTCTGTATCTGCAAATG AACAGCCTG AGAGCTGAGGACACGGCT GTGTATTACTGTGCGAGAGACTGGATCGGGTACTTTGACTACTGGGGCCAGGGAAC

CCTGGTCACCGTC
TCCTCAGCCTCCACCAAGGGCCCATCG-
GTCTTCCCCCTG GCACCC TCCTCCAAGAGCAC-
CTCTGGGGGC ACAGCGGCCCTGGGCTGCCTGGT-
CAAGGACTACTTCCCCGAACCGGTGACGGTGTCG
TGGAACTCAGGC GCCCTGACCAGCGGCGTGCA-
CACCTTCCCGGCTGTCCTACAGTCCTCAGGAC
TCTACTCCCTCAGCAGC GTGGTGACCGTGCCCTC-
CAGCAGCCTGGGCACCCAGACCTA-
CATCTGCAACGTGAATC ACAAGCCCAGC AACAC-
CAAGGTGGACAAGAAAGCAGAGCCCAAATCTCAT
CACCATC ACCATCAC

M2-35H (SEQ ID NO:109)

CAGGTGCAGCTGGTGGAGTCTGGGGGAG-
GCGTGGTCCAGCCTGGGAGGTCCCT-
GAGACTCTCCTGTGCA GCCTCTGGATTCACGAT-
CAGTTACTATGGTATACACTGGGTCCGCCAGGTTC
CAGGCAAGGGACTAGAG TGGGTGGAACTTATAT-
CATACGATGGAAGCAATAAATACTACG-
CAGACTCCGTGAAGGGCCGATTCACC ATCTCCA-
GAGACAATTCCAAGAACACTCTGTATCTGCAAAT
GAACAGCCTG AGAGCTGAGGACACGGCT GTGTAT-
TACTGTGCGAGAGACTGGATCGGG-
TACTTTGACTACTGGGGCCAGGGAAC-
CCTGGTCACCGTC
TCCTCAGCCTCCACCAAGGGCCCATCG-
GTCTTCCCCCTGGCACCC TCCTCCAAGAGCAC-
CTCTGGGGGC ACAGCGGCCCTGGGCTGCCTGGT-
CAAGGACTACTTCCCCGAACCGGTGACGGTGTCG
TGGAACTCAGGC GCCCTGACCAGCGGCGTGCA-
CACCTTCCCGGCTGTCCTACAGTCCTCAGGACT
CTACTCCCTCAGCAGC GTGGTGACCGTGCCCTC-
CAGCAGCCTGGGCACCCAGACCTA-
CATCTGCAACGTGAATCA CAAGCCCAGC AACAC-
CAAGGTGGACAAGAAAGCAGAGCCCAAATCTCA
TCACCAT CACCATCAC

Translated amino acid sequences of sequenced antibodies. M1-H Heavy Chain Variable and CH1 Regions $10^{-9}$ M Affinity Cut (SEQ ID NOS: 64, 54, 66, 68, 70, 56, 58, 60, and 62, respectively)

```
                 1                                                    50
M1_10H QVQLVQSGGG LVHPGGSLRL SCEGSGFIFR NHPIHWVRQA PGKGLEWVSV
 M1_1H QVQLVESGGG VVQPGKSLRL SCAASEFTIS YYGMHWVRQV PGKGLEWVAA
M1_21H QVQLVQSGGG VVQPGKSLRL SCAASGFTFS YYGMHWVRQV PGKGLEWVAA
M1_23H QVQLVQSGGG VVQPGRSLRL SCAASGFTFS NYGMHWVRQA PGKGLEWVAA
M1_25H QVQLVESGGG LVQPGGSLRL SCAASGFTFS YYGMHWVRQV PGKGLEWVAA
 M1_3H DVQLVQSGGG VVQPGRSLRL SCAASGFTFS YYGMHWVRQA PGKGLEWVTL
 M1_4H QVQLVESGGG VVQPGKSLRL SCAASGFTFS YYGMHWVRQV PGKGLEWVAA
 M1_5H QVQLVESGGG VVQPGRSLRL SCAASGFTFS YYGMHWVRQA PGKGLEWVTL
 M1_8H QVQLVQSGGG VVQPGKSLKL SCAASGFTFS YYGMHWVRQA PGKGLEWVAA 51                                                   100
M1_10H SGIGGDTYY. ADSVKGRFSI SRDNAKNSLY LQMNSLRAED MAVYYCAREY
 M1_1H VWYDESTTYS PDSVKGRFTI SRDDSKNTLY LQMNSLRAED TAVYYCARDR
M1_21H VWYDGSTTYS PDSVKGRFTI SRDDSKNTLY LQMSSLRAED TAVYYCARDR
M1_23H IWYDGSKTYN ADSVKGRFTI SRDNSKNTLY LQMNSLRAED TAVYYCARDG
M1_25H VWYDGSTTYP PDSVKGRFTI SRDDSKNTLY LQMNSLRAED TAVYYCARDR
 M1_3H ITYDGDNKYY ADSVKGRFTI SRDNSKNTLY LQMNSLRAED TAVYYCARDG
 M1_4H VWYDGSTTYS PDSVKGRFTI SRDDSKNTLY LQMNSLRAED TAVYYCARDR
 M1_5H ITYDGDNKYY ADSVKGRFTI SRDNSKNTLY LQMNSLPAED TAVYYCARDG
 M1_8H VWYDGSNTYS PDSVKGRFTI SRDDSKNTVY LQMNSLRAED TAVYYCARDR 101                                                   150
M1_10H YYGSGSYRVD YYYYGMDVWG QGTTVTVSSA STKGPSVFPL APSSKSTSGG
 M1_1H VG........ ....LFDYWG QGTLVTVSSA STKGPSVFPL APSSKSTSGG
M1_21H VG........ ....LFDYWG QGTLVTVSSA STKGPSVFPL APSSKSTSGG
M1_23H IG........ ....YFDYWG QGTLVTVSSA STKGPSVFPL APSSKSTSGG
M1_25H VG........ ....LFDYWG QGTLVTVSSA STKGPSVFPL APSSKSTSGG
 M1_3H IG........ ....YFDYWG QGTLVTVSSA STKGPSVFPL APSSKSTSGG
 M1_4H VG........ ....LFDYWG QGTLVTVSSA STKGPSVFPL APSSKSTSGG
 M1_5H IG........ ....YFDYWG QGTLVTVSSA STKGPSVFPL APSSKSTSGG
 M1_8H VG........ ....LFDYWG QGTLVTVSSA STKGPSVFPL APSSKSTSGG 151                                                   200
M1_10H TAALGCLVKD YFPEPVTVSW NSGALTSGVH TFPAVLQSSG LYSLSSVVTV
 M1_1H TAALGCLVKD YFPEPVTVSW NSGALTSGVH TFPAVLQSSG LYSLSSVVTV
M1_21H TAALGCLVKD YFPEPVTVSW NSGALTSGVH TFPAVLQSSG LYSLSSVVTV
M1_23H TAALGCLVKD YFPEPVTVSW NSGALTSGVH TFPAVLQSSG LYSLSSVVTV
M1_25H TAALGCLVKD YFPEPVTVSW NSGALTSGVH TFPAVLQSSG LYSLSSVVTV
 M1_3H TAALGCLVKD YFPEPVTVSW NSGALTSGVH TFPAVLQSSG LYSLSSVVTV
 M1_4H TAALGCLVKD YFPEPVTVSW NSGALTSGVH TFPAVLQSSG LYSLSSVVTV
 M1_5H TAALGCLVKD YFPEPVTVSW NSGALTSGVH TFPAVLQSSG LYSLSSVVTV
 M1_8H TAALGCLVKD YFPEPVTVSW NSGALTSGVH TFPAVLQSSG LYSLSSVVTV 201                                      237
M1_10H PSSSLGTQTY ICNVNHKPSN TKVDKKAEPK SHHHHHH
 M1_1H PSSSLGTQTY ICNVNHKPSN TKVDKKAEPK SHHHHHH
M1_21H PSSSLGTQTY ICNVNHKPSN TKVDKKAEPK SHHHHHH
M1_23H PSSSLGTQTY ICNVNHKPSN TKVDKKAEPK SHHHHHH
M1_25H PSSSLGTQTY ICNVNHKPSN TKVDKKAEPK SHHHHHH
 M1_3H PSSSLGTQTY ICNVNHKPSN TKVDKKAEPK SHHHHHH
 M1_4H PSSSLGTQTY ICNVNHKPSN TKVDKKAGPK SHHHHHH
 M1_5H PSSSLGTQTY ICNVNHKPSN TKVDKKAEPK SHHHHHH
 M1_8H PSSSLGTQTY ICNVNHKPSN TKVDKKAEPK SHHHHHH
```

M1-L Kappa Chain Variable and Constant Regions $10^{-9}$ M Affinity Cut (SEQ ID NOS: 46, 36, 48, 50, 52, 38, 40, 42, and 44, respectively)

```
         1                                                 50
M1_10L DVVMTQSPAT LSLSPGERAT LSCRASQSVS S.YLAWYQQK PGQAPRLLIY
 M1_1L EIVLTQSPAT LSLSPGERAT LSCRASQGVS S.YLAWYQQK PGQAPRLLIY
M1_21L AIRMTQSPSF LSASVGDRVT ITCRASQSIS S.YLNWYQQK PGKAPKLLIY
M1_23L EIVLTQSPGT LSLSPGERAT LSCRASQSVS SSYLAWYQQK PGQAPRLLIY
M1_25L EIVLTQSPGT LSLSPGERAT LSCRASQSVS SSYLAWYQQK PGQAPRLLIY
 M1_3L EIVMTQSPAT LSLSPGERAT LSCRASQSVS SSYLAWYQQK PGQAPRLLIY
 M1_4L EIVLTQSPGT LSLSPGERAT LSCRASQSVS SSYLAWYQQK PGQAPRLHIY
 M1_5L EIVMTQSPGT LSLSPGERAT LSCRASQSVS SSYLAWYQQK PGQAPRLLIY
 M1_8L EIVMTQSPGT LSLSPGERAT LSCRASQSVS STYLAWYQQK PGQAPRLLIY 51                                                100
M1_10L DASNRATGIP ARFSGSGSGT DFTLTISSLE PEDFAVYYCQ QRSNWP.PTF
 M1_1L DASNRATGIP ARPSGSGSGT DFTLTISSLE PEDFAVYYCQ QRSNWP.RTF
M1_21L AASSLQSGVP SRFSVSGSGT DLTLTISSLQ PEDFATYYCQ CGYSTP.FTF
M1_23L GASSPATGIP DRFSGSGSGT DFTLTISRLE PEDFAVYYCQ QYGSSPPYTF
M1_25L GASSRATGIP NRFSGSGSGT DFTLTISRLE PEDFAVYYCQ QYGSS..FTF
 M1_3L GASSRATGIP DRFSGSGSGT DFTLTISRLE PEDFAVYYCQ QYGSSPPFTF
 M1_4L GASRRATGIP DRFSGSGSGT DFTLTISRLE PEDFAVYYCQ QFGSS..FTF
 M1_5L GASSRATGIP DRFSGSGSGT DFTLTISRLE PEDFAVYYCQ QYGSSPIFTF
 M1_8L GASSRATGIP DRFSGSGSGT DFTLTISRLE PEDFAVYYCQ QYVSS..FTF 101                                               150
M1_10L GGGTKVEIKR TVAAPSVFIF PPSDEQLKSG TASVVCLLNN FYPREAKVQW
 M1_1L GQGTKVEIKR TVAAPSVFIF PPSDEQLKSG TASVVCLLNN FYPREAKVQW
M1_21L GPGTKVDIKR TVAAPSVFIF PPSDEQLKSG TASVVCLLNN FYPREAKVQW
M1_23L GQGTKLEIKR TVAAPSVFIF PPSDEQLKSG TASVVCLLNN FYPREAKVQW
M1_25L GPGTKVDIKR TVAAPSVFIF PPSDEQLKSG TASVVCLLNN FYPREAKVQW
 M1_3L GPGTKVDIKR TVAAPSVFIF PPSDEQLKSG TASVVCLLNN FYPREAKVQW
 M1_4L GPGTKVDIKR TVAAPSVFIF PPSDEQLKSG TASVVCLLNN FYPREAKVQW
 M1_5L GPGTKVDIKR TVAAPSVFIF PPSDEQLKSG TASVVCLLNN FYPREAKVQW
 M1_8L GPGTKVDIKR TVAAPSVFIF PPSDEQLKSG TASVVCLLNN FYPREAKVQW 151                                               200
M1_10L KVDNALQSGN SQESVTEQDS KDSTYSLSST LTLSKADYEK HKVYACEVTH
 M1_1L KVDNALQSGN SQESVTEQDS KDSTYSLSST LTLSKADYEK HKVYACEVTH
M1_21L KVDNALQSGN SQESVTEQDS KDSTYSLSST LTLSKADYEK HKVYACEVTH
M1_23L RVDNALQSGN SQESVTEQDS KDSTYSLSST LTLSKADYEK HKVYACEVTH
M1_25L KVDNALQSGN SQESVTEQDS KDSTYSLSST LTLSKADYEK HKVYACEVTH
 M1_3L KVDNALQSGN SQESVTEQDS KDSTYSLSST LTLSKADYEK HKVYACEVTH
 M1_4L KVDNALQSGN SQESVTEQDS KDSTYSLSST LTLSKADYEK HKVYACEVTH
 M1_5L KVDNALQSGN SQESVTEQDS KDSTYSLSST LTLSKADYEK HKVYACEVTH
 M1_8L KVDMALQSGW SQESVTEQDS KDSTYSLSST LTLSKADYEK HKVYACEVTH 201             226
M1_10L QGLSSPVTKS FNRGESYPYD VPDYAS
 M1_1L QGLSSPVTKS FNRGESYPYD VPDYAS
M1_21L QGLSSPVTKS FNRGESYPYD VPDYAS
M1_23L QGLSSPVTKS FNPGESYPYD VPDYAS
M1_25L QGLSSPVTKS FNRGESYPYD VPDYAN
 M1_3L QGLSSPVTKS FNRGESYPYD VPDYAS
 M1_4L QGLSSPVTKS FNRGESYPYD VPDYAS
 M1_5L QGLSSPVTKS FNRGESYPYD VPDYAS
 M1_8L QGLSSPVTKS FNRGESYPYD VPDYAS
```

M2-H Heavy Chain VH-CH1 Sequence $10^{-10}$ M Affinity Cut (SEQ ID NOS: 92, 94, 96, 98, 100, 102, 104, 106, 108, and 110, respectively)

```
         1                                                 50
M2_11H QVQLVESGGG VVQPGRSLRL SCAASGFTFS YYGMHWVRQA PGKGLEWVTL
M2_12H DVQLVESGGG VVHPGRSLRL SCAASGFTFS YYGMHWVRQA PGKGLEWMTL
M2_16H QVQLVQSGGG VVQPGKSLRL SCAASGFSLS YYGMHWVRQV PGKGLEWVAA
M2_18H QVQLVQSGGG VVQPGKSLRL SCAASGFSFS YYGMHWVRQV PGKGLEWVAA
M2_20H QVQLVQSGGG VVQPGRSLRL SCAASGFTFS YYGMHWVRQA PGKGLEWVSL
M2_31H QVQLVESGGV VVQPGRSLRL SCAASGFTFS YYGIHWVRQV PGKGLEWVAL
M2_32H QVQLVQSGGG LVHPGGSLRL SCEGSGFIFR NHPIHINRQA PGKGLEWVSV
M2_33H QVQLVQSGGG VVQPGRSLRL SCAASGFTFS YYGMHWVRQA PGKGLEWMTL
M2_34H QVQLVESGGG VVQPGRSLRL SCAASGFTFS YYGIHNVRQV PGKGLEWVVL
M2_35H QVQLVESGGG WQPGRSLPIL SCAASGFTIS YYGIHWVRQV PGKGLEWVEL
```

```
            51                                               100
M2_11H  ITYDGDNKYY ADSVKGRFTI SRDNSKNTLY LQMNSLRAED TAVYYCARDG
M2_12H  ISYDGDNKYY ADSVKGRFTI SRENSKNTLY LQMNSLRAED TAVYYCARDG
M2_16H  VWYDGSTRYS PDSVKGRFTI SRDDSKNTLY LQMNSLRAED TAVYYCARDR
M2_18H  VWYDGSTTYS PDSVKGRFTI SPDDSKNTLY LQMNSLRAED TAVYYCARDR
M2_20H  ITYDGRNKYY ADSVKGRFTI SRENSKNTLY LQMNSLRTED TAEYYCARDG
M2_31H  ISYDGSNKYY ADSVKGRFTI SRDNSKNTLY LQMNSLRAED TAVYYCARDW
M2_32H  SGIGG.DTYY ADSVKGRFSI SRDWAKNSLY LQMNSLRAED MAVYYCAREY
M2_33H  ITYDGDNKYY ADSVKGRFTI SRDNSKNTLY LQMNSLRAED TAVYYCARDG
M2_34H  ISYDGSNKYY ADSVKGRFTI SRDNSKNTLY LQMNSLRAED TAVYYCARDW
M2_35H  ISYDGSNKYY ADSVKGRFTI SRDNSKNTLY LQMNSLRAED TAVYYCARDW 101                                              150
M2_11H  IG........ ....YFDYWG QGTLVTVSSA STKGPSVFPL APSSKSTSGG
M2_12H  IG........ ....YFDYWG QGTLVTVSSA STKGPSVFPL APSSKSTSGG
M2_16H  VG........ ....LFDYWG QGTLVTVSSA STKGPSVFPL APSSKSTSGG
M2_18H  VG........ ....LFDYWG QGTLVTVSSA STKGPSVFPL APSSKSTSGG
M2_20H  IG........ ....YFDYWG QGILVTVSSA STKGPSVFPL APSSKSTSGG
M2_31H  IG........ ....YFDYWG QGTLVTVSSA STKGPSVFPL APSSKSTSGG
M2_32H  YYGSGSYRVD YYYYGMDVWG QGTTVTVSSA STKGPSVFPL APSSKSTSGG
M2_33H  IG........ ....YFDYWG QGTLVTVSSA STKGPSVFPL APSSKSTSGG
M2_34H  IG........ ....YFDYWG QGTLVTVSSA STKGPSVFPL APSSKSTSGG
M2_35H  IG........ ....YFDYWG QGTLVTVSSA STKGPSVFPL APSSKSTSGG 151                                              200
M2_11H  TAALGCLVKD YFPEPVTVSW NSGALTSGVH TFPAVLQSSG LYSLSSVVTV
M2_12H  TAALGCLVKD YFPEPVTVSW NSGALTSGVH TFPAVLQSSG LYSLSSVVTV
M2_16H  TAALGCLVKD YFPEPVTVSW NSGALTSGVH TFPAVLQSSG LYSLSSVVTV
M2_18H  TAALGCLVKD YFPEPVTVSW NSGALTSGVH TFPAVLQSSG LYSLSSVVTV
M2_20H  TAALGCLVKD YFPEPVTVSW KSGALTSGVH TFPAVLQSSG LYSLSSVVTV
M2_31H  TAALGCLVKD YFPEPVTVSW NSGALTSGVH TFPAVLQSSG LYSLSSVVTV
M2_32H  TAALGCLVKD YFPEPVTVSW NSGALTSGVH TFPAVLQSSG LYSLSSVVTV
M2_33H  TAALGCLVKD YFPEPVTVSW NSGALTSGVH TFPAVLQSSG LYSLSSVVTV
M2_34H  TAALGCLVKD YFPEPVTVSW NSGALTSGVH TFPAVLQSSG LYSLSSVVTV
M2_35H  TAALGCLVKD YFPEPVTVSW NSGALTSGVH TFPAVLQSSG LYSLSSVVTV 201                          237
M2_11H  PSSSLGTQTY ICNVNHKPSN TKVDKKAEPK SHHHHHH
M2_12H  PSSSLGTQTY ICNVNHKPSS TKVDKKAEPK SHHHHHH
M2_16H  PSSSLGTQTY ICNVNHKPSN TKVDKKAEPK SHHHHHH
M2_18H  PSSSLGTQTY ICNVNHKPSN TKVDKKAEPK SHHHHHH
M2_20H  PSSSLGTQTY ICNVNHKPSN TKVDKKAEPK SHHHHHH
M2_31H  PSSSLGTQTY ICNVNHKPSN TKVDKKAEPK SHHHHHH
M2_32H  PSSSLGTQTY ICNVNHKPSN TKVDKKAEPK SHHHHHH
M2_33H  PSSSLGTQTY ICNVNHKPSN TKVDKKAEPK SHHHHHH
M2_34H  PSSSLGTQTY ICNVNHKPSN TKVDKKAEPK SHHHHHH
M2_35H  PSSSLGTQTY ICNVNHKPSN TKVDKKAEPK SHHHHHH
```

M2-L Kappa Chain VKCK $10^{-10}$ M Affinity Cut (Thu Sep 23) (SEQ ID NOS: 72, 74, 76, 78, 80, 82, 84, 86, 88, and 90, respectively)

```
            1                                                50
M2_11L  EIVMTQSPGT LSLSPGERAT LSCRASQGVS SSYLAWYQQK PGQAPRLLIY
M2_12L  EIVMTQSPGT LSLSPGERAT LSCRASQGVS SSYLAWYQQK PGQAPRLLIY
M2_16L  EIVMTQSPGT LSLSPGERAT LSCRASQSVS SSYLAWYQQK PGQAPRLLIY
M2_18L  EIVMTQSPGT LSLSPGERAT LSCRASQSVS STYLAWYQQK PGQAPRLLIY
M2_20L  EIVMTQSPGT LSLSPGERAT LSCRASQSVS SSYLAWYQQK PGQAPRLLIY
M2_31L  EIVLTQSPAT LSLSPGERAT LSCRASQSVS S.YLAWYQQK PGQAPRLLIY
M2_32L  EIVLTQSPAT LSLSPGERAT LSCRASQSVS S.YLAWYQQK PGQAPRLLIY
M2_33L  EIVLTQSPGT LSLSPGERAT LSCRASQSVS SSYLAWYQQK PGQAPRLLIY
M2_34L  EIVLTQSPAT LSLSPGERAT LSCPASQSVS S.YLAWYQQK PGQAPRLLIY
M2_35L  EIVLTQSPAT LSLSPGERAT LSCRASQSVS S.YLAWYQQK PGQAPRLLIY 51                                               100
M2_11L  GASSRATGIP DRFSGSGSGT DFTLTISRLE PEDFAVYYCQ QYGSSPPFTF
M2_12L  GASSRATGIP DRFSGSGSGT DFTLTISSLE PEDFAVYYCQ QYGSSPPYTF
M2_16L  GASSRATGIP DRFSVSGSGT DFTLTISRLE PEDFAVYYCQ QYGSS..FTF
M2_18L  GASSRATGIP DRFSGSGSGT DFTLTISRLE PEDFAVYYCQ QYVSS..FTF
M2_20L  GASRRATGIP DRFSGSGSGT DFTLTISRLE PEDFAVYYCQ QYGSSPMYTF
M2_31L  DASNRATGIP ARFSGSGSGT DFTLTISSLE PEDFAVYYCQ QRTNWP.RTF
M2_32L  DASNRAAGIP ARFSGSGSGT DFTLTISSLE PEDFAVYYCQ QRNNWP.LTF
M2_33L  GASSRATGIP DRFSGSGSGT DFTLTISRLE PEDFAVYYCQ QYGSSPPYTF
M2_34L  DASNRATGIP ARFSGSGSGT DFTLTISSLE PEDFAVYYCQ QRTNWP.RTF
M2_35L  DASNRATGIP ARFSGSGSGT DFTLTISSLE PEDFAVYYCQ QRTNWP.RTF
```

```
                        -continued
           101                                              150
M2_11L GPGTKVDIKR TVAAPSVFIF PPSDEQLRSG TASVVCLLNN FYPREAKVQW
M2_12L GQGTKLEIKR TVAAPSVFIF PPSDEQLKSG TASVVCLLNN FYPREAKVQW
M2_16L GPGTKVDIKR TVAAPSVFIF PPSDEQLKSG TASVVCLLNN FYPREAKVQW
M2_18L GPGTKVDIKR TVAAPSVFIF PPSDEQLKSG TASVVCLLNN FYPREAKVQW
M2_20L GQGTKLEIKR TVAAPSVFIF PPSDEQLKSG TASVVCLLNN FYPREAKVQW
M2_31L GQGTKVEIKR TVAAPSVFIF PPSDEQLKSG TASVVCLLNN FYPREAKVQW
M2_32L GGGTKVEIKR TVAAPSVFIF PPSDEQLKSG TASVVCLLNN FYPREAKVQW
M2_33L GQGTKLEIKR TVAAPSVFIF PPSDEQLKSG TASVVCLLNN FYPREAKVQW
M2_34L GQGTKVEIKR TVAAPSVFIF PPSDEQLKSG TASVVCLLNN FYPREAKVQW
M2_35L GQGTKVEIKR TVAAPSVFIF PPSDEQLKSG TASVVCLLNN FYPREAKVQW 151                                              200
M2_11L KVDNALQSGN SQESVTEQDS KDSTYSLSST LTLSKADYEK HKVYACEVTH
M2_12L KVDNALQSGN SQESVTEQDS KDSTYSLSST LTLSKADYEK HKVYACEVTH
M2_16L KVDNALQSGN SQESVTEQDS KDSTYSLSST LTLSKADYEK HKVYACEVTH
M2_18L KVDNALQSGN SQESVTEQDS KDSTYSLSST LTLSKADYEK HKVYACEVTH
M2_20L KVDNALQSGN SQESVTEQDS KDSTYSLSST LTLSKADYEK HKVYACEVTH
M2_31L KVDNALQSGN SQESVTEQDS KDSTYSLSST LTLSKADYEK HKVYACEVTH
M2_32L KVDNALQSGN SQESVTEQDS KDSTYSLSST LTLSKADYEK HKVYACEVTH
M2_33L KVDNALQSGN SQESVTEQDS KDSTYSLSST LTLSKADYEK HKVYACEVTH
M2_34L KVDNALQSGN SQESVTEQDS KDSTYSLSST LTLSKADYEK HKVYACEVTH
M2_35L KVDNALQSGN SQESVTEQDS KDSTYSLSST LTLSKADYEK HKVYACEVTH 201              226
M2_11L QGLSSPVTKS FNRGESYPYD VPDYAS
M2_12L QGLSSPVTKS FNRGESYPYD VPDYAS
M2_16L QGLSSPVTKS FNRGESYPYD VPDYAS
M2_18L QGLSSPVTKS FNRGESYPYD VPDYAS
M2_20L QGLSSPVTKS FNRGESYPYD VPDYAS
M2_31L QGLSSPVTKS FNRGESYPYD VPDYAS
M2_32L QGLSSPVTKS FNRGESYPYD VPDYAS
M2_33L QGLSSPVTKS FNRGESYPYD VPDYAS
M2_34L QGLSSPVTKS FNRGESYPYD VPDYAS
M2_35L QGLSSPVTKS FNRGESYPYD VPDYAS
```

EXAMPLE 23

Cloning of the Human Interleukin-8 Antigen into the pEF1 Vector

PCR primers A and B (5' and 3' respectively, Table 5) were made corresponding to the coding sequence at the 5'-end of the human interleukin-8 antigen and the coding sequence at the 3'-end of human interleukin-8 (Genbank accession number M28130). The 5' primer also contains 21 base pairs of pEF1/Myc-His (A) vector sequence (Invitrogen, San Diego, Calif.) at its 5'-end corresponding to the EcoRI site and sequence immediately upstream. The 3' primer contains an additional 24 base-pairs of vector sequence, including the PmeI site and sequence immediately downstream, at its 5' end. The vector sequence at the 5'-ends of these primers will form, upon treatment with T4 DNA polymerase, single-stranded overhangs that are specific and complementary to those on the vector as described in Example 14.

The PCR amplification of the interleukin-8 gene insert was first done on a 50 µl reaction scale containing 50 pmol of 5' primer (A), 50 pmol of 3' primer (B), 1 unit of Expand polymerase, 5 µl 2 mM dNTPs, 5 µl× Expand reaction buffer, 1 µl of Clontech Quick-clone human liver cDNA (Clontech Laboratories, Palo Alto, Calif.) as template, and water to 50 µl. The reaction was carried out in a Perkin-Elmer thermal cycler as described in Example 15. A second PCR amplification was performed on a 3×100 µl reaction scale in order to prepare sufficient material for cloning, with each reaction containing 100 pmol of 5' primer (A), 100 pmol of 3' primer (B), 2.5 units of Expand polymerase, 10 µl 2 mM dNTPs, 10 µl 10× Expand reaction buffer, 2 µl of the first PCR reaction as template, and water to 100 µl. The PCR products were precipitated and fractionated by agarose gel electrophoresis and full-length products excised from the gel, purified, and resuspended in water (Example 14). The pEF1/Myc-His (A) vector was prepared to receive insert by digestion with PmeI and EcoRI (New England BioLabs, Beverly, Mass.). The insert and EcoRI/PmeI digested pEF1/Myc-His (A) vector were prepared for T4 exonuclease digestion by adding 1.0 µl of 10× Buffer A to 1.0 µg of DNA and bringing the final volume to 9 µL with water. The samples were digested for 4 minutes at 30° C. with 1 µl (1 U/µl) of T4 DNA polymerase. The T4 DNA polymerase was heat inactivated by incubation at 70° C. for 10 minutes. The samples were cooled, briefly spun, and 20 ng of the digested insert added to 100 ng of digested pEF1/Myc-His (A) vector in a fresh microfuge tube. After the addition of 1.0 µl of 10× annealing buffer, the volume was brought to 10 µl with water. The mixture was heated to 70° C. for 2 minutes and cooled over 20 minutes to room temperature, allowing the insert and vector to anneal. The annealed DNA was diluted one to four with distilled water and electroporated (example 8) into 30 µl of electrocompetent E. coli strain, DH10B. The transformed cells were diluted to 1.0 ml with 2×YT broth and 10 µl, 100 µl, 300 µl plated on LB agar plates supplemented with ampicillin (75 µg/ml) and grown overnight at 37° C. Colonies were picked and grown overnight in 2×YT (75 µg/ml ampicillin at 37° C. The following day glycerol freezer stocks were made for long term storage at −80° C. The sequence of these clones (pEF1-IL8) was verified at MacConnell Research (San Diego, Calif.) by the dideoxy chain termination method using a Sequathern sequencing kit (Epicenter Technologies, Madison, Wis.), oligonucleotide primers C and D (Table 5) that bind on the 5' and 3' side of the insert in the pEF1/Myc-His (A) vector, respectively, and a LI-COR 4000L automated sequencer (LI-COR, Lincoln, Nebr.).

TABLE 5

PCR and Sequencing Primer Sequences

A- 5'
(TAGTCCAGTGTGGTGGAATTCGCCACCATGACTTCCAAGCTGGCCGT)
(SEQ ID NO:111)

B- 5'
(CGAGGCTGATCAGCGGGTTTAAACTTATGAATTCTCAGCCCTCTTCAA)
(SEQ ID NO:112)

C- 5'
(CATTCTCAAGCCTCAGACAGTGG)(SEQ ID NO:113)

D- 5'
(CAGACAATGCGATGCAATTTCC)(SEQ ID NO:114)

EXAMPLE 24

Cloning of the Human Myelin Proteolipid Protein (PLP) Antigen into the pEF1 Vector PCR primers A and B (5' and 3' respectively, Table 6) were made corresponding to the coding sequence at the 5'-end of the human PLP antigen and the coding sequence at the 3'-end of human PLP (Genbank accession number M54927). The 5' primer also contains 21 base pairs of pEF1/Myc-His (A) vector sequence (Invitrogen, San Diego, Calif.) at its 5'-end corresponding to the EcoRI site and sequence immediately upstream. The 3' primer contains an additional 24 base-pairs of vector sequence, including the PmeI site and sequence immediately downstream, at its 5' end. The vector sequence at the 5'-ends of these primers will form, upon treatment with T4 DNA polymerase, single-stranded overhangs that are specific and complementary to those on the vector as described in Example 14.

The PCR amplification of the PLP gene insert was done on a 2×100 µl reaction scale containing 100 pmol of 5' primer (A), 100 pmol of 3' primer (B), 2.5 units of Expand polymerase, 10 µl 2 mM dNTPs, 10 µl 10×Expand reaction buffer, 1 µl of Clontech Quick-clone human brain cDNA (Clontech Laboratories, Palo Alto, Calif.) as template, and water to 100 µl. The reaction was carried out in a Perkin-Elmer thermal cycler as described in Example 15. The PCR products were precipitated and fractionated by agarose gel electrophoresis and full-length products excised from the gel, purified, and resuspended in water (Example 14). The pEF1/Myc-His (A) vector was prepared to receive insert by digestion with PmeI and EcoRI (New England BioLabs, Beverly, Mass.). The insert and EcoRI/PmeI digested pEF1/Myc-His (A) vector were prepared for T4 exonuclease digestion by adding 1.0 µl of 10× Buffer A to 1.0 µg of DNA and bringing the final volume to 9 µl with water. The samples were digested for 4 minutes at 30° C. with 1 µl (1 U/µl) of T4 DNA polymerase. The T4 DNA polymerase was heat inactivated by incubation at 70° C. for 10 minutes. The samples were cooled, briefly spun, and 45 ng of the digested insert added to 100 ng of digested pEF1/Myc-His (A) vector in a fresh microfuge tube. After the addition of 1.0 µl of 10× annealing buffer, the volume was brought to 10 µl with water. The mixture was heated to 70° C. for 2 minutes and cooled over 20 minutes to room temperature, allowing the insert and vector to anneal. The annealed DNA was diluted one to four with distilled water and electroporated (example 8) into 30 µl of electrocompetent E. coli strain, DH10B. The transformed cells were diluted to 1.0 ml with 2×YT broth and 10 µl, 100 µl, 300 µl plated on LB agar plates supplemented with ampicillin (75 µg/ml) and grown overnight at 37° C. Colonies were picked and grown overnight in 2×YT (75 µg/ml ampicillin at 37° C. The following day glycerol freezer stocks were made for long term storage at −80° C. The sequence of these clones (pEF1-PLP) was verified at MacConnell Research (San Diego, Calif.) by the dideoxy chain termination method using a Sequatherm sequencing kit (Epicenter Technologies, Madison, Wis.), oligonucleotide primers C and D (Table 6) that bind on the 5' and 3' side of the insert in the pEF1/Myc-His (A) vector, respectively, and a LI-COR 4000L automated sequencer (LI-COR, Lincoln, Nebr.).

TABLE 6

PCR and Sequencing Primer Sequences

A- 5'
(TAGTCCAGTGTGGTGGAATTCGCCACCATGGGCTTGTTAGAGTGCTGTG)
(SEQ ID NO:115)

B- 5'
(CGAGGCTGATCAGCGGGTTTAAACTCAGAACTTGGTGCCTCGGCCCAT)
(SEQ ID NO:116)

C- 5'
(CATTCTCAAGCCTCAGACAGTGG)(SEQ ID NO:117)

D- 5'
(CAGACAATGCGATGCAATTTCC)(SEQ ID NO:118)

EXAMPLE 25

Purification of pEF1-IL8 and pEF1-PLP Plasmids and Stable Transfection of PLP in COS-7 Cells A single colony of E. coli containing pEF1-IL8 (Example 23) or pEF1-PLP (Example 24) plasmid was cultured in LB containing 50 µg/ml of ampicillin for 8 h at 37° C. with shaking at 300 rpm. The cultures were then diluted 1/500 in 500 ml of selective LB and incubated for 12–16 h at 37° C. with shaking. The bacterial cells were harvested by centrifugation at 6,000×g for 20 min at 4° C. and the plasmids were purified using the EndoFree™ Plasmid Mega Kit (Qiagen, Valencia, Calif.) according to the directions supplied by the manufacturer. Purified plasmid for DNA immunizations were resuspended in endotoxin-free saline (0.15 M) and stored immediately at −20° C.

Expression of PLP was performed by transfection of the COS-7 cell line (CRL-1651) with linearized pEF1-PLP. The plasmid was linearized by digestion with the restriction enzyme PmeI (Invitrogen, San Diego, Calif.) for 16–18 h at 37° C. Following digestion, the reaction was incubated at 65° C. for 20 min to inactivate the enzyme. The linearized pEF1-PLP was purified using the QIAquick Spin Kit (Qiagen, Valencia, Calif.) according to the procedure provided with the kit. COS-7 cells were cultured in T-75 tissue culture flasks (CoStar, Corning, Inc., Corning, N.Y.) in Dulbecco's Modification of Eagle's Medium (DMEM; Cellgro, Herndon, Va.) containing 10% fetal bovine serum (JRH Biosciences, Lenexa, Kans.) at 37° C. in 5% $CO_2$. A 12-well tissue culture plate was seeded with 4×10e4 COS-7 cells per well. When the cells reached 40–80% confluency (usually in 24 h), transfections were performed using a range of DNA concentrations and various amounts of Effectene Transfection Reagent (Qiagen, Valencia, Calif.) according to the directions provided by the manufacturer. Twenty-four hours post-transfection, the medium was replaced with fresh DMEM containing 600 µg/ml of G418 (Invitrogen, San Diego, Calif.) for selection of transfected cells. Expression of PLP was confirmed by indirect immunofluorescence analysis using a rabbit anti-PLP polyclonal serum (Biogenesis, United Kingdom). Alternatively, an anti-Myc or anti-His antibody can also be used to test expression of the construct.

The efficacy of the pEF1-IL8 construct was confirmed by a transient transfection in COS-7 cells. IL-8 production was quantified in cell culture supernatants by a standard curve using IL-8 specific monoclonal antibodies and IL-8.

EXAMPLE 26

Preparation of Membrane Vesicles for Panning

Transfected cells are gently dissociated from the flask using Cell Dissociation Buffer (Life Technologies, Gaithersburg, Md.), washed three times in sterile 0.01M phosphate buffered saline, pH 7.4 and maintained at 4° C. during manipulations. The cell suspension is passed through a 30-gauge needle ten times then centrifuged at 2,000×g for 10 min. The supernatant containing membrane fragments is collected and sonicated on ice for 30s two times and pausing for 30s between each sonication. The sizes and size distribution of membrane vesicles are assessed using a particle sizer (Particle Sizing Systems, Holland, Pa.). Only preparations containing vesicles between 40–100 nm are used for panning phage antibody libraries. For panning, phage antibodies that bind to right-side out membrane vesicles or non-sealed membranes containing glycoproteins are captured by binding to wheat germ agglutinin (Lindsay et al. (1981) *Biochim Biophys Acta*, 640:791–801) coated magnetic latex. The preparation of lectin magnetic latex is performed in a similar fashion as avidin magnetic latex described in Example 10.

Alternatively, a biotin-phospholipid, N-((6-biotinoyl)amino)hexanoyl)-1,2-dihexadecanoyl-sn-glycero-3-phosphoethanolamine, triethylammonium salt (biotin-X DHPE; Molecular Probes, Inc, Eugene, Oreg.), is dissolved in chloroform/methanol (2:1) in a test tube then evaporated to dryness under nitrogen (Rivnay et al. (1987) *Methods in Enzymology* 149:119–123, Academic Press, Inc., San Diego, Calif.). The supernatant containing cell membranes is added to the tube coated with biotin-phospholipids and sonicated as described above. Phage antibodies binding to the biotinylated vesicles are captured using avidin magnetic latex as described in Example 13.

EXAMPLE 27

ELISA Assays for Serum Titers and Specific Antibody Detection

In general, antigens were immobilized either directly by absorption onto microtiter plate wells or antigens were biotinylated and bound to microtiter plate wells that already had streptavidin or NeutrAvidin™ (Pierce, Rockford, Ill.) bound to them by adsorption. In the case of direct adsorption, fifty microliters of troponin complex antigen (Bio-tech International Inc., Seattle, Wash., 2 µg/ml) were adsorbed to wells of a 96-well microwell plate (Falcon, Becton Dickinson Labware, Franklin Lakes, N.J.) overnight at 4° C. Excess antigen was removed and the wells were blocked with 200 µl of 10 mM TRIS, 150 mM NaCl, 10 mM $MgCl_2$, 0.1 mM $ZnCl_2$, 0.1% polyvinyl alcohol, 1% bovine serum albumin, 0.1% $NaN_3$, pH 8.0 (block buffer). After washing the plates three times with 3001 µl of BBST (20 mM borate, 150 mM NaCl, 0.1% $NaN_3$, 0.02% Tween 20), the wells were filled with 100 1 of 2-fold serial dilutions (in block buffer) of the mouse sera beginning at a 1:50 dilution. The wells were incubated with sera for 1 h at ambient temperature then washed as described above. After washing, the wells were filled with 100 µl of alkaline phosphatase-conjugated anti-human IgG Fc specific antibody (Jackson ImmunoResearch Laboratories, Inc., West Grove, Pa.) diluted 1:250 in block buffer. After 1 h of incubation at ambient temperature, the wells were washed and 2001 µl of the substrate phenolphthalein monophosphate (JBL Scientific Inc., San Luis Obispo, Calif.), 6 mg/ml in 0.2 M 2-amino-2-methyl-1-propanol, 0.5 M Tris, pH 10.2) was added to each well. The kinetics was measured for 1 min at an optical density of 560 nm (Molecular Devices, Sunnyvale, Calif.). The titer of the serum was the reciprocal of the dilution at which the signal was greater than two times that of the background signal (Table 7). Test bleeds (TB) were drawn nine days after three biweekly immunizations with TIC antigen (TB-1), nine days after the $4^{th}$ immunization (TB-2), and nine days after the $5^{th}$ immunization (TB-3).

TABLE 7

| | Antibody titers | | |
|---|---|---|---|
| Mouse ID | TB-1 | TB-2 | TB-3 |
| A | — | — | — |
| B | — | 3,200 | 12,800 |
| C | — | — | — |
| D | — | 50 | 200 |
| B | — | — | — |

To detect specific antibodies that had been expressed in *E. coli* and either obtained directly from disrupted cells or as purified antibody, biotinylated antigens troponin TIC complex, oxidized troponin I and IL-8 (Examples 9 and 33) were immobilized on 96-well polystyrene microtiter plates that had streptavidin or NeutrAvidin™ immobilized on them using a concentration of $10^{-8}$ M biotinylated antigen. Dilutions of the antibody preparations were incubated for one hour with the immobilized antigens and unbound antibody was washed away as described above. The presence of bound antibody was detected using goat-anti-human antibody conjugated to alkaline phosphatase that is specific for the human kappa chain (Southern Biotechnology Associates, Birmingham, Ala.) and the method described above.

EXAMPLE 28

Isolation of RNA from Bone Marrow from Mice Immunized with Oxidized Troponin I

Five HCo7 mice were immunized with oxidized troponin I (Example 32) as described in Example 1. Immediately post-splenectomy, muscle and connective tissues were removed from the femur. The cleaned femur was transferred to a sterile 35 mm petri dish containing 0.6 ml of sample lysis buffer (Buffer RLT; QIAamp RNA Isolation Kit, Qiagen, Valencia, Calif.). The bone was split longitudinally with a sterile No. 15 scalpel and the exposed marrow was teased out of the bone into the lysis buffer using a 27 gauge needle. The head of the femur was further split and scraped to remove all remaining marrow. The lysis buffer containing bone marrow cells and small bone fragments was transferred to a QIAshredder spin column for complete homogenization of cells and processed according to the manufacturer's protocol. Bone fragments were effectively removed from the sample as they failed to enter the QIAshredder spin column. Subsequent isolation of total RNA using the QIAamp spin column and a DNase1 digestion step were performed according to the procedures provided by the manufacturer.

EXAMPLE 29

DNA Immunizations

Plasmid DNA (pEF1-IL8, Example 25 and pEF1-PLP, Example 25) were suspended in endotoxin-free saline at a concentration of 1 mg/ml for DNA immunizations. Prior to injections, the mice were anaesthetized and the hind limbs were shaved to allow improved accessibility to the tibialis anterior muscle. Fifty microliters of the DNA suspension was injected slowly into each muscle (50 µg of DNA per injection site) using a 27 gauge needle. Mice were immunized on day 0 and day 14 and test bleeds were performed on day 14 (TB-1) and day 21 (TB-2). RNA was isolated on day 21 by the procedure described in Example 1.

Serum titer assays were performed on pre-immune sera collected prior to immunizations and test bleeds as described in Example 27 for the mice immunized with pEF1-IL8 The plates were coated with unlabeled IL8, and sera were tested at a starting dilution of 1:20.

TABLE 8

| | Antibody Titers | | |
|---|---|---|---|
| Mouse ID | Pre-immune | TB-1 | TB-2 |
| A | — | — | 20 |
| B | — | — | — |
| C | — | — | — |

EXAMPLE 30

Amplification of Human Antibody Sequence cDNA by PCR from Spleens of Mice Exhibiting no Serum Titer to TIC Five HCo7 mice were immunized with troponin complex (Bio-tech International Inc., Seattle, Wash.) as described in Example 1. The RNA from spleens C and E described in Example 27 was purified as described in Example 1 and cDNA was made as described in Example 2. The cDNA was amplified by PCR as described in Example 3 for HCo7 mice except 5 µL of cDNA was used for the double stranded PCR of the heavy chain for spleen E, and the 3' primer for the double stranded PCR was done using oligonucleotide 1008 for both spleens.

```
Oligonucleotide 1008
5'-CAC CGT CAC CGG TTC GGG GA (SEQ ID NO:119)
```

EXAMPLE 31

Amplification of Human Antibody RNA by One Step Reverse Transcription-Polymerase Chain Reaction (RT-PCR)

The total RNA purified from spleen (Example 29 for IL8) or bone marrow (Example 28) described above was used directly as template. The RNA from the bone marrow of mice A and E were pooled and RNA from the bone marrow of mice C and D were pooled for the bone marrow PCR. Superscript™ One-Step RT-PCR with PLATINUM® Taq (Gibco/BRL, Gaithersburg, Md.) was used as described in the product insert. The oligonucleotides described for HCo7 mice in Example 3 were used except oligonucleotide 1008 (Example 30) was the 3' oligonucleotide for the heavy chain instead of oligonucleotide 952. One 25 µL reaction was performed for each primer pair with 12.5 pmol of 5' primer, 12.5 pmol of 3' primer, and 0.625 µg of RNA. Amplification was done using a GeneAmp® 9600 thermal cycler (Perkin Elmer, Foster City, Calif.) with the following program: 45° C. for 30 min; 94° C. for 2 min; 40 cycles of 94° C. for 15 sec, 55° C. for 30 sec, and 72° C. for 60 sec; 72° C. for 7 min; 4° C. The dsDNA products of the PCR process were then subjected to asymmetric PCR using only 3' primer to generate substantially only the anti-sense strand of the target genes, as described in Example 3.

EXAMPLE 32

Preparation of Oxidized Troponin I

Cardiac troponin I (Bio-tech International Inc., Seattle, Wash.) was dialyzed extensively against 100 mM potassium phosphate, 50 mM potassium borate, 1 M NaCl, pH 7.0. After dialysis, 1 M $H_2O_2$ was added to the protein at a final concentration of 20 mM, and the mixture was incubated at room temperature for 30 minutes. The troponin I oxidized solution was transferred to dialysis tubing and dialyzed against 100 mM potassium phosphate, 50 mM potassium borate, 1 M NaCl, 1.4 ug/ml Catalase, pH 7.0 for 3 hr at room temperature. After 3 hr, the protein was dialyzed twice against 100 mM potassium phosphate, 50 mM potassium borate, 1M NaCl, pH 7.0, then once against 100 mM potassium phosphate, 50 mM potassium borate, 0.5M NaCl, pH 7.0 for at least 4 hr each at 2–8° C.

EXAMPLE 33

Preparation of Biotinylated Troponin Complex (TIC) and Biotinylated Oxidized Troponin Troponin complex and oxidized troponin were dialyzed against a minimum of 100 volumes of 20 mM borate, 150 mM NaCl, pH 8 (BBS) with 2 mM $CaCl_2$ at 2–8° C. for at least 4 hr. The buffer was changed at least once prior to biotinylation. Troponin complex and oxidized troponin were reacted with biotin-XX-NHS ester (Molecular Probes, Eugene, Oreg., stock solution at 40 mM in dimethylformamide) at a final concentration of 0.1 mM for TIC and 0.2 mM for oxidized troponin for 1 hr at room temperature. After 1 hr, the proteins were extensively dialyzed into BBS with 2 mM $CaCl_2$ to remove unreacted small molecules.

EXAMPLE 34

Enrichment of Polyclonal Phage from Mice Immunized with TIC but Exhibiting no Serum Titers of Antibody The RNA from spleens C and E (Example 27) was amplified by PCR (Example 30), and first round antibody phage was prepared as described in Example 7 using BS47 uracil template. The mice from where the spleens originated did not have an antibody serum titer in the test bleeds. Four electroporations of mutagenesis DNA were done from 2 different spleens (2 electroporations from each spleen) yielding 4 different phage samples. Phage were set up for the first round of panning by mixing 0.92 mL phage, 30 µL 300 mg/mL BSA, 2 µL 1M CaCl$_2$, 50 µL 1M TRIS, pH 8.0 and 10 µL 10$^{-7}$M TIC-biotin (Example 33), and incubating overnight at 2–8° C. The antibody phage samples were panned with avidin magnetic latex as described in Example 13. The only difference is the panning buffer also contained 2 mM CaCl$_2$. This panning buffer was used for every panning step described in this example.

The resulting 2nd round antibody phage samples were enriched for polyvalent display by panning with 7F11 magnetic latex as described in Example 13. Panning with TIC-biotin was set up for each sample by mixing 900 µL 7F11/decapeptide enriched phage, 2 µL 1M CaCl$_2$, 100 µL panning buffer, and 10 µL 10$^{-7}$ M TIC-biotin. After overnight incubation at 2–8° C., the phage samples were panned with avidin magnetic latex as described above.

The resulting 3rd round antibody phage samples were again enriched for polyvalent display and the eluted phage were set up with TIC-biotin as described above. After overnight incubation at 2–8° C., the phage samples were panned with avidin magnetic latex as described above. Aliquots of each sample were plated on 100 mm LB agar plates to determine the percentage of kappa positives (Example 12). The percentage of kappa positives for the 3rd round of panning was between 91–97%.

The 4th round antibody phage samples were titered as described in Example 13. The two phage samples from each spleen were pooled to give spleen C pool and spleen E pool. The pooled antibody phage was set up in duplicate for a 4th round of functional panning as described above using 900 µL panning buffer, 100 µL 4th round pooled-antibody phage. One sample (foreground) received 10 µL 10$^{-7}$M TIC-biotin and the other sample (background) did not receive TIC-biotin and served as a blank to monitor non-specific binding of phage to the magnetic latex. After overnight incubation at 2–8° C., the phage samples were panned with avidin magnetic latex as described above. The next day, the 5th round antibody phage was eluted and the number of plaques was counted on the foreground and background plates. The foreground:background ratio was 148:1 for spleen C and 190:1 for spleen E. The antibody phage populations were subcloned into the expression vector and electroporated as described in Example 15, except oligonucleotides 1161 and 1178 were used to amplify the antibody gene insert of spleen C and oligonucleotides 1161 and 1182 were used to amplify the antibody gene insert of spleen E

```
Primer 1161 5' TC GCT GCC AAA CCA GCC ATG GCC
(SEQ ID NO:120)

Primer 1178 5'-GT GAT AAA CTA CCG CAT TA AAG
CTT ATC GAT GAT AAG CTG TCA A TTA GTG ATG GTG
GTG ATG AGA TTT GG (SEQ ID NO:121)

Primer 1182 5'-GT GAT AAA CTA CCG CAT TA AAG
CTT ATC GAT GAT AAG CTG TCA A TTA GTG ATG GTG
GTG ATG ACA TTT GG (SEQ ID NO:122)
```

Figure 8:
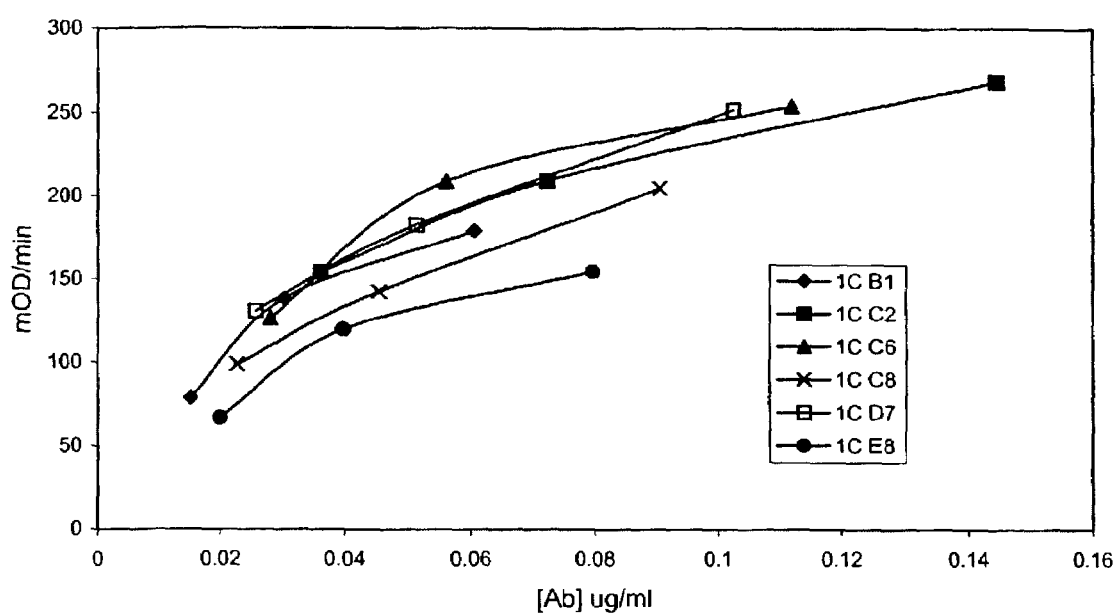
FIG. 8: ELISA for monoclonal antibodies to troponin derived from HuMAb mice showing zero titer.

FIG. 8 shows ELISA data of six monoclonals from the above experiment confirming specific binding to the target antigen.

EXAMPLE 35

Enrichment of Polyclonal Phage from Mice Immunized with DNA

RNA purified from the spleens of 3 HCo7 mice immunized with the pEF1-IL8 plasmid (Example 29) was amplified by PCR (Example 31), and first round antibody phage was prepared as described in Example 7 using BS47 uracil template. Six electroporations of mutagenesis DNA were done (2 electroporations from each spleen) yielding 6 different phage samples. Phage were set up for the first round of panning by mixing 0.92 mL phage, 52.5 µL 5% casein, 30 µL 300 mg/mL BSA, 50 µL 1M TRIS, pH 8.0 and 10 µL 10$^{-7}$M IL8-biotin (Example 9) and incubating 3 hr at room temperature. The antibody phage samples were panned with avidin magnetic latex as described in Example 13. The only difference is the panning buffer also contained 0.25% casein (Sigma, St. Louis, Mo.). This panning buffer was used for every panning step described in this example.

The resulting 2nd round antibody phage samples were enriched for polyvalent display by panning with 7F11 magnetic latex as described in Example 13. Panning with IL8-biotin was set up for each sample by mixing 900 µL 7F11/decapeptide enriched phage, 100 µL panning buffer, and 10 µL 10$^{-7}$ M IL8-biotin. After 3 hr incubation at room temperature, the phage samples were panned with avidin magnetic latex as described above.

The resulting 3rd round antibody phage samples were again enriched for polyvalent display and the eluted phage were set up with IL8-biotin as described above. After 3 hr incubation at room temperature, the phage samples were panned with avidin magnetic latex as described above. Aliquots of each sample were plated on 100 mm LB agar plates to determine the percentage of kappa positives (Example 12). The percentage of kappa positives for the 3rd round of panning was between 93–100%.

The 4th round antibody phage samples were titered as described in Example 13 and the phage were mixed into one pool. The pooled antibody phage was set up in duplicate for a 4th round of functional panning as described above using 900 µL panning buffer, 100 µL 4th round pooled-antibody phage. One sample (foreground) received 10 µL 10$^{-7}$M IL8-biotin and the other sample (background) did not receive IL8-biotin and served as a blank to monitor non-specific binding of phage to the magnetic latex. After overnight incubation at 2–8° C., the phage samples were panned with avidin magnetic latex as described above. The next day, the 5th round antibody phage was eluted and the number of plaques was counted on the foreground and background plates. The foreground:background ratio was 109:1. The antibody phage populations were subcloned into the expression vector and electroporated as described in Example 15, except oligonucleotides 1161 and 1178 were used to amplify the antibody gene inserts (Example 34).

Figure 9:
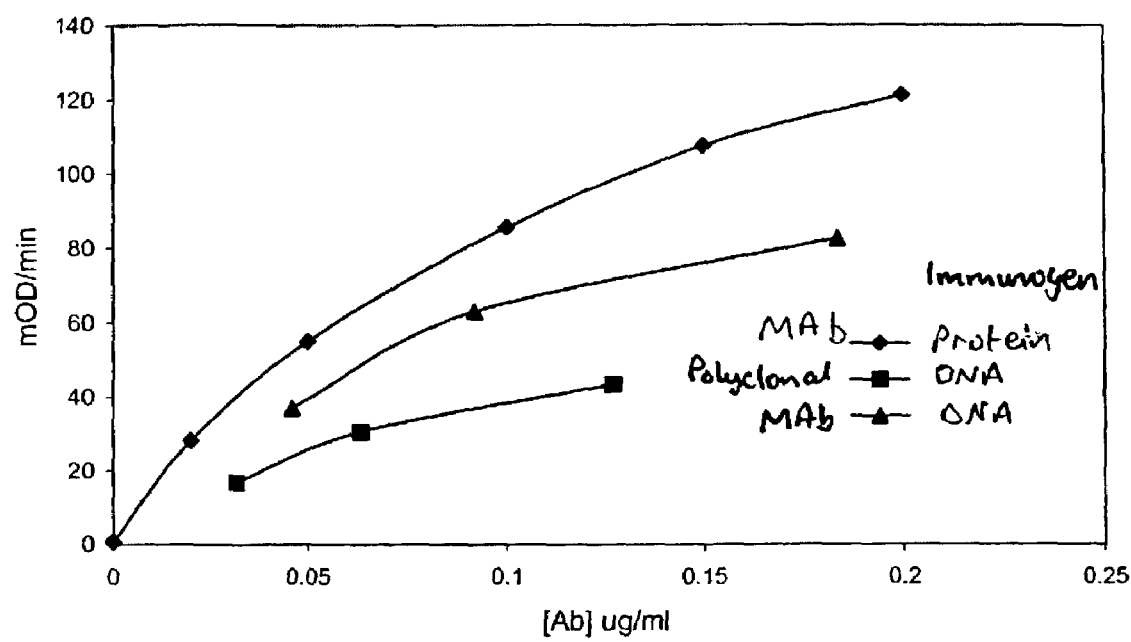
FIG. 9: ELISA for poly and monoclonal antibodies to IL-8 prepared by immunization with DNA compared with a monoclonal prepared by immunization with purified IL-8.

A randomly selected IL-8 monoclonal antibody (53B10) and the IL-8 polyclonal antibody (53B omni) were expressed and purified as described in Example 16. The solution phase equilibrium dissociation constants were determined for both preparations using a KinExA™ 3000 instrument (Sapidyne Instruments Inc., Boise, Id.) following the protocols and parameters suggested by the manufacturer. Briefly, an antibody solution is allowed to come to equilibrium with serial dilutions of native antigen (IL-8) (see FIG. 9). Free antibody is then captured and quantified on a solid phase support that is coated with biotinylated antigen (Example 9). Using the antigen and free antibody concentrations, data analysis software designed by Sapidyne calculates the $K_d$. Assays of the polyclonal preparation derived from the DNA-immunized mice resulted in a $K_d$ determination of 2.8 pM (range 138 pM–9.1 fM). The selected monoclonal has a $K_d$ of 2.9 pM (range 379 pM–9 fM). For comparison, a monoclonal from a mouse immunized with purified IL-8 (MED002 1.25.2) has a $K_d$ of 16 pM (range 85 pM–55 fM).

EXAMPLE 36

Enrichment of Polyclonal Phage from Mice Immunized with Oxidized Troponin with the RNA Purified from Bone Marrow RNA purified from the bone marrow of four HCo7 mice was amplified by PCR (Example 31), and first round antibody phage was prepared as described in Example 7 using BS47 uracil template. Four electroporations of mutagenesis DNA were done (2 electroporations from each spleen combination) yielding 4 different phage samples. Phage were set up for the first round of panning by mixing 0.92 mL phage, 52.5 µL 5% casein, 30 µL 300 mg/mL BSA, 50 µL 1M TRIS, pH 8.0 and 10 µL $10^{-7}$M oxidized troponin 1-biotin (Example 33, ox-TnI-biotin) and incubating 3 hr at room temperature. The antibody phage samples were panned with avidin magnetic latex as described in Example 13. The only difference is high salt conjugate diluent (1% bovine serum albumin (from 30% BSA, Bayer, Kankakee, Ill.), 10 mM MOPS, 650 mM NaCl, 1 mM $MgCl_2$, 0.1 mM $ZnCl_2$, 0.25% casein, 0.1% polyvinyl alcohol (80% hydrolyzed, Aldrich Chemical Co., Milwaukee, Wis.), pH 7.0) was used instead of the panning buffer. This buffer (HSCD) was used for every avidin magnetic latex panning step described in this example The panning buffer described in Example 35 was used for the 7F11 enrichment panning.

The resulting 2nd round antibody phage samples were enriched for polyvalent display by panning with 7F11 magnetic latex as described in Example 13. Panning with ox-TnI-biotin was set up for each sample by mixing 900 µL 7F11/decapeptide enriched phage, 100 µL panning buffer, and 10 µL $10^{-7}$ M ox-TnI-biotin. After 3 hr incubation at room temperature, the phage samples were panned with avidin magnetic latex as described above.

The resulting 3rd round antibody phage samples were again enriched for polyvalent display and the eluted phage were set up with ox-TnI-biotin as described above. After 3 hr incubation at room temperature, the phage samples were panned with avidin magnetic latex as described above. Aliquots of each sample were plated on 100 mm LB agar plates to determine the percentage of kappa positives (Example 12). The percentage of kappa positives for the 3rd round of panning was between 98–100%.

The 4th round antibody phage samples were titered as described in Example 13 and the phage were mixed into one pool. The pooled antibody phage was set up in duplicate for a 4th round of functional panning as described above using 900 µL panning buffer, 100 µL 4th round pooled-antibody phage. One sample (foreground) received 10 µL $10^{-7}$M ox-TnI-biotin and the other sample (background) did not receive ox-TnI-biotin and served as a blank to monitor non-specific binding of phage to the magnetic latex. After overnight incubation at 2–8° C., the phage samples were panned with avidin magnetic latex as described above. The next day, the 5th round antibody phage was eluted and the number of plaques was counted on the foreground and background plates. The foreground:background ratio was 2.5:1.

Figure 10:
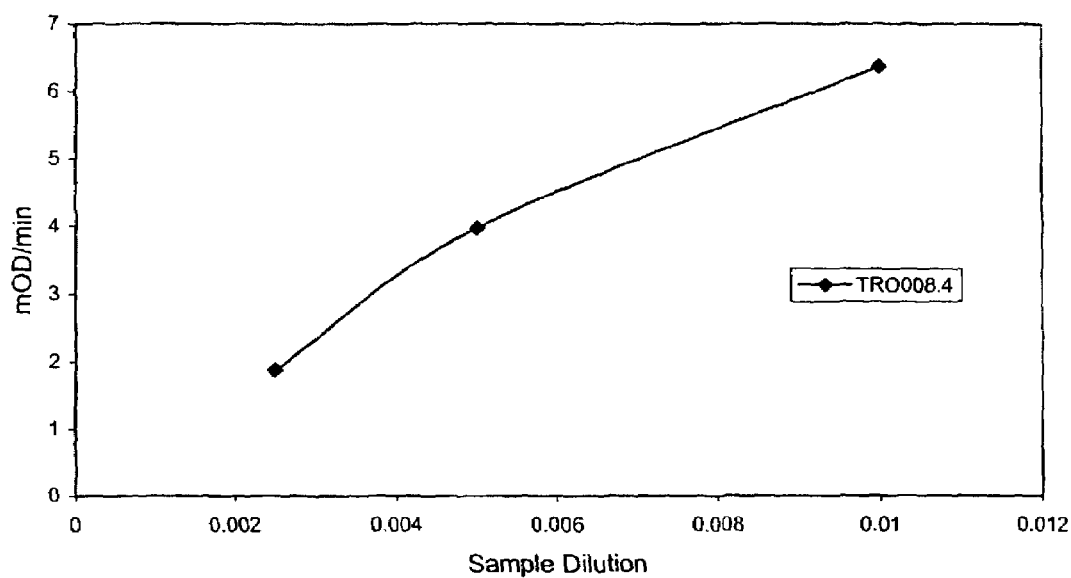
FIG. 10: ELISA of polyclonal antibodies to oxidized troponin prepared from bone marrow of HuMAb mice.

The 5th round antibody phage was set up in duplicate for a 5th round of functional panning as described above using 900 µL panning buffer, 100 µL 5th round antibody phage. One sample (foreground) received 10 µL $10^{-7}$M ox-TnI-biotin and the other sample (background) did not receive ox-TnI-biotin and served as a blank to monitor non-specific binding of phage to the magnetic latex. After 3 hr incubation at room temperature, the phage samples were panned with avidin magnetic latex as described above. The next day, the 6th round antibody phage was eluted and the number of plaques was counted on the foreground and background plates. The foreground:background ratio was 36:1. The antibody phage populations were subcloned into the expression vector and electroporated as described in Example 15, except oligonucleotides 1161 and 1178 were used to amplify the antibody gene inserts (Example 34). ELISA data of a crude population of cells expressing polyclonal antibody is shown in FIG. 10 confirming specific binding.

EXAMPLE 37

DNA Sequence Analysis of Random Clones

Six random clones, each, were picked from the spleenC and spleenE subcloned populations (Example 34) and used to inoculate 50 ml cultures for plasmid isolation and subsequent DNA sequencing of the antibody inserts. After overnight growth in 2×YT (10 µg/ml tetracycline) at 37° C., the recombinant plasmid was purified using a Qiagen Plasmid Midi kit (Qiagen, Valencia, Calif.) following manufacturer's recommendations. The sequence corresponding to the kappa and heavy chain variable and constant regions for each monoclonal was determined at MacConnell Research (San Diego, Calif.). Sequencing was done by the dideoxy chain termination method using a Sequatherm sequencing kit (Epicenter Technologies, Madison, Wis.), oligonucleotide primers C and D (Table 3) that bind on the 5' and 3' side of the Fab cassette in the pBR vector, respectively, and a LI-COR 4000L automated sequencer (LI-COR, Lincoln, Nebr.).

TRO005 Kappa Chains DNA Sequences

1C.B1 (SEQ ID NO:123)

CGAAATAGTGATGACGCAgtcTCCAGC-CACCCTGTCTTTGTCTCCAGGGGAAA-GAGCCACCCTCTCCTG CAGGGCCAGTCAGAGT-GTTTACAGCTACTTAGTCTGGTACCAACAGAAACC TGGCCAGGCTCCCAGGCT CCTCATCTATGATG-CATCCAACAGGGCCACTGGCATCCCAGC-CAGGTTCAGTGGCAGTGGGTCTGGGAC AGACT-TCACTCTCACCATCAGCAGCCTAGAGCCTGAAG ATTTTGCATTTTATT ACTGTCAGCAGCGTAC GAAC-CGGCCGTACACTTTTGGCCAGGGGAC-CAAGCTGGAGATCAAACGAACTGTGGCT-GCACCATCTGT CTTCATCTTCCCGCCATCTGATGAG-CAGTTGAAATCTGGAACTGCCTCTGTTGTGT GCCT-GCTGAATAA CTTCTATCCCAGAGAGGCCAAAGTA-CAGTGGAAGGTGGATAACGCCCTCCAATCGGGTA ACTCCCAGGA GAGTGTCACAGAGCAGGACAG-CAAGGACAGCACCTACAGCCTCAGC AGCACCCT-GACGCTGAGCAAAGC AGACTACGAGAAACA- CAAAGTCTACGCCTGCGAAGTCACCCATCAGGGCCTGAGCT CGCCCGTCACAAA GAGCTTCAACAGGGGAGAGTCTTATCCATATGATGTGCCAGATTATGCG AGC

1C.C2 (SEQ ID NO:125)

GAGCTCGTGATGACACAGTCTCCAGCCACCCTGTCTTTGTCTCCAGGGGAAAGAGCCACCCTCTCCTGC AGGGCCAGTCAGAGTGTTTACAGCTACTTAGTCTGGTACCAACAGAAACCTGGCCAGGCTCCCAGGCTC CTCATCTATGATGCATCCAACAGGGCCACTGGCATCCCAGCCAGGTTCAGTGGCAGTGGGTCTGGGACA GACTTCACTCTCACCATCAGCAGCCTAGAGCCTGAAGATTTTGCAGTTTATT ACTGTCAGCAGCGTAcG AACTGGCCGTGGACGTTCGGCCAAGGGACCAAGGTGGAAATCAAACGAACTGTGGCTGCACCATCTGTC TTCATCTTCCCGCCATCTGATGAGCAGTTGAAATCTGGAACT GCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGC AGCACCCTGACGCTGAGCAAAGCA GACTACGAGAAACACAAAGTCTACGCCTGCGAAGTCACCCATCAGGGCCTGAGCTCGCCCGTCACAAAG
AGCTTCAACAGGGGAGAGTCTTATCCATATGGTGTGCCAGATTATGCG AGC

1C.C6 (SEQ ID NO:127)

GAGCTCGTGATGACCCAGACTCCACTCTCCCTGTCTTTGTCTCCAGGGGAAAGAGCCACCCTCTCCTGC AGGGCCAGTCAGAGTATTTACAACTACTTAGCCTGGTACCAACAG AAACCTGGCCAGGCTCCCAGGCTC CTCATCTATGATGCATCCAACAGGGCCACTGGCATCCCAGCCAGGTTCAGTGGCAGTGGGTCTGGGACA GACTTCACTCTCACCATCAGCAGCCTAGAGCCTGAAGATTTTGCAGTTTAT TACTGTCAGCAGCGTAcG AACTGGCCGTGGACGTTCGGCCAAGGGACCAAGGTGGAAATCAAACGAACCGTG GCTGCACCATCTGTC TTCATCTTCCCGCCATCTGATGAGCAGTTGAAATCTGGAACTGCCTCTGTTGTGT GCCTGCTGAATAAC TTCTATCCCAGAGAGGCCAAAGTACAGTGGAAGGTGGATAACGCCCTCCAATCGGGTA ACTCCCAGGAG AGTGTCACAGAGCAGGACAGCAAGGACAGCACCTACAGCCTCA GC AGCACCCTGACGCTGAGCAAAGCA GACTACGAGAAACACAAAGTCTACGCCTGCGAAGTCACCCATCAGGGCCTGAGCTCGCCCGTCACAAAG
AGCTTCAACAGGGGAGAGTCTTATCCATATGATGTGCCAGATTATGCG AGC

1C.C8 (SEQ ID NO:129)

GAAATTGTGTTGACGCAgtcTCCAGGCACCCTGTCTTTGTCTCCAGGGGAAAGAGCCACCCTCTCCTGC AGGGCCAGTCAGAGTATTTACAACTACTTAGCCTGGTACCAACAGAAACCTGGCCAGGCTCCCAGGCTC CTCATCTATGATGCATCCAACAGGGCCACTGGCATCCCAGCCAGGTTCAGTGGCAGTGGGTCTGGGACA GACTTCACTCTCACCATCAGCAGCCTAGAGCCTGAAGATTTTGCAGTTTATT ACTGTCAGCAGCGTACG AACTGGCCGTGGACGTTCGGCCAAGGGACCAAGGTGGAAATCAAACGAACTGTGGCTGCACCATCTGTC TTCATCTTCCCGCCATCTGATGAGCAGTTGAAATCTGGAACT GCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGC AGCACCCTGACGCTGAGCAAAGCA GACTACGAGAAACACAAAGTCTACGCCTGCGAAGTCACCCATCAGGGCCTGAGCTCGCCCGTCACAAAG
AGCTTCAACAGGGGAGAGTCTTATCCATATGATGTGCCAGATTATGCG AGC

1C.D7 (SEQ ID NO:131)

GAGCTCGTGATGACCCAGTCTCCAGCCACCCTGTCTTTGTCTCCAGGGGAAAGAGCCACCCTCTCCTGC AGGGCCAGTCAGAGTATTTACAACTACTTAGCCTGGTACCAACAGAAACCTGGCCAGGCTCCCAGGCTC CTCATCTATGATGCATCCAACAGGGCCACTGGCATCCCAGCCAGGTTCAGTGGCAGTGGGTCTGGGACA GACTTCACTCTCACCATCAGCAGCCTAGAGCCTGAAG ATTTTGCAGTTTATT ACTGTCAGCAGCGTACG AACTGGCCGTGGACGTTCGGCCAAGGGACCAAGGTGGAAATCAAACGAACTGTGGCTGCACCATCTGTC TTCATCTTCCCGCCATCTGATGAGCAGTTGAAATCTGGAACT GCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGC AGCACCCTGACGCTGAGCAAAGCA GACTACGAGAAACACAAAGTCTACGCCTGCGAAGTCACCCATCAGGGCCTGAGCTCGCCCGTCACAAAG
AGCTTCAACAGGGGAGAGTCTTATCCATATGATGTGCCAGATTATGCG AGC

1C.E8 (SEQ ID NO:133)

GAGCTCGTGATGACCCAGACTCCACTCTCCCTGTCTTTGTCTCCAGGGGAAAGAGCCACCCTCTCCTGC AGGGCCAGTCAGAATGTTTACAGCTACTTAGCCTGGTACCAACAG AAACCTGGCCAGGCTCCCAGGCTC CTCATCTATGATGCATCCAACAGGGCCCCTGGCATCCCAGCCAGGTTCAGTGGCAGTGGGTCTGGGACA GACTTCACTCTCACCATCAGCAGCCTAGAGCCTGAAGATTTTGCAGTTTATT ACTGTCAGCAGCGTACG AACTGGCCGTGGACGTTCGGCCAAGGGACCAAGGTGGAAATCAAACGAACTGTG GCTGCACCATCTGTC TTCATCTTCCCGCCATCTGATGAGCAGTTGAAATCTGGAACTGCCTCTGTTGTGT GCCTGCTGAATAAC TTCTATCCCAGAGAGGCCAAAGTACAGTGGAAGGTGGATAACGCCCTCCAATCGGGTA ACTCCCAGGAG AGTGTCACAGAGCAGGACAGCAAGGACAGCACCTACAGCCTC AGCAGCACCCTGACGCTGAGCAAAGCA GACTACGAGAAACACAAAGTCTACGCCTGCGAAGTCACCCATCAGGGC CTGAGCTCGCCCGTCACAAAG
AGCTTCAACAGGGGAGAGTCTTATCCATATGATGTGCCAGATTATGCGAGC 3E.1 (SEQ ID NO:135)

GAAATAGTGATGACGCAgTCTCCAGGCACCCTGTCTTTGTCTCCAGGGGAAAGAGCCACCCTCTCCTGC AGGGCCAGTCAGAGTGTTAGCAGCCGCTACTTAGCCTGGTACCAGCAGAAACCTGGCCAGGCTCCCAGG CTCCTCATCTATGGTG

CATCCAGCAGGGCCACTGGCATCCCAGACAGGTTCAGTGGCAGTGGGTCTGGG ACAGACTCACTCTCGCCATCAGCAGACTGGAGCCTGAAGATTTTGCAGTGTATTTCTGTCAGCAGTAT GGTAGCTCAATCACCTTCGGCCAAGGGACACGACTGGAGATTAAACGAACTGTGGCTGCACCATCTGTCTTCATCTTCCCGCCATCTGATGAGCAGTTGAAATCTGGAACTGCCTCTGTTGTGT GCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGC AGCACCCTGACGCTGAGCAAAGCA GACTACGAGAAACACAAAGTCTACGCCTGCGAAGTCACCCATCAGGGCCTGAGCT CGCCCGTCACAAAG AGCTTCAACAGGGGAGAGTCTTATCCATATGATGTGCCAGATTATGCG AGC 3E.2 (SEQ ID NO:137)

CCAGCCATGGCCAACATCCAGATGACCCAGTCTCCATCCTCACTGTCTGCATCTGTAGGAGACAGAGTC ACCATCACTTGTCGGGCGAGTCAGGGTATTAGCAGCTGGTTAGCCTGGTATCAGCAGAAACCAGAGAAA GCCCCTAAGTCCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTG AAGATTTTGCAACTTATTACTGC CAACAGTATAATAGTTACCCATTCACTTTCGGCCCTGGGACCAAAGTGGATATCAAACGAACTGTGGCT GCACCATCTGTCTTCATCTTCCGCCATCTGATGAGCAGTTGAAATCT GGAACTGCCTCTGTTGTGTGC CTGCTGAATAACTTCTATCCAGAGAGGCCAAAGTACAGTGGAAGGTGGATAACG CCCTCCAATCGGGT AACTCCCAGGAGAGTGTCACAGAGCAGGACAGCAAGGACAGC ACCTACAGCCTCAGCAGCACCCTGACG CTGAGCAAAGCAGACTACGAGAAACACAAAGTCTACGCCTGCG AAGTC ACCC ATCAGGGCCTGAGCTCG CCCGTCACAAAGAGCTTCAACAGGGGAGAGTCTTATCCATATGATGTGCCA GATTATGCGAGC 3E.3 (SEQ ID NO:139)

GACATCCAGATGATCCAGTCTCCATCCTCCCCGTCTGCATCTGTAGGAGACAGAGTCACCATCACTTGC CGGGCAAGTCAGGGCATTAGCAGTGCTTTAGCCTGGTATCAGCAGAAACCAGGGAAAGCTCCTAAGCTC CTGATCTATGATGCCTCCAGTTTGGAAAGTGGGGTCCCATCAAGGTTCAGCGGCAGTGGATCTGGGACA GATTTCACTCTCACCATCAGCAGCCTGCAGCCTGAAGATTTTGCAACTTATT ACTGCCAACAGTATAAT AGTTACCCGCTCACTTTCGGCGGAGGGACCAAGGTGGAGATCAAACGAACTGTGGCTGCACCATCTGTC TTCATCTTCCGCCATCTGATGAGCAGTTGAAATCTGGAACTGCCTCTGTTGTGTGCCTGCTGAATAAC TTCTATCCCAGAGAGGCCAAAGTACAGTGGAAGGTGGATAACGCCCTCCAA TCGGGTAACTCCCAGGAG AGTGTCACAGAGCAGGACAGCAAGGACAGCACCTACAGCCTCAGCAGCACCCTGACGCTGAGCAAAGCA GACTACGAGAAACACAAAGTCTACGCCTGCGAAGTCACCC ATCAGGG CCTGAGCTCGCCCGTCACAAAG AGCTTCAACAGGGGAGAGTCTTATCCATATGATGTGCCAGATTATGCGAGC 3E.4 (SEQ ID NO:141)

GAAATAGTGATGACGCAgcTCCAGGCACCCTGTCTTTGTCTCCAGGGGAAAGAGCCACCCTCTCCTGCA GGGCCAGTCAGAGTGTTAGCAGCCGCTACTTAGCCTGGTACCAGCAGAAACCT GGCCAGGCTCCCAGGC TCCTCATCTATGGTGCATCCAGCAGGGCCACTGGCATCCCAGACAGGTTCAGTGGCAGTGGGTCTGGGA CAGACTCACTCTCGCCATCAGCAGACTGGAGCCTGAGGATTTTGCAGTGTAT TTCTGTCAGCAGTATG GTAGCTCAATCACCTTCGGCCAAGGGACACGACTGGAGATTAAACGAACTGTGGCTGCACCATCTGTCT TCATCTTCCCGCCATCTGATGAGCAGTTGAAATCTGGAACTG CCTCTGTTGTGT GCCTGCTGAATAACT TCTATCCCAGAGAGGCCAAAGTACAGTGGAAGGTGGATAACGCCCTCCAATCGGGTAACTCCCAGGAGA GTGTCACAGAGCAGGACAGCAAGGACAGCACCTACAGCCTC AGCAGCACCCT GACGCTGAGCAAAGCAG ACTACGAGAAACACAAAGTCTACGCCTGCGAAGTCACCCATCAGGGCCTGAGCTCGCCC GTCACAAAGA GCTCAACAGGGGAGAGTCTTATCCATATGATGTGCCA GATTATGCG AGC 3E.8 (SEQ ID NO:143)

CCAGCCATGGCCGCCATCCAGTTGACCCAGTCTCCATCCTCCCTGTCTGCATCTGTAGGAGACAGAGTC ACCATCACTTGCCGGGCAAGTCAGGGCATTAGCAGTGCTTTAGCCT GGTATCAGCAGAAACCAGAGAAA GCTCCTAAGCTCCTGATCTATGATGCCTCCAGTTTGGAAAGTGGGGTCCCATCAAGGTTCAGCGGCAGT GGATCTGGGACAGATTTCACTCTCACCATCAGCAGCCTGCAGCCTG AAGATTTTGCAACTTATTACTGC CAACAGTATAATAGTTACCCGTGGACGTTCGGCCAAGGGACCAAGGTGGAAATCAAACGAACTGTGGCT GCACCATCTGTCTTCATCTTCCGCCATCTGATGAGCAGTTGAAATCTGGAAC TGCCTCTGTTGTGTGC CTGCTGAATAACTTCTATCCAGAGAGGCCAAAGTACAGTGGAAGGTGGATAACG CCCTCCAATCGGGT AACTCCCAGGAGAGTGTCACAGAGCAGGACAGCAAGGACAGCCCTACAGCCTCAGCAGCACCCTGACG CTGAGCAAAGCAGACTACGAGAAACACAAAGTCTACGCCTGCGAAGTCACC CATCAGGGCCTGAGCTCG CCCGTCACAAAGAGCTTCAACAGGGGAGAGTCTTATCCATATGATGTGCC AGATTATGCGAGC 3E.9 (SEQ ID NO:145)

CCAGCCATGGCCGAGCTCGTGATGACCCAGTCTCCATCCTCACTGTCTGCATCTGTAGGAGACAGAGTC ACCATCACTTGTCGGGCGAGTCAGGGTATTAGCAGCTGGTTAGCCTGGTAT CAGCAGAAACCAGAGAAA GCCCCTAAGTCCCTGATCTATGCTGCATCCAGTTTGCAAAGTGGGGTCCCATCAAGGTTCAGCGGCAGT GGATCTGGGACAGATTTCACTCTCACCATCAGCAGCCTGCAGCCTG AAGATTTTGCAACTTATTACTGC CAACAGTATAATAGTTACCCGATCACCTTCGGCCAAGGGACGACTGGAGATTAAACGA ACTGGCT GCACCATCTGTCTTCATCTTCCGCCATCTGATGAGCAGTTGAAATCTGGAAC TGCCTCTGTTGTGTGC CTGCTGGATAACTTCTATCCCAGAGAGGCCAAAGTACAGTGGAAGGTGGATAACG CCCTCCAATCGGGT AACTCCCAGGAGAGTGTCA

CAGAGCAGGACAGCAAGGACAGC ACCTACAGC-CTCAGCAGCACCCTGACG CTGAGCAAAGCAGAC-TACGAGAAACACAAAGTCTACGCCTGCGAAGTCAC CC ATCAGGGCCTGAGCTCG CCCGTCACAAA-GAGCTTCAACAGGGGAGAGTCTTATC-CATATGATGTGCCA GATTATGCGAGC

TRO005 HEAVY CHAINS DNA SEQUENCES

1C.B1 (SEQ ID NO:147)

CAGGTGCAGCTGGTGGAGTCTGGGGGAG-GCGTGGTCCAGCCTGGGAGGTCCCT-GAGACTCTCCTGT GCAGCCTCTGGATTCACCCTCA-GAAGCTATGCTATGCACTGGGTCCGCCAGGCTCC AGGCAAGGGG CTGGAGTGGGTGGCAGTTATAT-CATATGATGGAAGCTATAAGTCCTACG-CAGACTCCGTGAAGGGC CGATTCATCAGCTCCA-GAGACAATTCCAAGAACACGCTGTCTCTGCAAAT GAACAGCCTGAGAGCT GAGGACACGGCTGTG-TATTTCTGTGCGAGGGCTATGGTTCGGG-GAGTTATCTTTGACTACTGGGGC CAGGGAACCCT-TGTCACCGTCTCCTCAGCCTCCACCAAGGGCCCA TCG GTCTTCCCCCTGGCACCC TCCTCCAAGAG-CACCTCTGGGGGCACAGCGGC-CCTGGGCTGCCTGGTCAAGGACTACTTCCCCGAA CCGGTGACGGTGTCGTGGAACTCAG-GCGCCCTGACCAGCGGC GTGCACACC TTCCCG-GCTGTCCTA CAGTCCTCAGGACTCTACTCCCTCAG-CAGCGTGGTGACCGTGCCCTCCAGCAGCTTGGGC ACCCAG ACCTACATCTGCAACGTGAATCACAAGC-CCAGCAACACCAAGGT GGACAA GAAAGCAGAGC-CCAAA TCTCATCACCATCACCATCAC

1C.C2 (SEQ ID NO:149)

GAGGTGCAGCTGGTGCAGTCTGGGGGAG-GCGTGGTCCAGCCTGGGAGGTCCCT-GAGACTCTCCTGT GCAGCCTCTGAATTCACCTT-TCAGTAACTATGCTTTTCACTGGGTCCGCCAGGCT CCAGGCAAGGGG CTGGAGTGGGTGGCAATTATAT-CATATGATGGAAGCCATAAATACTACG-CAGACTCCGTGACGGGC CGATTCACCATCTCCA-GAGACAATTCCAAGAACACGCTGTATCTGCAAAT GAACAGCCTGAGAGCT GAGGACACGGCTGTGTAC-TACTGTGCGAGGGCGATGGTTCGGG-GAGTTATCTTTGACTACTGGGGC CAGGGAAC CCTGGTCACCGTCTCCTCAGCCTCCACCAAGGGC CCATCG GTCTTCCCCCTGGCACCC TCCTCCAA-GAGCACCTCTGGGGGCACAGCGGC-CCTGGGCTGCCTGGTCAAGGACTACTTCCCCGAA CCGGTGACGGTGTCGTGGAACTCAG-GCGCCCTGACCAGCGGC TGCACAC CTTCCCGGCT-GTCCTA CAGTCCTCAGGACTCTACTCCCTCAG-CAGCGTGGTGACCGTGCCCTCCAGCAGCTTGGGC ACCCAG ACCTACATCTGCAACGTGAATCACAAGC-CCAGCAACACCAAGGT GGACAAGAAAGCAGAGC-CCAAA TCTCATCACCATCACCATCAC

1C.C6 (SEQ ID NO:151)

GAGGTGCAGCTGGTGCAGTCTGGGGGAG-GCTTGGTACAGCCTGGGGGGTCCCT-GAGACTCTCCTGT GCAGCCTCTGGATTCACCTT-TAGCAACTATGCCATGAGCTGGGTCCGCCAGGCT CCAGGGAAGGGG CTGGAGTGGGTCTCAGCTAT-TAATTATGGTGGTGGTAGCACATAC-TACGCAGACTCCGTGAAGGGC CGGTTCAC-CATCTCCAGAGACAATTCCAAGAACACGCTGTAT CTGCAAATGAACAGCC TGAGAGCC GAGGACACG-

GCCGTATATTACTGTGCGAAACATATG-GTTCGGGGAGTCCTCTTTGACTACTGGGGC CAG GGAACCCTGGTCACCGTCTCCTCAGC-CTCCACCAAGGGCCCATCG GTCTTCCCCCTG-GCACCC TCCTCCAAGAGCACCTCTGGGGGCA-CAGCGGCCCTGGGCTGCCTGGTCAAGGACTACTT CCCCGAA CCGGTGACGGTGTCGTGGAACTCAG-GCGCCCTGACCAGCGGCG TGCACACC TTCCCG-GCTGTCCTA CAGTCCTCAGGACTCTACTCCCTCAG-CAGCGTGGTGACCGTGCCCTCCAGCAGCTTGGGC ACCCAG ACCTACATCTGCAACGTGAATCACAAGC-CCAGCAACACC AAGGT GGACAA GAAAGCA-GAGCCCAAA TCTCATCACCATCACCATCAC

1C.C8 (SEQ ID NO:153)

CAGGTGCAGCTGGTGCAGTCTGGGGGAG-GCGTGGTCCAGCCTGGGAGGTCCCT-GAGACTCTCCTGT GCAGCCTCTGGATTCACCT-TCAGTAACTATGCTTTTCACTGGGTCCGCCAGGCT CCAGGCAAGGGG CTGGAGTGGGTGGCAATTATAT-CATATGATGGAAGCCATAAATACTACG-CAGACTCCGTGACGGGC CGATTCACCATCTCCA-GAGACAATTCCAAGAACACGCTGTATCTGCAAAT GAACAGCCTGAGAGCT GAGGACACGGCTGTGTAC-TACTGTGCGAGGGCGATGGTTCGGG-GAGTTATCTTTGACTACTGGGGC CAGGGAAC-CCTGGTCACCGTCTCCTCAGCCTCCACCAAGGGC CCATCG GTCTTCCCCCTGGCACCC TCCTCCAA-GAGCACCTCTGGGGGCATAGCGGC-CCTGGGCTGCCTGGTCAAGGACTACTTCCCCGAA CCGGTGACGGTGTCGTGGAACTCAG-GCGCCCTGACCAGCGGCG TGCACACCTTCCC GGCTGTCCTA CAGTCCTCAGGACTCTACTCCCT-CAGCAGCGTGGTGACCGTGCCCTCCAG-CAGCTTGGCACCCAG ACCTACATCTGCAACGT-GAATCACAAGCCCAGCAACACC AAGGTGGACAA GAAAGCAGAGCCCAAA TCTCATCACCATCACCAT-CAC

1C.D7 (SEQ ID NO:155)

CAGGTGCAGCTGGTGGAGTCTGGGGGAG-GCGTGGTCCAGCCTGGGAGGTCCCT-GAGACTGTCCTGT GCAGCCTCTGGATTCACCT-TCAGTAACTATGCTATGCACTGGGTCCGCCAGGCT CCAGGCAAGGGG CTGGAGTGGGTGGCAATTATCT-CATATGATGGAACCTATAAATATTACG-CAGACTCCGTGAAGGGC CGATTCACCATCTCCA-GAGACAATTCCAAGAACACGCTGTATCTGCAAAT GAACAGCCTGAGAGCT GAGGACACGGCTGTGTAT-TACTGTGCGAGGGCTATGGTTCGGG-GAGTTATCTTTGACTACTGGGGC CAGGGAGC-CCTGGTCACCGTCTCCTCAGCCTCCACCAAGGG CCCATCGGTCTTCCCCCTGGCACCC TCCTCCAA-GAGCACCTCTGGGGGCACAGCGGC-CCTGGGCTGCCTGGTCAAGGACTACTTCCCCGAA CCGGTGACGGTGTCGTGGAACTCAG-GCGCCCTGACCAGCGGCGTGCACAC CTTCCCG-GCTGTCCTA CAGTCCTCAGGACTCTACTCCCTCAG-CAGCGTGGTGACCGTGCCCTCCAGCAGCTTGGGC GCCCAG ACCTACATCTGCAACGTGAATCACAAGC-CCAGCAACACCAAGGTGGACAA GAAAGCAGAGC-CCAAA TCTCATCACCATCACCATCAC

1C.E8 (SEQ ID NO:157)

CAGGTGCAGCTGGTGCAGTCTGGGGGAG-GCGTGGTCCAGCCTGGGAGGTCCCT-GAGACTCTCCTGT GCAGCCTCTGGATTCACCT-TCAGTAACTATGCTTTTCACTGGGTCCGCCAGGCT

CCAGGCAAGGGG CTGGAGTGGGTGGCAATTATAT-
CATATGATGGAAGCCATAAATACTACG-
CAGACTCCGTGACGGGC CGATTCACCACCTCCA-
GAGACAATTCCAAGAACACGCTGTATCTGCAAAT
GAACAGCCTGAGAGCT GAGGACACGGCTGTGTAC-
TACTGTGCGAGGGCGATGGTTCGGG-
GAGTTATCTTTGACTACTGGGGC CAGGGAAC-
CCTGGTCACCGTCTCCTCAGCCTCCACCAAGGGC
CCATCG GTCTTCCCCCTGGCACCC TCCTCCAA-
GAGCACCTCTGGGGGCACAGCGGC-
CCTGGGCTGCCTGGTCAAGGACTACTTCCCCGAA
CCGGTGACGGTGTCGTGGAACTCAG-
GCGCCCTGACCAGCGGCG TGCACAC CTTCCCG-
GCTGTCCTA CAGTCCTCAGGACTCTACTCCCTCAG-
CAGCGTGGTGACCGTGCCCTCCAGCAGCTTGGGC
ACCCAG ACCTACATCTGCAACGTGAATCACAAGC-
CCAGCAACACCAAGGTG GACAA GAAAGCAGAGC-
CCAAA TCTCATCACCATCACCATCAC 3E.1 (SEQ ID NO:159)

CAGGTGCAGCTGGTGCAGTCTGGGGGAG-
GCGTGGTCCAGTCTGGGAGGTCCCT-
GAGACTCTCCTGT GCAGCCTCTGGAATCACCGT-
CAGGAACTATGCTATGCACTGGGTCCGCCAGGTT
CCAGGCAAGGGG CTGGAGTGGGTGGCAGTTATAT-
CATATGATGGAAGCAATAAATACTACG-
CAGACTCCGTGAAGGGC CGATTCACCCTCTCCA-
GAGACAATTCCAAGAACACGCTGTATCTGCAAAT
GAACAGCCTGAGAGCT GAGGACACGGCTGTGTAT-
TACTGTGCGAGAGAGGACTACTACGG-
TATGGACGTCTGGGGCCAAGGG ACCACGGTCAC-
CGTCTCCTCAGCCTCCACCAAGGGCCCATCGGTC
TTCCCCCTGGCACCCTCCTCC AAGAGCAC-
CTCTGGGGGCACAGCGGCCCTGGGCTGC-
CTGGTCAAGGACTACTTCCCCGAACCGGTG ACG-
GTGTCGTGGAACTCAGGCGCCCTGACCAGCGGC
GTGCACACCTTCCCGGC TGTCCTACAGTCC TCAG-
GACTCTACTCCCTCAGCAGCGTGGTGAC-
CGTGCCCTCCAGCAGCTTGGGCACCCAGACCTAC
ATCTGCAACGTGAATCACAAGCCCAG-
CAACACCAAGGTGGACAA GAAAGC AGAGC-
CCAAATGTCAT CACCATCACCATCAC 3E.2 (SEQ ID NO:161)

CAGGTGCAGCTGGTGCAGTCTGGGGCA-
GAGGTGAAAAAGCCCGGGGAGTCTCT-
GAAGATCTCCTGT AAGGGTTCTGGATACAGCTT-
TACCAACTACTGGATCGGCTGGGTGCGCCAGATG
CCCGGGAAAGGC CTGGAGTGGATGGGGTTCATC-
TATTCTGATGACTCTGTTACCAGATA-
CAGCCCGTCCTTCCAAGGC CAGGTCACCATCT-
CAGCCGACAAGTCCATCAGTACCGCCTACCTGCA
GTG GACCAGCCTGAAGGCC TCGGACACCGCCAT-
GTATTACTGTACGAGAGATGGTC-
CCGAAGCTTTTGATATCTGGGGCCAAGGG
ACAATGGTCACCGTCTCTTCAGCCTC-
CACCAAGGGCCCATCGGTCTTCCCCCTG-
GCACCCTCCTCC AAGAGCACCTCTGGGGGCA-
CAGCGGCCCTGGGCTGCCTGGTCAAGGACTACTT
CCCCGAACCGGTG ACGGTGTCGTGGAACTCAG-
GCGCCCTGACCAGCGGCGTGCACACCT-
TCCCGGCTGTCCTACAGTCC TCAGGACTCTACTC-
CCTCAGCAGCGTGGTGACCGTGCCCTCCAGCAGC
TTGGGC ACCCAGACCTAC ATCTGCAACGTGAAT-
CACAAGCCCAGCAACACCAAGGTGGA-
CAAGAAAGCAGAGCCCAAATGTCAT CACCATCAC-
CATCAC 3E.3 (SEQ ID NO:163)

CAGGTGCAGCTGGTGCAGTCTGGGGCA-
GAGGTGAAAAAGCCCGGGGAGTCTCT-
GAAGATCTCCTGT AAGGGTTCTGGATACAGCTT-
TACCAACTACTGGATCGGCTGGGTGCGCCAGATG
CCCGGGAAAGGC CTGGAGTGGATGGGGTTCATC-
TATTCTGATGACTCTGTTACCAGATA-
CAGCCCGTCCTTCCAAGGC CAGGTCACCATCT-
CAGCCGACAAGTCCATCAGTACCGCCTACCTGCA
GTGG AGCAGCCTGAAGGCC TCGGACACCGCCAT-
GTATTACTGTACGAGAGATGGTC-
CCGAAGCTTTTGATATCTGGGGCCAAGGG
ACAATGGTCACCGTCTCCTCAGCCTC-
CACCAAGGGCCCATCGGTCTTCCCCCTG-
GCACCCTCCTCC AAGAGCACCTCTGGGGGCA-
CAGCGGCCCTGGGCTGCCTGGTCAAGGACTACTT
CCCCGAACCGGTG ACGGTGTCGTGGAACTCAG-
GCGCCCTGACCAGCGGCGTGCACACCT-
TCCCGGCTGTCCTACAGTCC TCAGGACTCTACTC-
CCTCAGCAGCGTGGTGACCGTGCCCTCCAGCAGC
TTGGGC ACCCAGACCTAC ATCTGCAACGTGAAT-
CACAAGCCCAGCAACACCAAGGTGGA-
CAAGAAAGCAGAGCCCAAATGTCAT CACCATCAC-
CATCAC 3E.4 (SEQ ID NO:165)

CAGGTGCAGCTGGTGCAGTCTGGGGGAG-
GCGTGGTCCAGTCTGGGAGGTCCCT-
GAGACTCTCCTGT GCAGCCTCTGGAATCACCGT-
CAGGAACTATGCTATGCACTGGGTCCGCCAGGTTC
AGGCAAGGGG CTGGAGTGGGTGGCAGTTATAT-
CATATGATGGAAGCAATAAATACTACG-
CAGACTCCGTGAAGGGC CGATTCACCCTCTCCA-
GAGACAATTCCAAGAACACGCTGTATCTGCAAAT
GAACAGCCTGAGAGCT GAGGACACGGCTGTGTAT-
TACTGTGCGAGAGAGGACTACTACGG-
TATGGACGTCTGGGGCCAAGGG ACCACGGTCAC-
CGTCTCCTCAGCCTCCACCAAGGGCCCATCGGTCT
TCCCCCTGGCACCCTCCTCC AAGAGCAC-
CTCTGGGGGCACAGCGGCCCTGGGCTGC-
CTGGTCAAGGACTACTTCCCCGAACCGGTG ACG-
GTGTCGTGGAACTCAGGCGCCCTGACCAGCGGCG
TGCACACCTTCCCGGCTGTCCTACAGTCC TCAG-
GACTCTACTCCCTCAGCAGCGTGGTGAC-
CGTGCCCTCCAGCAGCTTGGGCACCCAGACCTAC
ATCTGCAACGTGAATCACAAGCCCAG-
CAACACCAAGGTGGACAAGAAAGC AGAGC-
CCAAATGTCAT CACCATCACCATCAC 3E.8 (SEQ ID NO:167)

CAGGTGCAGCTGGTGGAGTCTGGGGGAG-
GCGTGGTCCAGCCTGGGAGGTCCCT-
GAGACTCTCCTGT GCAGCGTCTGGATTCACCT-
TCAGGAGATATGGCATGCACTGGGTCCGCCAGGC
TCCAGGCAAGGGG CTGGAGTGGGTGGCAGT-
TATATCATATGATGGAAGCAATAAATAC-
TACGCAGACTCCGTGAAGGGC CGATTCACCCTC-
CCCAGAGACAATTCCAAGAACACGCTGTATCTGC
AAAT GAACAGCCTGAGAGCT GAGGACACGGCT-
GTGTATTACTGTGCGAGAGAGGACTAC-
TACGGTATGGACGTCTGGGGCCAAGGG ACCACG-
GTCACCGTCTCCTCAGCCTCCACCAAGGGCCCAT
CGGTC TTCCCCCTGGCACCCTCCTCC AAGAGCAC-
CTCTGGGGGCACAGCGCCCTGGGCTGC-
CTGGTCAAGGACTACTTCCCCGAACCGGTG ACG-
GTGTCGTGGAAGTCAGGCGCCCTGACCAGCGGC
GTGCACACCTTCCCGGC TGTCCTACAGTCC TCAG-

GACTCTACTCCCTCAGCAGCGTGGTGAC-
CGTGCCCTCCAGCAGCTTGGGCACCCAGACCTAC
ATCTGCAACGTGAATCACAAGCCCAG-
CAACACCAAGGTGGACAA GAAAGC AGAGC-
CCAAATGTCAT CACCATCACCATCAC 3E.9 (SEQ ID NO:169)

CAGGTGCAGCTGGTGCAGTCTGGGGCA-
GAGGTGAAAAAGCCCGGGGAGTCTCT-
GAAGATCTCCTGT AAGGGTTCTGGATACAGCTT-
TACCAACTACTGGATCGGCTGGGTGCGCCAGATG
CCCGGGAAAGGC CTGGAGTGGATGGGGATCATC-
TATTCTGATGACTCTGTTACCAGATA-
CAGCCCGTCCTTCCAAGGC CAGGTCACCATCT-
CAGCCGACAAGTCCATCAGTACCGCCTACCTGCA
GTGG AGCAGCCTGAAGGCC TCGGACACCGCCAT-
GTATTACTGTACGAGAGATGGTC-

CCGAAGCTTTTGATATCTGGGGCCAAGGG
ACAATGGTCACCGTCTCTTCAGCCTC-
CACCAAGGGCCCATCGGTCTTCCCCCTG-
GCACCCTCCTCC AAGAGCACCTCTGGGGGCA-
CAGCGGCCCTGGGCTGCCTGGTCAAGGACTACTT
CCCCGAACCGGTG ACGGTGTCGTGGAACTCAG-
GCGCCCTGACCAGCGGCGTGCACACCT-
TCCCGGCTGTCCTACAGTCC TCAGGACTCTACTC-
CCTCAGCAGCGTGGTGACCGTGCCCTCCAGCAGC
TTGGGC ACCCAGACCTAC ATCTGCAACGTGAAT-
CACAAGCCCAGCAACACCAAGGTGGA-
CAAGAAAGCAGAGCCCAAATGTCAT CACCATCAC-
CATCAC

Alignment: TRO005 HuMab Kappa Chain (SEQ ID
NOS:124, 126, 136, 130, 132, 134, 128, 138, 140, 142, 144,
and 146, respectively)

```
             1                                                  50
1CB1K  EIVMTQSPAT LSLSPGERAT LSCRASQSVY S.YLVWYQQK PGQAPRLLIY
1CC2K  ELVMTQSPAT LSLSPGERAT LSCRASQSVY S.YLVWYQQK PGQAPRLLIY
 3E1K  EIVMTQSPGT LSLSPGEPAT LSCRASQSVS SRYLAWYQQK PGQAPRLLIY
1CC8K  EIVLTQSPGT LSLSPGERAT LSCRASQSIY N.YLAWYQQK PGQAPRLLIY
1CD7K  ELVMTQSPAT LSLSPGERAT LSCRASQSIY N.YLAWYQQK PGQAPRLLIY
1CE8K  ELVMTQTPLS LSLSPGERAT LSCRASQNVY S.YLAWYQQK PGQAPRLLIY
1CC6K  ELVMTQTPLS LSLSPGEPAT LSCRASQSIY N.YLAWYQQK PGQAPRLLIY
 3E2K  NIQMTQSPSS LSASVGDRVT ITCRASQGIS S.WLAWYQQK PEKAPKSLIY
 3E3K  DIQMIQSPSS PSASVGDRVT ITCRASQGIS S.ALAWYQQK PGKAPKLLIY
 3E4K  EIVMTQSPGT LSLSPGERAT LSCRASQSVS SRYLAWYQQK PGQAPRLLIY
 3E8K  AIQLTQSPSS LSLSVGDRVT ITCRASQCIS S.ALAWYQQK PEKAPKLLIY
 3E9K  ELVMTQSPSS LSASVGDRVT ITCRASQGIS S.WLAWYQQK PEKAPKSLIY 51                                                 100
1CB1K  DASNRATGIP ARFSGSGSGT DFTLTISSLE PEDFAFYYCQ QRTNRPYTFG
1CC2K  DASNRATGIP ARFSGSGSGT DFTLTISSLE PEDFAVYYCQ QRTNWPWTFG
 3E1K  GASSRATGIP DRFSGSGSGT DFTLAISRLE PEDFAVYFCQ QYG.SSITFG
1CC8K  DASNPATGIP ARFSGSGSGT DFTLTISSLE PEDFAVYYCQ QRTNWPWTFG
1CD7K  DASNRATGIP ARFSGSGSGT DFTLTISSLE PEDFAVYYCQ QRTNWPWTFG
1CE8K  DASNRAPGIP ARFSGSGSGT DFTLTISSLE PEDFAVYYCQ QRTNWPWTFG
1CC6K  DASNRATGIP ARFSGSGSGT DFTLTISSLE PEDFAVYYCQ QRTNWPWTFG
 3E2K  AASSLQSGVP SRFSGSGSGT DFTLTISSLQ PEDFATYYCQ QYNSYPFTFG
 3E3K  DASSLESGVP SRFSGSGSGT DFTLTISSLQ PEDFATYYCQ QYNSYPLTFG
 3E4K  GASSRATGIP DRFSGSGSGT DFTLAISRLE PEDFAVYFCQ QYG.SSITFG
 3E8K  DASSLESGVP SRFSGSGSGT DFTLTISSLQ PEDFATYYCQ QYNSYPWTFG
 3E9K  AASSLQSGVP SRFSGSGSGT DFTLTISSLQ PEDFATYYCQ QYNSYPITFG 101                                                 150
1CB1K  QGTKLEIKRT VAAPSVFIFP PSDEQLKSGT ASVVCLLNNF YPREAKVQWK
1CC2K  QGTKVEIKRT VAAPSVFIFP PSDEQLKSGT ASVVCLLNHF YPREAKVQWK
 3E1K  QGTRLEIKRT VAAPSVFIFP PSDEQLKSGT ASVVCLLNNF YPREAKVQWK
1CC8K  QGTKVEIKRT VAAPSVFIFP PSDEQLKSGT ASVVCLLNNF YPREAKVQWK
1CD7K  QGTKVEIKRT VAAPSVFIFP PSDEQLKSGT ASVVCLLNNF YPREAXVQWK
1CE8K  QGTKVEIKRT VAAPSVFIFP PSDEQLKSGT ASVVCLLNNF YPREAKVQWK
1CCGK  QGTKVEIKRT VAAPSVFIFP PSDEQLKSGT ASVVCLLNNF YPREAXVQWK
 3E2K  PGTKVDIKRT VAAPSVFIFP PSDEQLKSGT ASVVCLLNNF YPREAKVQWK
 3E3K  GGTKVEIKRT VAAPSVFIFP PSDEQLKSGT ASVVCLLNNF YPREAKVQWK
 3E4K  QGTRLEIKRT VAAPSVFIFP PSDEQLKSGT ASVVCLLNNF YPREAKVQWK
 3E8K  QGTKVEIKRT VAAPSVFIFP PSDEQLKSGT ASVVCLLNNF YPREAKVQWK
 3E9K  QGTRLEIKRT VAAPSVFIFP PSDEQLKSGT ASVVCLLDNF YPREAKVQWK 151                                                 200
1CB1K  VDNALQSGNS QESVTEQDSK DSTYSLSSTL TLSKADYEKH KVYACEVTHQ
1CC2K  VDNALQSGNS QESVTEQDSK DSTYSLSSTL TLSKADYEKH KVYACEVTHQ
 3E1K  VDNALQSGNS QESVTEQDSK DSTYSLSSTL TLSKADYEKH KVYACEVTHQ
1CC8K  VDNALQSGNS QESVTEQDSK DSTYSLSSTL TLSKADYEKH KVYACEVTHQ
1CD7K  VDNALQSGNS QESVTEQDSK DSTYSLSSTL TLSKADYEKH KVYACEVTHQ
1CE8K  VDNALQSGNS QESVTEQDSK DSTYSLSSTL TLSKADYEKH KVYACEVTHQ
1CC6K  VDNALQSGNS QESVTEQDSK DSTYSLSSTL TLSKADYEKH KVYACEVTHQ
 3E2K  VDNALQSGNS QESVTEQDSK DSTYSLSSTL TLSKADYEKH KVYACEVTHQ
 3E3K  VDNALQSGNS QESVTEQDSK DSTYSLSSTL TLSKADYEKM KVYACEVTHQ
 3E4K  VDNALQSGNS QESVTEQDSK DSTYSLSSTL TLSKADYEKH KVYACEVTHQ
 3E8K  VDNALQSGNS QESVTEQDSK DSTYSLSSTL TLSKADYEKH KVYACEVTHQ
 3E9K  VDNALQSGNS QESVTEQDSK DSTYSLSSTL TLSKADYEKH KVYACEVTHQ 201        225
1CB1K  GLSSPVTKSF NRGESYPYDV PDYAS
1CC2K  GLSSPVTKSF NRGESYPYGV PDYAS
```

```
3E1K  GLSSPVTKSF NRGESYPYDV PDYAS
1CC8K GLSSPVTKSF NRGESYPYDV PDYAS
1CD7K GLSSPVTKSF NRGESYPYDV PDYAS
1CE8K GLSSPVTKSF NPGESYPYDV PDYAS
1CC6K GLSSPVTKSF NRGESYPYDV PDYAS
3E2K  GLSSPVTKSF NRGESYPYDV PDYAS
3E3K  GLSSPVTKSF NRGESYPYDV PDYAS
3E4K  GLSSPVTKSF NRGESYPYDV PDYAS
3E8K  GLSSPVTKSF NRGESYPYDV PDYAS
3E9K  GLSSPVTKSF NRGESYPYDV PDYAS
```

Alignment: TRO005 HuMab Heavy Chain (SEQ ID NOS:148, 150, 160, 154, 156, 158, 152, 162, 164, 166, 168, and 170, respectively)

```
         1                                                  50
1CB1H  QVQLVESGGG VVQPGRSLRL SCAASGFTLR SYAMHWVRQA PGKGLEWVAV
1CC2H  EVQLVQSGGG VVQPGRSLRL SCAASEFTFS NYAFHWVRQA PGKGLEWVAI
3E1H   QVQLVQSGGG VVQSGRSLRL SCAASGITVR NYAFHWVRQV PGKGLEWVAV
1CC8H  QVQLVQSGGG VVQPGRSLRL SCAASGFTFS NYAFHWVRQA PGKGLEWVAI
1CD7H  QVQLVESGGG VVQPGRSLRL SCAASGFTFS NYAMHWVRQA PGKGLEWVAI
1CE8H  QVQLVQSGGG VVQPGRSLRL SCAASGFTFS NYAFHNVRQA PCKGLEWVAI
1CC6H  EVQLVQSGGG LVQPGGSLRL SCAASGFTFS NYAMSWVRQA PGKGLEWVSA
3E2H   QVQLVQSGAE VKKPGESLKI SCKGSGYSFT NYWIGWVRQM PGKGLEWMGF
3E3H   QVQLVQSGAE VKKPGESLKI SCKGSGYSFT NYWIGWVRQM PGKGLEWMGF
3E4H   QVQLVQSGGG VVQSGRSLRL SCAASGITVR NYAMHWVRQV PGKGLEWVAV
3E8H   QVQLVESGGG VVQPGRSLRL SCAASGFTFR RYGMHWVRQA PGKGLEWVAV
3E9H   QVQLVQSGAE VKKPGESLKI SCKGSGYSFT NYWIGWVRQM PGKGLEWMGI 51                                                100
1CB1H  ISYDGSYKSY ADSVKGRFIS SRDNSKNTLS LQMNSLRAED TAVYFCARAM
1CC2H  ISYDGSHKYY ADSVTGRFTI SRDNSKNTLY LQMNSLRAED TAVYYCARAM
3E1H   ISYDGSNKYY ADSVKGRFTL SRDNSKNTLY LQMNSLRAED TAVYYCARED
1CC8H  ISYDGSHKYY ADSVTGRFTI SRDNSKNTLY LQMNSLRAED TAVYYCARAM
1CD7H  ISYDGTYKYY ADSVKGRFTI SRDNSKNTLY LQMNSLRAED TAVYYCARAM
1CE8H  ISYDGSHKYY ADSVTGRFTT SRDNSKNTLY LQMNSLPAED TAVYYCARAM
1CC6H  INYGGGSTYY ADSVKGRFTI SRDNSKNTLY LQMNSLRAED TAVYYCAKHM
3E2H   IYSDDSVTRY SPSFQGQVTI SADKSISTAY LQWSSLKASD TANYYCTRDG
3E3H   IYSDDSVTRY SPSFQGQVTI SADKSISTAY LQWSSLKASD TAMYYCTRDG
3E4H   ISYDGSNKYY ADSVKGRFTL SRDNSKNTLY LQMNSLRAED TAVYYCARED
3E8H   ISYDGSNKYY ADSVKGRFTL PRDNSKNTLY LQMNSLRAED TAVYYCARED
3E9H   IYSDDSVTRY SPSFQGQVTI SADKSISTAY LQWSSLKASD TAMYYCTRDG 101                                                150
1CB1H  VRGVIFDYWG QGTLVTVSSA STKGPSVFPL APSSKSTSGG TAALGCLVKD
1CC2H  VRGVIFDYWG QGTLVTVSSA STKGPSVFPL APSSKSTSGG TAALGCLVKD
3E1H   YYG..MDVWG QGTTVTVSSA STKGPSVFPL APSSKSTSGG TAALGCLVKD
1CC8H  VRGVIFDYWG QGTLVTVSSA STKGPSVFPL APSSKSTSGG IAALGCLVKD
1CD7H  VRGVIFDYWG QGALVTVSSA STKGPSVFPL APSSKSTSGG TAALGCLVKD
1CE8H  VRGVIFDYWG QGTLVTVSSA STKGPSVFPL APSSKSTSGG TAALGCLVKD
1CC6H  VRGVLFDYWG QGTLVTVSSA STKGPSVFPL APSSKSTSGG TAALGCLVKD
3E2H   PEA..FDIWG QGTMVTVSSA STKGPSVFPL APSSKSTSGG TAALGCLVKD
3E3H   PEA..FDIWG QGTMVTVSSA STKGPSVFPL APSSKSTSGG TAALGCLVKD
3E4H   YYG..MDVWG QGTTVTVSSA STKGPSVFPL APSSKSTSGG TAALGCLVKD
3E8H   YYG..MDVWG QGTTVTVSSA STKGPSVFPL APSSKSTSGG TAALGCLVKD
3E9H   PEA..FDIWG QGTMVTVSSA STKGPSVFPL APSSKSTSGG TAALGCLVKD 151                                                200
1CB1H  YFPEPVTVSW NSGALTSGVH TFPAVLQSSG LYSLSSVVTV PSSSLGTQTY
1CC2H  YFPEPVTVSW NSGALTSGVH TFPAVLQSSG LYSLSSVVTV PSSSLGTQTY
3E1H   YFPEPVTVSW NSGALTSGVH TFPAVLQSSG LYSLSSVVTV PSSSLGTQTY
1CC8H  YFPEPVTVSW NSGALTSGVH TFPAVLQSSG LYSLSSVVTV PSSSLGTQTY
1CD7H  YFPEPVTVSW NSGALTSGVH TFPAVLQSSG LYSLSSVVTV PSSSLGTQTY
1CE8H  YFPEPVTVSW NSGALTSGVH TFPAVLQSSG LYSLSSVVTV PSSSLGTQTY
1CCGH  YFPEPVTVSW NSGALTSGVH TFPAVLQSSG LYSLSSVVTV PSSSLGTQTY
3E2H   YFPEPVTVSW NSGALTSGVH TFPAVLQSSG LYSLSSVVTV PSSSLGTQTY
3E3H   YFPEPVTVSW NSGALTSGVH TFPAVLQSSG LYSLSSVVTV PSSSLGTQTY
3E4H   YFPEPVTVSW NSGALTSGVH TFPAVLQSSG LYSLSSVVTV PSSSLGTQTY
3E8H   YFPEPVTVSW NSGALTSGVH TFPAVLQSSG LYSLSSVVTV PSSSLGTQTY
3E9H   YFPEPVTVSW NSGALTSGVH TFPAVLQSSG LYSLSSVVTV PSSSLGTQTY 201                    227
1CB1H  ICNVNHKPSN TKVDKKAEPK SHHHHHH
1CC2H  ICNVNHKPSN TKVDKKAEPK SHHHHHH
3E1H   ICNVNHKPSN TKVDKKAEPK CHHHHHH
1CC8H  ICNVNHKPSN TKVDKKAEPK SHHHHHH
1CD7H  ICNVNHKPSN TKVDKKAEPK SHHHHHH
```

```
-continued
1CE8H  ICNVNHKPSN  TKVDCKAEPK  SHHHHHH
1CC6H  ICNVNHKPSN  TKVDKKAEPK  SHHHHHH
3E2H   ICNTNHKPSN  TKVDKKAEPK  CHHHHHH
3E3H   ICNVNHKPSN  TKVDKKAEPK  CHHHHHH
3E4H   ICNVNHKPSN  TKVDKKAEPK  CHHHHHH
3E8H   ICNVNHKPSN  TKVDKKAEPK  CHHHHHH
3E9H   ICNVNHKPSN  TKVDKKAEPK  CHHHHHH
```

EXAMPLE 38

Growth of E. coli Cultures and Purification of Recombinant Antibodies and Antigens A shake flask inoculum is generated overnight from a −70° C. cell bank in an Innova 4330 incubator shaker (New Brunswick Scientific, Edison, N.J.) set at 37° C., 300 rpm. The inoculum is used to seed a 20 L fermenter (Applikon, Foster City, Calif.) containing defined culture medium (Pack, et al., Bio/Technology 11:1271–1277 (1993)) supplemented with 3 g/L L-leucine, 3 g/L L-isoleucine, 12 g/L casein digest (Difco, Detroit, Mich.), 12.5 g/L glycerol and 10 mg/ml tetracycline. The temperature, pH and dissolved oxygen in the fermenter are controlled at 26° C., 6.0–6.8 and 25% saturation, respectively. Foam is controlled by addition of polypropylene glycol (Dow, Midland, Mich.). Glycerol is added to the fermenter in a fed-batch mode. Fab expression is induced by addition of L(+)-arabinose (Sigma, St. Louis, Mo.) to 2 g/L during the late logarithmic growth phase. Cell density is measured by optical density at 600 nm in an UV-1201 spectrophotometer (Shimadzu, Columbia, Md.). Final Fab concentrations are typically 100–500 mg/L. Following run termination and adjustment of pH to 6.0, the culture is passed twice through an M-210B-EH Microfluidizer (Microfluidics, Newton, Mass.) at 17000 psi. The high pressure homogenization of the cells releases the Fab into the culture supernatant.

The first step in purification is expanded bed immobilized metal affinity chromatography (EB-IMAC). Streamline Chelating resin (Pharmacia, Piscataway, N.J.) is charged with 0.1 M NiCl$_2$. It is then expanded and equilibrated in 50 mM acetate, 200 mM NaCl, 10 mM imidazole, 0.01% NaN$_3$, pH 6.0 buffer flowing in the upward direction. A stock solution is used to bring the culture homogenate to 10 mM imidazole, following which, it is diluted two-fold or higher in equilibration buffer to reduce the wet solids content to less than 5% by weight. It is then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed is converted to a packed bed and the Fab is eluted with 20 mM borate, 150 mM NaCl, 200 mM imidazole, 0.01% NaN$_3$, pH 8.0 buffer flowing in the downward direction. The second step in purification uses ion-exchange chromatography (IEC). Q Sepharose FastFlow resin (Pharmacia, Piscataway, N.J.) is equilibrated in 20 mM borate, 37.5 mM NaCl, 0.01% NaN$_3$, pH 8.0. The Fab elution pool from the EB-IMAC step is diluted four-fold in 20 mM borate, 0.01% NaN$_3$, pH 8.0 and loaded onto the IEC column. After washing, the Fab is eluted with a 37.5–200 mM NaCl salt gradient. The elution fractions are evaluated for purity using an Xcell II SDS-PAGE system (Novex, San Diego, Calif.) prior to pooling. Finally, the Fab pool is concentrated and diafiltered into 20 mM borate, 150 mM NaCl, 0.01% NaN$_3$, pH 8.0 buffer for storage. This is achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/mL solution.

EXAMPLE 39

Generation of Cmu Targeted Mice

The following example describes the making of mice with disrupted, and thus non-functional, immunoglobulin genes Construction of a CMD targeting vector To disrupt the mouse immunoglobulin gene, a vector containing a fragment of a murine Ig heavy chain locus is transfected into a mouse embryonic cell. The mouse Ig heavy chain sequence "targets" the vector to the mouse immunoglobulin gene locus. The following describes construction of this immunoglobulin gene "targeting" vector.

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481–485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in E. coli.

The targeting vector was constructed as follows (See FIG. 6). A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the SmaI site in Cmu1 3' to the XbaI site located just downstream of the last Cmu exon, was inserted.

The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65–74) and containing the pgk polyadenylation site (PvuII/HindIII fragment; Boer et al. (1990) Biochemical Genetics 28: 299–308). This cassette was obtained from the plasmid pKJ1 (described by Tybulewicz et al. (1991) Cell 65: 1153–1163) from which the neo cassette was excised as an EcoRI/HindIII fragment and subcloned into EcoRI/HindIII digested pGEM-7Zf(+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences.

The resulting plasmid was linearized with Not I, and a herpes simplex virus thymidine kinase (tk) cassette was inserted to allow for enrichment of ES clones (mouse embryo-derived stem cells) bearing homologous recombinants, as described by Mansour et al. (1988) Nature 336: 348–352. This cassette consists of the coding sequences of the tk gene bracketed by the mouse pgk promoter and polyadenylation site, as described by Tybulewicz et al. (1991) Cell 65: 1153–1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and analysis of targeted ES cells.

The vector containing the murine Ig heavy chain gene fragment is then inserted into a mouse embryonic stem cell (an ES cell). The following describes the construction of this immunoglobulin gene-containing vector "targeted" ES cell and analysis of the ES cells' DNA after the vector has been inserted (i.e., transfected) into the cell.

AB-1 ES cells (McMahon, A. P. and Bradley, A., (1990) Cell 62: 1073–1085) were grown on mitotically inactive SNL76/7 cell feeder layers (ibid.) essentially as described (Robertson, E. J. (1987) in Teratocarcinomas and Embryonic Stem Cells: a Practical Approach (E. J. Robertson, ed.) Oxford: IRL Press, p. 71–112). The linearized CMD targeting vector was electroporated into AB-1 cells by the methods described Hasty et al. (Hasty, P. R. et al. (1991) Nature 350: 243–246). Electroporated cells were plated into 100 mm dishes at a density of 1–2×106 cells/dish. After 24 hours, G418 (200 micrograms/ml of active component) and FIAU (5×10-7 M) were added to the medium, and drug-resistant clones were allowed to develop over 8–9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 bp SacI fragment, probe A (FIG. 6), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmul exon.

Generation of mice bearing the mutated mu gene.

The three targeted ES clones, designated number 264, 272, and 408, were thawed and injected into C57BL/6J blastocysts as described by Bradley (Bradley, A. (1987) in Teratocarcinomas and Embryonic Stem Cells: a Practical Approach. (E. J. Robertson, ed.) Oxford: IRL Press, p. 113–151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene.

To determine whether the insertion of the neo cassette (including the Ig heavy chain sequence) into Cmul has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647–656). Four agouti offspring were generated. Serum was obtained from these animals at the age of 1 month and assayed by ELISA for the presence of murine IgM. Two of the four offspring were completely lacking IgM (Table 9). Genotyping of the four animals by Southern blot analysis of DNA from tail biopsies by BglI digestion and hybridization with probe A (FIG. 6), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmul mutation. Mice heterozygous for the JHD mutation display wild type levels of serum Ig. These data demonstrate that the Cmul mutation inactivates expression of the mu gene.

TABLE 9

| Mouse | Serum IgM (micrograms/ml) | Ig H chain genotype |
| --- | --- | --- |
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

EXAMPLE 40

Generation of HCo12 Transgenic Mice

The following describes the generation of transgenic mice containing human immunoglobulin heavy chain gene sequence that can generate human immunoglobulins. Because these mice cannot make endogenous (i.e., mouse) immunoglobulins, upon challenge with antigen, e.g., a human polypeptide, only human sequence immunoglobulins are made by the transgenic mouse.

The HCo12 Human Heavy Chain Transgene.

The HCo12 transgene was generated by coinjection of the 80 kb insert of pHC2 (Taylor et al., 1994, Int. Immunol., 6: 579–591) and the 25 kb insert of pVx6. The plasmid pVx6 was constructed as described below. An 8.5 kb HindIII/SalI DNA fragment, comprising the germline human VH1–18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human VH5-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287–6295), to generate the plasmid p251 f.

A new cloning vector derived from pGP1f, pGP1k (Seq. ID #1), was digested with EcoRV/BamHI, and ligated to a 10 kb EcoRV/BamHI DNA fragment, comprising the germline human VH3-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251 f. The resulting plasmid, pVx4, was digested with XhoI and ligated with the 8.5 kb XhoI/SalI insert of p343.7.16.

A plasmid clone was obtained with the $V_H$1-18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J×DBA/2J)F2 embryos as described by Hogan et al. (B. Hogan et al., Manipulating the Mouse Embryo, A Laboratory Manual, 2nd edition, 1994, Cold Spring Harbor Laboratory Press, Plainview N.Y.).

Three independent lines of transgenic mice comprising sequences from both Vx6 and HC2 were established from mice that developed from the injected embryos. These lines of transgenic mice are designated (HCo12)14881, (HCo12) 15083, and (HCo12)15087. Each of the three lines were then bred with mice comprising the CMD mutation described in Example 23, the JKD mutation (Chen et al. 1993, EMBO J. 12: 811–820), and the (KCo5)9272 transgene (Fishwild et al. 1996, Nature Biotechnology 14: 845–851). The resulting mice express human heavy and kappa light chain transgenes (and produce human sequence heavy and kappa light chain antibodies) in a background homoygous for disruption of the endogenous mouse heavy and kappa light chain loci.

Two different strains of mice were used to generate hybridomas and monoclonal antibodies reactive to human IL-8. Strain ((CMD)++; (JKD)++; (HCo7)11952+/++; (KCo5)9272+/++), and strain ((CMD)++; (JKD)++; (HCo12)15087+/++; (KCo5)9272+/+). Each of these strains are homozygous for disruptions of the endogenous heavy chain (CMD) and kappa light chain (JKD) loci. Both strains also comprise a human kappa light chain transgene (HCo7), with individual animals either hemizygous or homozygous for insertion #11952. The two strains differ in the human heavy chain transgene used. Mice were hemizygous or homozygous for either the HCo7 or the HCo12 transgene. The CMD mutation is described above in Example 23, above. The generation of(HCo12)15087 mice is described above. The JKD mutation (Chen et al 1993, EMBO J. 12: 811–820) and the (KCo5)9272 (Fishwild et al. 1996, Nature Biotechnology 14: 845–851) and (HCo7)11952 mice, are described in U.S. Pat. No. 5,770,429 (Lonberg & Kay, Jun. 23, 1998).

What is claimed is:

1. A method of producing a human antibody display library, comprising:
   introducing a nucleic acid encoding a protein immunogen into a transgenic mouse whose genome comprises a plurality of human immunoglobulin genes that can be expressed to produce a plurality of human antibodies,
   isolating a population of nucleic acids encoding human antibody chains from lymphatic cells of the transgenic mouse;
   forming a library of display packages displaying the antibody chains, wherein a library member comprises a nucleic acid encoding an antibody chain, and the antibody chain is displayed from the package.

2. The method of claim 1, wherein the transgenic mouse lacks a titer to the immunogen greater than ten fold the background titer before the introducing step.

3. The method of claim 2, wherein the transgenic mouse lacks a detectable titer to the immunogen when the isolating step is performed.

4. The method of claim 2, wherein the nucleic acid encodes a membrane bound receptor.

5. The method of claim 2, further comprising
   contacting library members with a target, whereby library members displaying an antibody chain and binding partner (if present) with specific affinity for the target bind to the target, to produce a subpopulation of display packages;
   wherein the subpopulation of display packages comprises at least ten different display packages comprising at least ten nucleic acids encoding at least ten antibody chains, and at least 50% of the nucleic acids encode human antibody chains, which in combination with the binding partner (if present) show at least $10^{10}$ $M^{-1}$ affinity for the target and no library member constitutes more than 50% of the library.

6. The method of claim 5, wherein the at least 50% of the nucleic acids encode human antibody chains, which human antibody chains in combination with a binding partner (if present) show at least $10^{12}$ $M^{-1}$ affinity for the target.

7. The method of claim 1, wherein the protein immunogen is a natural protein.

8. The method of claim 1, wherein the natural protein is a natural human protein.

9. The method of claim 1, wherein the nucleic acid encodes a membrane bound protein.

10. The method of claim 1, wherein the nucleic acid encodes an EST.

11. The method of claim 1, further comprising
    contacting library members with a target, whereby library members displaying an antibody chain and binding partner (if present) with specific affinity for the target bind to the target, to produce a subpopulation of display packages;
    wherein the subpopulation of display packages comprises at least ten different display packages comprising at least ten nucleic acids encoding at least ten antibody chains, and at least 50% of the nucleic acids encode human antibody chains, which in combination with a binding partner (if present) show at least $10^{10}$ $M^{-1}$ affinity for the target and no library member constitutes more than 50% of the library.

12. The method of claim 11, wherein the at least 50% of the nucleic acids encode human antibody chains, which human antibody chain in combination with a binding partner (if present) show at least $10^{12}$ $M^{-1}$ affinity for the target.

* * * * *